US009493525B2

(12) United States Patent
Reed

(10) Patent No.: US 9,493,525 B2
(45) Date of Patent: Nov. 15, 2016

(54) AKT LIGANDS AND POLYNUCLEOTIDES ENCODING AKT LIGANDS

(71) Applicant: Intrexon Corporation, Blacksburg, VA (US)

(72) Inventor: Thomas D. Reed, Arlington, VA (US)

(73) Assignee: Intrexon Corporation, Blacksburg, VA (US)

( * ) Notice: Subject to any disclaimer, the term of this patent is extended or adjusted under 35 U.S.C. 154(b) by 134 days.

(21) Appl. No.: 14/335,550

(22) Filed: Jul. 18, 2014

(65) Prior Publication Data
US 2015/0104874 A1 Apr. 16, 2015

Related U.S. Application Data

(60) Division of application No. 13/605,803, filed on Sep. 6, 2012, now Pat. No. 8,815,530, which is a continuation of application No. 13/039,001, filed on Mar. 2, 2011, now Pat. No. 8,263,357, which is a division of application No. 11/758,422, filed on Jun. 5, 2007, now Pat. No. 7,943,732.

(60) Provisional application No. 60/803,913, filed on Jun. 5, 2006.

(51) Int. Cl.
*C12Q 1/48* (2006.01)
*C12N 15/00* (2006.01)
*C12N 1/20* (2006.01)
*C12P 21/06* (2006.01)
*C07H 21/04* (2006.01)
*C07K 14/47* (2006.01)
*C07K 14/00* (2006.01)
*C12N 15/62* (2006.01)
*C07K 14/435* (2006.01)

(52) U.S. Cl.
CPC ............. *C07K 14/47* (2013.01); *C07K 14/00* (2013.01); *C07K 14/435* (2013.01); *C12N 15/62* (2013.01); *C07K 2319/01* (2013.01); *C07K 2319/41* (2013.01); *C07K 2319/43* (2013.01); *C07K 2319/60* (2013.01)

(58) Field of Classification Search
CPC ........ C12N 15/00; C12N 1/20; C07H 21/04; C12P 21/06; C12Q 1/48
See application file for complete search history.

(56) References Cited

U.S. PATENT DOCUMENTS

| 7,071,295 | B2 | 7/2006 | Reed |
| 7,943,732 | B2 | 5/2011 | Reed |
| 8,153,598 | B2 | 4/2012 | Reed |
| 8,263,357 | B2 | 9/2012 | Reed |
| 8,283,445 | B2 | 10/2012 | Reed |
| 2004/0013517 | A1 | 1/2004 | Adrian |
| 2004/0185556 | A1 | 9/2004 | Reed |
| 2004/0203027 | A1 | 10/2004 | Reed |
| 2008/0032947 | A1 | 2/2008 | Reed |
| 2008/0050808 | A1 | 2/2008 | Reed et al. |
| 2008/0051360 | A1 | 2/2008 | Reed et al. |
| 2008/0213834 | A1 | 9/2008 | Reed et al. |
| 2008/0220475 | A1 | 9/2008 | Reed et al. |
| 2009/0186379 | A1 | 7/2009 | Reed |
| 2009/0215173 | A1 | 8/2009 | Reed |
| 2009/0215866 | A1 | 8/2009 | Reed |
| 2010/0279378 | A1 | 11/2010 | Bachinsky et al. |

FOREIGN PATENT DOCUMENTS

| WO | WO 2005/040336 A2 | 5/2005 |
| WO | WO 2005/083125 A2 | 9/2005 |
| WO | WO 2005/116231 AI | 12/2005 |
| WO | WO 2007/048103 A2 | 4/2007 |
| WO | WO 2007/076166 A2 | 7/2007 |
| WO | WO 2008/119058 A2 | 10/2008 |

OTHER PUBLICATIONS

Alessi, D.R. et al., "Molecular basis for the substrate specificity of protein kinase B; comparison with MAPKAP kinase-1 and p70 S6 kinase," *FEBS Letters*, 399:333-338, Elsevier Inc., The Netherlands (1996).
Altiok, S. et al., "Heregulin Induces Phosphorylation of BRCA 1 through Phosphalidylinositol 3-Kinase/AKT in Breast Cancer Cells," *J. Biol. Chem.* 274:32274-32278, The American Society for Biochemistry and Molecular Biology, Inc., United States (1999).
Berwick, D.C. et al., "The Identification of ATP-citrate Lyase as a Protein Kinase B (Akl) Substrate in Primary Adipocytes", *J. Biol. Chem.* 277:33895-33900, The American Society for Biochemistry and Molecular Biology, Inc., United States (2002).
Biggs, W.H. et al., "Protein Kinase B/Akl-mediated phosphorylation promotes nuclear exclusion of the winged helix transcription factor FKHR1", *Proc. Natl. Acad. ScL USA* 96:7421-7426, National Academy of Sciences, United States (Jun. 1999).
Blume-Jensen, P. et al., "The Kit receptor promotes cell survival via activation of PI 3-kinase and subsequent Akl—mediated phosphorylation of Bad on Ser136", *Curr. Biol.* 8:779-782, Elsevier Inc., The Netherlands (1998).
Brazil, D.P. et al., "PKB Binding Proteins: Getting in on the Akl", *Cell* 111:293-303, Elsevier, Inc., The Netherlands (2002).
Brunet, A. et al., "Akl Promotes Cell Survival by Phosphorylating and Inhibiting a Forkhead Transcription Factor", *Cell* 96:857-868, Elsevier Inc., The Netherlands (1999).
Cardone, M.H. et al., "Regulation of Cell Death Protease Caspase-9 by Phosphorylation", *Science* 282:1318-1321, American Society for the Advancement of Science, United States (1998).

(Continued)

*Primary Examiner* — Maryam Monshipouri
(74) *Attorney, Agent, or Firm* — Sterne, Kessler, Goldstein & Fox P.L.L.C.

(57) ABSTRACT

The invention relates to kinase ligands and polyligands. In particular, the invention relates to ligands, homopolyligands, and heteropolyligands that modulate AKT activity. The ligands, homopolyligands, and heteropolyligands are utilized as research tools or as therapeutics. The invention includes linkage of the ligands, homopolyligands, and heteropolyligands to a cellular localization signal, epitope tag and/or a reporter. The invention also includes polynucleotides encoding the ligands, homopolyligands, and heteropolyligands.

20 Claims, 15 Drawing Sheets

(56) References Cited

OTHER PUBLICATIONS

Cha, T. et al., "Akt-Mediated Phosphorylation of EZH2 Suppresses Methylation of Lysine 27 in Histone H3", *Science* 310:306-310, American Society for the Advancement of Science, United States (2005).

Chen, H. et al., "Interaction of Akt-Phosphorylated Ataxin-1 with 14-3-3 Mediates Neurodegeneration in Spinocerebellar Ataxia Type 1", *Cell* 113:457-468, Elsevier, Inc., The Netherlands (2003).

Cross, D.A.E. et al., "Inhibition of glycogen synthase kinase-3 by insulin mediated by protein kinase B", *Nature* 378:785-789, Macmillan Magazines Ltd., United Kingdom (1995).

Datta, S.R. et al., "Cellular survival: a play in three Akts", *Genes Dev.* 13:2905-2927, Cold Spring Harbor Laboratory Press, United States (1999).

del Peso, L. et al., "Interleukin 3-Induced Phosphorylation of BAD Through the Protein Kinase Akt", *Science* 278:687-689, American Society for the Advancement of Science, United States (1997).

Deprez, J. et al., "Phosphorylation and Activation of Heart 6-Phosphofructo-2-kinase by Protein Kinase B and 13 Other Protein Kinases of the Insulin Signaling Cascades", *J. Biol. Chem.* 272:17269-17275, The American Society for Biochemistry and Molecular Biology, Inc., United States (1997).

Du, K. et al., "TRB3: A tribbles Homolog That Inhibits Akt/PKB Activation by Insulin in Liver", *Science* 300:1574-1577, American Society for the Advancement of Science, United States (2003).

Gingras, A. et al., "4E-BP1, a repressor of mRNA translation, is phosphorylated and inactivated by the Akt (PKB) signaling pathway", *Genes Dev.* 12:502-513, Cold Spring Harbor Laboratory Press, United States (1998).

Haghighi, K. et al.,"Superinhibition of Sarcoplasmic Reticulum Function by Phospholamban Induces Cardiac Contractile Failure," *J. Biol. Chem.* 276:24145-24152, The American Society for Biochemistry and Molecular Biology, Inc., United States (2001).

Hanada, M. et al., "Structure, regulation and function of PKB/AKT—a major therapeutic target", *Biochimica et Biophysica ACTA* 3-16, Elsevier Inc., The Netherlands (2004).

Humbert, S. et al., "The IGF-1/Akt Pathway Is Neuroprotective in Huntington's Disease and involves Huntingtin Phosphorylation by Akt", *Dev. Cell*, 2:831-837, Elsevier Inc., The Netherlands (2002).

Hurt, K.J. et al., "Akt-dependent phosphorylation of endothelial nitric-oxide synthase mediates penile erection", *Proc. Natl. Acad. Sci. USA*, 99:4061-4066, National Academy of Sciences, United States (2002).

Ji, Y. et al., "Targeted Inhibition ofCa2+;calmodulin-dependant Protein Kinase II in Cardiac Longitudinal Sarcoplasmic Reticulum Results in Decreased Phospholamban Phosphorylation at Threonine 17," *J. Biol. Chem.* 278:25063-25071, The American Society for Biochemistry and Molecular Biology, Inc., United States (2003).

Jiang, Z.Y., et al., "Identification of WNK1 as a Substrate of Aki/Protein Kinase B and a negative Regulator of Insulin-stimulated Mitogenesis in 3T3-L 1 Cells", *J. Biol. Chem.*, 280: 21622-21628, The American Society for Biochemistry and Molecular Biology, Inc., United States (2005).

Kane, S. et al., "A Method to Identify Serine Kinase Substrates", *J. Biol. Chem.*, 277: 22115-22118, The American Society for Biochemistry and Molecular Biology, Inc., United States (2002).

Kimura, Y. et al., "Phospholamban Regulates the Ca2+-ATPase through Intramembrane Interactions," *J. Biol. Chem.* 271: 21726-21731, The American Society for Biochemistry and Molecular Biology, Inc., United States (1996).

Kimura, Y. et al., "Phospholamban Inhibitory Function Is Activated by Depolymerization," *J. Biol. Chem.* 272: 15061-15064,The American Society for Biochemistry and Molecular Biology, Inc., United States (1997).

Kitamura, T. et al., "Insulin-Induced Phosphorylation and Activation of Cyclic Nucleotide Phosphodiesterase 3B by the Serine-Threonine Kinase Akt", *Mol. Cell. Biol.* 19: 6286-6296, American Society of Microbiology, United States (1999).

Kovacina, K.S. et al., "Identification of a Proline-rich Akt Substrate as a 14-3-3 binding Partner", *J. Biol. Chem.* 278: 10189-4079, The American Society for Biochemistry and Molecular Biology, Inc., United States (2003).

Kwon, T. et al., "Akt Protein Kinase Inhibits Rac1-GTP Binding through Phosphorylation at Serine 71 of Rac1", *J. Biol. Chem.* 275: 423-428, The American Society for Biochemistry and Molecular Biology, Inc., United States (2000).

Lawlor, M. A. et al., "PKB/Akt: a key mediator of cell proliferation, survival and insulin responses?", *J. Cell Sci.* 114:2903-2910, The Company for Biologists Ltd. (2001).

Lee, M. et al., "Akt-Mediated Phosphorylation of the G Protein-Coupled receptor EDG-1 Is Required for Endothelial Cell Chemotaxis", *Mol. Cell*, 8: 693-704, Elsevier Inc., The Netherlands (2001).

Li, J., et al., "Modulation of Insulin receptor Substrate-1 Tyrosine Phosphorylation by an Aki/Phosphatidylinositol 3—Kinase Pathway", *J. Biol. Chem.* 274:9351-9356, The American Society for Biochemistry and Molecular Biology, Inc., United States (1999).

Lynch, D.K. et al., "PKB-mediated negative feedback tightly regulates mitogenic signalling via Gab2," *EMBO J.* 21:72-82, European Molecular Biology Organization, United Kingdom (2002).

Maira, S. et al., Carboxyl-terminal Modulator Protein (CTMP), a Negative Regulator of PKB/Akt and v-Akt at the Plasma Membrane, *Science* 294:374-380, American Society for the Advancement of Science, United States (2001).

Michell, B.J. et al., "The Akt kinase signals directly to endothelial nitric oxide synthase," *Curr. Biol.* 9:845-848, Elsevier Inc., The Netherlands (1999).

Miinea, C.P. et al., "AS160, the Akt substrate regulating GLUT4 translocation, has a functional Rab GTPase—activating protein domain," *J. Biochem.* 391:87-93, Oxford University Press, United Kingdom (2005).

Nakae, J. et al. "The forkhead transcription factor Foxo1 (Fkhr) confers insulin sensitivity onto glucose-6- phosphatase expression," *J. Clin. Invest.* 108:1359-1367, American Society for Clinical Investigation, United States (2001).

Obata, T. et al., "Peptide and Protein Library Screening Defines Optimal Substrate Motifs for AKT/PKB," *J. Biol. Chem.* 275:36108-36115, The American Society for Biochemistry and Molecular Biology, Inc., United States (2000).

Ozes, O.N. et al., "NF-kB activation by tumour necrosis factor requires the Akt serine-threonine kinase," *Nature* 401:401:82-85, Macmillan Magazines Ltd., London (1999).

Plomgaard, P. et al., "Tumor Necrosis Factor-a induces Skeletal Muscle Insulin Resistance in Healthy Human Subjects via inhibition of Akt Substrate 160 Phosphorylation", *Diabetes* 54:2939-2945, American Diabetes Association, United States (2005).

Powell, D.W. et al., "Identification of 14-3-3 as a Protein Kinase B/Akt Substrate," *J. Biol. Chem.* 277:21639-21642, The American Society for Biochemistry and Molecular Biology, Inc., United States (2002).

Rena, G. et al., "Phosphorylation of the Transcription Factor Forkhead Family Member FKHR by Protein Kinase B," *J. Biol. Chem.* 274:17179-171832, The American Society for Biochemistry and Molecular Biology, Inc., United States (1999).

Saito, A. et al., "Neuroprotective Role of a Proline-Rich Akt Substrate in Apoptotic neuronal Cell Death after Stroke: Relationships with Nerve Growth Factor," *J. Neurosci.*, 24:1584-1593, Society for Neuroscience, United States (2004).

Sano, H. et al., "Insulin-stimulated Phosphorylation of aRab GTPase-activating Protein Regulates GLUT4 Translocation," *J. Biol. Chem.* 278:14599-14602, The American Society for Biochemistry and Molecular Biology, Inc., United States (2003).

Song, G. et al., "The activation of Aki/PKB signaling pathway and cell survival," *J. Cell. Mol. Med.* 9:59-71, Wiley-Blackwell (2005).

Tee, A.R. et al., "Inactivation of the Tuberous Sclerosis Complex-1 and -2 Gene Products Occurs by Phosphoinositide 3-Kinase/Akt-dependent and—independent Phosphorylation of Tuberin," *J. Biol. Chem.* 278:37288-37296, The American Society for Biochemistry and Molecular Biology, Inc., United States (2003).

Toker, A. et al., "Aki/Protein Kinase B Is Regulated by Autophosphorylation at the Hypothetical PDK-2 Site," *J. Biol.*

(56) References Cited

OTHER PUBLICATIONS

*Chem.* 275:8271-8274, The American Society for Biochemistry and Molecular Biology, Inc., United States (2000).

Viglietto, G. et al., "Cytoplasmic relocalization and inhibition of the cyclindependent kinases inhibitor p27 by PKB/Akt-medicated phosphorylation in breast cancer," *Nat. Med.* 8:1136-1144, Nature Publishing Group (2002).

Vitari, A.G. et al., "WNK1, the kinase mutated in an inherited high-blood-pressure syndrome, is a novel PKB (protein kinase B)/Akt substrate," *J. Biochem. Soc.* 378:257-268 (2004).

Wang, L. et al., "Receptor-Independent Activation of GABAergic Neurotransmission and Receptor-Dependent Nontranscriptional Activation of Phosphatidylinositol 3-kinase/Protein Kinase Akt Pathway in Short-Term Cardiovascular Actions of Dexamethasone at the Nucleus T ractus Solitarii of the Rat," *Mol. Pharmacol.*, 67:489-498 (2005).

Wolfrum, C. et al., "Insulin regulates the activity of forkhead transcription factor Hnf-3B/Foxa-2 by Akt-mediated phosphorylation and nuclear/cytosolic localization," *Proc. Natl. Acad. Sci. USA* 100:11624-11629, National Academy of Sciences, United States (2003).

Yang, J. et al., "Crystal structure of an activated Aki/Protein Kinase B ternary complex with GSK3-peptide and AMP—PNP," *Nat. Struc. Biol.* 9: 940-944, Nature Publishing Group (2002).

Yang, L. et al., "Induction of Androgen Receptor Expression by Phosphatidylinositol 3-Kinase/Akt Downstream Substrate, FOX03a, and Their Roles in Apoptosis of LNCaP Prostate Cancer Cells," *J. Biol. Chem.* 280:33558-33565, The American Society for Biochemistry and Molecular Biology, Inc., United States (2005).

Zheng, W. et al., "Insulin-like Growth Factor-1-induced Phosphorylation of the Forkhead Family Transcription Factor FKHRL 1 Is Medicated by Akt Kinase in PC12 Cells," *J. Biol. Chem.* 275:39152-39158, The American Society for Biochemistry and Molecular Biology, Inc., United States (2002).

Zhou, B. P. et al., "Novel Targets of Akt, p21, and MDM2," *Semin. Oncol.* 29:62-70, Elsevier Inc., The Netherlands (2002).

Zhou, G. et al., "Akt Phosphorylation of Serine 21 on Pak1 Modulates Nck Binding and Cell Migration," *Mol. Cell. Biol.* 23:8058-8069, American Society of Microbiologists, United States (2003).

Zimmermann, S. et al., "Phosphorylation and Regulation of Raf by Akt (Protein Kinase B)," *Science* 286:1741-1744, American Society for the Advancement of Science, United States (1999).

Hanada, M. et al., "Structure, regulation and function of PKB/AKT—a major therapeutic target", *Biochimica et Biophysica ACTA* 1697: 3-16, Elsevier Inc., The Netherlands (2004).

Office Action mailed Jan. 27, 2012 in U.S. Appl. No. 13/039,001, filed Mar. 2, 2011, inventor Thomas D. Reed.

Office Action mailed Dec. 14, 2005 in U.S. Appl. No. 10/724,532, filed Nov. 29, 2003, inventor Thomas D. Reed.

Office Action mailed Apr. 23, 2010, in U.S. Appl. No. 11/758,422, filed Jun. 5, 2007, inventor Thomas D. Reed.

Office Action mailed Aug. 5, 2013, in U.S. Appl. No. 13/605,803, filed Sep. 6, 2012, inventor Thomas D. Reed.

Office Action mailed Jan. 10, 2014, in U.S. Appl. No. 13/605,803, filed Sep. 6, 2012, inventor Thomas D. Reed.

Notice of Allowance mailed Apr. 24, 2014, in U.S. Appl. No. 13/605,803, filed Sep. 6, 2012, inventor Thomas D. Reed.

Office Action mailed Jul. 29, 2005 in U.S. Appl. No. 10/724,532, filed Nov. 29, 2003.

| LIGAND X | LIGAND X |
|---|---|

FIGURE 1A

| LIGAND X | LIGAND X | LIGAND X |
|---|---|---|

FIGURE 1B

| LIGAND X | LIGAND X | LIGAND X | LIGAND X | LIGAND X |
|---|---|---|---|---|

FIGURE 1C

| LIGAND X | SPACER | LIGAND X |
|---|---|---|

FIGURE 2A

| LIGAND X | SPACER | LIGAND X | SPACER | LIGAND X |
|---|---|---|---|---|

FIGURE 2B

| LIGAND X | LIGAND X | SPACER | LIGAND X | SPACER | LIGAND X |
|---|---|---|---|---|---|

FIGURE 2C

| LIGAND X | LIGAND Y |
|---|---|

FIGURE 3A

| LIGAND X | LIGAND Y | LIGAND Z |
|---|---|---|

FIGURE 3B

| LIGAND X | LIGAND Y | LIGAND X | LIGAND Z | LIGAND A |
|---|---|---|---|---|

FIGURE 3C

| LIGAND A | LIGAND B | LIGAND C | LIGAND D |
|---|---|---|---|

FIGURE 3D

| LIGAND A | LIGAND A | LIGAND B | LIGAND C |
|---|---|---|---|

FIGURE 3E

| LIGAND B | SPACER | LIGAND A |

FIGURE 4A

| LIGAND X | SPACER | LIGAND Y | SPACER | LIGAND Z |

FIGURE 4B

| LIGAND X | LIGAND Y | SPACER | LIGAND Y | LIGAND X |

FIGURE 4C

| LIGAND A | SPACER | LIGAND B | SPACER | LIGAND C | SPACER | LIGAND D |

FIGURE 4D

| LIGAND A | LIGAND A | SPACER | LIGAND B | LIGAND C |

FIGURE 4E

| LIGAND A | LIGAND B | LIGAND C | LIGAND D | EPITOPE | LOCALIZATION SIGNAL |

FIGURE 8A

| LOCALIZATION SIGNAL | LIGAND X | LIGAND Y | EPITOPE |

FIGURE 8B

| EPITOPE | LIGAND X | SPACER | LIGAND X | LOCALIZATION SIGNAL |

FIGURE 8C

| LOCALIZATION SIGNAL | LIGAND X | SPACER | LIGAND Y | EPITOPE |

FIGURE 8D

| EPITOPE | LIGAND X | LIGAND Y | LIGAND B | LOCALIZATION SIGNAL |

FIGURE 8E

| LOCALIZATION SIGNAL | LIGAND Z | SPACER | LIGAND Y | LIGAND B | EPITOPE |

FIGURE 8F

| EPITOPE | LIGAND B | LOCALIZATION SIGNAL |

FIGURE 8G

| PROMOTER | LIGAND or POLYLIGAND | EPITOPE | LOCALIZATION SIGNAL | STOP | POLY-A |

FIGURE 9A

| PROMOTER | OPTIONAL REPORTER | OPTIONAL EPITOPE | LIGAND or POLYLIGAND | OPTIONAL LOCALIZATION SIGNAL | STOP | POLY-A |

FIGURE 9B

| PROMOTER | LIGAND or POLYLIGAND | REPORTER | LOCALIZATION SIGNAL | STOP | POLY-A |

FIGURE 9C

| PROMOTER | LIGAND or POLYLIGAND | OPTIONAL EPITOPE | OPTIONAL REPORTER | OPTIONAL LOCALIZATION SIGNAL | STOP | POLY-A |

FIGURE 9D

| PROMOTER | LIGAND or POLYLIGAND | LOCALIZATION SIGNAL | STOP | POLY-A |

FIGURE 9E

| PROMOTER | LOCALIZATION SIGNAL | LIGAND or POLYLIGAND | STOP | POLY-A |

FIGURE 9F

| PROMOTER | LIGAND or POLYLIGAND | STOP | POLY-A |

FIGURE 9G

SEQUENCE LISTING

```
<160> NUMBER OF SEQ ID NOS: 261

<210> SEQ ID NO 1
<211> LENGTH: 46
<212> TYPE: PRT
<213> ORGANISM: Artificial Sequence
<220> FEATURE:
<223> OTHER INFORMATION: Synthetic Polyligand

<400> SEQUENCE: 1

Ala Arg Lys Arg Glu Arg Ala Tyr Ala Phe Gly His His Ala Arg Pro
1               5                   10                  15

Arg Ala Ala Ala Phe Ala Asn Arg Met Arg Gly Arg Leu Gly Ala Val
            20                  25                  30

Asp Gly Asp Leu Pro Arg Pro Arg Leu Asn Ala Ala Asp Phe
        35                  40                  45

<210> SEQ ID NO 2
<211> LENGTH: 138
<212> TYPE: DNA
<213> ORGANISM: Artificial Sequence
<220> FEATURE:
<223> OTHER INFORMATION: Synthetic Polyligand

<400> SEQUENCE: 2
gccaggaaga gggagagggc ctacgccttc ggccaccacg ccaggcccag ggccgccgcc        60
```

```
ttcgccaaca ggatgagggg caggctgggc gccgtggacg gcgacctgcc caggcccagg    120
ctgaacgccg ccgacttc                                                  138

<210> SEQ ID NO 3
<211> LENGTH: 138
<212> TYPE: DNA
<213> ORGANISM: Artificial Sequence
<220> FEATURE:
<223> OTHER INFORMATION: Synthetic Polyligand

<400> SEQUENCE: 3
gccaggaaga gggagagggc ctacgccttc ggccaccacg ccaggcccag ggccgccgcc    60
ttcgccaaca ggatgagggg caggctcgga gccgtggacg gcgacctgcc caggcccagg    120
ctgaacgccg ccgacttc                                                  138

<210> SEQ ID NO 4
<211> LENGTH: 81
<212> TYPE: PRT
<213> ORGANISM: Artificial Sequence
<220> FEATURE:
<223> OTHER INFORMATION: Synthetic Polyligand

<400> SEQUENCE: 4
```

Glu Ala Val Ser Glu Gly Ser Ser Ser Gly Arg Ala Arg Glu Ala Ala
1               5                   10                  15

Gly Ala Pro Thr Ser Ser Lys Asp Asn Tyr Leu Gln Glu Arg Pro Leu
            20                  25                  30

Thr Asn Lys Leu Lys Arg Lys Arg Arg Pro Ala Ser Gly Leu His Pro
        35                  40                  45

Glu Asp Phe Ile Lys Lys His Lys Ser Arg Met Tyr Ser Gln Cys Val
    50                  55                  60

Arg Met Arg His Leu Ala Gln Glu Arg Arg Phe Tyr Gln Leu Thr Lys
65                  70                  75                  80

Leu

```
<210> SEQ ID NO 5
<211> LENGTH: 243
<212> TYPE: DNA
<213> ORGANISM: Artificial Sequence
<220> FEATURE:
<223> OTHER INFORMATION: Synthetic Polyligand

<400> SEQUENCE: 5
gaggccgtga gcgagggcag ctccagcggc agggccaggg aggccgccgg cgcccccacc    60
agcagcaagg acaactacct gcaggagagg cccctgacca acaagctgaa gaggaagagg    120
aggcccgcca gcggcctgca ccccgaggac ttcatcaaga agcacaagag caggatgtac    180
agccagtgcg tgaggatgag gcacctggcc caggagagga ggttctacca gctgaccaag    240
ctg                                                                  243

<210> SEQ ID NO 6
<211> LENGTH: 243
<212> TYPE: DNA
<213> ORGANISM: Artificial Sequence
<220> FEATURE:
<223> OTHER INFORMATION: Synthetic Polyligand

<400> SEQUENCE: 6
gaggccgtga gcgagggcag ctccagcggc agggccaggg aggccgctgg agcccccacc    60
```

```
agcagcaagg acaactacct gcaagagaga cccctgacca caagctgaa gaggaagagg      120 aggcccgcca gcggcctgca ccccgaggac ttcatcaaga agcacaagag caggatgtat      180
agccagtgcg tgaggatgag gcacctggcc caggaggga ggttctacca gctcaccaag      240
ctg                                                                   243
```

<210> SEQ ID NO 7
<211> LENGTH: 91
<212> TYPE: PRT
<213> ORGANISM: Artificial Sequence
<220> FEATURE:
<223> OTHER INFORMATION: Synthetic Polyligand

<400> SEQUENCE: 7

```
Tyr Cys Arg Ile Tyr Ser Leu Val Arg Thr Arg Ser Arg Arg Leu Ala
1               5                   10                  15

Phe Arg Lys Asn Ile Ser Lys Ala Ser Arg Ser Ala Gly Ala Gly Pro
            20                  25                  30

Leu Leu Asp Leu Gln Glu Asn Arg Pro Ala Arg Gln Arg Ile Arg Ala
        35                  40                  45

Cys Val Ser Ala Glu Asn Phe Leu Gln Ile Gln Gly Ala Gly Ala Pro
    50                  55                  60

Glu Ile Asp Pro Asp Phe Glu Pro Leu Pro Arg Pro Arg Ser Cys Ala
65                  70                  75                  80

Trp Pro Leu Pro Arg Pro Glu Phe Ser Gln Ser
                85                  90
```

<210> SEQ ID NO 8
<211> LENGTH: 273
<212> TYPE: DNA
<213> ORGANISM: Artificial Sequence
<220> FEATURE:
<223> OTHER INFORMATION: Synthetic Polyligand

<400> SEQUENCE: 8

```
tactgcagga tctatagcct ggtgaggaca agaagcagga gactggcctt caggaagaac       60
atcagcaagg cctccaggag cgccggcgct ggacccctgc tcgacctgca ggagaacagg      120
cccgccaggc agagaatcag ggcctgcgtg agcgctgaga acttcctgca gatccagggc      180
gccggagctc ccgagatcga ccccgatttt gaacctctgc ccaggcctag atcctgcgcc      240 tggccctcc ctagacccga gttcagccag agc                                  273
```

<210> SEQ ID NO 9
<211> LENGTH: 273
<212> TYPE: DNA
<213> ORGANISM: Artificial Sequence
<220> FEATURE:
<223> OTHER INFORMATION: Synthetic Polyligand

<400> SEQUENCE: 9

```
tactgtagga tctatagcct ggtgaggaca agaagcagga gactggcctt caggaagaac       60
atcagcaagg cttccaggag cgctggcgct ggacccctgc tcgacctcca ggagaacagg      120
cccgccaggc agagaatcag agcctgcgtg agcgctgaga acttcctcca gatccaagga      180
gccggagccc ccgagatcga ccccgatttt gaacctctgc ccaggcccag atcctgcgcc      240 tggccctcc ctagacccga gttcagccag agc                                  273
```

<210> SEQ ID NO 10
<211> LENGTH: 906

<212> TYPE: PRT
<213> ORGANISM: Homo Sapiens

<400> SEQUENCE: 10

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45

Pro Pro Gly Ala Ser Leu Leu Leu Leu Gln Gln Gln Gln Gln Gln Gln
    50                  55                  60

Gln Gln Gln Gln Gln Gln Gln Gln Glu Thr Ser Pro Arg Gln Gln Gln
65                  70                  75                  80

Gln Gln Gln Gln Gly Glu Asp Gly Ser Pro Gln Ala His Arg Arg Gly
                85                  90                  95

Pro Thr Gly Tyr Leu Val Leu Asp Glu Glu Gln Gln Pro Ser Gln Pro
            100                 105                 110

Gln Ser Ala Leu Glu Cys His Pro Glu Arg Gly Cys Val Pro Glu Pro
        115                 120                 125

Gly Ala Ala Val Ala Ala Ser Lys Gly Leu Pro Gln Gln Leu Pro Ala
    130                 135                 140

Pro Pro Asp Glu Asp Ser Ala Ala Pro Ser Thr Leu Ser Leu Leu
145                 150                 155                 160

Ala Pro Thr Phe Pro Gly Leu Ser Ser Cys Ser Ala Asp Leu Lys Asp
                165                 170                 175

Ile Leu Ser Glu Ala Ser Thr Met Gln Leu Leu Gln Gln Gln Gln Gln
            180                 185                 190

Glu Ala Val Ser Glu Gly Ser Ser Ser Gly Arg Ala Arg Glu Ala Ser
        195                 200                 205

Gly Ala Pro Thr Ser Ser Lys Asp Asn Tyr Leu Gly Gly Thr Ser Thr
    210                 215                 220

Ile Ser Asp Asn Ala Lys Glu Leu Cys Lys Ala Val Ser Val Ser Met
225                 230                 235                 240

Gly Leu Gly Val Glu Ala Leu Glu His Leu Ser Pro Gly Glu Gln Leu
                245                 250                 255

Arg Gly Asp Cys Met Tyr Ala Pro Leu Leu Gly Val Pro Pro Ala Val
            260                 265                 270

Arg Pro Thr Pro Cys Ala Pro Leu Ala Glu Cys Lys Gly Ser Leu Leu
        275                 280                 285

Asp Asp Ser Ala Gly Lys Ser Thr Glu Asp Thr Ala Glu Tyr Ser Pro
    290                 295                 300

Phe Lys Gly Gly Tyr Thr Lys Gly Leu Glu Gly Glu Ser Leu Gly Cys
305                 310                 315                 320

Ser Gly Ser Ala Ala Gly Ser Ser Gly Thr Leu Glu Leu Pro Ser
                325                 330                 335

Thr Leu Ser Leu Tyr Lys Ser Gly Ala Leu Asp Glu Ala Ala Ala Tyr
            340                 345                 350

Gln Ser Arg Asp Tyr Tyr Asn Phe Pro Leu Ala Leu Ala Gly Pro Pro
        355                 360                 365

Pro Pro Pro Pro Pro His Pro His Ala Arg Ile Lys Leu Glu Asn
    370                 375                 380

Pro Leu Asp Tyr Gly Ser Ala Trp Ala Ala Ala Ala Gln Cys Arg
385                 390                 395                 400

-continued

```
Tyr Gly Asp Leu Ala Ser Leu His Gly Ala Gly Ala Gly Pro Gly
            405                 410                 415

Ser Gly Ser Pro Ser Ala Ala Ser Ser Trp His Thr Leu Phe
            420                 425                 430

Thr Ala Glu Glu Gly Gln Leu Tyr Gly Pro Cys Gly Gly Gly Gly
            435                 440                 445

Gly Gly Gly Gly Gly Gly Gly Gly Gly Glu Ala Gly Ala Val
    450                 455                 460

Ala Pro Tyr Gly Tyr Thr Arg Pro Pro Gln Gly Leu Ala Gly Gln Glu
465                 470                 475                 480

Ser Asp Phe Thr Ala Pro Asp Val Trp Tyr Pro Gly Gly Met Val Ser
            485                 490                 495

Arg Val Pro Tyr Pro Ser Pro Thr Cys Val Lys Ser Glu Met Gly Pro
                500                 505                 510

Trp Met Asp Ser Tyr Ser Gly Pro Tyr Gly Asp Met Arg Leu Glu Thr
            515                 520                 525

Ala Arg Asp His Val Leu Pro Ile Asp Tyr Tyr Phe Pro Pro Gln Lys
    530                 535                 540

Thr Cys Leu Ile Cys Gly Asp Glu Ala Ser Gly Cys His Tyr Gly Ala
545                 550                 555                 560

Leu Thr Cys Gly Ser Cys Lys Val Phe Phe Lys Arg Ala Ala Glu Gly
                565                 570                 575

Lys Gln Lys Tyr Leu Cys Ala Ser Arg Asn Asp Cys Thr Ile Asp Lys
            580                 585                 590

Phe Arg Arg Lys Asn Cys Pro Ser Cys Arg Leu Arg Lys Cys Tyr Glu
    595                 600                 605

Ala Gly Met Thr Leu Gly Ala Arg Lys Leu Lys Lys Leu Gly Asn Leu
    610                 615                 620

Lys Leu Gln Glu Glu Gly Glu Ala Ser Ser Thr Thr Ser Pro Thr Glu
625                 630                 635                 640

Glu Thr Thr Gln Lys Leu Thr Val Ser His Ile Glu Gly Tyr Glu Cys
                645                 650                 655

Gln Pro Ile Phe Leu Asn Val Leu Glu Ala Ile Glu Pro Gly Val Val
            660                 665                 670

Cys Ala Gly His Asp Asn Asn Gln Pro Asp Ser Phe Ala Ala Leu Leu
            675                 680                 685

Ser Ser Leu Asn Glu Leu Gly Glu Arg Gln Leu Val His Val Val Lys
    690                 695                 700

Trp Ala Lys Ala Leu Pro Gly Leu Arg Asn Leu His Val Asp Asp Gln
705                 710                 715                 720

Met Ala Val Ile Gln Tyr Ser Trp Met Gly Leu Met Val Phe Ala Met
                725                 730                 735

Gly Trp Arg Ser Phe Thr Asn Val Asn Ser Arg Met Leu Tyr Phe Ala
            740                 745                 750

Pro Asp Leu Val Phe Asn Glu Tyr Arg Met His Lys Ser Arg Met Tyr
            755                 760                 765

Ser Gln Cys Val Arg Met Arg His Leu Ser Gln Glu Phe Gly Trp Leu
    770                 775                 780

Gln Ile Thr Pro Gln Glu Phe Leu Cys Met Lys Ala Met Leu Leu Phe
785                 790                 795                 800

Ser Ile Ile Pro Val Asp Gly Leu Lys Asn Gln Lys Phe Phe Asp Glu
                805                 810                 815
```

```
Leu Arg Met Asn Tyr Ile Lys Glu Leu Asp Arg Ile Ile Ala Cys Lys
            820                 825                 830

Arg Lys Asn Pro Thr Ser Cys Ser Arg Arg Phe Tyr Gln Leu Thr Lys
            835                 840                 845

Leu Leu Asp Ser Val Gln Pro Ile Ala Arg Glu Leu His Gln Phe Thr
            850                 855                 860

Phe Asp Leu Leu Ile Lys Ser His Met Val Ser Val Asp Phe Pro Glu
865                 870                 875                 880

Met Met Ala Glu Ile Ile Ser Val Gln Val Pro Lys Ile Leu Ser Gly
            885                 890                 895

Lys Val Lys Pro Ile Tyr Phe His Thr Gln
            900                 905

<210> SEQ ID NO 11
<211> LENGTH: 661
<212> TYPE: PRT
<213> ORGANISM: Homo Sapiens

<400> SEQUENCE: 11

Met Glu Gly Ala Ala Pro Val Ala Gly Asp Arg Pro Asp Leu Gly
1               5                   10                  15

Leu Gly Ala Pro Gly Ser Pro Arg Glu Ala Val Ala Gly Ala Thr Ala
            20                  25                  30

Ala Leu Glu Pro Arg Lys Pro His Gly Val Lys Arg His His His Lys
            35                  40                  45

His Asn Leu Lys His Arg Tyr Glu Leu Gln Glu Thr Leu Gly Lys Gly
        50                  55                  60

Thr Tyr Gly Lys Val Lys Arg Ala Thr Glu Arg Phe Ser Gly Arg Val
65                  70                  75                  80

Val Ala Ile Lys Ser Ile Arg Lys Asp Lys Ile Lys Asp Glu Gln Asp
                85                  90                  95

Met Val His Ile Arg Arg Glu Ile Glu Ile Met Ser Ser Leu Asn His
            100                 105                 110

Pro His Ile Ile Ser Ile Tyr Glu Val Phe Glu Asn Lys Asp Lys Ile
            115                 120                 125

Val Ile Ile Met Glu Tyr Ala Ser Lys Gly Glu Leu Tyr Asp Tyr Ile
            130                 135                 140

Ser Glu Arg Arg Arg Leu Ser Glu Arg Glu Thr Arg His Phe Phe Arg
145                 150                 155                 160

Gln Ile Val Ser Ala Val His Tyr Cys His Lys Asn Gly Val Val His
                165                 170                 175

Arg Asp Leu Lys Leu Glu Asn Ile Leu Leu Asp Asp Asn Cys Asn Ile
            180                 185                 190

Lys Ile Ala Asp Phe Gly Leu Ser Asn Leu Tyr Gln Lys Asp Lys Phe
            195                 200                 205

Leu Gln Thr Phe Cys Gly Ser Pro Leu Tyr Ala Ser Pro Glu Ile Val
            210                 215                 220

Asn Gly Arg Pro Tyr Arg Gly Pro Glu Val Asp Ser Trp Ala Leu Gly
225                 230                 235                 240

Val Leu Leu Tyr Thr Leu Val Tyr Gly Thr Met Pro Phe Asp Gly Phe
                245                 250                 255

Asp His Lys Asn Leu Ile Arg Gln Ile Ser Ser Gly Glu Tyr Arg Glu
            260                 265                 270

Pro Thr Gln Pro Ser Asp Ala Arg Gly Leu Ile Arg Trp Met Leu Met
            275                 280                 285
```

Val Asn Pro Asp Arg Arg Ala Thr Ile Glu Asp Ile Ala Asn His Trp
    290                 295                 300

Trp Val Asn Trp Gly Tyr Lys Ser Ser Val Cys Asp Cys Asp Ala Leu
305                 310                 315                 320

His Asp Ser Glu Ser Pro Leu Leu Ala Arg Ile Ile Asp Trp His His
                325                 330                 335

Arg Ser Thr Gly Leu Gln Ala Asp Thr Glu Ala Lys Met Lys Gly Leu
            340                 345                 350

Ala Lys Pro Thr Thr Ser Glu Val Met Leu Glu Arg Gln Arg Ser Leu
        355                 360                 365

Lys Lys Ser Lys Lys Glu Asn Asp Phe Ala Gln Ser Gly Gln Asp Ala
370                 375                 380

Val Pro Glu Ser Pro Ser Lys Leu Ser Ser Lys Arg Pro Lys Gly Ile
385                 390                 395                 400

Leu Lys Lys Arg Ser Asn Ser Glu His Arg Ser His Ser Thr Gly Phe
                405                 410                 415

Ile Glu Gly Val Val Gly Pro Ala Leu Pro Ser Thr Phe Lys Met Glu
            420                 425                 430

Gln Asp Leu Cys Arg Thr Gly Val Leu Leu Pro Ser Ser Pro Glu Ala
        435                 440                 445

Glu Val Pro Gly Lys Leu Ser Pro Lys Gln Ser Ala Thr Met Pro Lys
450                 455                 460

Lys Gly Ile Leu Lys Lys Thr Gln Gln Arg Glu Ser Gly Tyr Tyr Ser
465                 470                 475                 480

Ser Pro Glu Arg Ser Glu Ser Ser Glu Leu Leu Asp Ser Asn Asp Val
                485                 490                 495

Met Gly Ser Ser Ile Pro Ser Pro Ser Pro Asp Pro Ala Arg Val
            500                 505                 510

Thr Ser His Ser Leu Ser Cys Arg Arg Lys Gly Ile Leu Lys His Ser
        515                 520                 525

Ser Lys Tyr Ser Ala Gly Thr Met Asp Pro Ala Leu Val Ser Pro Glu
530                 535                 540

Met Pro Thr Leu Glu Ser Leu Ser Glu Pro Gly Val Pro Ala Glu Gly
545                 550                 555                 560

Leu Ser Arg Ser Tyr Ser Arg Pro Ser Ser Val Ile Ser Asp Asp Ser
                565                 570                 575

Val Leu Ser Ser Asp Ser Phe Asp Leu Leu Asp Leu Gln Glu Asn Arg
            580                 585                 590

Pro Ala Arg Gln Arg Ile Arg Ser Cys Val Ser Ala Glu Asn Phe Leu
        595                 600                 605

Gln Ile Gln Asp Phe Glu Gly Leu Gln Asn Arg Pro Arg Pro Gln Tyr
610                 615                 620

Leu Lys Arg Tyr Arg Asn Arg Leu Ala Asp Ser Ser Phe Ser Leu Leu
625                 630                 635                 640

Thr Asp Met Asp Asp Val Thr Gln Val Tyr Lys Gln Ala Leu Glu Ile
                645                 650                 655

Cys Ser Lys Leu Asn
            660

<210> SEQ ID NO 12
<211> LENGTH: 1299
<212> TYPE: PRT
<213> ORGANISM: Homo Sapiens

```
<400> SEQUENCE: 12

Met Glu Pro Pro Ser Cys Ile Gln Asp Glu Pro Phe Pro His Pro Leu
1               5                   10                  15

Glu Pro Glu Pro Gly Val Ser Ala Gln Pro Gly Pro Gly Lys Pro Ser
            20                  25                  30

Asp Lys Arg Phe Arg Leu Trp Tyr Val Gly Gly Ser Cys Leu Asp His
        35                  40                  45

Arg Thr Thr Leu Pro Met Leu Pro Trp Leu Met Ala Glu Ile Arg Arg
    50                  55                  60

Arg Ser Gln Lys Pro Glu Ala Gly Cys Gly Ala Pro Ala Ala Arg
65              70                  75                  80

Glu Val Ile Leu Val Leu Ser Ala Pro Phe Leu Arg Cys Val Pro Ala
                85                  90                  95

Pro Gly Ala Gly Ala Ser Gly Gly Thr Ser Pro Ser Ala Thr Gln Pro
            100                 105                 110

Asn Pro Ala Val Phe Ile Phe Glu His Lys Ala Gln His Ile Ser Arg
        115                 120                 125

Phe Ile His Asn Ser His Asp Leu Thr Tyr Phe Ala Tyr Leu Ile Lys
    130                 135                 140

Ala Gln Pro Asp Asp Pro Glu Ser Gln Met Ala Cys His Val Phe Arg
145                 150                 155                 160

Ala Thr Asp Pro Ser Gln Val Pro Asp Val Ile Ser Ser Ile Arg Gln
                165                 170                 175

Leu Ser Lys Ala Ala Met Lys Glu Asp Ala Lys Pro Ser Lys Asp Asn
            180                 185                 190

Glu Asp Ala Phe Tyr Asn Ser Gln Lys Phe Glu Val Leu Tyr Cys Gly
        195                 200                 205

Lys Val Thr Val Thr His Lys Lys Ala Pro Ser Ser Leu Ile Asp Asp
    210                 215                 220

Cys Met Glu Lys Phe Ser Leu His Glu Gln Gln Arg Leu Lys Ile Gln
225                 230                 235                 240

Gly Glu Gln Arg Gly Pro Asp Pro Gly Glu Asp Leu Ala Asp Leu Glu
                245                 250                 255

Val Val Val Pro Gly Ser Pro Gly Asp Cys Leu Pro Glu Glu Ala Asp
            260                 265                 270

Gly Thr Asp Thr His Leu Gly Leu Pro Ala Gly Ala Ser Gln Pro Ala
        275                 280                 285

Leu Thr Ser Ser Arg Val Cys Phe Pro Glu Arg Ile Leu Glu Asp Ser
    290                 295                 300

Gly Phe Asp Glu Gln Gln Glu Phe Arg Ser Arg Cys Ser Ser Val Thr
305                 310                 315                 320

Gly Val Gln Arg Arg Val His Glu Gly Ser Gln Lys Ser Gln Pro Arg
                325                 330                 335

Arg Arg His Ala Ser Ala Pro Ser His Val Gln Pro Ser Asp Ser Glu
            340                 345                 350

Lys Asn Arg Thr Met Leu Phe Gln Val Gly Arg Phe Glu Ile Asn Leu
        355                 360                 365

Ile Ser Pro Asp Thr Lys Ser Val Val Leu Glu Lys Asn Phe Lys Asp
    370                 375                 380

Ile Ser Ser Cys Ser Gln Gly Ile Lys His Val Asp His Phe Gly Phe
385                 390                 395                 400

Ile Cys Arg Glu Ser Pro Glu Pro Gly Leu Ser Gln Tyr Ile Cys Tyr
                405                 410                 415
```

-continued

Val Phe Gln Cys Ala Ser Glu Ser Leu Val Asp Val Met Leu Thr
            420             425             430

Leu Lys Gln Ala Phe Ser Thr Ala Ala Leu Gln Ser Ala Lys Thr
            435             440             445

Gln Ile Lys Leu Cys Glu Ala Cys Pro Met His Ser Leu His Lys Leu
    450             455             460

Cys Glu Arg Ile Glu Gly Leu Tyr Pro Pro Arg Ala Lys Leu Val Ile
465             470             475             480

Gln Arg His Leu Ser Ser Leu Thr Asp Asn Glu Gln Ala Asp Ile Phe
            485             490             495

Glu Arg Val Gln Lys Met Lys Pro Val Ser Asp Gln Glu Glu Asn Glu
            500             505             510

Leu Val Ile Leu His Leu Arg Gln Leu Cys Glu Ala Lys Gln Lys Thr
            515             520             525

His Val His Ile Gly Glu Gly Pro Ser Thr Ile Ser Asn Ser Thr Ile
            530             535             540

Pro Glu Asn Ala Thr Ser Ser Gly Arg Phe Lys Leu Asp Ile Leu Lys
545             550             555             560

Asn Lys Ala Lys Arg Ser Leu Thr Ser Ser Leu Glu Asn Ile Phe Ser
            565             570             575

Arg Gly Ala Asn Arg Met Arg Gly Arg Leu Gly Ser Val Asp Ser Phe
            580             585             590

Glu Arg Ser Asn Ser Leu Ala Ser Glu Lys Asp Tyr Ser Pro Gly Asp
            595             600             605

Ser Pro Gly Thr Pro Pro Ala Ser Pro Pro Ser Ser Ala Trp Gln
            610             615             620

Thr Phe Pro Glu Glu Asp Ser Asp Ser Pro Gln Phe Arg Arg Arg Ala
625             630             635             640

His Thr Phe Ser His Pro Pro Ser Ser Thr Lys Arg Lys Leu Asn Leu
            645             650             655

Gln Asp Gly Arg Ala Gln Gly Val Arg Ser Pro Leu Leu Arg Gln Ser
            660             665             670

Ser Ser Glu Gln Cys Ser Asn Leu Ser Ser Val Arg Arg Met Tyr Lys
            675             680             685

Glu Ser Asn Ser Ser Ser Ser Leu Pro Ser Leu His Thr Ser Phe Ser
            690             695             700

Ala Pro Ser Phe Thr Ala Pro Ser Phe Leu Lys Ser Phe Tyr Gln Asn
705             710             715             720

Ser Gly Arg Leu Ser Pro Gln Tyr Glu Asn Glu Ile Arg Gln Asp Thr
            725             730             735

Ala Ser Glu Ser Ser Asp Gly Glu Gly Arg Lys Arg Thr Ser Ser Thr
            740             745             750

Cys Ser Asn Glu Ser Leu Ser Val Gly Gly Thr Ser Val Thr Pro Arg
            755             760             765

Arg Ile Ser Trp Arg Gln Arg Ile Phe Leu Arg Val Ala Ser Pro Met
            770             775             780

Asn Lys Ser Pro Ser Ala Met Gln Gln Gln Asp Gly Leu Asp Arg Asn
785             790             795             800

Glu Leu Leu Pro Leu Ser Pro Leu Ser Pro Thr Met Glu Glu Glu Pro
            805             810             815

Leu Val Ile Phe Leu Ser Gly Glu Asp Asp Pro Glu Lys Ile Glu Glu
            820             825             830

```
Arg Lys Lys Ser Lys Glu Leu Arg Ser Leu Trp Arg Lys Ala Ile His
            835                 840                 845
Gln Gln Ile Leu Leu Arg Met Glu Lys Glu Asn Gln Lys Leu Glu
    850                 855                 860
Gly Ala Ser Arg Asp Glu Leu Gln Ser Arg Lys Val Lys Leu Asp Tyr
865                 870                 875                 880
Glu Glu Val Gly Ala Cys Gln Lys Glu Val Leu Ile Thr Trp Asp Lys
                885                 890                 895
Lys Leu Leu Asn Cys Arg Ala Lys Ile Arg Cys Asp Met Glu Asp Ile
                900                 905                 910
His Thr Leu Leu Lys Glu Gly Val Pro Lys Ser Arg Arg Gly Glu Ile
            915                 920                 925
Trp Gln Phe Leu Ala Leu Gln Tyr Arg Leu Arg His Arg Leu Pro Asn
    930                 935                 940
Lys Gln Gln Pro Pro Asp Ile Ser Tyr Lys Glu Leu Leu Lys Gln Leu
945                 950                 955                 960
Thr Ala Gln Gln His Ala Ile Leu Val Asp Leu Gly Arg Thr Phe Pro
                965                 970                 975
Thr His Pro Tyr Phe Ser Val Gln Leu Gly Pro Gly Gln Leu Ser Leu
            980                 985                 990
Phe Asn Leu Leu Lys Ala Tyr Ser  Leu Leu Asp Lys Glu  Val Gly Tyr
            995                1000                1005
Cys Gln Gly Ile Ser Phe Val  Ala Gly Val Leu Leu  Leu His Met
    1010                1015                1020
Ser Glu Glu Gln Ala Phe Glu  Met Leu Lys Phe Leu  Met Tyr Asp
    1025                1030                1035
Leu Gly Phe Arg Lys Gln Tyr  Arg Pro Asp Met Met  Ser Leu Gln
    1040                1045                1050
Ile Gln Met Tyr Gln Leu Ser  Arg Leu Leu His Asp  Tyr His Arg
    1055                1060                1065
Asp Leu Tyr Asn His Leu Glu  Glu Asn Glu Ile Ser  Pro Ser Leu
    1070                1075                1080
Tyr Ala Ala Pro Trp Phe Leu  Thr Leu Phe Ala Ser  Gln Phe Ser
    1085                1090                1095
Leu Gly Phe Val Ala Arg Val  Phe Asp Ile Ile Phe  Leu Gln Gly
    1100                1105                1110
Thr Glu Val Ile Phe Lys Val  Ala Leu Ser Leu Leu  Ser Ser Gln
    1115                1120                1125
Glu Thr Leu Ile Met Glu Cys  Glu Ser Phe Glu Asn  Ile Val Glu
    1130                1135                1140
Phe Leu Lys Asn Thr Leu Pro  Asp Met Asn Thr Ser  Glu Met Glu
    1145                1150                1155
Lys Ile Ile Thr Gln Val Phe  Glu Met Asp Ile Ser  Lys Gln Leu
    1160                1165                1170
His Ala Tyr Glu Val Glu Tyr  His Val Leu Gln Asp  Glu Leu Gln
    1175                1180                1185
Glu Ser Ser Tyr Ser Cys Glu  Asp Ser Glu Thr Leu  Glu Lys Leu
    1190                1195                1200
Glu Arg Ala Asn Ser Gln Leu  Lys Arg Gln Asn Met  Asp Leu Leu
    1205                1210                1215
Glu Lys Leu Gln Val Ala His  Thr Lys Ile Gln Ala  Leu Glu Ser
    1220                1225                1230
Asn Leu Glu Asn Leu Leu Thr  Arg Glu Thr Lys Met  Lys Ser Leu
```

```
            1235                1240                1245
Ile Arg Thr Leu Glu Gln Glu Lys Met Ala Tyr Gln Lys Thr Val
        1250                1255                1260

Glu Gln Leu Arg Lys Leu Leu Pro Ala Asp Ala Leu Ala Asn Cys
    1265                1270                1275

Asp Leu Leu Arg Asp Leu Asn Cys Asn Pro Asn Asn Lys Ala
1280                1285                1290

Lys Ile Gly Asn Lys Pro
    1295

<210> SEQ ID NO 13
<211> LENGTH: 1307
<212> TYPE: PRT
<213> ORGANISM: Mus musculus

<400> SEQUENCE: 13

Met Glu Ser Pro Ser Cys Ile Gln Asp Glu Pro Phe Pro His Pro Leu
1               5                   10                  15

Glu Pro Glu Pro Ser Ala Pro Ala Gln Pro Gly Ala Thr Lys Pro Gly
            20                  25                  30

Asp Lys Arg Phe Arg Leu Trp Tyr Val Gly Gly Ser Cys Leu Asp Arg
        35                  40                  45

Arg Thr Thr Leu Pro Met Leu Pro Trp Leu Met Ala Glu Ile Arg Arg
    50                  55                  60

Arg Ser Gln Lys Pro Asp Ala Gly Gly Cys Gly Ala Pro Ala Ala Arg
65                  70                  75                  80

Glu Val Ile Leu Val Leu Ser Ala Pro Phe Leu Arg Cys Val Pro Ala
                85                  90                  95

Pro Gly Ala Gly Val Gly Gly Ala Gly Ser Gly Ala Val Gln Pro
            100                 105                 110

Asn Thr Gly Val Phe Ile Phe Glu His Lys Ala Gln His Ile Ser Arg
        115                 120                 125

Phe Ile His Asn Ser His Asp Leu Thr Tyr Phe Ala Tyr Leu Ile Lys
    130                 135                 140

Ala Gln Pro Asp Asp Pro Glu Ser Gln Met Ala Cys His Val Phe Arg
145                 150                 155                 160

Ala Thr Asp Pro Asn Gln Val Pro Asp Val Ile Ser Ser Ile Arg Gln
                165                 170                 175

Leu Ser Lys Ala Ala Met Lys Glu Asp Ser Lys Pro Ser Lys Asp Asn
            180                 185                 190

Glu Asp Ala Phe Tyr Asn Ser Gln Lys Phe Glu Val Leu Tyr Cys Gly
        195                 200                 205

Arg Val Ile Val Thr His Lys Lys Ala Pro Ser Ser Leu Ile Asp Asp
    210                 215                 220

Cys Lys Asp Lys Phe Ser Leu His Glu Gln Gln Arg Leu Lys Leu Gln
225                 230                 235                 240

Gly Glu Arg Gly Gly Asp Pro Gly Asp Glu Met Gly Val Leu Glu Val
                245                 250                 255

Glu Ser Pro Val Ser Pro Asp Asp Ser Leu Pro Glu Lys Ala Asp Gly
            260                 265                 270

Thr Val Asn Ser Pro Arg Ala Leu Pro Ser Leu Ala Ser Leu Pro Ala
        275                 280                 285

Leu Ala Ser Gln Pro Ala Leu Ala Ser Ser Arg Val Cys Phe Pro Glu
    290                 295                 300
```

```
Arg Ile Leu Glu Asp Cys Gly Phe Asp Glu Gln Glu Phe Arg Ser
305                 310                 315                 320

Arg Cys Ser Ser Val Thr Gly Val Met Gln Lys Lys Val His Glu Asn
            325                 330                 335

Asn Gln Lys Thr Gln Pro Arg Arg His Ala Ser Ala Pro Ser His
        340                 345                 350

Val Gln Pro Ser Asp Ser Glu Lys Asn Arg Thr Met Leu Phe Gln Val
    355                 360                 365

Gly Arg Phe Glu Ile Asn Leu Ile Ser Pro Asp Thr Lys Ser Val Val
370                 375                 380

Leu Glu Lys Asn Phe Lys Asp Ile Ser Cys Ser Gln Gly Ile Lys
385                 390                 395                 400

His Val Asp His Phe Gly Phe Ile Cys Arg Glu Ser Pro Glu Pro Gly
            405                 410                 415

Leu Ser Gln Tyr Ile Cys Tyr Val Phe Gln Cys Ala Asn Glu Ser Leu
            420                 425                 430

Val Asp Glu Val Met Leu Thr Leu Lys Gln Ala Phe Ser Thr Ala Ala
        435                 440                 445

Ala Leu Gln Ser Ala Lys Thr Gln Ile Lys Leu Cys Glu Thr Cys Pro
450                 455                 460

Met His Ser Leu His Lys Leu Cys Glu Arg Ile Glu Gly Leu Tyr Pro
465                 470                 475                 480

Pro Arg Ala Lys Leu Val Ile Gln Arg His Leu Ser Ser Leu Thr Asp
                485                 490                 495

Asn Glu Gln Ala Asp Ile Phe Glu Arg Val Gln Lys Met Lys Pro Ile
            500                 505                 510

Ser Asp Gln Glu Glu Asn Glu Leu Val Ile Leu His Leu Arg Gln Leu
        515                 520                 525

Cys Glu Ala Lys Gln Arg Thr His Val His Ile Gly Glu Gly Pro Ala
530                 535                 540

Ile Ile Ser Asn Ser Thr Ile Pro Glu Asn Val Thr Ser Gly Gly Arg
545                 550                 555                 560

Phe Lys Leu Asp Val Leu Lys Asn Lys Ala Lys Arg Ser Leu Thr Ser
                565                 570                 575

Ser Leu Glu Asn Ile Phe Ser Arg Gly Ala Asn Arg Met Arg Gly Arg
            580                 585                 590

Leu Gly Ser Met Asp Ser Phe Glu Arg Ala Asn Ser Leu Ala Ser Glu
        595                 600                 605

Lys Asp Phe Ser Pro Gly Asp Ser Pro Gly Thr Pro Pro Ala Ser
610                 615                 620

Pro Leu Ser Ser Ala Trp His Ala Phe Pro Glu Glu Asp Ser Asp Ser
625                 630                 635                 640

Pro Gln Phe Arg Arg Arg Ala His Thr Phe Ser His Pro Pro Ser Ser
                645                 650                 655

Ser Arg Arg Lys Leu Asn Leu Gln Asp Gly Lys Ala His Gly Leu Arg
            660                 665                 670

Ser Pro Leu Leu Arg Gln Ser Ser Glu Gln Cys Ser Ile Val Pro
        675                 680                 685

Ser Ala Arg Arg Met Tyr Lys Glu Ser Asn Ser Ser Cys Ser Leu Pro
690                 695                 700

Ser Leu His Thr Ser Phe Ser Ala Pro Ser Phe Thr Ala Pro Ser Phe
705                 710                 715                 720

Leu Lys Ser Phe Tyr Gln Asn Ser Gly Arg Leu Ser Pro Gln Tyr Glu
```

```
                    725                 730                 735
Asn Glu Ile Arg Gln Asp Thr Ala Ser Glu Ser Ser Asp Gly Glu Gly
                740                 745                 750
Arg Lys Arg Thr Ser Thr Cys Ser Asn Glu Ser Leu Asn Ala Gly
            755                 760                 765
Gly Thr Pro Val Thr Pro Arg Val Ser Trp Arg Gln Arg Ile Phe
770                 775                 780
Leu Arg Val Ala Ser Pro Val Asn Lys Ser Pro Ser Ala Met Gln Gln
785                 790                 795                 800
Gln Lys Asp Gly Leu Asp Arg Thr Glu Leu Leu Pro Leu Ser Pro Leu
                805                 810                 815
Ser Pro Thr Met Glu Glu Pro Leu Ile Ile Phe Leu Ser Gly Asp
            820                 825                 830
Glu Asp Thr Glu Lys Val Glu Glu Lys Lys Ser Lys Glu Leu Lys
            835                 840                 845
Ser Leu Trp Lys Lys Ala Ile His Gln Gln Ile Leu Leu Leu Arg Met
850                 855                 860
Glu Lys Glu Asn Gln Lys Leu Glu Glu Ala Arg Arg Asp Glu Leu Gln
865                 870                 875                 880
Ser Arg Lys Val Lys Leu Asp Tyr Glu Glu Val Gly Thr Cys Gln Lys
                885                 890                 895
Glu Ile Leu Ile Ala Trp Asp Lys Lys Leu Leu Asn Cys Arg Thr Lys
            900                 905                 910
Ile Arg Cys Asp Met Glu Asp Ile His Thr Ser Leu Lys Glu Gly Val
            915                 920                 925
Pro Lys Ser Arg Arg Gly Glu Ile Trp Gln Phe Leu Ala Leu Gln Tyr
930                 935                 940
Arg Leu Arg His Arg Leu Pro Asn Lys His Gln Pro Pro Asp Thr Ser
945                 950                 955                 960
Tyr Lys Glu Leu Leu Lys Gln Leu Thr Ala Gln Gln His Ala Ile Leu
                965                 970                 975
Val Asp Leu Gly Arg Thr Phe Pro Thr His Pro Tyr Phe Ser Val Gln
            980                 985                 990
Leu Gly Ala Gly Gln Leu Ser Leu  Phe Asn Leu Leu  Lys Ala Tyr Ser
            995                 1000                1005
Leu Leu Asp Lys Glu Val Gly  Tyr Cys Gln Gly Ile  Ser Phe Val
        1010                1015                1020
Ala Gly Val Leu Leu Leu His  Met Ser Glu Glu Gln  Ala Phe Glu
        1025                1030                1035
Met Leu Lys Phe Leu Met Tyr  Asp Leu Gly Phe Arg  Lys Gln Tyr
        1040                1045                1050
Arg Pro Asp Met Met Ser Leu  Gln Ile Gln Met Tyr  Gln Leu Ser
        1055                1060                1065
Arg Leu Leu His Asp Tyr His  Arg Glu Leu Tyr Asn  His Leu Glu
        1070                1075                1080
Glu Asn  Glu Ile Ser Pro Ser  Leu Tyr Ala Ala Pro  Trp Phe Leu
        1085                1090                1095
Thr Leu Phe Ala Ser Gln Phe  Pro Leu Gly Phe Val  Ala Arg Val
        1100                1105                1110
Phe Asp  Ile Ile Phe Leu Gln  Gly Thr Glu Val Ile  Phe Lys Val
        1115                1120                1125
Ala Leu Ser Leu Leu Ser Ser  Gln Glu Ala Leu Ile  Met Glu Cys
        1130                1135                1140
```

```
Glu Asn Phe Glu Asn Ile Val Glu Phe Leu Lys Ser Thr Leu Pro
    1145                1150                1155

Asp Met Asn Thr Thr Glu Met Glu Lys Ile Ile Thr Gln Val Phe
1160                1165                1170

Glu Met Asp Ile Ser Lys Gln Leu His Ala Tyr Glu Val Glu Tyr
    1175                1180                1185

His Val Leu Gln Asp Glu Leu Leu Glu Ser Ser Tyr Ala Cys Glu
    1190                1195                1200

Asp Asn Glu Ser Leu Glu Lys Leu Glu Arg Ala Asn Asn Gln Leu
    1205                1210                1215

Lys Arg Gln Asn Met Asp Leu Leu Glu Lys Leu Gln Val Ala His
    1220                1225                1230

Ala Lys Ile Gln Ala Leu Glu Ser Asn Leu Glu Thr Leu Leu Thr
    1235                1240                1245

Arg Glu Thr Lys Met Lys Ala Leu Ile Arg Thr Leu Glu Gln Asp
    1250                1255                1260

Lys Met Ala Tyr Gln Lys Thr Val Glu Gln Ile Arg Lys Leu Leu
    1265                1270                1275

Pro Ala Asp Ala Leu Ala Asn Cys Glu Leu Leu Leu Lys Asp Leu
    1280                1285                1290

Thr His Pro Thr Asn Asp Lys Ala Lys Ala Gly Asn Lys Pro
    1295                1300                1305

<210> SEQ ID NO 14
<211> LENGTH: 1374
<212> TYPE: PRT
<213> ORGANISM: Homo Sapiens

<400> SEQUENCE: 14

Met Ser Thr Glu Ala Asp Glu Gly Ile Thr Phe Ser Val Pro Pro Phe
1               5                   10                  15

Ala Pro Ser Gly Phe Cys Thr Ile Pro Glu Gly Gly Ile Cys Arg Arg
                20                  25                  30

Gly Gly Ala Ala Ala Val Gly Glu Gly Glu Glu His Gln Leu Pro Pro
            35                  40                  45

Pro Pro Pro Gly Ser Phe Trp Asn Val Glu Ser Ala Ala Ala Pro Gly
        50                  55                  60

Ile Gly Cys Pro Ala Ala Thr Ser Ser Ser Ala Thr Arg Gly Arg
65                  70                  75                  80

Gly Ser Ser Val Gly Gly Ser Arg Arg Thr Thr Val Ala Tyr Val
                85                  90                  95

Ile Asn Glu Ala Ser Gln Gly Gln Leu Val Val Ala Glu Ser Glu Ala
                100                 105                 110

Leu Gln Ser Leu Arg Glu Ala Cys Glu Thr Val Gly Ala Thr Leu Glu
            115                 120                 125

Thr Leu His Phe Gly Lys Leu Asp Phe Gly Glu Thr Thr Val Leu Asp
        130                 135                 140

Arg Phe Tyr Asn Ala Asp Ile Ala Val Val Glu Met Ser Asp Ala Phe
145                 150                 155                 160

Arg Gln Pro Ser Leu Phe Tyr His Leu Gly Val Arg Glu Ser Phe Ser
                165                 170                 175

Met Ala Asn Asn Ile Ile Leu Tyr Cys Asp Thr Asn Ser Asp Ser Leu
                180                 185                 190

Gln Ser Leu Lys Glu Ile Ile Cys Gln Lys Asn Thr Met Cys Thr Gly
```

-continued

```
                195                 200                 205
Asn Tyr Thr Phe Val Pro Tyr Met Ile Thr Pro His Asn Lys Val Tyr
210                 215                 220

Cys Cys Asp Ser Ser Phe Met Lys Gly Leu Thr Glu Leu Met Gln Pro
225                 230                 235                 240

Asn Phe Glu Leu Leu Leu Gly Pro Ile Cys Leu Pro Leu Val Asp Arg
                245                 250                 255

Phe Ile Gln Leu Leu Lys Val Ala Gln Ala Ser Ser Ser Gln Tyr Phe
                260                 265                 270

Arg Glu Ser Ile Leu Asn Asp Ile Arg Lys Ala Arg Asn Leu Tyr Thr
                275                 280                 285

Gly Lys Glu Leu Ala Ala Glu Leu Ala Arg Ile Arg Gln Arg Val Asp
290                 295                 300

Asn Ile Glu Val Leu Thr Ala Asp Ile Val Asn Leu Leu Leu Ser
305                 310                 315                 320

Tyr Arg Asp Ile Gln Asp Tyr Asp Ser Ile Val Lys Leu Val Glu Thr
                325                 330                 335

Leu Glu Lys Leu Pro Thr Phe Asp Leu Ala Ser His His Val Lys
                340                 345                 350

Phe His Tyr Ala Phe Ala Leu Asn Arg Arg Asn Leu Pro Gly Asp Arg
                355                 360                 365

Ala Lys Ala Leu Asp Ile Met Ile Pro Met Val Gln Ser Glu Gly Gln
370                 375                 380

Val Ala Ser Asp Met Tyr Cys Leu Val Gly Arg Ile Tyr Lys Asp Met
385                 390                 395                 400

Phe Leu Asp Ser Asn Phe Thr Asp Thr Glu Ser Arg Asp His Gly Ala
                405                 410                 415

Ser Trp Phe Lys Lys Ala Phe Glu Ser Glu Pro Thr Leu Gln Ser Gly
                420                 425                 430

Ile Asn Tyr Ala Val Leu Leu Leu Ala Ala Gly His Gln Phe Glu Ser
                435                 440                 445

Ser Phe Glu Leu Arg Lys Val Gly Val Lys Leu Ser Ser Leu Leu Gly
                450                 455                 460

Lys Lys Gly Asn Leu Glu Lys Leu Gln Ser Tyr Trp Glu Val Gly Phe
465                 470                 475                 480

Phe Leu Gly Ala Ser Val Leu Ala Asn Asp His Met Arg Val Ile Gln
                485                 490                 495

Ala Ser Glu Lys Leu Phe Lys Leu Lys Thr Pro Ala Trp Tyr Leu Lys
                500                 505                 510

Ser Ile Val Glu Thr Ile Leu Ile Tyr Lys His Phe Val Lys Leu Thr
                515                 520                 525

Thr Glu Gln Pro Val Ala Lys Gln Glu Leu Val Asp Phe Trp Met Asp
                530                 535                 540

Phe Leu Val Glu Ala Thr Lys Thr Asp Val Thr Val Arg Phe Pro
545                 550                 555                 560

Val Leu Ile Leu Glu Pro Thr Lys Ile Tyr Gln Pro Ser Tyr Leu Ser
                565                 570                 575

Ile Asn Asn Glu Val Glu Glu Lys Thr Ile Ser Ile Trp His Val Leu
                580                 585                 590

Pro Asp Asp Lys Lys Gly Ile His Glu Trp Asn Phe Ser Ala Ser Ser
                595                 600                 605

Val Arg Gly Val Ser Ile Ser Lys Phe Glu Glu Arg Cys Cys Phe Leu
610                 615                 620
```

```
Tyr Val Leu His Asn Ser Asp Asp Phe Gln Ile Tyr Phe Cys Thr Glu
625                 630                 635                 640

Leu His Cys Lys Lys Phe Phe Glu Met Val Asn Thr Ile Thr Glu Glu
                645                 650                 655

Lys Gly Arg Ser Thr Glu Glu Gly Asp Cys Glu Ser Asp Leu Leu Glu
            660                 665                 670

Tyr Asp Tyr Glu Tyr Asp Glu Asn Gly Asp Arg Val Val Leu Gly Lys
        675                 680                 685

Gly Thr Tyr Gly Ile Val Tyr Ala Gly Arg Asp Leu Ser Asn Gln Val
    690                 695                 700

Arg Ile Ala Ile Lys Glu Ile Pro Glu Arg Asp Ser Arg Tyr Ser Gln
705                 710                 715                 720

Pro Leu His Glu Glu Ile Ala Leu His Lys His Leu Lys His Lys Asn
                725                 730                 735

Ile Val Gln Tyr Leu Gly Ser Phe Ser Glu Asn Gly Phe Ile Lys Ile
            740                 745                 750

Phe Met Glu Gln Val Pro Gly Gly Ser Leu Ser Ala Leu Leu Arg Ser
        755                 760                 765

Lys Trp Gly Pro Leu Lys Asp Asn Glu Gln Thr Ile Gly Phe Tyr Thr
770                 775                 780

Lys Gln Ile Leu Glu Gly Leu Lys Tyr Leu His Asp Asn Gln Ile Val
785                 790                 795                 800

His Arg Asp Ile Lys Gly Asp Asn Val Leu Ile Asn Thr Tyr Ser Gly
                805                 810                 815

Val Leu Lys Ile Ser Asp Phe Gly Thr Ser Lys Arg Leu Ala Gly Ile
            820                 825                 830

Asn Pro Cys Thr Glu Thr Phe Thr Gly Thr Leu Gln Tyr Met Ala Pro
        835                 840                 845

Glu Ile Ile Asp Lys Gly Pro Arg Gly Tyr Gly Lys Ala Ala Asp Ile
850                 855                 860

Trp Ser Leu Gly Cys Thr Ile Ile Glu Met Ala Thr Gly Lys Pro Pro
865                 870                 875                 880

Phe Tyr Glu Leu Gly Glu Pro Gln Ala Ala Met Phe Lys Val Gly Met
                885                 890                 895

Phe Lys Val His Pro Glu Ile Pro Glu Ser Met Ser Ala Glu Ala Lys
            900                 905                 910

Ala Phe Ile Leu Lys Cys Phe Glu Pro Asp Pro Asp Lys Arg Ala Cys
        915                 920                 925

Ala Asn Asp Leu Leu Val Asp Glu Phe Leu Lys Val Ser Ser Lys Lys
930                 935                 940

Lys Lys Thr Gln Pro Lys Leu Ser Ala Leu Ser Ala Gly Ser Asn Glu
945                 950                 955                 960

Tyr Leu Arg Ser Ile Ser Leu Pro Val Pro Val Leu Val Glu Asp Thr
                965                 970                 975

Ser Ser Ser Ser Glu Tyr Gly Ser Val Ser Pro Asp Thr Glu Leu Lys
            980                 985                 990

Val Asp Pro Phe Ser Phe Lys Thr Arg Ala Lys Ser Cys Gly Glu Arg
        995                 1000                1005

Asp Val Lys Gly Ile Arg Thr Leu Phe Leu Gly Ile Pro Asp Glu
    1010                1015                1020

Asn Phe Glu Asp His Ser Ala Pro Pro Ser Pro Glu Glu Lys Asp
    1025                1030                1035
```

Ser Gly Phe Phe Met Leu Arg Lys Asp Ser Glu Arg Arg Ala Thr
    1040                1045                1050

Leu His Arg Ile Leu Thr Glu Asp Gln Asp Lys Ile Val Arg Asn
    1055                1060                1065

Leu Met Glu Ser Leu Ala Gln Gly Ala Glu Pro Lys Leu Lys
    1070                1075                1080

Trp Glu His Ile Thr Thr Leu Ile Ala Ser Leu Arg Glu Phe Val
    1085                1090                1095

Arg Ser Thr Asp Arg Lys Ile Ile Ala Thr Thr Leu Ser Lys Leu
    1100                1105                1110

Lys Leu Glu Leu Asp Phe Asp Ser His Gly Ile Ser Gln Val Gln
    1115                1120                1125

Val Val Leu Phe Gly Phe Gln Asp Ala Val Asn Lys Val Leu Arg
    1130                1135                1140

Asn His Asn Ile Lys Pro His Trp Met Phe Ala Leu Asp Ser Ile
    1145                1150                1155

Ile Arg Lys Ala Val Gln Thr Ala Ile Thr Ile Leu Val Pro Glu
    1160                1165                1170

Leu Arg Pro His Phe Ser Leu Ala Ser Glu Ser Asp Thr Ala Asp
    1175                1180                1185

Gln Glu Asp Leu Asp Val Glu Asp Asp His Glu Glu Gln Pro Ser
    1190                1195                1200

Asn Gln Thr Val Arg Arg Pro Gln Ala Val Ile Glu Asp Ala Val
    1205                1210                1215

Ala Thr Ser Gly Val Ser Thr Leu Ser Ser Thr Val Ser His Asp
    1220                1225                1230

Ser Gln Ser Ala His Arg Ser Leu Asn Val Gln Leu Gly Arg Met
    1235                1240                1245

Lys Ile Glu Thr Asn Arg Leu Leu Glu Glu Leu Val Arg Lys Glu
    1250                1255                1260

Lys Glu Leu Gln Ala Leu Leu His Arg Ala Ile Glu Glu Lys Asp
    1265                1270                1275

Gln Glu Ile Lys His Leu Lys Leu Lys Ser Gln Pro Ile Glu Ile
    1280                1285                1290

Pro Glu Leu Pro Val Phe His Leu Asn Ser Ser Gly Thr Asn Thr
    1295                1300                1305

Glu Asp Ser Glu Leu Thr Asp Trp Leu Arg Val Asn Gly Ala Asp
    1310                1315                1320

Glu Asp Thr Ile Ser Arg Phe Leu Ala Glu Asp Tyr Thr Leu Leu
    1325                1330                1335

Asp Val Leu Tyr Tyr Val Thr Arg Asp Asp Leu Lys Cys Leu Arg
    1340                1345                1350

Leu Arg Gly Gly Met Leu Cys Thr Leu Trp Lys Ala Ile Ile Asp
    1355                1360                1365

Phe Arg Asn Lys Gln Thr
    1370

<210> SEQ ID NO 15
<211> LENGTH: 815
<212> TYPE: PRT
<213> ORGANISM: Homo Sapiens

<400> SEQUENCE: 15

Met Lys Ser Asn Gln Glu Arg Ser Asn Glu Cys Leu Pro Pro Lys Lys
1               5                   10                  15

```
Arg Glu Ile Pro Ala Thr Ser Arg Ser Ser Glu Glu Lys Ala Pro Thr
             20                  25                  30

Leu Pro Ser Asp Asn His Arg Val Glu Gly Thr Ala Trp Leu Pro Gly
         35                  40                  45

Asn Pro Gly Gly Arg Gly His Gly Gly Gly Arg His Gly Pro Ala Gly
     50                  55                  60

Thr Ser Val Glu Leu Gly Leu Gln Gln Gly Ile Gly Leu His Lys Ala
65                  70                  75                  80

Leu Ser Thr Gly Leu Asp Tyr Ser Pro Pro Ser Ala Pro Arg Ser Val
                 85                  90                  95

Pro Val Ala Thr Thr Leu Pro Ala Ala Tyr Ala Thr Pro Gln Pro Gly
            100                 105                 110

Thr Pro Val Ser Pro Val Gln Tyr Ala His Leu Pro His Thr Phe Gln
        115                 120                 125

Phe Ile Gly Ser Ser Gln Tyr Ser Gly Thr Tyr Ala Ser Phe Ile Pro
    130                 135                 140

Ser Gln Leu Ile Pro Pro Thr Ala Asn Pro Val Thr Ser Ala Val Ala
145                 150                 155                 160

Ser Ala Ala Gly Ala Thr Thr Pro Ser Gln Arg Ser Gln Leu Glu Ala
                165                 170                 175

Tyr Ser Thr Leu Leu Ala Asn Met Gly Ser Leu Ser Gln Thr Pro Gly
            180                 185                 190

His Lys Ala Glu Gln Gln Gln Gln Gln Gln Gln Gln Gln Gln Gln Gln
        195                 200                 205

His Gln His Gln Gln Gln Gln Gln Gln Gln Gln Gln Gln Gln Gln Gln
    210                 215                 220

Gln His Leu Ser Arg Ala Pro Gly Leu Ile Thr Pro Gly Ser Pro Pro
225                 230                 235                 240

Pro Ala Gln Gln Asn Gln Tyr Val His Ile Ser Ser Ser Pro Gln Asn
                245                 250                 255

Thr Gly Arg Thr Ala Ser Pro Pro Ala Ile Pro Val His Leu His Pro
            260                 265                 270

His Gln Thr Met Ile Pro His Thr Leu Thr Leu Gly Pro Pro Ser Gln
        275                 280                 285

Val Val Met Gln Tyr Ala Asp Ser Gly Ser His Phe Val Pro Arg Glu
    290                 295                 300

Ala Thr Lys Lys Ala Glu Ser Ser Arg Leu Gln Gln Ala Ile Gln Ala
305                 310                 315                 320

Lys Glu Val Leu Asn Gly Glu Met Glu Lys Ser Arg Arg Tyr Gly Ala
                325                 330                 335

Pro Ser Ser Ala Asp Leu Gly Leu Gly Lys Ala Gly Gly Lys Ser Val
            340                 345                 350

Pro His Pro Tyr Glu Ser Arg His Val Val His Pro Ser Pro Ser
        355                 360                 365

Asp Tyr Ser Ser Arg Asp Pro Ser Gly Val Arg Ala Ser Val Met Val
    370                 375                 380

Leu Pro Asn Ser Asn Thr Pro Ala Ala Asp Leu Glu Val Gln Gln Ala
385                 390                 395                 400

Thr His Arg Glu Ala Ser Pro Ser Thr Leu Asn Asp Lys Ser Gly Leu
                405                 410                 415

His Leu Gly Lys Pro Gly His Arg Ser Tyr Ala Leu Ser Pro His Thr
            420                 425                 430
```

Val Ile Gln Thr Thr His Ser Ala Ser Glu Pro Leu Pro Val Gly Leu
             435                 440                 445

Pro Ala Thr Ala Phe Tyr Ala Gly Thr Gln Pro Val Ile Gly Tyr
450                 455                 460

Leu Ser Gly Gln Gln Ala Ile Thr Tyr Ala Gly Ser Leu Pro Gln
465                 470                 475                 480

His Leu Val Ile Pro Gly Thr Gln Pro Leu Leu Ile Pro Val Gly Ser
                 485                 490                 495

Thr Asp Met Glu Ala Ser Gly Ala Ala Pro Ala Ile Val Thr Ser Ser
                500                 505                 510

Pro Gln Phe Ala Ala Val Pro His Thr Phe Val Thr Thr Ala Leu Pro
                515                 520                 525

Lys Ser Glu Asn Phe Asn Pro Glu Ala Leu Val Thr Gln Ala Ala Tyr
                530                 535                 540

Pro Ala Met Val Gln Ala Gln Ile His Leu Pro Val Val Gln Ser Val
545                 550                 555                 560

Ala Ser Pro Ala Ala Ala Pro Pro Thr Leu Pro Pro Tyr Phe Met Lys
                565                 570                 575

Gly Ser Ile Ile Gln Leu Ala Asn Gly Glu Leu Lys Lys Val Glu Asp
                580                 585                 590

Leu Lys Thr Glu Asp Phe Ile Gln Ser Ala Glu Ile Ser Asn Asp Leu
                595                 600                 605

Lys Ile Asp Ser Ser Thr Val Glu Arg Ile Glu Asp Ser His Ser Pro
                610                 615                 620

Gly Val Ala Val Ile Gln Phe Ala Val Gly Glu His Arg Ala Gln Val
625                 630                 635                 640

Ser Val Glu Val Leu Val Glu Tyr Pro Phe Phe Val Phe Gly Gln Gly
                645                 650                 655

Trp Ser Ser Cys Cys Pro Glu Arg Thr Ser Gln Leu Phe Asp Leu Pro
                660                 665                 670

Cys Ser Lys Leu Ser Val Gly Asp Val Cys Ile Ser Leu Thr Leu Lys
                675                 680                 685

Asn Leu Lys Asn Gly Ser Val Lys Lys Gly Gln Pro Val Asp Pro Ala
                690                 695                 700

Ser Val Leu Leu Lys His Ser Lys Ala Asp Gly Leu Ala Gly Ser Arg
705                 710                 715                 720

His Arg Tyr Ala Glu Gln Asn Gly Ile Asn Gln Gly Ser Ala Gln
                725                 730                 735

Met Leu Ser Glu Asn Gly Glu Leu Lys Phe Pro Glu Lys Met Gly Leu
                740                 745                 750

Pro Ala Ala Pro Phe Leu Thr Lys Ile Glu Pro Ser Lys Pro Ala Ala
                755                 760                 765

Thr Arg Lys Arg Arg Trp Ser Ala Pro Glu Ser Arg Lys Leu Glu Lys
                770                 775                 780

Ser Glu Asp Glu Pro Pro Leu Thr Leu Pro Lys Pro Ser Leu Ile Pro
785                 790                 795                 800

Gln Glu Val Lys Ile Cys Ile Glu Gly Arg Ser Asn Val Gly Lys
                805                 810                 815

<210> SEQ ID NO 16
<211> LENGTH: 1100
<212> TYPE: PRT
<213> ORGANISM: Rattus norvegicus

<400> SEQUENCE: 16

-continued

```
Met Ser Ala Lys Ala Ile Ser Glu Gln Thr Gly Lys Glu Leu Leu Tyr
1               5                   10                  15

Lys Tyr Ile Cys Thr Thr Ser Ala Ile Gln Asn Arg Phe Lys Tyr Ala
            20                  25                  30

Arg Val Thr Pro Asp Thr Asp Trp Ala His Leu Leu Gln Asp His Pro
        35                  40                  45

Trp Leu Leu Ser Gln Ser Leu Val Val Lys Pro Asp Gln Leu Ile Lys
    50                  55                  60

Arg Arg Gly Lys Leu Gly Leu Val Gly Val Asn Leu Ser Leu Asp Gly
65                  70                  75                  80

Val Lys Ser Trp Leu Lys Pro Arg Leu Gly His Glu Ala Thr Val Gly
                85                  90                  95

Lys Ala Lys Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
        115                 120                 125

Gly Asp Tyr Val Leu Phe His His Glu Gly Gly Val Asp Val Gly Asp
    130                 135                 140

Val Asp Thr Lys Ala Gln Lys Leu Leu Val Gly Val Asp Glu Lys Leu
145                 150                 155                 160

Asn Ala Glu Asp Ile Lys Arg His Leu Val His Ala Pro Glu Asp
                165                 170                 175

Lys Lys Glu Ile Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
        195                 200                 205

Lys Asp Gly Val Tyr Ile Leu Asp Leu Ala Ala Lys Val Asp Ala Thr
    210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Glu Ala Tyr Ile Ala Asp Leu
                245                 250                 255

Asp Ala Lys Ser Gly Ala Ser Leu Lys Leu Thr Leu Asn Pro Lys
            260                 265                 270

Gly Arg Ile Trp Thr Met Val Ala Gly Gly Ala Ser Val Val Tyr
        275                 280                 285

Ser Asp Thr Ile Cys Asp Leu Gly Gly Val Asn Glu Leu Ala Asn Tyr
    290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Asp Gly Lys
                325                 330                 335

Ile Leu Ile Ile Gly Gly Ser Ile Ala Asn Phe Thr Asn Val Ala Ala
            340                 345                 350

Thr Phe Lys Gly Ile Val Arg Ala Ile Arg Asp Tyr Gln Gly Ser Leu
        355                 360                 365

Lys Glu His Glu Val Thr Ile Phe Val Arg Arg Gly Gly Pro Asn Tyr
    370                 375                 380

Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415
```

```
Met Ala Trp Ala Pro Ala Ile Pro Asn Gln Pro Pro Thr Ala Ala His
                420                 425                 430

Thr Ala Asn Phe Leu Leu Asn Ala Ser Gly Ser Thr Ser Thr Pro Ala
            435                 440                 445

Pro Ser Arg Thr Ala Ser Phe Ser Glu Ser Arg Ala Asp Glu Val Ala
465         450                 455                 460

Pro Ala Lys Lys Ala Lys Pro Ala Met Pro Gln Asp Ser Val Pro Ser
465                 470                 475                 480

Pro Arg Ser Leu Gln Gly Lys Ser Ala Thr Leu Phe Ser Arg His Thr
                485                 490                 495

Lys Ala Ile Val Trp Gly Met Gln Thr Arg Ala Val Gln Gly Met Leu
            500                 505                 510

Asp Phe Asp Tyr Val Cys Ser Arg Asp Glu Pro Ser Val Ala Ala Met
            515                 520                 525

Val Tyr Pro Phe Thr Gly Asp His Lys Gln Lys Phe Tyr Trp Gly His
            530                 535                 540

Lys Glu Ile Leu Ile Pro Val Phe Lys Asn Met Ala Asp Ala Met Lys
545                 550                 555                 560

Lys His Pro Glu Val Asp Val Leu Ile Asn Phe Ala Ser Leu Arg Ser
                565                 570                 575

Ala Tyr Asp Ser Thr Met Glu Thr Met Asn Tyr Ala Gln Ile Arg Thr
            580                 585                 590

Ile Ala Ile Ile Ala Glu Gly Ile Pro Glu Ala Leu Thr Arg Lys Leu
            595                 600                 605

Ile Lys Lys Ala Asp Gln Lys Gly Val Thr Ile Ile Gly Pro Ala Thr
610                 615                 620

Val Gly Gly Ile Lys Pro Gly Cys Phe Lys Ile Gly Asn Thr Gly Gly
625                 630                 635                 640

Met Leu Asp Asn Ile Leu Ala Ser Lys Leu Tyr Arg Pro Gly Ser Val
            645                 650                 655

Ala Tyr Val Ser Arg Ser Gly Gly Met Ser Asn Glu Leu Asn Asn Ile
            660                 665                 670

Ile Ser Arg Thr Thr Asp Gly Val Tyr Glu Gly Val Ala Ile Gly Gly
            675                 680                 685

Asp Arg Tyr Pro Gly Ser Thr Phe Met Asp His Val Leu Arg Tyr Gln
            690                 695                 700

Asp Thr Pro Gly Val Lys Met Ile Val Val Leu Gly Glu Ile Gly Gly
705                 710                 715                 720

Thr Glu Glu Tyr Lys Ile Cys Arg Gly Ile Lys Glu Gly Arg Leu Thr
                725                 730                 735

Lys Pro Val Val Cys Trp Cys Ile Gly Thr Cys Ala Thr Met Phe Ser
                740                 745                 750

Ser Glu Val Gln Phe Gly His Ala Gly Ala Cys Ala Asn Gln Ala Ser
            755                 760                 765

Glu Thr Ala Val Ala Lys Asn Gln Ala Leu Lys Glu Ala Gly Val Phe
            770                 775                 780

Val Pro Arg Ser Phe Asp Glu Leu Gly Glu Ile Ile Gln Ser Val Tyr
785                 790                 795                 800

Glu Asp Leu Val Ala Lys Gly Ala Ile Val Pro Ala Gln Glu Val Pro
                805                 810                 815

Pro Pro Thr Val Pro Met Asp Tyr Ser Trp Ala Arg Glu Leu Gly Leu
            820                 825                 830

Ile Arg Lys Pro Ala Ser Phe Met Thr Ser Ile Cys Asp Glu Arg Gly
```

```
                      835                 840                 845
Gln Glu Leu Ile Tyr Ala Gly Met Pro Ile Thr Glu Val Phe Lys Glu
    850                 855                 860

Glu Met Gly Ile Gly Gly Val Leu Gly Leu Leu Trp Phe Gln Arg Arg
865                 870                 875                 880

Leu Pro Lys Tyr Ser Cys Gln Phe Ile Glu Met Cys Leu Met Val Thr
                885                 890                 895

Ala Asp His Gly Pro Ala Val Ser Gly Ala His Asn Thr Ile Ile Cys
            900                 905                 910

Ala Arg Ala Gly Lys Asp Leu Val Ser Ser Leu Thr Ser Gly Leu Leu
        915                 920                 925

Thr Ile Gly Asp Arg Phe Gly Gly Ala Leu Asp Ala Ala Ala Lys Met
    930                 935                 940

Phe Ser Lys Ala Phe Asp Ser Gly Ile Ile Pro Met Glu Phe Val Asn
945                 950                 955                 960

Lys Met Lys Lys Glu Gly Lys Leu Ile Met Gly Ile Gly His Arg Val
                965                 970                 975

Lys Ser Ile Asn Asn Pro Asp Met Arg Val Gln Ile Leu Lys Asp Phe
            980                 985                 990

Val Lys Gln His Phe Pro Ala Thr Pro Leu Leu Asp Tyr Ala Leu Glu
        995                1000                1005

Val Glu Lys Ile Thr Thr Ser Lys Lys Pro Asn Leu Ile Leu Asn
    1010                1015                1020

Val Asp Gly Phe Ile Gly Val Ala Phe Val Asp Met Leu Arg Asn
    1025                1030                1035

Cys Gly Ser Phe Thr Arg Glu Glu Ala Asp Glu Tyr Val Asp Ile
    1040                1045                1050

Gly Ala Leu Asn Gly Val Phe Val Leu Gly Arg Ser Met Gly Phe
    1055                1060                1065

Ile Gly His Tyr Leu Asp Gln Lys Arg Leu Lys Gln Gly Leu Tyr
    1070                1075                1080

Arg His Pro Trp Asp Asp Ile Ser Tyr Val Leu Pro Glu His Met
    1085                1090                1095

Ser Met
    1100

<210> SEQ ID NO 17
<211> LENGTH: 1101
<212> TYPE: PRT
<213> ORGANISM: Homo Sapiens

<400> SEQUENCE: 17

Met Ser Ala Lys Ala Ile Ser Glu Gln Thr Gly Lys Glu Leu Leu Tyr
1               5                   10                  15

Lys Phe Ile Cys Thr Thr Ser Ala Ile Gln Asn Arg Phe Lys Tyr Ala
                20                  25                  30

Arg Val Thr Pro Asp Thr Asp Trp Ala Arg Leu Leu Gln Asp His Pro
            35                  40                  45

Trp Leu Leu Ser Gln Asn Leu Val Val Lys Pro Asp Gln Leu Ile Lys
        50                  55                  60

Arg Arg Gly Lys Leu Gly Leu Val Gly Val Asn Leu Thr Leu Asp Gly
65                  70                  75                  80

Val Lys Ser Trp Leu Lys Pro Arg Leu Gly Gln Glu Ala Thr Val Gly
                85                  90                  95
```

-continued

Lys Ala Thr Gly Phe Leu Lys Asn Phe Leu Ile Glu Pro Phe Val Pro
            100                 105                 110

His Ser Gln Ala Glu Glu Phe Tyr Val Cys Ile Tyr Ala Thr Arg Glu
            115                 120                 125

Gly Asp Tyr Val Leu Phe His His Glu Gly Val Asp Val Gly Asp
            130                 135             140

Val Asp Ala Lys Ala Gln Lys Leu Leu Val Gly Val Asp Glu Lys Leu
145                 150                 155                 160

Asn Pro Glu Asp Ile Lys Lys His Leu Leu Val His Ala Pro Glu Asp
                    165                 170                 175

Lys Lys Glu Ile Leu Ala Ser Phe Ile Ser Gly Leu Phe Asn Phe Tyr
            180                 185                 190

Glu Asp Leu Tyr Phe Thr Tyr Leu Glu Ile Asn Pro Leu Val Val Thr
            195                 200                 205

Lys Asp Gly Val Tyr Val Leu Asp Leu Ala Ala Lys Val Asp Ala Thr
        210                 215                 220

Ala Asp Tyr Ile Cys Lys Val Lys Trp Gly Asp Ile Glu Phe Pro Pro
225                 230                 235                 240

Pro Phe Gly Arg Glu Ala Tyr Pro Glu Ala Tyr Ile Ala Asp Leu
                245                 250                 255

Asp Ala Lys Ser Gly Ala Ser Leu Lys Leu Thr Leu Leu Asn Pro Lys
            260                 265                 270

Gly Arg Ile Trp Thr Met Val Ala Gly Gly Ala Ser Val Val Tyr
            275                 280                 285

Ser Asp Thr Ile Cys Asp Leu Gly Gly Val Asn Glu Leu Ala Asn Tyr
        290                 295                 300

Gly Glu Tyr Ser Gly Ala Pro Ser Glu Gln Gln Thr Tyr Asp Tyr Ala
305                 310                 315                 320

Lys Thr Ile Leu Ser Leu Met Thr Arg Glu Lys His Pro Asp Gly Lys
                325                 330                 335

Ile Leu Ile Ile Gly Gly Ser Ile Ala Asn Phe Thr Asn Val Ala Ala
            340                 345                 350

Thr Phe Lys Gly Ile Val Arg Ala Ile Arg Asp Tyr Gln Gly Pro Leu
        355                 360                 365

Lys Glu His Glu Val Thr Ile Phe Val Arg Arg Gly Gly Pro Asn Tyr
        370                 375                 380

Gln Glu Gly Leu Arg Val Met Gly Glu Val Gly Lys Thr Thr Gly Ile
385                 390                 395                 400

Pro Ile His Val Phe Gly Thr Glu Thr His Met Thr Ala Ile Val Gly
                405                 410                 415

Met Ala Leu Gly His Arg Pro Ile Pro Asn Gln Pro Pro Thr Ala Ala
            420                 425                 430

His Thr Ala Asn Phe Leu Leu Asn Ala Ser Gly Ser Thr Ser Thr Pro
        435                 440                 445

Ala Pro Ser Arg Thr Ala Ser Phe Ser Glu Ser Arg Ala Asp Glu Val
        450                 455                 460

Ala Pro Ala Lys Lys Ala Lys Pro Ala Met Pro Gln Asp Ser Val Pro
465                 470                 475                 480

Ser Pro Arg Ser Leu Gln Gly Lys Ser Thr Thr Leu Phe Ser Arg His
                485                 490                 495

Thr Lys Ala Ile Val Trp Gly Met Gln Thr Arg Ala Val Gln Gly Met
            500                 505                 510

Leu Asp Phe Asp Tyr Val Cys Ser Arg Asp Glu Pro Ser Val Ala Ala

```
                515                 520                 525
Met Val Tyr Pro Phe Thr Gly Asp His Lys Gln Lys Phe Tyr Trp Gly
    530                 535                 540

His Lys Glu Ile Leu Ile Pro Val Phe Lys Asn Met Ala Asp Ala Met
545                 550                 555                 560

Arg Lys His Pro Glu Val Asp Val Leu Ile Asn Phe Ala Ser Leu Arg
                565                 570                 575

Ser Ala Tyr Asp Ser Thr Met Glu Thr Met Asn Tyr Ala Gln Ile Arg
            580                 585                 590

Thr Ile Ala Ile Ile Ala Glu Gly Ile Pro Glu Ala Leu Thr Arg Lys
        595                 600                 605

Leu Ile Lys Lys Ala Asp Gln Lys Gly Val Thr Ile Ile Gly Pro Ala
    610                 615                 620

Thr Val Gly Gly Ile Lys Pro Gly Cys Phe Lys Ile Gly Asn Thr Gly
625                 630                 635                 640

Gly Met Leu Asp Asn Ile Leu Ala Ser Lys Leu Tyr Arg Pro Gly Ser
                645                 650                 655

Val Ala Tyr Val Ser Arg Ser Gly Gly Met Ser Asn Glu Leu Asn Asn
            660                 665                 670

Ile Ile Ser Arg Thr Thr Asp Gly Val Tyr Glu Gly Val Ala Ile Gly
        675                 680                 685

Gly Asp Arg Tyr Pro Gly Ser Thr Phe Met Asp His Val Leu Arg Tyr
    690                 695                 700

Gln Asp Thr Pro Gly Val Lys Met Ile Val Val Leu Gly Glu Ile Gly
705                 710                 715                 720

Gly Thr Glu Glu Tyr Lys Ile Cys Arg Gly Ile Lys Glu Gly Arg Leu
                725                 730                 735

Thr Lys Pro Ile Val Cys Trp Cys Ile Gly Thr Cys Ala Thr Met Phe
            740                 745                 750

Ser Ser Glu Val Gln Phe Gly His Ala Gly Ala Cys Ala Asn Gln Ala
        755                 760                 765

Ser Glu Thr Ala Val Ala Lys Asn Gln Ala Leu Lys Glu Ala Gly Val
    770                 775                 780

Phe Val Pro Arg Ser Phe Asp Glu Leu Gly Glu Ile Ile Gln Ser Val
785                 790                 795                 800

Tyr Glu Asp Leu Val Ala Asn Gly Val Ile Val Pro Ala Gln Glu Val
                805                 810                 815

Pro Pro Pro Thr Val Pro Met Asp Tyr Ser Trp Ala Arg Glu Leu Gly
            820                 825                 830

Leu Ile Arg Lys Pro Ala Ser Phe Met Thr Ser Ile Cys Asp Glu Arg
        835                 840                 845

Gly Gln Glu Leu Ile Tyr Ala Gly Met Pro Ile Thr Glu Val Phe Lys
    850                 855                 860

Glu Glu Met Gly Ile Gly Gly Val Leu Gly Leu Leu Trp Phe Gln Lys
865                 870                 875                 880

Arg Leu Pro Lys Tyr Ser Cys Gln Phe Ile Glu Met Cys Leu Met Val
                885                 890                 895

Thr Ala Asp His Gly Pro Ala Val Ser Gly Ala His Asn Thr Ile Ile
            900                 905                 910

Cys Ala Arg Ala Gly Lys Asp Leu Val Ser Ser Leu Thr Ser Gly Leu
        915                 920                 925

Leu Thr Ile Gly Asp Arg Phe Gly Gly Ala Leu Asp Ala Ala Ala Lys
    930                 935                 940
```

```
Met Phe Ser Lys Ala Phe Asp Ser Gly Ile Ile Pro Met Glu Phe Val
945                 950                 955                 960

Asn Lys Met Lys Lys Glu Gly Lys Leu Ile Met Gly Ile Gly His Arg
            965                 970                 975

Val Lys Ser Ile Asn Asn Pro Asp Met Arg Val Gln Ile Leu Lys Asp
        980                 985                 990

Tyr Val Arg Gln His Phe Pro Ala Thr Pro Leu Leu Asp Tyr Ala Leu
    995                 1000                1005

Glu Val Glu Lys Ile Thr Thr Ser Lys Lys Pro Asn Leu Ile Leu
    1010                1015                1020

Asn Val Asp Gly Leu Ile Gly Val Ala Phe Val Asp Met Leu Arg
    1025                1030                1035

Asn Cys Gly Ser Phe Thr Arg Glu Glu Ala Asp Glu Tyr Ile Asp
    1040                1045                1050

Ile Gly Ala Leu Asn Gly Ile Phe Val Leu Gly Arg Ser Met Gly
    1055                1060                1065

Phe Ile Gly His Tyr Leu Asp Gln Lys Arg Leu Lys Gln Gly Leu
    1070                1075                1080

Tyr Arg His Pro Trp Asp Asp Ile Ser Tyr Val Leu Pro Glu His
    1085                1090                1095

Met Ser Met
    1100

<210> SEQ ID NO 18
<211> LENGTH: 204
<212> TYPE: PRT
<213> ORGANISM: Mus musculus

<400> SEQUENCE: 18

Met Gly Thr Pro Lys Gln Pro Ser Leu Ala Pro Ala His Ala Leu Gly
1               5                   10                  15

Leu Arg Lys Ser Asp Pro Gly Ile Arg Ser Leu Gly Ser Asp Ala Gly
            20                  25                  30

Gly Arg Arg Trp Arg Pro Ala Ala Gln Ser Met Phe Gln Ile Pro Glu
        35                  40                  45

Phe Glu Pro Ser Glu Gln Glu Asp Ala Ser Ala Thr Asp Arg Gly Leu
    50                  55                  60

Gly Pro Ser Leu Thr Glu Asp Gln Pro Gly Pro Tyr Leu Ala Pro Gly
65                  70                  75                  80

Leu Leu Gly Ser Asn Ile His Gln Gln Gly Arg Ala Ala Thr Asn Ser
                85                  90                  95

His His Gly Gly Ala Gly Ala Met Glu Thr Arg Ser Arg His Ser Ser
            100                 105                 110

Tyr Pro Ala Gly Thr Glu Glu Asp Glu Gly Met Glu Glu Glu Leu Ser
        115                 120                 125

Pro Phe Arg Gly Arg Ser Arg Ser Ala Pro Pro Asn Leu Trp Ala Ala
    130                 135                 140

Gln Arg Tyr Gly Arg Glu Leu Arg Arg Met Ser Asp Glu Phe Glu Gly
145                 150                 155                 160

Ser Phe Lys Gly Leu Pro Arg Pro Lys Ser Ala Gly Thr Ala Thr Gln
                165                 170                 175

Met Arg Gln Ser Ala Gly Trp Thr Arg Ile Ile Gln Ser Trp Trp Asp
            180                 185                 190

Arg Asn Leu Gly Lys Gly Gly Ser Thr Pro Ser Gln
```

<210> SEQ ID NO 19
<211> LENGTH: 1863
<212> TYPE: PRT
<213> ORGANISM: Homo Sapiens

<400> SEQUENCE: 19

Met Asp Leu Ser Ala Leu Arg Val Glu Glu Val Gln Asn Val Ile Asn
1               5                   10                  15

Ala Met Gln Lys Ile Leu Glu Cys Pro Ile Cys Leu Glu Leu Ile Lys
            20                  25                  30

Glu Pro Val Ser Thr Lys Cys Asp His Ile Phe Cys Lys Phe Cys Met
        35                  40                  45

Leu Lys Leu Leu Asn Gln Lys Lys Gly Pro Ser Gln Cys Pro Leu Cys
    50                  55                  60

Lys Asn Asp Ile Thr Lys Arg Ser Leu Gln Glu Ser Thr Arg Phe Ser
65                  70                  75                  80

Gln Leu Val Glu Glu Leu Leu Lys Ile Ile Cys Ala Phe Gln Leu Asp
                85                  90                  95

Thr Gly Leu Glu Tyr Ala Asn Ser Tyr Asn Phe Ala Lys Lys Glu Asn
            100                 105                 110

Asn Ser Pro Glu His Leu Lys Asp Glu Val Ser Ile Ile Gln Ser Met
        115                 120                 125

Gly Tyr Arg Asn Arg Ala Lys Arg Leu Leu Gln Ser Glu Pro Glu Asn
    130                 135                 140

Pro Ser Leu Gln Glu Thr Ser Leu Ser Val Gln Leu Ser Asn Leu Gly
145                 150                 155                 160

Thr Val Arg Thr Leu Arg Thr Lys Gln Arg Ile Gln Pro Gln Lys Thr
                165                 170                 175

Ser Val Tyr Ile Glu Leu Gly Ser Asp Ser Ser Glu Asp Thr Val Asn
            180                 185                 190

Lys Ala Thr Tyr Cys Ser Val Gly Asp Gln Glu Leu Leu Gln Ile Thr
        195                 200                 205

Pro Gln Gly Thr Arg Asp Glu Ile Ser Leu Asp Ser Ala Lys Lys Ala
    210                 215                 220

Ala Cys Glu Phe Ser Glu Thr Asp Val Thr Asn Thr Glu His His Gln
225                 230                 235                 240

Pro Ser Asn Asn Asp Leu Asn Thr Thr Glu Lys Arg Ala Ala Glu Arg
                245                 250                 255

His Pro Glu Lys Tyr Gln Gly Ser Ser Val Ser Asn Leu His Val Glu
            260                 265                 270

Pro Cys Gly Thr Asn Thr His Ala Ser Ser Leu Gln His Glu Asn Ser
        275                 280                 285

Ser Leu Leu Leu Thr Lys Asp Arg Met Asn Val Glu Lys Ala Glu Phe
    290                 295                 300

Cys Asn Lys Ser Lys Gln Pro Gly Leu Ala Arg Ser Gln His Asn Arg
305                 310                 315                 320

Trp Ala Gly Ser Lys Glu Thr Cys Asn Asp Arg Arg Thr Pro Ser Thr
                325                 330                 335

Glu Lys Lys Val Asp Leu Asn Ala Asp Pro Leu Cys Glu Arg Lys Glu
            340                 345                 350

Trp Asn Lys Gln Lys Leu Pro Cys Ser Glu Asn Pro Arg Asp Thr Glu
        355                 360                 365

-continued

```
Asp Val Pro Trp Ile Thr Leu Asn Ser Ser Ile Gln Lys Val Asn Glu
    370                 375                 380

Trp Phe Ser Arg Ser Asp Glu Leu Leu Gly Ser Asp Ser His Asp
385                 390                 395                 400

Gly Glu Ser Glu Ser Asn Ala Lys Val Ala Asp Val Leu Asp Val Leu
                405                 410                 415

Asn Glu Val Asp Glu Tyr Ser Gly Ser Ser Glu Lys Ile Asp Leu Leu
                420                 425                 430

Ala Ser Asp Pro His Glu Ala Leu Ile Cys Lys Ser Glu Arg Val His
                435                 440                 445

Ser Lys Ser Val Glu Ser Asn Ile Glu Asp Lys Ile Phe Gly Lys Thr
450                 455                 460

Tyr Arg Lys Lys Ala Ser Leu Pro Asn Leu Ser His Val Thr Glu Asn
465                 470                 475                 480

Leu Ile Ile Gly Ala Phe Val Thr Glu Pro Gln Ile Ile Gln Glu Arg
                485                 490                 495

Pro Leu Thr Asn Lys Leu Lys Arg Lys Arg Pro Thr Ser Gly Leu
                500                 505                 510

His Pro Glu Asp Phe Ile Lys Lys Ala Asp Leu Ala Val Gln Lys Thr
                515                 520                 525

Pro Glu Met Ile Asn Gln Gly Thr Asn Gln Thr Glu Gln Asn Gly Gln
530                 535                 540

Val Met Asn Ile Thr Asn Ser Gly His Glu Asn Lys Thr Lys Gly Asp
545                 550                 555                 560

Ser Ile Gln Asn Glu Lys Asn Pro Asn Pro Ile Glu Ser Leu Glu Lys
                565                 570                 575

Glu Ser Ala Phe Lys Thr Lys Ala Glu Pro Ile Ser Ser Ser Ile Ser
                580                 585                 590

Asn Met Glu Leu Glu Leu Asn Ile His Asn Ser Lys Ala Pro Lys Lys
                595                 600                 605

Asn Arg Leu Arg Arg Lys Ser Ser Thr Arg His Ile His Ala Leu Glu
610                 615                 620

Leu Val Val Ser Arg Asn Leu Ser Pro Pro Asn Cys Thr Glu Leu Gln
625                 630                 635                 640

Ile Asp Ser Cys Ser Ser Ser Glu Glu Ile Lys Lys Lys Lys Tyr Asn
                645                 650                 655

Gln Met Pro Val Arg His Ser Arg Asn Leu Gln Leu Met Glu Gly Lys
                660                 665                 670

Glu Pro Ala Thr Gly Ala Lys Lys Ser Asn Lys Pro Asn Glu Gln Thr
                675                 680                 685

Ser Lys Arg His Asp Ser Asp Thr Phe Pro Glu Leu Lys Leu Thr Asn
690                 695                 700

Ala Pro Gly Ser Phe Thr Lys Cys Ser Asn Thr Ser Glu Leu Lys Glu
705                 710                 715                 720

Phe Val Asn Pro Ser Leu Pro Arg Glu Glu Lys Glu Glu Lys Leu Glu
                725                 730                 735

Thr Val Lys Val Ser Asn Asn Ala Glu Asp Pro Lys Asp Leu Met Leu
                740                 745                 750

Ser Gly Glu Arg Val Leu Gln Thr Glu Arg Ser Val Glu Ser Ser Ser
                755                 760                 765

Ile Ser Leu Val Pro Gly Thr Asp Tyr Gly Thr Gln Glu Ser Ile Ser
770                 775                 780

Leu Leu Glu Val Ser Thr Leu Gly Lys Ala Lys Thr Glu Pro Asn Lys
```

-continued

```
                785                 790                 795                 800
        Cys Val Ser Gln Cys Ala Ala Phe Glu Asn Pro Lys Gly Leu Ile His
                        805                 810                 815
        Gly Cys Ser Lys Asp Asn Arg Asn Asp Thr Glu Gly Phe Lys Tyr Pro
                        820                 825                 830
        Leu Gly His Glu Val Asn His Ser Arg Glu Thr Ser Ile Glu Met Glu
                        835                 840                 845
        Glu Ser Glu Leu Asp Ala Gln Tyr Leu Gln Asn Thr Phe Lys Val Ser
                850                 855                 860
        Lys Arg Gln Ser Phe Ala Pro Phe Ser Asn Pro Gly Asn Ala Glu Glu
        865                 870                 875                 880
        Glu Cys Ala Thr Phe Ser Ala His Ser Gly Ser Leu Lys Lys Gln Ser
                        885                 890                 895
        Pro Lys Val Thr Phe Glu Cys Glu Gln Lys Glu Glu Asn Gln Gly Lys
                        900                 905                 910
        Asn Glu Ser Asn Ile Lys Pro Val Gln Thr Val Asn Ile Thr Ala Gly
                        915                 920                 925
        Phe Pro Val Val Gly Gln Lys Asp Lys Pro Val Asp Asn Ala Lys Cys
                930                 935                 940
        Ser Ile Lys Gly Gly Ser Arg Phe Cys Leu Ser Ser Gln Phe Arg Gly
        945                 950                 955                 960
        Asn Glu Thr Gly Leu Ile Thr Pro Asn Lys His Gly Leu Leu Gln Asn
                        965                 970                 975
        Pro Tyr Arg Ile Pro Pro Leu Phe Pro Ile Lys Ser Phe Val Lys Thr
                        980                 985                 990
        Lys Cys Lys Lys Asn Leu Leu Glu Glu Asn Phe Glu Glu His Ser Met
                995                 1000                1005
        Ser Pro Glu Arg Glu Met Gly Asn Glu Asn Ile Pro Ser Thr Val
                1010                1015                1020
        Ser Thr Ile Ser Arg Asn Asn Ile Arg Glu Asn Val Phe Lys Glu
                1025                1030                1035
        Ala Ser Ser Ser Asn Ile Asn Glu Val Gly Ser Ser Thr Asn Glu
                1040                1045                1050
        Val Gly Ser Ser Ile Asn Glu Ile Gly Ser Ser Asp Glu Asn Ile
                1055                1060                1065
        Gln Ala Glu Leu Gly Arg Asn Arg Gly Pro Lys Leu Asn Ala Met
                1070                1075                1080
        Leu Arg Leu Gly Val Leu Gln Pro Glu Val Tyr Lys Gln Ser Leu
                1085                1090                1095
        Pro Gly Ser Asn Cys Lys His Pro Glu Ile Lys Lys Gln Glu Tyr
                1100                1105                1110
        Glu Glu Val Val Gln Thr Val Asn Thr Asp Phe Ser Pro Tyr Leu
                1115                1120                1125
        Ile Ser Asp Asn Leu Glu Gln Pro Met Gly Ser Ser His Ala Ser
                1130                1135                1140
        Gln Val Cys Ser Glu Thr Pro Asp Asp Leu Leu Asp Asp Gly Glu
                1145                1150                1155
        Ile Lys Glu Asp Thr Ser Phe Ala Glu Asn Asp Ile Lys Glu Ser
                1160                1165                1170
        Ser Ala Val Phe Ser Lys Ser Val Gln Lys Gly Glu Leu Ser Arg
                1175                1180                1185
        Ser Pro Ser Pro Phe Thr His Thr His Leu Ala Gln Gly Tyr Arg
                1190                1195                1200
```

```
Arg Gly Ala Lys Lys Leu Glu Ser Ser Glu Glu Asn Leu Ser Ser
    1205                1210                1215

Glu Asp Glu Glu Leu Pro Cys Phe Gln His Leu Leu Phe Gly Lys
    1220                1225                1230

Val Asn Asn Ile Pro Ser Gln Ser Thr Arg His Ser Thr Val Ala
    1235                1240                1245

Thr Glu Cys Leu Ser Lys Asn Thr Glu Asn Leu Leu Ser Leu
    1250                1255                1260

Lys Asn Ser Leu Asn Asp Cys Ser Asn Gln Val Ile Leu Ala Lys
    1265                1270                1275

Ala Ser Gln Glu His His Leu Ser Glu Glu Thr Lys Cys Ser Ala
    1280                1285                1290

Ser Leu Phe Ser Ser Gln Cys Ser Glu Leu Glu Asp Leu Thr Ala
    1295                1300                1305

Asn Thr Asn Thr Gln Asp Pro Phe Leu Ile Gly Ser Ser Lys Gln
    1310                1315                1320

Met Arg His Gln Ser Glu Ser Gln Gly Val Gly Leu Ser Asp Lys
    1325                1330                1335

Glu Leu Val Ser Asp Asp Glu Glu Arg Gly Thr Gly Leu Glu Glu
    1340                1345                1350

Asn Asn Gln Glu Glu Gln Ser Met Asp Ser Asn Leu Gly Glu Ala
    1355                1360                1365

Ala Ser Gly Cys Glu Ser Glu Thr Ser Val Ser Glu Asp Cys Ser
    1370                1375                1380

Gly Leu Ser Ser Gln Ser Asp Ile Leu Thr Thr Gln Gln Arg Asp
    1385                1390                1395

Thr Met Gln His Asn Leu Ile Lys Leu Gln Gln Glu Met Ala Glu
    1400                1405                1410

Leu Glu Ala Val Leu Glu Gln His Gly Ser Gln Pro Ser Asn Ser
    1415                1420                1425

Tyr Pro Ser Ile Ile Ser Asp Ser Ser Ala Leu Glu Asp Leu Arg
    1430                1435                1440

Asn Pro Glu Gln Ser Thr Ser Glu Lys Ala Val Leu Thr Ser Gln
    1445                1450                1455

Lys Ser Ser Glu Tyr Pro Ile Ser Gln Asn Pro Glu Gly Leu Ser
    1460                1465                1470

Ala Asp Lys Phe Glu Val Ser Ala Asp Ser Ser Thr Ser Lys Asn
    1475                1480                1485

Lys Glu Pro Gly Val Glu Arg Ser Ser Pro Ser Lys Cys Pro Ser
    1490                1495                1500

Leu Asp Asp Arg Trp Tyr Met His Ser Cys Ser Gly Ser Leu Gln
    1505                1510                1515

Asn Arg Asn Tyr Pro Ser Gln Glu Glu Leu Ile Lys Val Val Asp
    1520                1525                1530

Val Glu Glu Gln Gln Leu Glu Glu Ser Gly Pro His Asp Leu Thr
    1535                1540                1545

Glu Thr Ser Tyr Leu Pro Arg Gln Asp Leu Glu Gly Thr Pro Tyr
    1550                1555                1560

Leu Glu Ser Gly Ile Ser Leu Phe Ser Asp Asp Pro Glu Ser Asp
    1565                1570                1575

Pro Ser Glu Asp Arg Ala Pro Glu Ser Ala Arg Val Gly Asn Ile
    1580                1585                1590
```

-continued

```
Pro Ser Ser Thr Ser Ala Leu Lys Val Pro Gln Leu Lys Val Ala
    1595                1600                1605

Glu Ser Ala Gln Ser Pro Ala Ala Ala His Thr Thr Asp Thr Ala
    1610                1615                1620

Gly Tyr Asn Ala Met Glu Glu Ser Val Ser Arg Glu Lys Pro Glu
    1625                1630                1635

Leu Thr Ala Ser Thr Glu Arg Val Asn Lys Arg Met Ser Met Val
    1640                1645                1650

Val Ser Gly Leu Thr Pro Glu Glu Phe Met Leu Val Tyr Lys Phe
    1655                1660                1665

Ala Arg Lys His His Ile Thr Leu Thr Asn Leu Ile Thr Glu Glu
    1670                1675                1680

Thr Thr His Val Val Met Lys Thr Asp Ala Glu Phe Val Cys Glu
    1685                1690                1695

Arg Thr Leu Lys Tyr Phe Leu Gly Ile Ala Gly Gly Lys Trp Val
    1700                1705                1710

Val Ser Tyr Phe Trp Val Thr Gln Ser Ile Lys Glu Arg Lys Met
    1715                1720                1725

Leu Asn Glu His Asp Phe Glu Val Arg Gly Asp Val Val Asn Gly
    1730                1735                1740

Arg Asn His Gln Gly Pro Lys Arg Ala Arg Glu Ser Gln Asp Arg
    1745                1750                1755

Lys Ile Phe Arg Gly Leu Glu Ile Cys Cys Tyr Gly Pro Phe Thr
    1760                1765                1770

Asn Met Pro Thr Asp Gln Leu Glu Trp Met Val Gln Leu Cys Gly
    1775                1780                1785

Ala Ser Val Val Lys Glu Leu Ser Ser Phe Thr Leu Gly Thr Gly
    1790                1795                1800

Val His Pro Ile Val Val Gln Pro Asp Ala Trp Thr Glu Asp
    1805                1810                1815

Asn Gly Phe His Ala Ile Gly Gln Met Cys Glu Ala Pro Val Val
    1820                1825                1830

Thr Arg Glu Trp Val Leu Asp Ser Val Ala Leu Tyr Gln Cys Gln
    1835                1840                1845

Glu Leu Asp Thr Tyr Leu Ile Pro Gln Ile Pro His Ser His Tyr
    1850                1855                1860

<210> SEQ ID NO 20
<211> LENGTH: 479
<212> TYPE: PRT
<213> ORGANISM: Homo Sapiens

<400> SEQUENCE: 20

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
                20                  25                  30

Arg Lys Gln Glu Pro Ile Lys Asp Ala Leu Met Leu Phe Gln Arg Leu
            35                  40                  45

Gln Glu Lys Arg Met Leu Glu Glu Ser Asn Leu Ser Phe Leu Lys Glu
        50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95
```

```
Gln Ile Ser Ala Tyr Arg Val Met Leu Tyr Gln Ile Ser Glu Glu Val
                100                 105                 110

Ser Arg Ser Glu Leu Arg Ser Phe Lys Phe Leu Leu Gln Glu Glu Ile
            115                 120                 125

Ser Lys Cys Lys Leu Asp Asp Met Asn Leu Leu Asp Ile Phe Ile
130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
                180                 185                 190

Pro Asp Glu Phe Ser Asn Gly Glu Glu Leu Cys Gly Val Met Thr Ile
            195                 200                 205

Ser Asp Ser Pro Arg Glu Gln Asp Ser Glu Ser Gln Thr Leu Asp Lys
210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
                260                 265                 270

Thr Phe Glu Glu Leu His Phe Glu Ile Lys Pro His Asp Asp Cys Thr
            275                 280                 285

Val Glu Gln Ile Tyr Asp Ile Leu Lys Ile Tyr Gln Leu Met Asp His
            290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
                355                 360                 365

Ile Pro Val Glu Thr Asp Ser Glu Glu Gln Pro Tyr Leu Glu Met Asp
370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
            435                 440                 445

Glu Val Ser Asn Lys Asp Asp Lys Lys Asn Met Gly Lys Gln Met Pro
            450                 455                 460

Gln Pro Thr Phe Thr Leu Arg Lys Lys Leu Val Phe Pro Ser Asp
465                 470                 475

<210> SEQ ID NO 21
<211> LENGTH: 416
<212> TYPE: PRT
<213> ORGANISM: Homo Sapiens
```

<400> SEQUENCE: 21

```
Met Asp Glu Ala Asp Arg Arg Leu Leu Arg Cys Arg Leu Arg Leu
1               5                   10                  15

Val Glu Glu Leu Gln Val Asp Gln Leu Trp Asp Ala Leu Leu Ser Ser
                20                  25                  30

Glu Leu Phe Arg Pro His Met Ile Glu Asp Ile Gln Arg Ala Gly Ser
            35                  40                  45

Gly Ser Arg Arg Asp Gln Ala Arg Gln Leu Ile Asp Leu Glu Thr
        50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Phe Gly Asp Val Gly Ala Leu Glu Ser
130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Pro His Phe Met Val Glu Val Lys Gly Asp Leu Thr
        195                 200                 205

Ala Lys Lys Met Val Leu Ala Leu Leu Glu Leu Ala Gln Gln Asp His
210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
        355                 360                 365

Asp Ile Phe Glu Gln Trp Ala His Ser Glu Asp Leu Gln Ser Leu Leu
370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415
```

<210> SEQ ID NO 22
<211> LENGTH: 499
<212> TYPE: PRT
<213> ORGANISM: Homo Sapiens

<400> SEQUENCE: 22

Met Pro His Pro Arg Arg Tyr His Ser Ser Glu Arg Gly Ser Arg Gly
1               5                   10                  15

Ser Tyr Arg Glu His Tyr Arg Ser Lys His Lys Arg Arg Arg Arg Ser
                20                  25                  30

Arg Ser Trp Ser Ser Ser Asp Arg Thr Arg Arg Arg Arg Glu
            35                  40                  45

Asp Ser Tyr His Val Arg Ser Arg Ser Tyr Asp Asp Arg Ser Ser
50                  55                  60

Asp Arg Arg Val Tyr Asp Arg Arg Tyr Cys Gly Ser Tyr Arg Arg Asn
65                  70                  75                  80

Asp Tyr Ser Arg Asp Arg Gly Asp Ala Tyr Tyr Asp Thr Asp Tyr Arg
                85                  90                  95

His Ser Tyr Glu Tyr Gln Arg Glu Asn Ser Ser Tyr Arg Ser Gln Arg
                100                 105                 110

Ser Ser Arg Arg Lys His Arg Arg Arg Arg Arg Ser Arg Thr Phe
            115                 120                 125

Ser Arg Ser Ser Ser Gln His Ser Ser Arg Arg Ala Lys Ser Val Glu
130                 135                 140

Asp Asp Ala Glu Gly His Leu Ile Tyr His Val Gly Asp Trp Leu Gln
145                 150                 155                 160

Glu Arg Tyr Glu Ile Val Ser Thr Leu Gly Glu Gly Thr Phe Gly Arg
                165                 170                 175

Val Val Gln Cys Val Asp His Arg Arg Gly Gly Ala Arg Val Ala Leu
                180                 185                 190

Lys Ile Ile Lys Asn Val Glu Lys Tyr Lys Glu Ala Ala Arg Leu Glu
            195                 200                 205

Ile Asn Val Leu Glu Lys Ile Asn Glu Lys Asp Pro Asp Asn Lys Asn
210                 215                 220

Leu Cys Val Gln Met Phe Asp Trp Phe Asp Tyr His Gly His Met Cys
225                 230                 235                 240

Ile Ser Phe Glu Leu Leu Gly Leu Ser Thr Phe Asp Phe Leu Lys Asp
                245                 250                 255

Asn Asn Tyr Leu Pro Tyr Pro Ile His Gln Val Arg His Met Ala Phe
                260                 265                 270

Gln Leu Cys Gln Ala Val Lys Phe Leu His Asp Asn Lys Leu Thr His
            275                 280                 285

Thr Asp Leu Lys Pro Glu Asn Ile Leu Phe Val Asn Ser Asp Tyr Glu
290                 295                 300

Leu Thr Tyr Asn Leu Glu Lys Lys Arg Asp Glu Arg Ser Val Lys Ser
305                 310                 315                 320

Thr Ala Val Arg Val Val Asp Phe Gly Ser Ala Thr Phe Asp His Glu
                325                 330                 335

His His Ser Thr Ile Val Ser Thr Arg His Tyr Arg Ala Pro Glu Val
                340                 345                 350

Ile Leu Glu Leu Gly Trp Ser Gln Pro Cys Asp Val Trp Ser Ile Gly
            355                 360                 365

Cys Ile Ile Phe Glu Tyr Tyr Val Gly Phe Thr Leu Phe Gln Thr His

```
            370                 375                 380
Asp Asn Arg Glu His Leu Ala Met Met Glu Arg Ile Leu Gly Pro Ile
385                 390                 395                 400

Pro Ser Arg Met Ile Arg Lys Thr Arg Lys Gln Lys Tyr Phe Tyr Arg
                405                 410                 415

Gly Arg Leu Asp Trp Asp Glu Asn Thr Ser Ala Gly Arg Tyr Val Arg
                420                 425                 430

Glu Asn Cys Lys Pro Leu Arg Arg Tyr Leu Thr Ser Glu Ala Glu Glu
                435                 440                 445

His His Gln Leu Phe Asp Leu Ile Glu Ser Met Leu Glu Tyr Glu Pro
        450                 455                 460

Ala Lys Arg Leu Thr Leu Gly Glu Ala Leu Gln His Pro Phe Phe Ala
465                 470                 475                 480

Arg Leu Arg Ala Glu Pro Pro Asn Lys Leu Trp Asp Ser Ser Arg Asp
                485                 490                 495

Ile Ser Arg

<210> SEQ ID NO 23
<211> LENGTH: 341
<212> TYPE: PRT
<213> ORGANISM: Homo Sapiens

<400> SEQUENCE: 23

Met Thr Met Glu Ser Gly Ala Glu Asn Gln Gln Ser Gly Asp Ala Ala
1               5                   10                  15

Val Thr Glu Ala Glu Asn Gln Gln Met Thr Val Gln Ala Gln Pro Gln
                20                  25                  30

Ile Ala Thr Leu Ala Gln Val Ser Met Pro Ala Ala His Ala Thr Ser
            35                  40                  45

Ser Ala Pro Thr Val Thr Leu Val Gln Leu Pro Asn Gly Gln Thr Val
        50                  55                  60

Gln Val His Gly Val Ile Gln Ala Ala Gln Pro Ser Val Ile Gln Ser
65                  70                  75                  80

Pro Gln Val Gln Thr Val Gln Ser Ser Cys Lys Asp Leu Lys Arg Leu
                85                  90                  95

Phe Ser Gly Thr Gln Ile Ser Thr Ile Ala Glu Ser Glu Asp Ser Gln
                100                 105                 110

Glu Ser Val Asp Ser Val Thr Asp Ser Gln Lys Arg Arg Glu Ile Leu
            115                 120                 125

Ser Arg Arg Pro Ser Tyr Arg Lys Ile Leu Asn Asp Leu Ser Ser Asp
        130                 135                 140

Ala Pro Gly Val Pro Arg Ile Glu Glu Glu Lys Ser Glu Glu Glu Thr
145                 150                 155                 160

Ser Ala Pro Ala Ile Thr Thr Val Thr Val Pro Thr Pro Ile Tyr Gln
                165                 170                 175

Thr Ser Ser Gly Gln Tyr Ile Ala Ile Thr Gln Gly Gly Ala Ile Gln
                180                 185                 190

Leu Ala Asn Asn Gly Thr Asp Gly Val Gln Gly Leu Gln Thr Leu Thr
            195                 200                 205

Met Thr Asn Ala Ala Ala Thr Gln Pro Gly Thr Thr Ile Leu Gln Tyr
        210                 215                 220

Ala Gln Thr Thr Asp Gly Gln Gln Ile Leu Val Pro Ser Asn Gln Val
225                 230                 235                 240

Val Val Gln Ala Ala Ser Gly Asp Val Gln Thr Tyr Gln Ile Arg Thr
```

```
                              245                 250                 255
        Ala Pro Thr Ser Thr Ile Ala Pro Gly Val Met Ala Ser Ser Pro
                    260                 265                 270

Ala Leu Pro Thr Gln Pro Ala Glu Glu Ala Arg Lys Arg Glu Val
                275                 280                 285

Arg Leu Met Lys Asn Arg Glu Ala Ala Arg Glu Cys Arg Lys Lys
                290                 295                 300

Lys Glu Tyr Val Lys Cys Leu Glu Asn Arg Val Ala Val Leu Glu Asn
        305                 310                 315                 320

Gln Asn Lys Thr Leu Ile Glu Glu Leu Lys Ala Leu Lys Asp Leu Tyr
                        325                 330                 335

Cys His Lys Ser Asp
                    340

<210> SEQ ID NO 24
<211> LENGTH: 1431
<212> TYPE: PRT
<213> ORGANISM: Homo Sapiens

<400> SEQUENCE: 24

Met Thr Val Phe Arg Gln Glu Asn Val Asp Asp Tyr Tyr Asp Thr Gly
        1               5                   10                  15

Glu Glu Leu Gly Ser Gly Gln Phe Ala Val Val Lys Lys Cys Arg Glu
                    20                  25                  30

Lys Ser Thr Gly Leu Gln Tyr Ala Ala Lys Phe Ile Lys Lys Arg Arg
                35                  40                  45

Thr Lys Ser Ser Arg Arg Gly Val Ser Arg Glu Asp Ile Glu Arg Glu
            50                  55                  60

Val Ser Ile Leu Lys Glu Ile Gln His Pro Asn Val Ile Thr Leu His
        65                  70                  75                  80

Glu Val Tyr Glu Asn Lys Thr Asp Val Ile Leu Ile Leu Glu Leu Val
                        85                  90                  95

Ala Gly Gly Glu Leu Phe Asp Phe Leu Ala Glu Lys Glu Ser Leu Thr
                    100                 105                 110

Glu Glu Glu Ala Thr Glu Phe Leu Lys Gln Ile Leu Asn Gly Val Tyr
                115                 120                 125

Tyr Leu His Ser Leu Gln Ile Ala His Phe Asp Leu Lys Pro Glu Asn
            130                 135                 140

Ile Met Leu Leu Asp Arg Asn Val Pro Lys Pro Arg Ile Lys Ile Ile
        145                 150                 155                 160

Asp Phe Gly Leu Ala His Lys Ile Asp Phe Gly Asn Glu Phe Lys Asn
                        165                 170                 175

Ile Phe Gly Thr Pro Glu Phe Val Ala Pro Glu Ile Val Asn Tyr Glu
                    180                 185                 190

Pro Leu Gly Leu Glu Ala Asp Met Trp Ser Ile Gly Val Ile Thr Tyr
                195                 200                 205

Ile Leu Leu Ser Gly Ala Ser Pro Phe Leu Gly Asp Thr Lys Gln Glu
            210                 215                 220

Thr Leu Ala Asn Val Ser Ala Val Asn Tyr Glu Phe Glu Asp Glu Tyr
        225                 230                 235                 240

Phe Ser Asn Thr Ser Ala Leu Ala Lys Asp Phe Ile Arg Arg Leu Leu
                        245                 250                 255

Val Lys Asp Pro Lys Lys Arg Met Thr Ile Gln Asp Ser Leu Gln His
                    260                 265                 270
```

```
Pro Trp Ile Lys Pro Lys Asp Thr Gln Gln Ala Leu Ser Arg Lys Ala
            275                 280                 285

Ser Ala Val Asn Met Glu Lys Phe Lys Phe Ala Ala Arg Lys Lys
    290                 295                 300

Trp Lys Gln Ser Val Arg Leu Ile Ser Leu Cys Gln Arg Leu Ser Arg
305                 310                 315                 320

Ser Phe Leu Ser Arg Ser Asn Met Ser Val Ala Arg Ser Asp Asp Thr
                325                 330                 335

Leu Asp Glu Glu Asp Ser Phe Val Met Lys Ala Ile His Ala Ile
            340                 345                 350

Asn Asp Asp Asn Val Pro Gly Leu Gln His Leu Leu Gly Ser Leu Ser
            355                 360                 365

Asn Tyr Asp Val Asn Gln Pro Asn Lys His Gly Thr Pro Pro Leu Leu
    370                 375                 380

Ile Ala Ala Gly Cys Gly Asn Ile Gln Ile Leu Gln Leu Leu Ile Lys
385                 390                 395                 400

Arg Gly Ser Arg Ile Asp Val Gln Asp Lys Gly Gly Ser Asn Ala Val
                405                 410                 415

Tyr Trp Ala Ala Arg His Gly His Val Asp Thr Leu Lys Phe Leu Ser
            420                 425                 430

Glu Asn Lys Cys Pro Leu Asp Val Lys Asp Lys Ser Gly Glu Met Ala
    435                 440                 445

Leu His Val Ala Ala Arg Tyr Gly His Ala Asp Val Ala Gln Val Thr
    450                 455                 460

Cys Ala Ala Ser Ala Gln Ile Pro Ile Ser Arg Thr Lys Glu Glu
465                 470                 475                 480

Thr Pro Leu His Cys Ala Ala Trp His Gly Tyr Tyr Ser Val Ala Lys
                485                 490                 495

Ala Leu Cys Glu Ala Gly Cys Asn Val Asn Ile Lys Asn Arg Glu Gly
            500                 505                 510

Glu Thr Pro Leu Leu Thr Ala Ser Ala Arg Gly Tyr His Asp Ile Val
            515                 520                 525

Glu Cys Leu Ala Glu His Gly Ala Asp Leu Asn Ala Cys Asp Lys Asp
    530                 535                 540

Gly His Ile Ala Leu His Leu Ala Val Arg Arg Cys Gln Met Glu Val
545                 550                 555                 560

Ile Lys Thr Leu Leu Ser Gln Gly Cys Phe Val Asp Tyr Gln Asp Arg
                565                 570                 575

His Gly Asn Thr Pro Leu His Val Ala Cys Lys Asp Gly Asn Met Pro
            580                 585                 590

Ile Val Val Ala Leu Cys Glu Ala Asn Cys Asn Leu Asp Ile Ser Asn
    595                 600                 605

Lys Tyr Gly Arg Thr Pro Leu His Leu Ala Ala Asn Asn Gly Ile Leu
    610                 615                 620

Asp Val Val Arg Tyr Leu Cys Leu Met Gly Ala Ser Val Glu Ala Leu
625                 630                 635                 640

Thr Thr Asp Gly Lys Thr Ala Glu Asp Leu Ala Arg Ser Glu Gln His
                645                 650                 655

Glu His Val Ala Gly Leu Leu Ala Arg Leu Arg Lys Asp Thr His Arg
            660                 665                 670

Gly Leu Phe Ile Gln Gln Leu Arg Pro Thr Gln Asn Leu Gln Pro Arg
            675                 680                 685

Ile Lys Leu Lys Leu Phe Gly His Ser Gly Ser Gly Lys Thr Thr Leu
```

```
                690                 695                 700
Val Glu Ser Leu Lys Cys Gly Leu Leu Arg Ser Phe Arg Arg Arg
705                 710                 715                 720

Arg Pro Arg Leu Ser Ser Thr Asn Ser Ser Arg Phe Pro Ser Pro
            725                 730                 735

Leu Ala Ser Lys Pro Thr Val Ser Val Ser Ile Asn Asn Leu Tyr Pro
                740                 745                 750

Gly Cys Glu Asn Val Ser Val Arg Ser Arg Ser Met Met Phe Glu Pro
            755                 760                 765

Gly Leu Thr Lys Gly Met Leu Glu Val Phe Val Ala Pro Thr His His
        770                 775                 780

Pro His Cys Ser Ala Asp Asp Gln Ser Thr Lys Ala Ile Asp Ile Gln
785                 790                 795                 800

Asn Ala Tyr Leu Asn Gly Val Gly Asp Phe Ser Val Trp Glu Phe Ser
                805                 810                 815

Gly Asn Pro Val Tyr Phe Cys Cys Tyr Asp Tyr Phe Ala Ala Asn Asp
            820                 825                 830

Pro Thr Ser Ile His Val Val Phe Ser Leu Glu Glu Pro Tyr Glu
        835                 840                 845

Ile Gln Leu Asn Pro Val Ile Phe Trp Leu Ser Phe Leu Lys Ser Leu
    850                 855                 860

Val Pro Val Glu Glu Pro Ile Ala Phe Gly Gly Lys Leu Lys Asn Pro
865                 870                 875                 880

Leu Gln Val Val Leu Val Ala Thr His Ala Asp Ile Met Asn Val Pro
                885                 890                 895

Arg Pro Ala Gly Gly Glu Phe Gly Tyr Asp Lys Asp Thr Ser Leu Leu
            900                 905                 910

Lys Glu Ile Arg Asn Arg Phe Gly Asn Asp Leu His Ile Ser Asn Lys
        915                 920                 925

Leu Phe Val Leu Asp Ala Gly Ala Ser Gly Ser Lys Asp Met Lys Val
    930                 935                 940

Leu Arg Asn His Leu Gln Glu Ile Arg Ser Gln Ile Val Ser Val Cys
945                 950                 955                 960

Pro Pro Met Thr His Leu Cys Glu Lys Ile Ile Ser Thr Leu Pro Ser
                965                 970                 975

Trp Arg Lys Leu Asn Gly Pro Asn Gln Leu Met Ser Leu Gln Gln Phe
            980                 985                 990

Val Tyr Asp Val Gln Asp Gln Leu Asn Pro Leu Ala Ser Glu Glu Asp
        995                 1000                1005

Leu Arg Arg Ile Ala Gln Gln Leu His Ser Thr Gly Glu Ile Asn
    1010                1015                1020

Ile Met Gln Ser Glu Thr Val Gln Asp Val Leu Leu Asp Pro
    1025                1030                1035

Arg Trp Leu Cys Thr Asn Val Leu Gly Lys Leu Leu Ser Val Glu
    1040                1045                1050

Thr Pro Arg Ala Leu His His Tyr Arg Gly Arg Tyr Thr Val Glu
    1055                1060                1065

Asp Ile Gln Arg Leu Val Pro Asp Ser Asp Val Glu Glu Leu Leu
    1070                1075                1080

Gln Ile Leu Asp Ala Met Asp Ile Cys Ala Arg Asp Leu Ser Ser
    1085                1090                1095

Gly Thr Met Val Asp Val Pro Ala Leu Ile Lys Thr Asp Asn Leu
    1100                1105                1110
```

His Arg Ser Trp Ala Asp Glu Asp Glu Val Met Val Tyr Gly
1115                1120                1125

Gly Val Arg Ile Val Pro Val Glu His Leu Thr Pro Phe Pro Cys
1130                1135                1140

Gly Ile Phe His Lys Val Gln Val Asn Leu Cys Arg Trp Ile His
1145                1150                1155

Gln Gln Ser Thr Glu Gly Asp Ala Asp Ile Arg Leu Trp Val Asn
1160                1165                1170

Gly Cys Lys Leu Ala Asn Arg Gly Ala Glu Leu Leu Val Leu Leu
1175                1180                1185

Val Asn His Gly Gln Gly Ile Glu Val Gln Val Arg Gly Leu Glu
1190                1195                1200

Thr Glu Lys Ile Lys Cys Cys Leu Leu Leu Asp Ser Val Cys Ser
1205                1210                1215

Thr Ile Glu Asn Val Met Ala Thr Thr Leu Pro Gly Leu Leu Thr
1220                1225                1230

Val Lys His Tyr Leu Ser Pro Gln Gln Leu Arg Glu His His Glu
1235                1240                1245

Pro Val Met Ile Tyr Gln Pro Arg Asp Phe Phe Arg Ala Gln Thr
1250                1255                1260

Leu Lys Glu Thr Ser Leu Thr Asn Thr Met Gly Gly Tyr Lys Glu
1265                1270                1275

Ser Phe Ser Ser Ile Met Cys Phe Gly Cys His Asp Val Tyr Ser
1280                1285                1290

Gln Ala Ser Leu Gly Met Asp Ile His Ala Ser Asp Leu Asn Leu
1295                1300                1305

Leu Thr Arg Arg Lys Leu Ser Arg Leu Leu Asp Pro Pro Asp Pro
1310                1315                1320

Leu Gly Lys Asp Trp Cys Leu Leu Ala Met Asn Leu Gly Leu Pro
1325                1330                1335

Asp Leu Val Ala Lys Tyr Asn Thr Asn Asn Gly Ala Pro Lys Asp
1340                1345                1350

Phe Leu Pro Ser Pro Leu His Ala Leu Leu Arg Glu Trp Thr Thr
1355                1360                1365

Tyr Pro Glu Ser Thr Val Gly Thr Leu Met Ser Lys Leu Arg Glu
1370                1375                1380

Leu Gly Arg Arg Asp Ala Ala Asp Leu Leu Lys Ala Ser Ser
1385                1390                1395

Val Phe Lys Ile Asn Leu Asp Gly Asn Gly Gln Glu Ala Tyr Ala
1400                1405                1410

Ser Ser Cys Asn Ser Gly Thr Ser Tyr Asn Ser Ile Ser Ser Val
1415                1420                1425

Val Ser Arg
1430

<210> SEQ ID NO 25
<211> LENGTH: 381
<212> TYPE: PRT
<213> ORGANISM: Homo Sapiens

<400> SEQUENCE: 25

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr

```
            20                  25                  30
Gly Lys Leu Asn Ile Ser Ala Asp Lys Glu Asn Ser Ile Lys Leu Thr
            35                  40                  45

Ser Val Val Phe Ile Leu Ile Cys Phe Ile Ile Leu Glu Asn Ile
 50                  55                  60

Phe Val Leu Leu Thr Ile Trp Lys Thr Lys Lys Phe His Arg Pro Met
 65                  70                  75                  80

Tyr Tyr Phe Ile Gly Asn Leu Ala Leu Ser Asp Leu Leu Ala Gly Val
                    85                  90                  95

Ala Tyr Thr Ala Asn Leu Leu Leu Ser Gly Ala Thr Thr Tyr Lys Leu
                100                 105                 110

Thr Pro Ala Gln Trp Phe Leu Arg Glu Gly Ser Met Phe Val Ala Leu
                115                 120                 125

Ser Ala Ser Val Phe Ser Leu Leu Ala Ile Ala Ile Glu Arg Tyr Ile
                130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
                180                 185                 190

Thr Val Leu Pro Leu Tyr His Lys His Tyr Ile Leu Phe Cys Thr Thr
                195                 200                 205

Val Phe Thr Leu Leu Leu Ser Ile Val Ile Leu Tyr Cys Arg Ile
                210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Asn Val Ala Leu Leu Lys Thr
                245                 250                 255

Val Ile Ile Val Leu Ser Val Phe Ile Ala Cys Trp Ala Pro Leu Phe
                260                 265                 270

Ile Leu Leu Leu Leu Asp Val Gly Cys Lys Val Lys Thr Cys Asp Ile
                275                 280                 285

Leu Phe Arg Ala Glu Tyr Phe Leu Val Leu Ala Val Leu Asn Ser Gly
                290                 295                 300

Thr Asn Pro Ile Ile Tyr Thr Leu Thr Asn Lys Glu Met Arg Arg Ala
305                 310                 315                 320

Phe Ile Arg Ile Met Ser Cys Cys Lys Cys Pro Ser Gly Asp Ser Ala
                325                 330                 335

Gly Lys Phe Lys Arg Pro Ile Ile Ala Gly Met Glu Phe Ser Arg Ser
                340                 345                 350

Lys Ser Asp Asn Ser Ser His Pro Gln Lys Asp Glu Gly Asp Asn Pro
                355                 360                 365

Glu Thr Ile Met Ser Ser Gly Asn Val Asn Ser Ser
                370                 375                 380

<210> SEQ ID NO 26
<211> LENGTH: 382
<212> TYPE: PRT
<213> ORGANISM: Mus musculus

<400> SEQUENCE: 26

Met Val Ser Thr Ser Ile Pro Glu Val Lys Ala Leu Arg Ser Ser Val
  1               5                  10                  15
```

Ser Asp Tyr Gly Asn Tyr Asp Ile Ile Val Arg His Tyr Asn Tyr Thr
            20                  25                  30

Gly Lys Leu Asn Ile Gly Ala Glu Lys Asp His Gly Ile Lys Leu Thr
        35                  40                  45

Ser Val Val Phe Ile Leu Ile Cys Cys Phe Ile Ile Leu Glu Asn Ile
 50                  55                  60

Phe Val Leu Leu Thr Ile Trp Lys Thr Lys Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
130                 135                 140

Thr Met Leu Lys Met Lys Leu His Asn Gly Ser Asn Ser Ser Arg Ser
145                 150                 155                 160

Phe Leu Leu Ile Ser Ala Cys Trp Val Ile Ser Leu Ile Leu Gly Gly
                165                 170                 175

Leu Pro Ser Met Gly Trp Asn Cys Ile Ser Ser Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Val Ile Leu Tyr Cys Arg Ile
210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Ala Lys Thr Cys Asp
        275                 280                 285

Ile Leu Tyr Lys Ala Glu Tyr Phe Leu Val Leu Ala Val Leu Asn Ser
290                 295                 300

Gly Thr Asn Pro Ile Ile Tyr Thr Leu Thr Asn Lys Glu Met Arg Arg
305                 310                 315                 320

Ala Phe Ile Arg Ile Val Ser Cys Cys Lys Cys Pro Asn Gly Asp Ser
                325                 330                 335

Ala Gly Lys Phe Lys Arg Pro Ile Ile Pro Gly Met Glu Phe Ser Arg
            340                 345                 350

Ser Lys Ser Asp Asn Ser Ser His Pro Gln Lys Asp Asp Gly Asp Asn
        355                 360                 365

Pro Glu Thr Ile Met Ser Ser Gly Asn Val Asn Ser Ser Ser
370                 375                 380

<210> SEQ ID NO 27
<211> LENGTH: 1203
<212> TYPE: PRT
<213> ORGANISM: Homo Sapiens

<400> SEQUENCE: 27

Met Gly Asn Leu Lys Ser Val Ala Gln Glu Pro Gly Pro Pro Cys Gly
1               5                   10                  15

-continued

Leu Gly Leu Gly Leu Gly Leu Cys Gly Lys Gln Gly Pro Ala
          20              25              30

Thr Pro Ala Pro Glu Pro Ser Arg Ala Pro Ala Ser Leu Pro Pro
         35              40              45

Ala Pro Glu His Ser Pro Ser Ser Pro Leu Thr Gln Pro Pro Glu
 50              55              60

Gly Pro Lys Phe Pro Arg Val Lys Asn Trp Glu Val Gly Ser Ile Thr
 65              70              75              80

Tyr Asp Thr Leu Ser Ala Gln Ala Gln Gln Asp Gly Pro Cys Thr Pro
             85              90              95

Arg Arg Cys Leu Gly Ser Leu Val Phe Pro Arg Lys Leu Gln Gly Arg
             100             105             110

Pro Ser Pro Gly Pro Pro Ala Pro Glu Gln Leu Leu Ser Gln Ala Arg
             115             120             125

Asp Phe Ile Asn Gln Tyr Tyr Ser Ser Ile Lys Arg Ser Gly Ser Gln
 130             135             140

Ala His Glu Gln Arg Leu Gln Glu Val Glu Ala Glu Val Ala Ala Thr
145             150             155             160

Gly Thr Tyr Gln Leu Arg Glu Ser Glu Leu Val Phe Gly Ala Lys Gln
             165             170             175

Ala Trp Arg Asn Ala Pro Arg Cys Val Gly Arg Ile Gln Trp Gly Lys
             180             185             190

Leu Gln Val Phe Asp Ala Arg Asp Cys Arg Ser Ala Gln Glu Met Phe
             195             200             205

Thr Tyr Ile Cys Asn His Ile Lys Tyr Ala Thr Asn Arg Gly Asn Leu
210             215             220

Arg Ser Ala Ile Thr Val Phe Pro Gln Arg Cys Pro Gly Arg Gly Asp
225             230             235             240

Phe Arg Ile Trp Asn Ser Gln Leu Val Arg Tyr Ala Gly Tyr Arg Gln
             245             250             255

Gln Asp Gly Ser Val Arg Gly Asp Pro Ala Asn Val Glu Ile Thr Glu
             260             265             270

Leu Cys Ile Gln His Gly Trp Thr Pro Gly Asn Gly Arg Phe Asp Val
             275             280             285

Leu Pro Leu Leu Leu Gln Ala Pro Asp Asp Pro Pro Glu Leu Phe Leu
290             295             300

Leu Pro Pro Glu Leu Val Leu Glu Val Pro Leu Glu His Pro Thr Leu
305             310             315             320

Glu Trp Phe Ala Ala Leu Gly Leu Arg Trp Tyr Ala Leu Pro Ala Val
             325             330             335

Ser Asn Met Leu Leu Glu Ile Gly Gly Leu Glu Phe Pro Ala Ala Pro
             340             345             350

Phe Ser Gly Trp Tyr Met Ser Thr Glu Ile Gly Thr Arg Asn Leu Cys
             355             360             365

Asp Pro His Arg Tyr Asn Ile Leu Glu Asp Val Ala Val Cys Met Asp
             370             375             380

Leu Asp Thr Arg Thr Thr Ser Ser Leu Trp Lys Asp Lys Ala Ala Val
385             390             395             400

Glu Ile Asn Val Ala Val Leu His Ser Tyr Gln Leu Ala Lys Val Thr
             405             410             415

Ile Val Asp His His Ala Ala Thr Ala Ser Phe Met Lys His Leu Glu
             420             425             430

-continued

```
Asn Glu Gln Lys Ala Arg Gly Gly Cys Pro Ala Asp Trp Ala Trp Ile
            435                 440                 445

Val Pro Pro Ile Ser Gly Ser Leu Thr Pro Val Phe His Gln Glu Met
450                 455                 460

Val Asn Tyr Phe Leu Ser Pro Ala Phe Arg Tyr Gln Pro Asp Pro Trp
465                 470                 475                 480

Lys Gly Ser Ala Ala Lys Gly Thr Gly Ile Thr Arg Lys Lys Thr Phe
                485                 490                 495

Lys Glu Val Ala Asn Ala Val Lys Ile Ser Ala Ser Leu Met Gly Thr
                500                 505                 510

Val Met Ala Lys Arg Val Lys Ala Thr Ile Leu Tyr Gly Ser Glu Thr
            515                 520                 525

Gly Arg Ala Gln Ser Tyr Ala Gln Gln Leu Gly Arg Leu Phe Arg Lys
530                 535                 540

Ala Phe Asp Pro Arg Val Leu Cys Met Asp Glu Tyr Asp Val Val Ser
545                 550                 555                 560

Leu Glu His Glu Thr Leu Val Leu Val Val Thr Ser Thr Phe Gly Asn
                565                 570                 575

Gly Asp Pro Pro Glu Asn Gly Glu Ser Phe Ala Ala Ala Leu Met Glu
                580                 585                 590

Met Ser Gly Pro Tyr Asn Ser Ser Pro Arg Pro Glu Gln His Lys Ser
            595                 600                 605

Tyr Lys Ile Arg Phe Asn Ser Ile Ser Cys Ser Asp Pro Leu Val Ser
                610                 615                 620

Ser Trp Arg Arg Lys Arg Lys Glu Ser Ser Asn Thr Asp Ser Ala Gly
625                 630                 635                 640

Ala Leu Gly Thr Leu Arg Phe Cys Val Phe Gly Leu Gly Ser Arg Ala
                645                 650                 655

Tyr Pro His Phe Cys Ala Phe Ala Arg Ala Val Asp Thr Arg Leu Glu
                660                 665                 670

Glu Leu Gly Gly Glu Arg Leu Leu Gln Leu Gly Gln Gly Asp Glu Leu
            675                 680                 685

Cys Gly Gln Glu Glu Ala Phe Arg Gly Trp Ala Gln Ala Ala Phe Gln
690                 695                 700

Ala Ala Cys Glu Thr Phe Cys Val Gly Glu Asp Ala Lys Ala Ala Ala
705                 710                 715                 720

Arg Asp Ile Phe Ser Pro Lys Arg Ser Trp Lys Arg Gln Arg Tyr Arg
                725                 730                 735

Leu Ser Ala Gln Ala Glu Gly Leu Gln Leu Leu Pro Gly Leu Ile His
                740                 745                 750

Val His Arg Lys Met Phe Gln Ala Thr Ile Arg Ser Val Glu Asn
            755                 760                 765

Leu Gln Ser Ser Lys Ser Thr Arg Ala Thr Ile Leu Val Arg Leu Asp
770                 775                 780

Thr Gly Gly Gln Glu Gly Leu Gln Tyr Gln Pro Gly Asp His Ile Gly
785                 790                 795                 800

Val Cys Pro Pro Asn Arg Pro Gly Leu Val Glu Ala Leu Leu Ser Arg
                805                 810                 815

Val Glu Asp Pro Pro Ala Pro Thr Glu Pro Val Ala Val Glu Gln Leu
                820                 825                 830

Glu Lys Gly Ser Pro Gly Gly Pro Pro Gly Trp Val Arg Asp Pro
            835                 840                 845

Arg Leu Pro Pro Cys Thr Leu Arg Gln Ala Leu Thr Phe Phe Leu Asp
```

```
                850                 855                 860
Ile Thr Ser Pro Pro Pro Gln Leu Leu Arg Leu Ser Thr Leu
865                 870                 875                 880

Ala Glu Glu Pro Arg Glu Gln Gln Leu Glu Ala Leu Ser Gln Asp
                885                 890                 895

Pro Arg Arg Tyr Glu Glu Trp Lys Trp Phe Arg Cys Pro Thr Leu Leu
                900                 905                 910

Glu Val Leu Glu Gln Phe Pro Ser Val Ala Leu Pro Ala Pro Leu Leu
                915                 920                 925

Leu Thr Gln Leu Pro Leu Leu Gln Pro Arg Tyr Tyr Ser Val Ser Ser
                930                 935                 940

Ala Pro Ser Thr His Pro Gly Glu Ile His Leu Thr Val Ala Val Leu
945                 950                 955                 960

Ala Tyr Arg Thr Gln Asp Gly Leu Gly Pro Leu His Tyr Gly Val Cys
                965                 970                 975

Ser Thr Trp Leu Ser Gln Leu Lys Pro Gly Asp Pro Val Pro Cys Phe
                980                 985                 990

Ile Arg Gly Ala Pro Ser Phe Arg Leu Pro Pro Asp Pro Ser Leu Pro
                995                 1000                1005

Cys Ile Leu Val Gly Pro Gly Thr Gly Ile Ala Pro Phe Arg Gly
                1010                1015                1020

Phe Trp Gln Glu Arg Leu His Asp Ile Glu Ser Lys Gly Leu Gln
                1025                1030                1035

Pro Thr Pro Met Thr Leu Val Phe Gly Cys Arg Cys Ser Gln Leu
                1040                1045                1050

Asp His Leu Tyr Arg Asp Glu Val Gln Asn Ala Gln Gln Arg Gly
                1055                1060                1065

Val Phe Gly Arg Val Leu Thr Ala Phe Ser Arg Glu Pro Asp Asn
                1070                1075                1080

Pro Lys Thr Tyr Val Gln Asp Ile Leu Arg Thr Glu Leu Ala Ala
                1085                1090                1095

Glu Val His Arg Val Leu Cys Leu Glu Arg Gly His Met Phe Val
                1100                1105                1110

Cys Gly Asp Val Thr Met Ala Thr Asn Val Leu Gln Thr Val Gln
                1115                1120                1125

Arg Ile Leu Ala Thr Glu Gly Asp Met Glu Leu Asp Glu Ala Gly
                1130                1135                1140

Asp Val Ile Gly Val Leu Arg Asp Gln Gln Arg Tyr His Glu Asp
                1145                1150                1155

Ile Phe Gly Leu Thr Leu Arg Thr Gln Glu Val Thr Ser Arg Ile
                1160                1165                1170

Arg Thr Gln Ser Phe Ser Leu Gln Glu Arg Gln Leu Arg Gly Ala
                1175                1180                1185

Val Pro Trp Ala Phe Asp Pro Pro Gly Ser Asp Thr Asn Ser Pro
                1190                1195                1200

<210> SEQ ID NO 28
<211> LENGTH: 286
<212> TYPE: PRT
<213> ORGANISM: Homo Sapiens

<400> SEQUENCE: 28

Met Gly Gln Thr Gly Lys Lys Ser Glu Lys Gly Pro Val Cys Trp Arg
1               5                   10                  15
```

Lys Arg Val Lys Ser Glu Tyr Met Arg Leu Arg Gln Leu Lys Arg Phe
            20                  25                  30

Arg Arg Ala Asp Glu Val Lys Ser Met Phe Ser Ser Asn Arg Gln Lys
        35                  40                  45

Ile Leu Glu Arg Thr Glu Ile Leu Asn Gln Glu Trp Lys Gln Arg Arg
50                  55                  60

Ile Gln Pro Val His Ile Leu Thr Ser Val Ser Ser Leu Arg Gly Thr
65                  70                  75                  80

Arg Glu Cys Ser Val Thr Ser Asp Leu Asp Phe Pro Thr Gln Val Ile
                85                  90                  95

Pro Leu Lys Thr Leu Asn Ala Val Ala Ser Val Pro Ile Met Tyr Ser
            100                 105                 110

Trp Ser Pro Leu Gln Gln Asn Phe Met Val Glu Asp Glu Thr Val Leu
        115                 120                 125

His Asn Ile Pro Tyr Met Gly Asp Glu Val Leu Asp Gln Asp Gly Thr
    130                 135                 140

Phe Ile Glu Glu Leu Ile Lys Asn Tyr Asp Gly Lys Val His Gly Asp
145                 150                 155                 160

Arg Glu Cys Gly Phe Ile Asn Asp Glu Ile Phe Val Glu Leu Val Asn
                165                 170                 175

Ala Leu Gly Gln Tyr Asn Asp Asp Asp Asp Asp Asp Gly Asp Asp
            180                 185                 190

Pro Glu Glu Arg Glu Glu Lys Gln Lys Asp Leu Glu Asp His Arg Asp
        195                 200                 205

Asp Lys Glu Ser Arg Pro Pro Arg Lys Phe Pro Ser Asp Lys Ile Phe
210                 215                 220

Glu Ala Ile Ser Ser Met Phe Pro Asp Lys Gly Thr Ala Glu Glu Leu
225                 230                 235                 240

Lys Glu Lys Tyr Lys Glu Leu Thr Glu Gln Gln Leu Pro Gly Ala Leu
                245                 250                 255

Pro Pro Glu Cys Thr Pro Asn Ile Asp Gly Pro Asn Ala Lys Ser Val
            260                 265                 270

Gln Arg Glu Gln Ser Leu His Ser Phe His Thr Leu Phe Cys
        275                 280                 285

<210> SEQ ID NO 29
<211> LENGTH: 655
<212> TYPE: PRT
<213> ORGANISM: Homo Sapiens

<400> SEQUENCE: 29

Met Ala Glu Ala Pro Gln Val Val Glu Ile Asp Pro Asp Phe Glu Pro
1               5                   10                  15

Leu Pro Arg Pro Arg Ser Cys Thr Trp Pro Leu Pro Arg Pro Glu Phe
            20                  25                  30

Ser Gln Ser Asn Ser Ala Thr Ser Ser Pro Ala Pro Ser Gly Ser Ala
        35                  40                  45

Ala Ala Asn Pro Asp Ala Ala Ala Gly Leu Pro Ser Ala Ser Ala Ala
    50                  55                  60

Ala Val Ser Ala Asp Phe Met Ser Asn Leu Ser Leu Leu Glu Glu Ser
65                  70                  75                  80

Glu Asp Phe Pro Gln Ala Pro Gly Ser Val Ala Ala Val Ala Ala
                85                  90                  95

Ala Ala Ala Ala Ala Thr Gly Gly Leu Cys Gly Asp Phe Gln Gly
            100                 105                 110

```
Pro Glu Ala Gly Cys Leu His Pro Ala Pro Gln Pro Pro Pro
        115                 120                 125

Gly Pro Leu Ser Gln His Pro Pro Val Pro Pro Ala Ala Gly Pro
    130                 135                 140

Leu Ala Gly Gln Pro Arg Lys Ser Ser Ser Arg Arg Asn Ala Trp
145                 150                 155                 160

Gly Asn Leu Ser Tyr Ala Asp Leu Ile Thr Lys Ala Ile Glu Ser Ser
                165                 170                 175

Ala Glu Lys Arg Leu Thr Leu Ser Gln Ile Tyr Glu Trp Met Val Lys
                180                 185                 190

Ser Val Pro Tyr Phe Lys Asp Lys Gly Asp Ser Asn Ser Ser Ala Gly
            195                 200                 205

Trp Lys Asn Ser Ile Arg His Asn Leu Ser Leu His Ser Lys Phe Ile
    210                 215                 220

Arg Val Gln Asn Glu Gly Thr Gly Lys Ser Ser Trp Trp Met Leu Asn
225                 230                 235                 240

Pro Glu Gly Gly Lys Ser Gly Lys Ser Pro Arg Arg Ala Ala Ser
                245                 250                 255

Met Asp Asn Asn Ser Lys Phe Ala Lys Ser Arg Ser Arg Ala Ala Lys
                260                 265                 270

Lys Lys Ala Ser Leu Gln Ser Gly Gln Glu Gly Ala Gly Asp Ser Pro
            275                 280                 285

Gly Ser Gln Phe Ser Lys Trp Pro Ala Ser Pro Gly Ser His Ser Asn
    290                 295                 300

Asp Asp Phe Asp Asn Trp Ser Thr Phe Arg Pro Arg Thr Ser Ser Asn
305                 310                 315                 320

Ala Ser Thr Ile Ser Gly Arg Leu Ser Pro Ile Met Thr Glu Gln Asp
                325                 330                 335

Asp Leu Gly Glu Gly Asp Val His Ser Met Val Tyr Pro Pro Ser Ala
            340                 345                 350

Ala Lys Met Ala Ser Thr Leu Pro Ser Leu Ser Glu Ile Ser Asn Pro
    355                 360                 365

Glu Asn Met Glu Asn Leu Leu Asp Asn Leu Asn Leu Leu Ser Ser Pro
            370                 375                 380

Thr Ser Leu Thr Val Ser Thr Gln Ser Ser Pro Gly Thr Met Met Gln
385                 390                 395                 400

Gln Thr Pro Cys Tyr Ser Phe Ala Pro Pro Asn Thr Ser Leu Asn Ser
                405                 410                 415

Pro Ser Pro Asn Tyr Gln Lys Tyr Thr Tyr Gly Gln Ser Ser Met Ser
                420                 425                 430

Pro Leu Pro Gln Met Pro Ile Gln Thr Leu Gln Asp Asn Lys Ser Ser
            435                 440                 445

Tyr Gly Gly Met Ser Gln Tyr Asn Cys Ala Pro Gly Leu Leu Lys Glu
    450                 455                 460

Leu Leu Thr Ser Asp Ser Pro Pro His Asn Asp Ile Met Thr Pro Val
465                 470                 475                 480

Asp Pro Gly Val Ala Gln Pro Asn Ser Arg Val Leu Gly Gln Asn Val
                485                 490                 495

Met Met Gly Pro Asn Ser Val Met Ser Thr Tyr Gly Ser Gln Ala Ser
            500                 505                 510

His Asn Lys Met Met Asn Pro Ser Ser His Thr His Pro Gly His Ala
    515                 520                 525
```

-continued

```
Gln Gln Thr Ser Ala Val Asn Gly Arg Pro Leu Pro His Thr Val Ser
    530                 535                 540
Thr Met Pro His Thr Ser Gly Met Asn Arg Leu Thr Gln Val Lys Thr
545                 550                 555                 560
Pro Val Gln Val Pro Leu Pro His Pro Met Gln Met Ser Ala Leu Gly
                565                 570                 575
Gly Tyr Ser Ser Val Ser Ser Cys Asn Gly Tyr Gly Arg Met Gly Leu
                580                 585                 590
Leu His Gln Glu Lys Leu Pro Ser Asp Leu Asp Gly Met Phe Ile Glu
                595                 600                 605
Arg Leu Asp Cys Asp Met Glu Ser Ile Ile Arg Asn Asp Leu Met Asp
            610                 615                 620
Gly Asp Thr Leu Asp Phe Asn Phe Asp Asn Val Leu Pro Asn Gln Ser
625                 630                 635                 640
Phe Pro His Ser Val Lys Thr Thr Thr His Ser Trp Val Ser Gly
                645                 650                 655

<210> SEQ ID NO 30
<211> LENGTH: 673
<212> TYPE: PRT
<213> ORGANISM: Homo Sapiens

<400> SEQUENCE: 30

Met Ala Glu Ala Pro Ala Ser Pro Ala Pro Leu Ser Pro Leu Glu Val
1               5                   10                  15
Glu Leu Asp Pro Glu Phe Glu Pro Gln Ser Arg Pro Arg Ser Cys Thr
                20                  25                  30
Trp Pro Leu Gln Arg Pro Glu Leu Gln Ala Ser Pro Ala Lys Pro Ser
            35                  40                  45
Gly Glu Thr Ala Ala Asp Ser Met Ile Pro Glu Glu Glu Asp Asp Glu
    50                  55                  60
Asp Asp Glu Asp Gly Gly Gly Arg Ala Gly Ser Ala Met Ala Ile Gly
65                  70                  75                  80
Gly Gly Gly Gly Ser Gly Thr Leu Gly Ser Gly Leu Leu Leu Glu Asp
                85                  90                  95
Ser Ala Arg Val Leu Ala Pro Gly Gly Gln Asp Pro Gly Ser Gly Pro
                100                 105                 110
Ala Thr Ala Ala Gly Gly Leu Ser Gly Gly Thr Gln Ala Leu Leu Gln
            115                 120                 125
Pro Gln Gln Pro Leu Pro Pro Gln Pro Gly Ala Ala Gly Gly Ser
130                 135                 140
Gly Gln Pro Arg Lys Cys Ser Ser Arg Arg Asn Ala Trp Gly Asn Leu
145                 150                 155                 160
Ser Tyr Ala Asp Leu Ile Thr Arg Ala Ile Glu Ser Ser Pro Asp Lys
                165                 170                 175
Arg Leu Thr Leu Ser Gln Ile Tyr Glu Trp Met Val Arg Cys Val Pro
            180                 185                 190
Tyr Phe Lys Asp Lys Gly Asp Ser Asn Ser Ser Ala Gly Trp Lys Asn
        195                 200                 205
Ser Ile Arg His Asn Leu Ser Leu His Ser Arg Phe Met Arg Val Gln
    210                 215                 220
Asn Glu Gly Thr Gly Lys Ser Ser Trp Trp Ile Ile Asn Pro Asp Gly
225                 230                 235                 240
Gly Lys Ser Gly Lys Ala Pro Arg Arg Arg Ala Val Ser Met Asp Asn
                245                 250                 255
```

```
Ser Asn Lys Tyr Thr Lys Ser Arg Gly Arg Ala Ala Lys Lys Lys Ala
            260                 265                 270

Ala Leu Gln Thr Ala Pro Glu Ser Ala Asp Asp Ser Pro Ser Gln Leu
        275                 280                 285

Ser Lys Trp Pro Gly Ser Pro Thr Ser Arg Ser Ser Asp Glu Leu Asp
    290                 295                 300

Ala Trp Thr Asp Phe Arg Ser Arg Thr Asn Ser Asn Ala Ser Thr Val
305                 310                 315                 320

Ser Gly Arg Leu Ser Pro Ile Met Ala Ser Thr Glu Leu Asp Glu Val
                325                 330                 335

Gln Asp Asp Asp Ala Pro Leu Ser Pro Met Leu Tyr Ser Ser Ser Ala
            340                 345                 350

Ser Leu Ser Pro Ser Val Ser Lys Pro Cys Thr Val Glu Leu Pro Arg
        355                 360                 365

Leu Thr Asp Met Ala Gly Thr Met Asn Leu Asn Asp Gly Leu Thr Glu
    370                 375                 380

Asn Leu Met Asp Asp Leu Leu Asp Asn Ile Thr Leu Pro Pro Ser Gln
385                 390                 395                 400

Pro Ser Pro Thr Gly Gly Leu Met Gln Arg Ser Ser Ser Phe Pro Tyr
                405                 410                 415

Thr Thr Lys Gly Ser Gly Leu Gly Ser Pro Thr Ser Ser Phe Asn Ser
            420                 425                 430

Thr Val Phe Gly Pro Ser Ser Leu Asn Ser Leu Arg Gln Ser Pro Met
        435                 440                 445

Gln Thr Ile Gln Glu Asn Lys Pro Ala Thr Phe Ser Ser Met Ser His
    450                 455                 460

Tyr Gly Asn Gln Thr Leu Gln Asp Leu Leu Thr Ser Asp Ser Leu Ser
465                 470                 475                 480

His Ser Asp Val Met Met Thr Gln Ser Asp Pro Leu Met Ser Gln Ala
                485                 490                 495

Ser Thr Ala Val Ser Ala Gln Asn Ser Arg Arg Asn Val Met Leu Arg
            500                 505                 510

Asn Asp Pro Met Met Ser Phe Ala Ala Gln Pro Asn Gln Gly Ser Leu
        515                 520                 525

Val Asn Gln Asn Leu Leu His His Gln His Gln Thr Gln Gly Ala Leu
    530                 535                 540

Gly Gly Ser Arg Ala Leu Ser Asn Ser Val Ser Asn Met Gly Leu Ser
545                 550                 555                 560

Glu Ser Ser Ser Leu Gly Ser Ala Lys His Gln Gln Ser Pro Val
                565                 570                 575

Ser Gln Ser Met Gln Thr Leu Ser Asp Ser Leu Ser Gly Ser Ser Leu
            580                 585                 590

Tyr Ser Thr Ser Ala Asn Leu Pro Val Met Gly His Glu Lys Phe Pro
        595                 600                 605

Ser Asp Leu Asp Leu Asp Met Phe Asn Gly Ser Leu Glu Cys Asp Met
    610                 615                 620

Glu Ser Ile Ile Arg Ser Glu Leu Met Asp Ala Asp Gly Leu Asp Phe
625                 630                 635                 640

Asn Phe Asp Ser Leu Ile Ser Thr Gln Asn Val Val Gly Leu Asn Val
                645                 650                 655

Gly Asn Phe Thr Gly Ala Lys Gln Ala Ser Ser Gln Ser Trp Val Pro
            660                 665                 670
```

Gly

<210> SEQ ID NO 31
<211> LENGTH: 501
<212> TYPE: PRT
<213> ORGANISM: Homo Sapiens

<400> SEQUENCE: 31

```
Met Arg Ile Gln Pro Gln Lys Ala Ala Ile Ile Asp Leu Asp Pro
1               5                   10                  15

Asp Phe Glu Pro Gln Ser Arg Pro Arg Ser Cys Thr Trp Pro Leu Pro
                20                  25                  30

Arg Pro Glu Ile Ala Asn Gln Pro Ser Glu Pro Pro Val Glu Pro
                35                  40                  45

Asp Leu Gly Glu Lys Val His Thr Glu Gly Arg Ser Glu Pro Ile Leu
50                      55                  60

Leu Pro Ser Arg Leu Ser Glu Pro Ala Gly Pro Gln Pro Gly Ile
65                  70                  75                  80

Leu Gly Ala Val Thr Gly Pro Arg Lys Gly Ser Arg Arg Asn Ala
                    85                  90                      95

Trp Gly Asn Gln Ser Tyr Ala Glu Phe Ile Ser Gln Ala Ile Glu Ser
                100                 105                 110

Ala Pro Glu Lys Arg Leu Thr Leu Ala Gln Ile Tyr Glu Trp Met Val
                115                 120                 125

Arg Thr Val Pro Tyr Phe Lys Asp Lys Gly Asp Ser Asn Ser Ser Ala
            130                 135                 140

Gly Trp Lys Asn Ser Ile Arg His Asn Leu Ser Leu His Ser Lys Phe
145                 150                 155                 160

Ile Lys Val His Asn Glu Ala Thr Gly Lys Ser Ser Trp Trp Met Leu
                165                 170                 175

Asn Pro Glu Gly Gly Lys Ser Gly Lys Ala Pro Arg Arg Ala Ala
                180                 185                 190

Ser Met Asp Ser Ser Lys Leu Leu Arg Gly Arg Ser Lys Ala Pro
            195                 200                 205

Lys Lys Lys Pro Ser Val Leu Pro Ala Pro Glu Gly Ala Thr Pro
210                 215                 220

Thr Ser Pro Val Gly His Phe Ala Lys Trp Ser Gly Ser Pro Cys Ser
225                 230                 235                 240

Arg Asn Arg Glu Glu Ala Asp Met Trp Thr Thr Phe Arg Pro Arg Ser
                245                 250                 255

Ser Ser Asn Ala Ser Ser Val Ser Thr Arg Leu Ser Pro Leu Arg Pro
                260                 265                 270

Glu Ser Glu Val Leu Ala Glu Glu Ile Pro Ala Ser Val Ser Ser Tyr
                275                 280                 285

Ala Gly Gly Val Pro Pro Thr Leu Asn Glu Gly Leu Glu Leu Leu Asp
                290                 295                 300

Gly Leu Asn Leu Thr Ser Ser His Ser Leu Leu Ser Arg Ser Gly Leu
305                 310                 315                 320

Ser Gly Phe Ser Leu Gln His Pro Gly Val Thr Gly Pro Leu His Thr
                325                 330                 335

Tyr Ser Ser Ser Leu Phe Ser Pro Ala Glu Gly Pro Leu Ser Ala Gly
                340                 345                 350

Glu Gly Cys Phe Ser Ser Ser Gln Ala Leu Glu Ala Leu Leu Thr Ser
                355                 360                 365
```

```
Asp Thr Pro Pro Pro Ala Asp Val Leu Met Thr Gln Val Asp Pro
370                 375                 380

Ile Leu Ser Gln Ala Pro Thr Leu Leu Leu Gly Gly Leu Pro Ser
385                 390                 395                 400

Ser Ser Lys Leu Ala Thr Gly Val Gly Leu Cys Pro Lys Pro Leu Glu
                405                 410                 415

Ala Arg Gly Pro Ser Ser Leu Val Pro Thr Leu Ser Met Ile Ala Pro
                420                 425                 430

Pro Pro Val Met Ala Ser Ala Pro Ile Pro Lys Ala Leu Gly Thr Pro
            435                 440                 445

Val Leu Thr Pro Pro Thr Glu Ala Ala Ser Gln Asp Arg Met Pro Gln
450                 455                 460

Asp Leu Asp Leu Asp Met Tyr Met Glu Asn Leu Glu Cys Asp Met Asp
465                 470                 475                 480

Asn Ile Ile Ser Asp Leu Met Asp Glu Gly Glu Gly Leu Asp Phe Asn
                485                 490                 495

Phe Glu Pro Asp Pro
            500

<210> SEQ ID NO 32
<211> LENGTH: 457
<212> TYPE: PRT
<213> ORGANISM: Homo Sapiens

<400> SEQUENCE: 32

Met Leu Gly Ala Val Lys Met Glu Gly His Glu Pro Ser Asp Trp Ser
1               5                   10                  15

Ser Tyr Tyr Ala Glu Pro Glu Gly Tyr Ser Ser Val Ser Asn Met Asn
                20                  25                  30

Ala Gly Leu Gly Met Asn Gly Met Asn Thr Tyr Met Ser Met Ser Ala
            35                  40                  45

Ala Ala Met Gly Ser Gly Ser Gly Asn Met Ser Ala Gly Ser Met Asn
50                  55                  60

Met Ser Ser Tyr Val Gly Ala Gly Met Ser Pro Ser Leu Ala Gly Met
65                  70                  75                  80

Ser Pro Gly Ala Gly Ala Met Ala Gly Met Gly Gly Ser Ala Gly Ala
                85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
            115                 120                 125

Asn Met Asn Ser Met Ser Pro Met Tyr Gly Gln Ala Gly Leu Ser Arg
130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
            195                 200                 205

His Ser Leu Ser Phe Asn Asp Cys Phe Leu Lys Val Pro Arg Ser Pro
210                 215                 220

Asp Lys Pro Gly Lys Gly Ser Phe Trp Thr Leu His Pro Asp Ser Gly
225                 230                 235                 240
```

```
Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Gly Ser
                260                 265                 270

Gly Lys Lys Ala Ala Gly Ala Gln Ala Ser Gln Ala Gln Leu Gly
                275                 280                 285

Glu Ala Ala Gly Pro Ala Ser Glu Thr Pro Ala Gly Thr Glu Ser Pro
            290                 295                 300

His Ser Ser Ala Ser Pro Cys Gln Glu His Lys Arg Gly Gly Leu Gly
305                 310                 315                 320

Glu Leu Lys Gly Thr Pro Ala Ala Leu Ser Pro Glu Pro Ala
                325                 330                 335

Pro Ser Pro Gly Gln Gln Gln Ala Ala His Leu Leu Gly Pro
                340                 345                 350

Pro His His Pro Gly Leu Pro Pro Glu Ala His Leu Lys Pro Glu His
                355                 360                 365

His Tyr Ala Phe Asn His Pro Phe Ser Ile Asn Asn Leu Met Ser Ser
            370                 375                 380

Glu Gln Gln His His His Ser His His His His Gln Pro His Lys Met
385                 390                 395                 400

Asp Leu Lys Ala Tyr Glu Gln Val Met His Tyr Pro Gly Tyr Gly Ser
                405                 410                 415

Pro Met Pro Gly Ser Leu Ala Met Gly Pro Val Thr Asn Lys Thr Gly
                420                 425                 430

Leu Asp Ala Ser Pro Leu Ala Ala Asp Thr Ser Tyr Tyr Gln Gly Val
                435                 440                 445

Tyr Ser Arg Pro Ile Met Asn Ser Ser
            450                 455

<210> SEQ ID NO 33
<211> LENGTH: 652
<212> TYPE: PRT
<213> ORGANISM: Homo Sapiens

<400> SEQUENCE: 33

Met Ala Glu Ala Pro Gln Val Val Glu Thr Asp Pro Asp Phe Glu Pro
1               5                   10                  15

Leu Pro Arg Gln Arg Ser Cys Thr Trp Pro Leu Pro Arg Pro Glu Phe
                20                  25                  30

Asn Gln Ser Asn Ser Thr Thr Ser Ser Pro Ala Pro Ser Gly Gly Ala
            35                  40                  45

Ala Ala Asn Pro Asp Ala Ala Ala Ser Leu Ala Ser Ala Ser Ala Val
        50                  55                  60

Ser Thr Asp Phe Met Ser Asn Leu Ser Leu Leu Glu Glu Ser Glu Asp
65                  70                  75                  80

Phe Ala Arg Ala Pro Gly Cys Val Ala Val Ala Ala Ala Ala Ala Ala
                85                  90                  95

Ser Arg Gly Leu Cys Gly Asp Phe Gln Gly Pro Glu Ala Gly Cys Val
                100                 105                 110

His Pro Ala Pro Pro Gln Pro Pro Thr Gly Pro Leu Ser Gln Pro
                115                 120                 125

Pro Pro Val Pro Pro Ser Ala Ala Ala Ala Gly Pro Leu Ala Gly
                130                 135                 140

Gln Pro Arg Lys Thr Ser Ser Ser Arg Arg Asn Ala Trp Gly Asn Leu
```

-continued

```
                145                 150                 155                 160
Ser Tyr Ala Asp Leu Ile Thr Lys Ala Ile Glu Ser Ser Ala Glu Lys
                    165                 170                 175
Arg Leu Thr Leu Ser Gln Ile Tyr Glu Trp Met Val Lys Ser Val Pro
                    180                 185                 190
Tyr Phe Lys Asp Lys Gly Asp Ser Asn Ser Ser Ala Gly Trp Lys Asn
                195                 200                 205
Ser Ile Arg His Asn Leu Ser Leu His Ser Lys Phe Ile Arg Val Gln
            210                 215                 220
Asn Glu Gly Thr Gly Lys Ser Ser Trp Trp Met Leu Asn Pro Glu Gly
225                 230                 235                 240
Gly Lys Ser Gly Lys Ser Pro Arg Arg Ala Ala Ser Met Asp Asn
                    245                 250                 255
Asn Ser Lys Phe Ala Lys Ser Arg Gly Arg Ala Ala Lys Lys Lys Ala
                260                 265                 270
Ser Leu Gln Ser Gly Gln Glu Gly Pro Gly Asp Ser Pro Gly Ser Gln
                275                 280                 285
Phe Ser Lys Trp Pro Ala Ser Pro Gly Ser His Ser Asn Asp Asp Phe
            290                 295                 300
Asp Asn Trp Ser Thr Phe Arg Pro Arg Thr Ser Ser Asn Ala Ser Thr
305                 310                 315                 320
Ile Ser Gly Arg Leu Ser Pro Ile Met Thr Glu Gln Asp Asp Leu Gly
                    325                 330                 335
Asp Gly Asp Val His Ser Leu Val Tyr Pro Pro Ser Ala Ala Lys Met
                340                 345                 350
Ala Ser Thr Leu Pro Ser Leu Ser Glu Ile Ser Asn Pro Glu Asn Met
                355                 360                 365
Glu Asn Leu Leu Asp Asn Leu Asn Leu Leu Ser Ser Pro Thr Ser Leu
            370                 375                 380
Thr Val Ser Thr Gln Ser Ser Pro Gly Ser Met Met Gln Gln Thr Pro
385                 390                 395                 400
Cys Tyr Ser Phe Ala Pro Pro Asn Thr Ser Leu Asn Ser Pro Ser Pro
                    405                 410                 415
Asn Tyr Ser Lys Tyr Thr Tyr Gly Gln Ser Ser Met Ser Pro Leu Pro
                420                 425                 430
Gln Met Pro Met Gln Thr Leu Gln Asp Ser Lys Ser Ser Tyr Gly Gly
                435                 440                 445
Leu Asn Gln Tyr Asn Cys Ala Pro Gly Leu Leu Lys Glu Leu Leu Thr
            450                 455                 460
Ser Asp Ser Pro Pro His Asn Asp Ile Met Ser Pro Val Asp Pro Gly
465                 470                 475                 480
Val Ala Gln Pro Asn Ser Arg Val Leu Gly Gln Asn Val Met Met Gly
                    485                 490                 495
Pro Asn Ser Val Met Pro Ala Tyr Gly Ser Gln Ala Ser His Asn Lys
                500                 505                 510
Met Met Asn Pro Ser Ser His Thr His Pro Gly His Ala Gln Gln Thr
            515                 520                 525
Ala Ser Val Asn Gly Arg Thr Leu Pro His Val Val Asn Thr Met Pro
                    530                 535                 540
His Thr Ser Ala Met Asn Arg Leu Thr Pro Val Lys Thr Pro Leu Gln
545                 550                 555                 560
Val Pro Leu Ser His Pro Met Gln Met Ser Ala Leu Gly Ser Tyr Ser
                    565                 570                 575
```

Ser Val Ser Ser Cys Asn Gly Tyr Gly Arg Met Gly Val Leu His Gln
            580                 585                 590

Glu Lys Leu Pro Ser Asp Leu Asp Gly Met Phe Ile Glu Arg Leu Asp
            595                 600                 605

Cys Asp Met Glu Ser Ile Ile Arg Asn Asp Leu Met Asp Gly Asp Thr
610                 615                 620

Leu Asp Phe Asn Phe Asp Asn Val Leu Pro Asn Gln Ser Phe Pro His
625                 630                 635                 640

Ser Val Lys Thr Thr Thr His Ser Trp Val Ser Gly
            645                 650

<210> SEQ ID NO 34
<211> LENGTH: 672
<212> TYPE: PRT
<213> ORGANISM: Mus musculus

<400> SEQUENCE: 34

Met Ala Glu Ala Pro Ala Ser Pro Val Pro Leu Ser Pro Leu Glu Val
1               5                   10                  15

Glu Leu Asp Pro Glu Phe Glu Pro Gln Ser Arg Pro Arg Ser Cys Thr
            20                  25                  30

Trp Pro Leu Gln Arg Pro Glu Leu Gln Ala Ser Pro Ala Lys Pro Ser
        35                  40                  45

Gly Glu Thr Ala Ala Asp Ser Met Ile Pro Glu Asp Asp Asp Glu
    50                  55                  60

Asp Asp Glu Asp Gly Gly Gly Arg Ala Ser Ser Ala Met Val Ile Gly
65                  70                  75                  80

Gly Gly Val Ser Ser Thr Leu Gly Ser Gly Leu Leu Leu Glu Asp Ser
            85                  90                  95

Ala Met Leu Leu Ala Pro Gly Gly Gln Asp Leu Gly Ser Gly Pro Ala
            100                 105                 110

Ser Ala Ala Gly Ala Leu Ser Gly Gly Thr Pro Thr Gln Leu Gln Pro
        115                 120                 125

Gln Gln Pro Leu Pro Gln Pro Gln Pro Gly Ala Ala Gly Gly Ser Gly
130                 135                 140

Gln Pro Arg Lys Cys Ser Ser Arg Arg Asn Ala Trp Gly Asn Leu Ser
145                 150                 155                 160

Tyr Ala Asp Leu Ile Thr Arg Ala Ile Glu Ser Ser Pro Asp Lys Arg
                165                 170                 175

Leu Thr Leu Ser Gln Ile Tyr Glu Trp Met Val Arg Cys Val Pro Tyr
            180                 185                 190

Phe Lys Asp Lys Gly Asp Ser Asn Ser Ser Ala Gly Trp Lys Asn Ser
        195                 200                 205

Ile Arg His Asn Leu Ser Leu His Ser Arg Phe Met Arg Val Gln Asn
    210                 215                 220

Glu Gly Thr Gly Lys Ser Ser Trp Trp Ile Ile Asn Pro Asp Gly Gly
225                 230                 235                 240

Lys Ser Gly Lys Ala Pro Arg Arg Ala Val Ser Met Asp Asn Ser
                245                 250                 255

Asn Lys Tyr Thr Lys Ser Arg Gly Arg Ala Ala Lys Lys Lys Ala Ala
                260                 265                 270

Leu Gln Ala Ala Pro Glu Ser Ala Asp Asp Ser Pro Ser Gln Leu Ser
            275                 280                 285

Lys Trp Pro Gly Ser Pro Thr Ser Arg Ser Ser Asp Glu Leu Asp Ala

```
            290                 295                 300
Trp Thr Asp Phe Arg Ser Arg Thr Asn Ser Asn Ala Ser Thr Val Ser
305                 310                 315                 320

Gly Arg Leu Ser Pro Ile Leu Ala Ser Thr Glu Leu Asp Asp Val Gln
                325                 330                 335

Asp Asp Asp Gly Pro Leu Ser Pro Met Leu Tyr Ser Ser Ser Ala Ser
                340                 345                 350

Leu Ser Pro Ser Val Ser Lys Pro Cys Thr Val Glu Leu Pro Arg Leu
                355                 360                 365

Thr Asp Met Ala Gly Thr Met Asn Leu Asn Asp Gly Leu Ala Glu Asn
            370                 375                 380

Leu Met Asp Asp Leu Leu Asp Asn Ile Ala Leu Pro Pro Ser Gln Pro
385                 390                 395                 400

Ser Pro Pro Gly Gly Leu Met Gln Arg Gly Ser Ser Phe Pro Tyr Thr
                405                 410                 415

Ala Lys Ser Ser Gly Leu Gly Ser Pro Thr Gly Ser Phe Asn Ser Thr
                420                 425                 430

Val Phe Gly Pro Ser Ser Leu Asn Ser Leu Arg Gln Ser Pro Met Gln
                435                 440                 445

Thr Ile Gln Glu Asn Arg Pro Ala Thr Phe Ser Ser Val Ser His Tyr
            450                 455                 460

Gly Asn Gln Thr Leu Gln Asp Leu Leu Ala Ser Asp Ser Leu Ser His
465                 470                 475                 480

Ser Asp Val Met Met Thr Gln Ser Asp Pro Leu Met Ser Gln Ala Ser
                485                 490                 495

Thr Ala Val Ser Ala Gln Asn Ala Arg Arg Asn Val Met Leu Arg Asn
                500                 505                 510

Asp Pro Met Met Ser Phe Ala Ala Gln Pro Thr Gln Gly Ser Leu Val
            515                 520                 525

Asn Gln Asn Leu Leu His His Gln His Gln Thr Gln Gly Ala Leu Gly
            530                 535                 540

Gly Ser Arg Ala Leu Ser Asn Ser Val Ser Asn Met Gly Leu Ser Asp
545                 550                 555                 560

Ser Ser Ser Leu Gly Ser Ala Lys His Gln Gln Ser Pro Ala Ser
                565                 570                 575

Gln Ser Met Gln Thr Leu Ser Asp Ser Leu Ser Gly Ser Ser Leu Tyr
                580                 585                 590

Ser Ala Ser Ala Asn Leu Pro Val Met Gly His Asp Lys Phe Pro Ser
            595                 600                 605

Asp Leu Asp Leu Asp Met Phe Asn Gly Ser Leu Glu Cys Asp Met Glu
            610                 615                 620

Ser Ile Ile Arg Ser Glu Leu Met Asp Ala Asp Gly Leu Asp Phe Asn
625                 630                 635                 640

Phe Asp Ser Leu Ile Ser Thr Gln Asn Val Val Gly Leu Asn Val Gly
                645                 650                 655

Asn Phe Thr Gly Ala Lys Gln Ala Ser Ser Gln Ser Trp Val Pro Gly
                660                 665                 670

<210> SEQ ID NO 35
<211> LENGTH: 676
<212> TYPE: PRT
<213> ORGANISM: Homo Sapiens

<400> SEQUENCE: 35
```

-continued

```
Met Ser Gly Gly Gly Asp Val Val Cys Thr Gly Trp Leu Arg Lys Ser
1               5                   10                  15

Pro Pro Glu Lys Lys Leu Arg Arg Tyr Ala Trp Lys Lys Arg Trp Phe
            20                  25                  30

Ile Leu Arg Ser Gly Arg Met Ser Gly Asp Pro Asp Val Leu Glu Tyr
                35                  40                  45

Tyr Lys Asn Asp His Ser Lys Lys Pro Leu Arg Ile Ile Asn Leu Asn
    50                  55                  60

Phe Cys Glu Gln Val Asp Ala Gly Leu Thr Phe Asn Lys Lys Glu Leu
65                  70                  75                  80

Gln Asp Ser Phe Val Phe Asp Ile Lys Thr Ser Glu Arg Thr Phe Tyr
                85                  90                  95

Leu Val Ala Glu Thr Glu Asp Met Asn Lys Trp Val Gln Ser Ile
                100                 105                 110

Cys Gln Ile Cys Gly Phe Asn Gln Ala Glu Glu Ser Thr Asp Ser Leu
            115                 120                 125

Arg Asn Val Ser Ser Ala Gly His Gly Pro Arg Ser Ser Pro Ala Glu
    130                 135                 140

Leu Ser Ser Ser Gln His Leu Leu Arg Glu Arg Lys Ser Ser Ala
145                 150                 155                 160

Pro Ser His Ser Ser Gln Pro Thr Leu Phe Thr Phe Glu Pro Pro Val
                165                 170                 175

Ser Asn His Met Gln Pro Thr Leu Ser Thr Ser Ala Pro Gln Glu Tyr
                180                 185                 190

Leu Tyr Leu His Gln Cys Ile Ser Arg Arg Ala Glu Asn Ala Arg Ser
                195                 200                 205

Ala Ser Phe Ser Gln Gly Thr Arg Ala Ser Phe Leu Met Arg Ser Asp
    210                 215                 220

Thr Ala Val Gln Lys Leu Ala Gln Gly Asn Gly His Cys Val Asn Gly
225                 230                 235                 240

Ile Ser Gly Gln Val His Gly Phe Tyr Ser Leu Pro Lys Pro Ser Arg
                245                 250                 255

His Asn Thr Glu Phe Arg Asp Ser Thr Tyr Asp Leu Pro Arg Ser Leu
                260                 265                 270

Ala Ser His Gly His Thr Lys Gly Ser Leu Thr Gly Ser Glu Thr Asp
                275                 280                 285

Asn Glu Asp Val Tyr Thr Phe Lys Thr Pro Ser Asn Thr Leu Cys Arg
                290                 295                 300

Glu Phe Gly Asp Leu Leu Val Asp Asn Met Asp Val Pro Ala Thr Pro
305                 310                 315                 320

Leu Ser Ala Tyr Gln Ile Pro Arg Thr Phe Thr Leu Asp Lys Asn His
                325                 330                 335

Asn Ala Met Thr Val Ala Thr Pro Gly Asp Ser Ala Ile Ala Pro Pro
                340                 345                 350

Pro Arg Pro Pro Lys Pro Ser Gln Ala Glu Thr Pro Trp Gly Ser
                355                 360                 365

Pro Gln Gln Arg Pro Pro Ile Ser Glu Asn Ser Arg Ser Val Ala Ala
    370                 375                 380

Thr Ile Pro Arg Arg Asn Thr Leu Pro Ala Met Asp Asn Ser Arg Leu
385                 390                 395                 400

His Arg Ala Ser Ser Cys Glu Thr Tyr Glu Tyr Pro Gln Arg Gly Gly
                405                 410                 415

Glu Ser Ala Gly Arg Ser Ala Glu Ser Met Ser Asp Gly Val Gly Ser
```

```
                    420                 425                 430
Phe Leu Pro Gly Lys Met Ile Val Gly Arg Ser Asp Ser Thr Asn Ser
            435                 440                 445

Glu Asp Asn Tyr Val Pro Met Asn Pro Gly Ser Ser Thr Leu Leu Ala
450                 455                 460

Met Glu Arg Ala Gly Asp Asn Ser Gln Ser Val Tyr Ile Pro Met Ser
465                 470                 475                 480

Pro Gly Ala His His Phe Asp Ser Leu Gly Tyr Pro Ser Thr Thr Leu
                485                 490                 495

Pro Val His Arg Gly Pro Ser Arg Gly Ser Glu Ile Gln Pro Pro Pro
            500                 505                 510

Val Asn Arg Asn Leu Lys Pro Asp Arg Lys Ala Lys Pro Thr Pro Leu
            515                 520                 525

Asp Leu Arg Asn Asn Thr Val Ile Asp Glu Leu Pro Phe Lys Ser Pro
            530                 535                 540

Ile Thr Lys Ser Trp Ser Arg Ala Asn His Thr Phe Asn Ser Ser Ser
545                 550                 555                 560

Ser Gln Tyr Cys Arg Pro Ile Ser Thr Gln Ser Ile Thr Ser Thr Asp
                565                 570                 575

Ser Gly Asp Ser Glu Glu Asn Tyr Val Pro Met Gln Asn Pro Val Ser
            580                 585                 590

Ala Ser Pro Val Pro Ser Gly Thr Asn Ser Pro Ala Pro Lys Lys Ser
            595                 600                 605

Thr Gly Ser Val Asp Tyr Leu Ala Leu Asp Phe Gln Pro Ser Ser Pro
            610                 615                 620

Ser Pro His Arg Lys Pro Ser Thr Ser Ser Val Thr Ser Asp Glu Lys
625                 630                 635                 640

Val Asp Tyr Val Gln Val Asp Lys Glu Lys Thr Gln Ala Leu Gln Asn
                645                 650                 655

Thr Met Gln Glu Trp Thr Asp Val Arg Gln Ser Ser Glu Pro Ser Lys
            660                 665                 670

Gly Ala Lys Leu
        675

<210> SEQ ID NO 36
<211> LENGTH: 665
<212> TYPE: PRT
<213> ORGANISM: Mus musculus

<400> SEQUENCE: 36

Met Ser Gly Gly Gly Asp Asp Val Val Cys Thr Gly Trp Leu Arg
1               5                   10                  15

Lys Ser Pro Pro Glu Lys Lys Leu Arg Arg Tyr Ala Trp Lys Lys Arg
                20                  25                  30

Trp Phe Ile Leu Arg Ser Gly Arg Met Ser Gly Asp Pro Asp Val Leu
            35                  40                  45

Glu Tyr Tyr Lys Asn Glu His Ser Lys Lys Pro Leu Arg Ile Ile Asn
        50                  55                  60

Leu Asn Leu Cys Glu Gln Val Asp Ala Gly Leu Thr Phe Asn Lys Lys
65                  70                  75                  80

Glu Leu Gln Asp Ser Phe Val Phe Asp Ile Lys Thr Ser Glu Arg Thr
                85                  90                  95

Phe Tyr Leu Val Ala Glu Thr Glu Ala Asp Met Asn Lys Trp Val Gln
            100                 105                 110
```

```
Ser Ile Cys Gln Ile Cys Gly Phe Asn Gln Ala Glu Glu Ser Thr Asp
        115                 120                 125

Ser Leu Arg Asn Leu Ser Ser Ala Ser His Gly Pro Arg Ser Ser Pro
130                 135                 140

Ala Glu Phe Ser Ser Ser Gln His Leu Leu Arg Glu Arg Lys Ser Ser
145                 150                 155                 160

Ala Pro Ser His Ser Ser Gln Pro Thr Leu Phe Thr Phe Glu Pro Pro
                165                 170                 175

Val Ser Ser His Met Gln Pro Thr Leu Ser Thr Ser Ala Pro Gln Glu
            180                 185                 190

Tyr Leu Tyr Leu His Gln Cys Ile Ser Arg Arg Thr Glu Asn Ala Arg
        195                 200                 205

Ser Ala Ser Phe Ser Gln Gly Thr Arg Gln Lys Ser Asp Thr Ala Val
210                 215                 220

Gln Lys Leu Ala Gln Ser Asn Gly His Cys Ile Asn Gly Val Gly Gly
225                 230                 235                 240

Gln Val His Gly Phe Tyr Ser Leu Pro Lys Pro Ser Arg His Asn Thr
                245                 250                 255

Glu Phe Lys Asp Ser Thr Tyr Asp Leu Pro Arg Ser Leu Ala Ser His
            260                 265                 270

Gly His Thr Lys Ser Ser Leu Thr Gly Ser Glu Thr Asp Asn Glu Asp
        275                 280                 285

Val Tyr Thr Phe Lys Met Pro Ser Asn Thr Leu Cys Arg Glu Leu Gly
        290                 295                 300

Asp Leu Leu Val Asp Asn Met Asp Val Pro Thr Thr Pro Leu Ser Ala
305                 310                 315                 320

Tyr Gln Ile Pro Arg Thr Phe Thr Leu Asp Lys Asn His Asn Ala Met
                325                 330                 335

Thr Val Ala Thr Pro Gly Asp Ser Ala Ile Ala Pro Pro Pro Arg Pro
            340                 345                 350

Pro Lys Pro Ser Gln Ala Glu Thr Ser Gln Trp Gly Ser Ile Gln Gln
        355                 360                 365

Arg Pro Pro Ile Ser Glu Asn Ser Arg Ser Val Ala Ala Thr Ile Pro
370                 375                 380

Arg Arg Asn Thr Leu Pro Ala Met Asp Asn Ser Arg Leu His Arg Ala
385                 390                 395                 400

Ser Ser Cys Glu Thr Tyr Glu Tyr Pro Ala Arg Gly Ser Gly Glu Ser
                405                 410                 415

Ala Ser Trp Ser Ala Glu Pro Pro Gly Lys Thr Ala Val Gly Arg Ser
            420                 425                 430

Asn Ser Ala Ser Ser Asp Asp Asn Tyr Val Pro Met Asn Pro Gly Ser
        435                 440                 445

Ser Thr Leu Leu Ala Met Glu Arg Pro Gly Asp Asn Ser Gln Ser Val
        450                 455                 460

Tyr Ile Pro Met Ser Pro Gly Pro His His Phe Asp Pro Leu Gly Tyr
465                 470                 475                 480

Pro Ser Thr Ala Leu Pro Ile His Arg Gly Pro Ser Arg Gly Ser Glu
                485                 490                 495

Ile Gln Pro Pro Val Asn Arg Asn Leu Lys Pro Asp Arg Lys Ala
            500                 505                 510

Lys Pro Thr Pro Leu Asp Leu Arg Asn Asn Thr Val Ile Asp Glu Leu
        515                 520                 525

Pro Phe Lys Ser Pro Val Thr Lys Ser Trp Ser Arg Ile Asn His Thr
```

```
                530                 535                 540
Phe Asn Ser Ser Ser Gln Tyr Cys Arg Pro Ile Ser Thr Gln Ser
545                 550                 555                 560

Ile Thr Ser Thr Asp Ser Gly Asp Ser Glu Glu Asn Tyr Val Pro Met
                565                 570                 575

Gln Asn Pro Val Ser Ala Ser Pro Val Pro Ser Gly Thr Asn Ser Pro
                580                 585                 590

Ala Pro Lys Lys Ser Thr Gly Ser Val Asp Tyr Leu Ala Leu Asp Phe
                595                 600                 605

Gln Pro Gly Ser Pro Ser Pro His Arg Lys Pro Ser Thr Ser Ser Val
                610                 615                 620

Thr Ser Asp Glu Lys Val Asp Tyr Val Gln Val Asp Lys Glu Lys Thr
625                 630                 635                 640

Gln Ala Leu Gln Asn Thr Met Gln Glu Trp Thr Asp Val Arg Gln Ser
                645                 650                 655

Ser Glu Pro Ser Lys Gly Ala Lys Leu
                660                 665
```

<210> SEQ ID NO 37
<211> LENGTH: 474
<212> TYPE: PRT
<213> ORGANISM: Homo Sapiens

<400> SEQUENCE: 37

```
Met Trp Arg Val Arg Lys Arg Gly Tyr Phe Gly Ile Trp Ser Phe Pro
1               5                   10                  15

Leu Ile Ile Ala Ala Val Cys Ala Gln Ser Val Asn Asp Pro Ser Asn
                20                  25                  30

Met Ser Leu Val Lys Glu Thr Val Asp Arg Leu Leu Lys Gly Tyr Asp
                35                  40                  45

Ile Arg Leu Arg Pro Asp Phe Gly Gly Pro Pro Val Ala Val Gly Met
                50                  55                  60

Asn Ile Asp Ile Ala Ser Ile Asp Met Val Ser Glu Val Asn Met Asp
65                  70                  75                  80

Tyr Thr Leu Thr Met Tyr Phe Gln Gln Ala Trp Arg Asp Lys Arg Leu
                85                  90                  95

Ser Tyr Asn Val Ile Pro Leu Asn Leu Thr Leu Asp Asn Arg Val Ala
                100                 105                 110

Asp Gln Leu Trp Val Pro Asp Thr Tyr Phe Leu Asn Asp Lys Lys Ser
                115                 120                 125

Phe Val His Gly Val Thr Val Lys Asn Arg Met Ile Arg Leu His Pro
                130                 135                 140

Asp Gly Thr Val Leu Tyr Gly Leu Arg Ile Thr Thr Thr Ala Ala Cys
145                 150                 155                 160

Met Met Asp Leu Arg Arg Tyr Pro Leu Asp Glu Gln Asn Cys Thr Leu
                165                 170                 175

Glu Ile Glu Ser Tyr Gly Tyr Thr Thr Asp Asp Ile Glu Phe Tyr Trp
                180                 185                 190

Arg Gly Asp Asp Asn Ala Val Thr Gly Val Thr Lys Ile Glu Leu Pro
                195                 200                 205

Gln Phe Ser Ile Val Asp Tyr Lys Leu Ile Thr Lys Lys Val Val Phe
                210                 215                 220

Ser Thr Gly Ser Tyr Pro Arg Leu Ser Leu Ser Phe Lys Leu Lys Arg
225                 230                 235                 240
```

```
Asn Ile Gly Tyr Phe Ile Leu Gln Thr Tyr Met Pro Ser Ile Leu Ile
                245                 250                 255

Thr Ile Leu Ser Trp Val Ser Phe Trp Ile Asn Tyr Asp Ala Ser Ala
            260                 265                 270

Ala Arg Val Ala Leu Gly Ile Thr Thr Val Leu Thr Met Thr Thr Ile
        275                 280                 285

Asn Thr His Leu Arg Glu Thr Leu Pro Lys Ile Pro Tyr Val Lys Ala
290                 295                 300

Ile Asp Met Tyr Leu Met Gly Cys Phe Val Phe Val Phe Met Ala Leu
305                 310                 315                 320

Leu Glu Tyr Ala Leu Val Asn Tyr Ile Phe Phe Gly Arg Gly Pro Gln
                325                 330                 335

Arg Gln Lys Lys Ala Ala Glu Lys Ala Ala Ser Ala Asn Asn Glu Lys
            340                 345                 350

Met Arg Leu Asp Val Asn Lys Met Asp Pro His Glu Asn Ile Leu Leu
        355                 360                 365

Ser Thr Leu Glu Ile Lys Asn Glu Met Ala Thr Ser Glu Ala Val Met
370                 375                 380

Gly Leu Gly Asp Pro Arg Ser Thr Met Leu Ala Tyr Asp Ala Ser Ser
385                 390                 395                 400

Ile Gln Tyr Arg Lys Ala Gly Leu Pro Arg His Ser Phe Gly Arg Asn
                405                 410                 415

Ala Leu Glu Arg His Val Ala Gln Lys Lys Ser Arg Leu Arg Arg Arg
            420                 425                 430

Ala Ser Gln Leu Lys Ile Thr Ile Pro Asp Leu Thr Asp Val Asn Ala
        435                 440                 445

Ile Asp Arg Trp Ser Arg Ile Phe Phe Pro Val Val Phe Ser Phe Phe
450                 455                 460

Asn Ile Val Tyr Trp Leu Tyr Tyr Val Asn
465                 470

<210> SEQ ID NO 38
<211> LENGTH: 490
<212> TYPE: PRT
<213> ORGANISM: Mus musculus

<400> SEQUENCE: 38

Met Ser Gly Gly Pro Ser Gly Gly Pro Gly Gly Ser Gly Arg
1               5                   10                  15

Ala Arg Thr Ser Ser Phe Ala Glu Pro Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Ser Gly Ser Gly Gly Gly Ser Gly Gly Pro
65                  70                  75                  80

Gly Ala Gly Thr Ser Phe Pro Pro Gly Val Lys Leu Gly Arg Asp
                85                  90                  95

Ser Gly Lys Val Thr Thr Val Ala Thr Val Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
130                 135                 140
```

Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
            165                 170                 175

Tyr Phe Phe Tyr Ser Ser Gly Glu Lys Lys Asp Glu Leu Tyr Leu Asn
            180                 185                 190

Leu Val Leu Glu Tyr Val Pro Glu Thr Val Tyr Arg Val Ala Arg His
            195                 200                 205

Phe Thr Lys Ala Lys Leu Ile Thr Pro Ile Ile Tyr Ile Lys Val Tyr
            210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
            245                 250                 255

Ala Val Leu Lys Leu Cys Asp Phe Gly Ser Ala Lys Gln Leu Val Arg
            260                 265                 270

Gly Glu Pro Asn Val Ser Tyr Ile Cys Ser Arg Tyr Tyr Arg Ala Pro
            275                 280                 285

Glu Leu Ile Phe Gly Ala Thr Asp Tyr Thr Ser Ser Ile Asp Val Trp
            290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
            325                 330                 335

Gly Thr Pro Thr Arg Glu Gln Ile Arg Glu Met Asn Pro Asn Tyr Thr
            340                 345                 350

Glu Phe Lys Phe Pro Gln Ile Lys Ala His Pro Trp Thr Lys Val Phe
            355                 360                 365

Lys Ser Ser Lys Thr Pro Pro Glu Ala Ile Ala Leu Cys Ser Ser Leu
370                 375                 380

Leu Glu Tyr Thr Pro Ser Ser Arg Leu Ser Pro Leu Glu Ala Cys Ala
385                 390                 395                 400

His Ser Phe Phe Asp Glu Leu Arg Arg Leu Gly Ala Gln Leu Pro Asn
            405                 410                 415

Asp Arg Pro Leu Pro Pro Leu Phe Asn Phe Ser Pro Gly Glu Leu Ser
            420                 425                 430

Ile Gln Pro Ser Leu Asn Ala Ile Leu Ile Pro Pro His Leu Arg Ser
            435                 440                 445

Pro Ala Gly Pro Ala Ser Pro Leu Thr Thr Ser Tyr Asn Pro Ser Ser
450                 455                 460

Gln Ala Leu Thr Glu Ala Gln Thr Gly Gln Asp Trp Gln Pro Ser Asp
465                 470                 475                 480

Ala Thr Thr Ala Thr Leu Ala Ser Ser Ser
            485                 490

<210> SEQ ID NO 39
<211> LENGTH: 483
<212> TYPE: PRT
<213> ORGANISM: Homo Sapiens

<400> SEQUENCE: 39

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly

-continued

```
             20                  25                  30
Gly Gly Gly Pro Gly Gly Ser Ala Ser Gly Pro Gly Gly Thr Gly Gly
             35                  40                  45
Gly Lys Ala Ser Val Gly Ala Met Gly Gly Val Gly Ala Ser Ser
 50                  55                  60
Ser Gly Gly Gly Pro Gly Gly Ser Gly Gly Gly Ser Gly Gly Pro
 65                  70                  75                  80
Gly Ala Gly Thr Ser Phe Pro Pro Gly Val Lys Leu Gly Arg Asp
                     85                  90                  95
Ser Gly Lys Val Thr Val Val Ala Thr Leu Gly Gln Gly Pro Glu
                100                 105                 110
Arg Ser Gln Glu Val Ala Tyr Thr Asp Ile Lys Val Ile Gly Asn Gly
                115                 120                 125
Ser Phe Gly Val Val Tyr Gln Ala Arg Leu Ala Glu Thr Arg Glu Leu
                130                 135                 140
Val Ala Ile Lys Lys Val Leu Gln Asp Lys Arg Phe Lys Asn Arg Glu
145                 150                 155                 160
Leu Gln Ile Met Arg Lys Leu Asp His Cys Asn Ile Val Arg Leu Arg
                165                 170                 175
Tyr Phe Phe Tyr Ser Ser Gly Glu Lys Lys Asp Glu Leu Tyr Leu Asn
                180                 185                 190
Leu Val Leu Glu Tyr Val Pro Glu Thr Val Tyr Arg Val Ala Arg His
                195                 200                 205
Phe Thr Lys Ala Lys Leu Thr Ile Pro Ile Leu Tyr Val Lys Val Tyr
                210                 215                 220
Met Tyr Gln Leu Phe Arg Ser Leu Ala Tyr Ile His Ser Gln Gly Val
225                 230                 235                 240
Cys His Arg Asp Ile Lys Pro Gln Asn Leu Leu Val Asp Pro Asp Thr
                245                 250                 255
Ala Val Leu Lys Leu Cys Asp Phe Gly Ser Ala Lys Gln Leu Val Arg
                260                 265                 270
Gly Glu Pro Asn Val Ser Tyr Ile Cys Ser Arg Tyr Tyr Arg Ala Pro
                275                 280                 285
Glu Leu Ile Phe Gly Ala Thr Asp Tyr Thr Ser Ser Ile Asp Val Trp
                290                 295                 300
Ser Ala Gly Cys Val Leu Ala Glu Leu Leu Gly Gln Pro Ile Phe
305                 310                 315                 320
Pro Gly Asp Ser Gly Val Asp Gln Leu Val Glu Ile Ile Lys Val Leu
                325                 330                 335
Gly Thr Pro Thr Arg Glu Gln Ile Arg Glu Met Asn Pro Asn Tyr Thr
                340                 345                 350
Glu Phe Lys Phe Pro Gln Ile Lys Ala His Pro Trp Thr Lys Val Phe
                355                 360                 365
Lys Ser Arg Thr Pro Pro Glu Ala Ile Ala Leu Cys Ser Ser Leu Leu
                370                 375                 380
Glu Tyr Thr Pro Ser Ser Arg Leu Ser Pro Leu Glu Ala Cys Ala His
385                 390                 395                 400
Ser Phe Phe Asp Glu Leu Arg Cys Leu Gly Thr Gln Leu Pro Asn Asn
                405                 410                 415
Arg Pro Leu Pro Pro Leu Phe Asn Phe Ser Ala Gly Glu Leu Ser Ile
                420                 425                 430
Gln Pro Ser Leu Asn Ala Ile Leu Ile Pro Pro His Leu Arg Ser Pro
                435                 440                 445
```

Ser Gly Thr Thr Thr Leu Thr Pro Ser Ser Gln Ala Leu Thr Glu Thr
            450                 455                 460

Pro Thr Ser Ser Asp Trp Gln Ser Thr Asp Ala Thr Pro Thr Leu Thr
465                 470                 475                 480

Asn Ser Ser

<210> SEQ ID NO 40
<211> LENGTH: 433
<212> TYPE: PRT
<213> ORGANISM: Homo Sapiens

<400> SEQUENCE: 40

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270

Leu Gly Thr Pro Thr Arg Glu Gln Ile Arg Glu Met Asn Pro Asn Tyr
        275                 280                 285

Thr Glu Phe Lys Phe Pro Gln Ile Lys Ala His Pro Trp Thr Lys Asp
    290                 295                 300

Ser Ser Gly Thr Gly His Phe Thr Ser Gly Val Arg Val Phe Arg Pro
305                 310                 315                 320

Arg Thr Pro Pro Glu Ala Ile Ala Leu Cys Ser Arg Leu Leu Glu Tyr
                325                 330                 335

```
Thr Pro Thr Ala Arg Leu Thr Pro Leu Glu Ala Cys Ala His Ser Phe
            340                 345                 350

Phe Asp Glu Leu Arg Asp Pro Asn Val Lys Leu Pro Asn Gly Arg Asp
            355                 360                 365

Thr Pro Ala Leu Phe Asn Phe Thr Thr Gln Glu Leu Ser Ser Asn Pro
        370                 375                 380

Pro Leu Ala Thr Ile Leu Ile Pro Pro His Ala Arg Ile Gln Ala Ala
385                 390                 395                 400

Ala Ser Thr Pro Thr Asn Ala Thr Ala Ala Ser Asp Ala Asn Thr Gly
                405                 410                 415

Asp Arg Gly Gln Thr Asn Asn Ala Ala Ser Ala Ser Ala Ser Asn Ser
            420                 425                 430

Thr

<210> SEQ ID NO 41
<211> LENGTH: 420
<212> TYPE: PRT
<213> ORGANISM: Mus musculus

<400> SEQUENCE: 41

Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140

His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
    210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
            260                 265                 270
```

-continued

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Val
        290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
            340                 345                 350

Gly Arg Asp Thr Pro Ala Leu Phe Asn Phe Thr Thr Gln Glu Leu Ser
        355                 360                 365

Ser Asn Pro Pro Leu Ala Thr Ile Leu Ile Pro Pro His Ala Arg Ile
370                 375                 380

Gln Ala Ala Ser Pro Pro Ala Asn Ala Thr Ala Ala Ser Asp Thr
385                 390                 395                 400

Asn Ala Gly Asp Arg Gly Gln Thr Asn Asn Ala Ala Ser Ala Ser Ala
                405                 410                 415

Ser Asn Ser Thr
            420

<210> SEQ ID NO 42
<211> LENGTH: 138
<212> TYPE: PRT
<213> ORGANISM: Mus musculus

<400> SEQUENCE: 42

Met Pro Glu Pro Val Lys Ser Val Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

Ser Arg Lys Glu Ser Tyr Ser Val Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Ser Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
            100                 105                 110

Ser Glu Gly Thr Lys Ala Val Thr Lys Tyr Thr Ser Ser Lys Ile Leu
        115                 120                 125

Trp Asn Lys Phe Tyr Tyr Leu Pro Ser Phe
    130                 135

<210> SEQ ID NO 43
<211> LENGTH: 126
<212> TYPE: PRT
<213> ORGANISM: Homo Sapiens

<400> SEQUENCE: 43

Met Pro Asp Pro Ala Lys Ser Ala Pro Ala Pro Lys Lys Gly Ser Lys
1               5                   10                  15

Lys Ala Val Thr Lys Ala Gln Lys Lys Asp Gly Lys Lys Arg Lys Arg
            20                  25                  30

```
Ser Arg Lys Glu Ser Tyr Ser Ile Tyr Val Tyr Lys Val Leu Lys Gln
        35                  40                  45

Val His Pro Asp Thr Gly Ile Ser Ser Lys Ala Met Gly Ile Met Asn
    50                  55                  60

Ser Phe Val Asn Asp Ile Phe Glu Arg Ile Ala Gly Glu Ala Ser Arg
65                  70                  75                  80

Leu Ala His Tyr Asn Lys Arg Ser Thr Ile Thr Ser Arg Glu Ile Gln
                85                  90                  95

Thr Ala Val Arg Leu Leu Leu Pro Gly Glu Leu Ala Lys His Ala Val
                100                 105                 110

Ser Glu Gly Thr Lys Ala Val Thr Lys Tyr Thr Ser Ser Lys
                115                 120                 125

<210> SEQ ID NO 44
<211> LENGTH: 3144
<212> TYPE: PRT
<213> ORGANISM: Homo Sapiens

<400> SEQUENCE: 44

Met Ala Thr Leu Glu Lys Leu Met Lys Ala Phe Glu Ser Leu Lys Ser
1               5                   10                  15

Phe Gln Gln Gln Gln Gln Gln Gln Gln Gln Gln Gln Gln Gln Gln Gln
                20                  25                  30

Gln Gln Gln Gln Gln Gln Gln Pro Pro Pro Pro Pro Pro Pro Pro Pro
                35                  40                  45

Pro Pro Pro Gln Leu Pro Gln Pro Pro Pro Gln Ala Gln Pro Leu Leu
        50                  55                  60

Pro Gln Pro Gln Pro Pro Pro Pro Pro Pro Pro Pro Gly Pro
65                  70                  75                  80

Ala Val Ala Glu Glu Pro Leu His Arg Pro Lys Lys Glu Leu Ser Ala
                85                  90                  95

Thr Lys Lys Asp Arg Val Asn His Cys Leu Thr Ile Cys Glu Asn Ile
                100                 105                 110

Val Ala Gln Ser Val Arg Asn Ser Pro Glu Phe Gln Lys Leu Leu Gly
                115                 120                 125

Ile Ala Met Glu Leu Phe Leu Leu Cys Ser Asp Asp Ala Glu Ser Asp
                130                 135                 140

Val Arg Met Val Ala Asp Glu Cys Leu Asn Lys Val Ile Lys Ala Leu
145                 150                 155                 160

Met Asp Ser Asn Leu Pro Arg Leu Gln Leu Glu Leu Tyr Lys Glu Ile
                165                 170                 175

Lys Lys Asn Gly Ala Pro Arg Ser Leu Arg Ala Ala Leu Trp Arg Phe
                180                 185                 190

Ala Glu Leu Ala His Leu Val Arg Pro Gln Lys Cys Arg Pro Tyr Leu
                195                 200                 205

Val Asn Leu Leu Pro Cys Leu Thr Arg Thr Ser Lys Arg Pro Glu Glu
            210                 215                 220

Ser Val Gln Glu Thr Leu Ala Ala Ala Val Pro Lys Ile Met Ala Ser
225                 230                 235                 240

Phe Gly Asn Phe Ala Asn Asp Asn Glu Ile Lys Val Leu Leu Lys Ala
                245                 250                 255

Phe Ile Ala Asn Leu Lys Ser Ser Ser Pro Thr Ile Arg Arg Thr Ala
                260                 265                 270

Ala Gly Ser Ala Val Ser Ile Cys Gln His Ser Arg Arg Thr Gln Tyr
```

-continued

```
            275                 280                 285
Phe Tyr Ser Trp Leu Leu Asn Val Leu Leu Gly Leu Val Pro Val
290                 295                 300
Glu Asp Glu His Ser Thr Leu Leu Ile Leu Gly Val Leu Leu Thr Leu
305                 310                 315                 320
Arg Tyr Leu Val Pro Leu Leu Gln Gln Val Lys Asp Thr Ser Leu
                325                 330                 335
Lys Gly Ser Phe Gly Val Thr Arg Lys Glu Met Glu Val Ser Pro Ser
                340                 345                 350
Ala Glu Gln Leu Val Gln Val Tyr Glu Leu Thr Leu His His Thr Gln
                355                 360                 365
His Gln Asp His Asn Val Val Thr Gly Ala Leu Glu Leu Leu Gln Gln
370                 375                 380
Leu Phe Arg Thr Pro Pro Glu Leu Leu Gln Thr Leu Thr Ala Val
385                 390                 395                 400
Gly Gly Ile Gly Gln Leu Thr Ala Ala Lys Glu Glu Ser Gly Gly Arg
                405                 410                 415
Ser Arg Ser Gly Ser Ile Val Glu Leu Ile Ala Gly Gly Ser Ser
                420                 425                 430
Cys Ser Pro Val Leu Ser Arg Lys Gln Lys Gly Lys Val Leu Leu Gly
                435                 440                 445
Glu Glu Glu Ala Leu Glu Asp Asp Ser Glu Ser Arg Ser Asp Val Ser
450                 455                 460
Ser Ser Ala Leu Thr Ala Ser Val Lys Asp Glu Ile Ser Gly Glu Leu
465                 470                 475                 480
Ala Ala Ser Ser Gly Val Ser Thr Pro Gly Ser Ala Gly His Asp Ile
                485                 490                 495
Ile Thr Glu Gln Pro Arg Ser Gln His Thr Leu Gln Ala Asp Ser Val
                500                 505                 510
Asp Leu Ala Ser Cys Asp Leu Thr Ser Ser Ala Thr Asp Gly Asp Glu
                515                 520                 525
Glu Asp Ile Leu Ser His Ser Ser Ser Gln Val Ser Ala Val Pro Ser
530                 535                 540
Asp Pro Ala Met Asp Leu Asn Asp Gly Thr Gln Ala Ser Ser Pro Ile
545                 550                 555                 560
Ser Asp Ser Ser Gln Thr Thr Thr Glu Gly Pro Asp Ser Ala Val Thr
                565                 570                 575
Pro Ser Asp Ser Ser Glu Ile Val Leu Asp Gly Thr Asp Asn Gln Tyr
                580                 585                 590
Leu Gly Leu Gln Ile Gly Gln Pro Gln Asp Glu Asp Glu Glu Ala Thr
                595                 600                 605
Gly Ile Leu Pro Asp Glu Ala Ser Glu Ala Phe Arg Asn Ser Ser Met
                610                 615                 620
Ala Leu Gln Gln Ala His Leu Leu Lys Asn Met Ser His Cys Arg Gln
625                 630                 635                 640
Pro Ser Asp Ser Ser Val Asp Lys Phe Val Leu Arg Asp Glu Ala Thr
                645                 650                 655
Glu Pro Gly Asp Gln Glu Asn Lys Pro Cys Arg Ile Lys Gly Asp Ile
                660                 665                 670
Gly Gln Ser Thr Asp Asp Ser Ala Pro Leu Val His Cys Val Arg
                675                 680                 685
Leu Leu Ser Ala Ser Phe Leu Leu Thr Gly Gly Lys Asn Val Leu Val
                690                 695                 700
```

```
Pro Asp Arg Asp Val Arg Val Ser Val Lys Ala Leu Ala Leu Ser Cys
705                 710                 715                 720

Val Gly Ala Ala Val Ala Leu His Pro Glu Ser Phe Phe Ser Lys Leu
            725                 730                 735

Tyr Lys Val Pro Leu Asp Thr Thr Glu Tyr Pro Glu Glu Gln Tyr Val
        740                 745                 750

Ser Asp Ile Leu Asn Tyr Ile Asp His Gly Asp Pro Gln Val Arg Gly
    755                 760                 765

Ala Thr Ala Ile Leu Cys Gly Thr Leu Ile Cys Ser Ile Leu Ser Arg
770                 775                 780

Ser Arg Phe His Val Gly Asp Trp Met Gly Thr Ile Arg Thr Leu Thr
785                 790                 795                 800

Gly Asn Thr Phe Ser Leu Ala Asp Cys Ile Pro Leu Leu Arg Lys Thr
            805                 810                 815

Leu Lys Asp Glu Ser Ser Val Thr Cys Lys Leu Ala Cys Thr Ala Val
        820                 825                 830

Arg Asn Cys Val Met Ser Leu Cys Ser Ser Tyr Ser Glu Leu Gly
    835                 840                 845

Leu Gln Leu Ile Ile Asp Val Leu Thr Leu Arg Asn Ser Ser Tyr Trp
850                 855                 860

Leu Val Arg Thr Glu Leu Leu Glu Thr Leu Ala Glu Ile Asp Phe Arg
865                 870                 875                 880

Leu Val Ser Phe Leu Glu Ala Lys Ala Glu Asn Leu His Arg Gly Ala
            885                 890                 895

His His Tyr Thr Gly Leu Leu Lys Leu Gln Glu Arg Val Leu Asn Asn
        900                 905                 910

Val Val Ile His Leu Leu Gly Asp Glu Asp Pro Arg Val Arg His Val
    915                 920                 925

Ala Ala Ala Ser Leu Ile Arg Leu Val Pro Lys Leu Phe Tyr Lys Cys
930                 935                 940

Asp Gln Gly Gln Ala Asp Pro Val Val Ala Val Ala Arg Asp Gln Ser
945                 950                 955                 960

Ser Val Tyr Leu Lys Leu Leu Met His Glu Thr Gln Pro Pro Ser His
            965                 970                 975

Phe Ser Val Ser Thr Ile Thr Arg Ile Tyr Arg Gly Tyr Asn Leu Leu
        980                 985                 990

Pro Ser Ile Thr Asp Val Thr Met Glu Asn Asn Leu Ser Arg Val Ile
    995                 1000                1005

Ala Ala Val Ser His Glu Leu Ile Thr Ser Thr Thr Arg Ala Leu
        1010                1015                1020

Thr Phe Gly Cys Cys Glu Ala Leu Cys Leu Leu Ser Thr Ala Phe
    1025                1030                1035

Pro Val Cys Ile Trp Ser Leu Gly Trp His Cys Gly Val Pro Pro
    1040                1045                1050

Leu Ser Ala Ser Asp Glu Ser Arg Lys Ser Cys Thr Val Gly Met
    1055                1060                1065

Ala Thr Met Ile Leu Thr Leu Leu Ser Ser Ala Trp Phe Pro Leu
    1070                1075                1080

Asp Leu Ser Ala His Gln Asp Ala Leu Ile Leu Ala Gly Asn Leu
    1085                1090                1095

Leu Ala Ala Ser Ala Pro Lys Ser Leu Arg Ser Ser Trp Ala Ser
    1100                1105                1110
```

-continued

| | | | | | | | | | | | |
|---|---|---|---|---|---|---|---|---|---|---|---|
| Glu | Glu | Glu | Ala | Asn | Pro | Ala | Ala | Thr | Lys | Gln | Glu | Val | Trp |
| 1115 | | | | | 1120 | | | | | 1125 | | | |

Pro Ala Leu Gly Asp Arg Ala Leu Val Pro Met Val Glu Gln Leu
1130                1135                1140

Phe Ser His Leu Leu Lys Val Ile Asn Ile Cys Ala His Val Leu
1145                1150                1155

Asp Asp Val Ala Pro Gly Pro Ala Ile Lys Ala Ala Leu Pro Ser
1160                1165                1170

Leu Thr Asn Pro Pro Ser Leu Ser Pro Ile Arg Arg Lys Gly Lys
1175                1180                1185

Glu Lys Glu Pro Gly Glu Gln Ala Ser Val Pro Leu Ser Pro Lys
1190                1195                1200

Lys Gly Ser Glu Ala Ser Ala Ala Ser Arg Gln Ser Asp Thr Ser
1205                1210                1215

Gly Pro Val Thr Thr Ser Lys Ser Ser Ser Leu Gly Ser Phe Tyr
1220                1225                1230

His Leu Pro Ser Tyr Leu Lys Leu His Asp Val Leu Lys Ala Thr
1235                1240                1245

His Ala Asn Tyr Lys Val Thr Leu Asp Leu Gln Asn Ser Thr Glu
1250                1255                1260

Lys Phe Gly Gly Phe Leu Arg Ser Ala Leu Asp Val Leu Ser Gln
1265                1270                1275

Ile Leu Glu Leu Ala Thr Leu Gln Asp Ile Gly Lys Cys Val Glu
1280                1285                1290

Glu Ile Leu Gly Tyr Leu Lys Ser Cys Phe Ser Arg Glu Pro Met
1295                1300                1305

Met Ala Thr Val Cys Val Gln Gln Leu Leu Lys Thr Leu Phe Gly
1310                1315                1320

Thr Asn Leu Ala Ser Gln Phe Asp Gly Leu Ser Ser Asn Pro Ser
1325                1330                1335

Lys Ser Gln Gly Arg Ala Gln Arg Leu Gly Ser Ser Ser Val Arg
1340                1345                1350

Pro Gly Leu Tyr His Tyr Cys Phe Met Ala Pro Tyr Thr His Phe
1355                1360                1365

Thr Gln Ala Leu Ala Asp Ala Ser Leu Arg Asn Met Val Gln Ala
1370                1375                1380

Glu Gln Glu Asn Asp Thr Ser Gly Trp Phe Asp Val Leu Gln Lys
1385                1390                1395

Val Ser Thr Gln Leu Lys Thr Asn Leu Thr Ser Val Thr Lys Asn
1400                1405                1410

Arg Ala Asp Lys Asn Ala Ile His Asn His Ile Arg Leu Phe Glu
1415                1420                1425

Pro Leu Val Ile Lys Ala Leu Lys Gln Tyr Thr Thr Thr Thr Cys
1430                1435                1440

Val Gln Leu Gln Lys Gln Val Leu Asp Leu Leu Ala Gln Leu Val
1445                1450                1455

Gln Leu Arg Val Asn Tyr Cys Leu Leu Asp Ser Asp Gln Val Phe
1460                1465                1470

Ile Gly Phe Val Leu Lys Gln Phe Glu Tyr Ile Glu Val Gly Gln
1475                1480                1485

Phe Arg Glu Ser Glu Ala Ile Ile Pro Asn Ile Phe Phe Phe Leu
1490                1495                1500

Val Leu Leu Ser Tyr Glu Arg Tyr His Ser Lys Gln Ile Ile Gly

```
              1505                1510                1515
Ile Pro Lys Ile Ile Gln Leu Cys Asp Gly Ile Met Ala Ser Gly
    1520                1525                1530

Arg Lys Ala Val Thr His Ala Ile Pro Ala Leu Gln Pro Ile Val
    1535                1540                1545

His Asp Leu Phe Val Leu Arg Gly Thr Asn Lys Ala Asp Ala Gly
    1550                1555                1560

Lys Glu Leu Glu Thr Gln Lys Glu Val Val Ser Met Leu Leu
    1565                1570                1575

Arg Leu Ile Gln Tyr His Gln Val Leu Glu Met Phe Ile Leu Val
    1580                1585                1590

Leu Gln Gln Cys His Lys Glu Asn Glu Asp Lys Trp Lys Arg Leu
    1595                1600                1605

Ser Arg Gln Ile Ala Asp Ile Ile Leu Pro Met Leu Ala Lys Gln
    1610                1615                1620

Gln Met His Ile Asp Ser His Glu Ala Leu Gly Val Leu Asn Thr
    1625                1630                1635

Leu Phe Glu Ile Leu Ala Pro Ser Ser Leu Arg Pro Val Asp Met
    1640                1645                1650

Leu Leu Arg Ser Met Phe Val Thr Pro Asn Thr Met Ala Ser Val
    1655                1660                1665

Ser Thr Val Gln Leu Trp Ile Ser Gly Ile Leu Ala Ile Leu Arg
    1670                1675                1680

Val Leu Ile Ser Gln Ser Thr Glu Asp Ile Val Leu Ser Arg Ile
    1685                1690                1695

Gln Glu Leu Ser Phe Ser Pro Tyr Leu Ile Ser Cys Thr Val Ile
    1700                1705                1710

Asn Arg Leu Arg Asp Gly Asp Ser Thr Ser Thr Leu Glu Glu His
    1715                1720                1725

Ser Glu Gly Lys Gln Ile Lys Asn Leu Pro Glu Glu Thr Phe Ser
    1730                1735                1740

Arg Phe Leu Leu Gln Leu Val Gly Ile Leu Leu Glu Asp Ile Val
    1745                1750                1755

Thr Lys Gln Leu Lys Val Glu Met Ser Glu Gln Gln His Thr Phe
    1760                1765                1770

Tyr Cys Gln Glu Leu Gly Thr Leu Leu Met Cys Leu Ile His Ile
    1775                1780                1785

Phe Lys Ser Gly Met Phe Arg Arg Ile Thr Ala Ala Ala Thr Arg
    1790                1795                1800

Leu Phe Arg Ser Asp Gly Cys Gly Gly Ser Phe Tyr Thr Leu Asp
    1805                1810                1815

Ser Leu Asn Leu Arg Ala Arg Ser Met Ile Thr Thr His Pro Ala
    1820                1825                1830

Leu Val Leu Leu Trp Cys Gln Ile Leu Leu Val Asn His Thr
    1835                1840                1845

Asp Tyr Arg Trp Trp Ala Glu Val Gln Gln Thr Pro Lys Arg His
    1850                1855                1860

Ser Leu Ser Ser Thr Lys Leu Leu Ser Pro Gln Met Ser Gly Glu
    1865                1870                1875

Glu Glu Asp Ser Asp Leu Ala Ala Lys Leu Gly Met Cys Asn Arg
    1880                1885                1890

Glu Ile Val Arg Arg Gly Ala Leu Ile Leu Phe Cys Asp Tyr Val
    1895                1900                1905
```

Cys Gln Asn Leu His Asp Ser Glu His Leu Thr Trp Leu Ile Val
1910                 1915                1920

Asn His Ile Gln Asp Leu Ile Ser Leu Ser His Glu Pro Pro Val
1925                 1930                1935

Gln Asp Phe Ile Ser Ala Val His Arg Asn Ser Ala Ala Ser Gly
1940                 1945                1950

Leu Phe Ile Gln Ala Ile Gln Ser Arg Cys Glu Asn Leu Ser Thr
1955                 1960                1965

Pro Thr Met Leu Lys Lys Thr Leu Gln Cys Leu Glu Gly Ile His
1970                 1975                1980

Leu Ser Gln Ser Gly Ala Val Leu Thr Leu Tyr Val Asp Arg Leu
1985                 1990                1995

Leu Cys Thr Pro Phe Arg Val Leu Ala Arg Met Val Asp Ile Leu
2000                 2005                2010

Ala Cys Arg Arg Val Glu Met Leu Leu Ala Ala Asn Leu Gln Ser
2015                 2020                2025

Ser Met Ala Gln Leu Pro Met Glu Glu Leu Asn Arg Ile Gln Glu
2030                 2035                2040

Tyr Leu Gln Ser Ser Gly Leu Ala Gln Arg His Gln Arg Leu Tyr
2045                 2050                2055

Ser Leu Leu Asp Arg Phe Arg Leu Ser Thr Met Gln Asp Ser Leu
2060                 2065                2070

Ser Pro Ser Pro Pro Val Ser Ser His Pro Leu Asp Gly Asp Gly
2075                 2080                2085

His Val Ser Leu Glu Thr Val Ser Pro Asp Lys Asp Trp Tyr Val
2090                 2095                2100

His Leu Val Lys Ser Gln Cys Trp Thr Arg Ser Asp Ser Ala Leu
2105                 2110                2115

Leu Glu Gly Ala Glu Leu Val Asn Arg Ile Pro Ala Glu Asp Met
2120                 2125                2130

Asn Ala Phe Met Met Asn Ser Glu Phe Asn Leu Ser Leu Leu Ala
2135                 2140                2145

Pro Cys Leu Ser Leu Gly Met Ser Glu Ile Ser Gly Gly Gln Lys
2150                 2155                2160

Ser Ala Leu Phe Glu Ala Ala Arg Glu Val Thr Leu Ala Arg Val
2165                 2170                2175

Ser Gly Thr Val Gln Gln Leu Pro Ala Val His His Val Phe Gln
2180                 2185                2190

Pro Glu Leu Pro Ala Glu Pro Ala Ala Tyr Trp Ser Lys Leu Asn
2195                 2200                2205

Asp Leu Phe Gly Asp Ala Ala Leu Tyr Gln Ser Leu Pro Thr Leu
2210                 2215                2220

Ala Arg Ala Leu Ala Gln Tyr Leu Val Val Val Ser Lys Leu Pro
2225                 2230                2235

Ser His Leu His Leu Pro Pro Glu Lys Glu Lys Asp Ile Val Lys
2240                 2245                2250

Phe Val Val Ala Thr Leu Glu Ala Leu Ser Trp His Leu Ile His
2255                 2260                2265

Glu Gln Ile Pro Leu Ser Leu Asp Leu Gln Ala Gly Leu Asp Cys
2270                 2275                2280

Cys Cys Leu Ala Leu Gln Leu Pro Gly Leu Trp Ser Val Val Ser
2285                 2290                2295

```
Ser Thr Glu Phe Val Thr His Ala Cys Ser Leu Ile Tyr Cys Val
    2300            2305            2310

His Phe Ile Leu Glu Ala Val Ala Val Gln Pro Gly Glu Gln Leu
    2315            2320            2325

Leu Ser Pro Glu Arg Arg Thr Asn Thr Pro Lys Ala Ile Ser Glu
    2330            2335            2340

Glu Glu Glu Glu Val Asp Pro Asn Thr Gln Asn Pro Lys Tyr Ile
    2345            2350            2355

Thr Ala Ala Cys Glu Met Val Ala Glu Met Val Glu Ser Leu Gln
    2360            2365            2370

Ser Val Leu Ala Leu Gly His Lys Arg Asn Ser Gly Val Pro Ala
    2375            2380            2385

Phe Leu Thr Pro Leu Leu Arg Asn Ile Ile Ile Ser Leu Ala Arg
    2390            2395            2400

Leu Pro Leu Val Asn Ser Tyr Thr Arg Val Pro Pro Leu Val Trp
    2405            2410            2415

Lys Leu Gly Trp Ser Pro Lys Pro Gly Gly Asp Phe Gly Thr Ala
    2420            2425            2430

Phe Pro Glu Ile Pro Val Glu Phe Leu Gln Glu Lys Glu Val Phe
    2435            2440            2445

Lys Glu Phe Ile Tyr Arg Ile Asn Thr Leu Gly Trp Thr Ser Arg
    2450            2455            2460

Thr Gln Phe Glu Glu Thr Trp Ala Thr Leu Leu Gly Val Leu Val
    2465            2470            2475

Thr Gln Pro Leu Val Met Glu Gln Glu Glu Ser Pro Pro Glu Glu
    2480            2485            2490

Asp Thr Glu Arg Thr Gln Ile Asn Val Leu Ala Val Gln Ala Ile
    2495            2500            2505

Thr Ser Leu Val Leu Ser Ala Met Thr Val Pro Val Ala Gly Asn
    2510            2515            2520

Pro Ala Val Ser Cys Leu Glu Gln Gln Pro Arg Asn Lys Pro Leu
    2525            2530            2535

Lys Ala Leu Asp Thr Arg Phe Gly Arg Lys Leu Ser Ile Ile Arg
    2540            2545            2550

Gly Ile Val Glu Gln Glu Ile Gln Ala Met Val Ser Lys Arg Glu
    2555            2560            2565

Asn Ile Ala Thr His His Leu Tyr Gln Ala Trp Asp Pro Val Pro
    2570            2575            2580

Ser Leu Ser Pro Ala Thr Thr Gly Ala Leu Ile Ser His Glu Lys
    2585            2590            2595

Leu Leu Leu Gln Ile Asn Pro Glu Arg Glu Leu Gly Ser Met Ser
    2600            2605            2610

Tyr Lys Leu Gly Gln Val Ser Ile His Ser Val Trp Leu Gly Asn
    2615            2620            2625

Ser Ile Thr Pro Leu Arg Glu Glu Glu Trp Asp Glu Glu Glu Glu
    2630            2635            2640

Glu Glu Ala Asp Ala Pro Ala Pro Ser Ser Pro Thr Ser Pro
    2645            2650            2655

Val Asn Ser Arg Lys His Arg Ala Gly Val Asp Ile His Ser Cys
    2660            2665            2670

Ser Gln Phe Leu Leu Glu Leu Tyr Ser Arg Trp Ile Leu Pro Ser
    2675            2680            2685

Ser Ser Ala Arg Arg Thr Pro Ala Ile Leu Ile Ser Glu Val Val
```

```
                2690                2695                2700
Arg Ser Leu Leu Val Val Ser Asp Leu Phe Thr Glu Arg Asn Gln
    2705                2710                2715
Phe Glu Leu Met Tyr Val Thr Leu Thr Glu Leu Arg Arg Val His
    2720                2725                2730
Pro Ser Glu Asp Glu Ile Leu Ala Gln Tyr Leu Val Pro Ala Thr
    2735                2740                2745
Cys Lys Ala Ala Ala Val Leu Gly Met Asp Lys Ala Val Ala Glu
    2750                2755                2760
Pro Val Ser Arg Leu Leu Glu Ser Thr Leu Arg Ser Ser His Leu
    2765                2770                2775
Pro Ser Arg Val Gly Ala Leu His Gly Val Leu Tyr Val Leu Glu
    2780                2785                2790
Cys Asp Leu Leu Asp Asp Thr Ala Lys Gln Leu Ile Pro Val Ile
    2795                2800                2805
Ser Asp Tyr Leu Leu Ser Asn Leu Lys Gly Ile Ala His Cys Val
    2810                2815                2820
Asn Ile His Ser Gln Gln His Val Leu Val Met Cys Ala Thr Ala
    2825                2830                2835
Phe Tyr Leu Ile Glu Asn Tyr Pro Leu Asp Val Gly Pro Glu Phe
    2840                2845                2850
Ser Ala Ser Ile Ile Gln Met Cys Gly Val Met Leu Ser Gly Ser
    2855                2860                2865
Glu Glu Ser Thr Pro Ser Ile Ile Tyr His Cys Ala Leu Arg Gly
    2870                2875                2880
Leu Glu Arg Leu Leu Leu Ser Glu Gln Leu Ser Arg Leu Asp Ala
    2885                2890                2895
Glu Ser Leu Val Lys Leu Ser Val Asp Arg Val Asn Val His Ser
    2900                2905                2910
Pro His Arg Ala Met Ala Ala Leu Gly Leu Met Leu Thr Cys Met
    2915                2920                2925
Tyr Thr Gly Lys Glu Lys Val Ser Pro Gly Arg Thr Ser Asp Pro
    2930                2935                2940
Asn Pro Ala Ala Pro Asp Ser Glu Ser Val Ile Val Ala Met Glu
    2945                2950                2955
Arg Val Ser Val Leu Phe Asp Arg Ile Arg Lys Gly Phe Pro Cys
    2960                2965                2970
Glu Ala Arg Val Val Ala Arg Ile Leu Pro Gln Phe Leu Asp Asp
    2975                2980                2985
Phe Phe Pro Pro Gln Asp Ile Met Asn Lys Val Ile Gly Glu Phe
    2990                2995                3000
Leu Ser Asn Gln Gln Pro Tyr Pro Gln Phe Met Ala Thr Val Val
    3005                3010                3015
Tyr Lys Val Phe Gln Thr Leu His Ser Thr Gly Gln Ser Ser Met
    3020                3025                3030
Val Arg Asp Trp Val Met Leu Ser Leu Ser Asn Phe Thr Gln Arg
    3035                3040                3045
Ala Pro Val Ala Met Ala Thr Trp Ser Leu Ser Cys Phe Phe Val
    3050                3055                3060
Ser Ala Ser Thr Ser Pro Trp Val Ala Ala Ile Leu Pro His Val
    3065                3070                3075
Ile Ser Arg Met Gly Lys Leu Glu Gln Val Asp Val Asn Leu Phe
    3080                3085                3090
```

```
Cys Leu Val Ala Thr Asp Phe Tyr Arg His Gln Ile Glu Glu Glu
    3095                3100                3105

Leu Asp Arg Arg Ala Phe Gln Ser Val Leu Glu Val Val Ala Ala
    3110                3115                3120

Pro Gly Ser Pro Tyr His Arg Leu Leu Thr Cys Leu Arg Asn Val
    3125                3130                3135

His Lys Val Thr Thr Cys
    3140

<210> SEQ ID NO 45
<211> LENGTH: 745
<212> TYPE: PRT
<213> ORGANISM: Homo Sapiens

<400> SEQUENCE: 45

Met Glu Arg Pro Pro Gly Leu Arg Pro Gly Ala Gly Pro Trp Glu
1               5                   10                  15

Met Arg Glu Arg Leu Gly Thr Gly Gly Phe Gly Asn Val Cys Leu Tyr
                20                  25                  30

Gln His Arg Glu Leu Asp Leu Lys Ile Ala Ile Lys Ser Cys Arg Leu
            35                  40                  45

Glu Leu Ser Thr Lys Asn Arg Glu Arg Trp Cys His Glu Ile Gln Ile
        50                  55                  60

Met Lys Lys Leu Asn His Ala Asn Val Val Lys Ala Cys Asp Val Pro
65                  70                  75                  80

Glu Glu Leu Asn Ile Leu Ile His Asp Val Pro Leu Leu Ala Met Glu
                85                  90                  95

Tyr Cys Ser Gly Gly Asp Leu Arg Lys Leu Leu Asn Lys Pro Glu Asn
            100                 105                 110

Cys Cys Gly Leu Lys Glu Ser Gln Ile Leu Ser Leu Leu Ser Asp Ile
        115                 120                 125

Gly Ser Gly Ile Arg Tyr Leu His Glu Asn Lys Ile Ile His Arg Asp
    130                 135                 140

Leu Lys Pro Glu Asn Ile Val Leu Gln Asp Val Gly Gly Lys Ile Ile
145                 150                 155                 160

His Lys Ile Ile Asp Leu Gly Tyr Ala Lys Asp Val Asp Gln Gly Ser
                165                 170                 175

Leu Cys Thr Ser Phe Val Gly Thr Leu Gln Tyr Leu Ala Pro Glu Leu
            180                 185                 190

Phe Glu Asn Lys Pro Tyr Thr Ala Thr Val Asp Tyr Trp Ser Phe Gly
        195                 200                 205

Thr Met Val Phe Glu Cys Ile Ala Gly Tyr Arg Pro Phe Leu His His
    210                 215                 220

Leu Gln Pro Phe Thr Trp His Glu Lys Ile Lys Lys Lys Asp Pro Lys
225                 230                 235                 240

Cys Ile Phe Ala Cys Glu Glu Met Ser Gly Glu Val Arg Phe Ser Ser
                245                 250                 255

His Leu Pro Gln Pro Asn Ser Leu Cys Ser Leu Ile Val Glu Pro Met
            260                 265                 270

Glu Asn Trp Leu Gln Leu Met Leu Asn Trp Asp Pro Gln Gln Arg Gly
        275                 280                 285

Gly Pro Val Asp Leu Thr Leu Lys Gln Pro Arg Cys Phe Val Leu Met
    290                 295                 300

Asp His Ile Leu Asn Leu Lys Ile Val His Ile Leu Asn Met Thr Ser
```

```
        305                 310                 315                 320
Ala Lys Ile Ile Ser Phe Leu Pro Pro Asp Glu Ser Leu His Ser
                    325                 330                 335

Leu Gln Ser Arg Ile Glu Arg Glu Thr Gly Ile Asn Thr Gly Ser Gln
                340                 345                 350

Glu Leu Leu Ser Glu Thr Gly Ile Ser Leu Asp Pro Arg Lys Pro Ala
            355                 360                 365

Ser Gln Cys Val Leu Asp Gly Val Arg Gly Cys Asp Ser Tyr Met Val
        370                 375                 380

Tyr Leu Phe Asp Lys Ser Lys Thr Val Tyr Glu Gly Pro Phe Ala Ser
385                 390                 395                 400

Arg Ser Leu Ser Asp Cys Val Asn Tyr Ile Val Gln Asp Ser Lys Ile
                405                 410                 415

Gln Leu Pro Ile Ile Gln Leu Arg Lys Val Trp Ala Glu Ala Val His
            420                 425                 430

Tyr Val Ser Gly Leu Lys Glu Asp Tyr Ser Arg Leu Phe Gln Gly Gln
        435                 440                 445

Arg Ala Ala Met Leu Ser Leu Leu Arg Tyr Asn Ala Asn Leu Thr Lys
    450                 455                 460

Met Lys Asn Thr Leu Ile Ser Ala Ser Gln Gln Leu Lys Ala Lys Leu
465                 470                 475                 480

Glu Phe Phe His Lys Ser Ile Gln Leu Asp Leu Glu Arg Tyr Ser Glu
                485                 490                 495

Gln Met Thr Tyr Gly Ile Ser Ser Glu Lys Met Leu Lys Ala Trp Lys
            500                 505                 510

Glu Met Glu Glu Lys Ala Ile His Tyr Ala Glu Val Gly Val Ile Gly
        515                 520                 525

Tyr Leu Glu Asp Gln Ile Met Ser Leu His Ala Glu Ile Met Glu Leu
    530                 535                 540

Gln Lys Ser Pro Tyr Gly Arg Arg Gln Gly Asp Leu Met Glu Ser Leu
545                 550                 555                 560

Glu Gln Arg Ala Ile Asp Leu Tyr Lys Gln Leu Lys His Arg Pro Ser
                565                 570                 575

Asp His Ser Tyr Ser Asp Ser Thr Glu Met Val Lys Ile Ile Val His
            580                 585                 590

Thr Val Gln Ser Gln Asp Arg Val Leu Lys Glu Leu Phe Gly His Leu
        595                 600                 605

Ser Lys Leu Leu Gly Cys Lys Gln Lys Ile Ile Asp Leu Leu Pro Lys
    610                 615                 620

Val Glu Val Ala Leu Ser Asn Ile Lys Glu Ala Asp Asn Thr Val Met
625                 630                 635                 640

Phe Met Gln Gly Lys Arg Gln Lys Glu Ile Trp His Leu Leu Lys Ile
                645                 650                 655

Ala Cys Thr Gln Ser Ser Ala Arg Ser Leu Val Gly Ser Ser Leu Glu
            660                 665                 670

Gly Ala Val Thr Pro Gln Thr Ser Ala Trp Leu Pro Pro Thr Ser Ala
        675                 680                 685

Glu His Asp His Ser Leu Ser Cys Val Val Thr Pro Gln Asp Gly Glu
    690                 695                 700

Thr Ser Ala Gln Met Ile Glu Glu Asn Leu Asn Cys Leu Gly His Leu
705                 710                 715                 720

Ser Thr Ile Ile His Glu Ala Asn Glu Glu Gln Gly Asn Ser Met Met
                725                 730                 735
```

```
Asn Leu Asp Trp Ser Trp Leu Thr Glu
            740                 745

<210> SEQ ID NO 46
<211> LENGTH: 1242
<212> TYPE: PRT
<213> ORGANISM: Homo Sapiens

<400> SEQUENCE: 46

Met Ala Ser Pro Pro Glu Ser Asp Gly Phe Ser Asp Val Arg Lys Val
1               5                   10                  15

Gly Tyr Leu Arg Lys Pro Lys Ser Met His Lys Arg Phe Phe Val Leu
            20                  25                  30

Arg Ala Ala Ser Glu Ala Gly Gly Pro Ala Arg Leu Glu Tyr Tyr Glu
        35                  40                  45

Asn Glu Lys Lys Trp Arg His Lys Ser Ser Ala Pro Lys Arg Ser Ile
    50                  55                  60

Pro Leu Glu Ser Cys Phe Asn Ile Asn Lys Arg Ala Asp Ser Lys Asn
65                  70                  75                  80

Lys His Leu Val Ala Leu Tyr Thr Arg Asp Glu His Phe Ala Ile Ala
                85                  90                  95

Ala Asp Ser Glu Ala Glu Gln Asp Ser Trp Tyr Gln Ala Leu Leu Gln
            100                 105                 110

Leu His Asn Arg Ala Lys Gly His His Asp Gly Ala Ala Ala Leu Gly
        115                 120                 125

Ala Gly Gly Gly Gly Ser Cys Ser Gly Ser Ser Gly Leu Gly Glu
130                 135                 140

Ala Gly Glu Asp Leu Ser Tyr Gly Asp Val Pro Gly Pro Ala Phe
145                 150                 155                 160

Lys Glu Val Trp Gln Val Ile Leu Lys Pro Lys Gly Leu Gly Gln Thr
                165                 170                 175

Lys Asn Leu Ile Gly Ile Tyr Arg Leu Cys Leu Thr Ser Lys Thr Ile
            180                 185                 190

Ser Phe Val Lys Leu Asn Ser Glu Ala Ala Ala Val Val Leu Gln Leu
        195                 200                 205

Met Asn Ile Arg Arg Cys Gly His Ser Glu Asn Phe Phe Phe Ile Glu
    210                 215                 220

Val Gly Arg Ser Ala Val Thr Gly Pro Gly Glu Phe Trp Met Gln Val
225                 230                 235                 240

Asp Asp Ser Val Val Ala Gln Asn Met His Glu Thr Ile Leu Glu Ala
                245                 250                 255

Met Arg Ala Met Ser Asp Glu Phe Arg Pro Arg Ser Lys Ser Gln Ser
            260                 265                 270

Ser Ser Asn Cys Ser Asn Pro Ile Ser Val Pro Leu Arg Arg His His
        275                 280                 285

Leu Asn Asn Pro Pro Ser Gln Val Gly Leu Thr Arg Arg Ser Arg
    290                 295                 300

Thr Glu Ser Ile Thr Ala Thr Ser Pro Ala Ser Met Val Gly Gly Lys
305                 310                 315                 320

Pro Gly Ser Phe Arg Val Arg Ala Ser Ser Asp Gly Glu Gly Thr Met
                325                 330                 335

Ser Arg Pro Ala Ser Val Asp Gly Ser Pro Val Ser Pro Ser Thr Asn
            340                 345                 350

Arg Thr His Ala His Arg His Arg Gly Ser Ala Arg Leu His Pro Pro
```

```
                355                 360                 365
Leu Asn His Ser Arg Ser Ile Pro Met Pro Ala Ser Arg Cys Ser Pro
370                 375                 380

Ser Ala Thr Ser Pro Val Ser Leu Ser Ser Ser Thr Ser Gly His
385                 390                 395                 400

Gly Ser Thr Ser Asp Cys Leu Phe Pro Arg Arg Ser Ser Ala Ser Val
                405                 410                 415

Ser Gly Ser Pro Ser Asp Gly Gly Phe Ile Ser Ser Asp Glu Tyr Gly
                420                 425                 430

Ser Ser Pro Cys Asp Phe Arg Ser Ser Phe Arg Ser Val Thr Pro Asp
                435                 440                 445

Ser Leu Gly His Thr Pro Pro Ala Arg Gly Glu Glu Glu Leu Ser Asn
450                 455                 460

Tyr Ile Cys Met Gly Gly Lys Gly Pro Ser Thr Leu Thr Ala Pro Asn
465                 470                 475                 480

Gly His Tyr Ile Leu Ser Arg Gly Gly Asn Gly His Arg Cys Thr Pro
                485                 490                 495

Gly Thr Gly Leu Gly Thr Ser Pro Ala Leu Ala Gly Asp Glu Ala Ala
                500                 505                 510

Ser Ala Ala Asp Leu Asp Asn Arg Phe Arg Lys Arg Thr His Ser Ala
                515                 520                 525

Gly Thr Ser Pro Thr Ile Thr His Gln Lys Thr Pro Ser Gln Ser Ser
530                 535                 540

Val Ala Ser Ile Glu Glu Tyr Thr Glu Met Met Pro Ala Tyr Pro Pro
545                 550                 555                 560

Gly Gly Gly Ser Gly Gly Arg Leu Pro Gly His Arg His Ser Ala Phe
                565                 570                 575

Val Pro Thr Arg Ser Tyr Pro Glu Glu Gly Leu Glu Met His Pro Leu
                580                 585                 590

Glu Arg Arg Gly Gly His His Arg Pro Asp Ser Ser Thr Leu His Thr
                595                 600                 605

Asp Asp Gly Tyr Met Pro Met Ser Pro Gly Val Ala Pro Val Pro Ser
610                 615                 620

Gly Arg Lys Gly Ser Gly Asp Tyr Met Pro Met Ser Pro Lys Ser Val
625                 630                 635                 640

Ser Ala Pro Gln Gln Ile Ile Asn Pro Ile Arg Arg His Pro Gln Arg
                645                 650                 655

Val Asp Pro Asn Gly Tyr Met Met Met Ser Pro Ser Gly Gly Cys Ser
                660                 665                 670

Pro Asp Ile Gly Gly Gly Pro Ser Ser Ser Ser Ser Ser Ser Asn Ala
                675                 680                 685

Val Pro Ser Gly Thr Ser Tyr Gly Lys Leu Trp Thr Asn Gly Val Gly
                690                 695                 700

Gly His His Ser His Val Leu Pro His Pro Lys Pro Pro Val Glu Ser
705                 710                 715                 720

Ser Gly Gly Lys Leu Leu Pro Cys Thr Gly Asp Tyr Met Asn Met Ser
                725                 730                 735

Pro Val Gly Asp Ser Asn Thr Ser Ser Pro Ser Asp Cys Tyr Tyr Gly
                740                 745                 750

Pro Glu Asp Pro Gln His Lys Pro Val Leu Ser Tyr Tyr Ser Leu Pro
                755                 760                 765

Arg Ser Phe Lys His Thr Gln Arg Pro Gly Glu Pro Glu Glu Gly Ala
770                 775                 780
```

-continued

```
Arg His Gln His Leu Arg Leu Ser Thr Ser Ser Gly Arg Leu Leu Tyr
785                 790                 795                 800

Ala Ala Thr Ala Asp Asp Ser Ser Ser Thr Ser Ser Asp Ser Leu
                805                 810                 815

Gly Gly Gly Tyr Cys Gly Ala Arg Leu Glu Pro Ser Leu Pro His Pro
                820                 825                 830

His His Gln Val Leu Gln Pro His Leu Pro Arg Lys Val Asp Thr Ala
                835                 840                 845

Ala Gln Thr Asn Ser Arg Leu Ala Arg Pro Thr Arg Leu Ser Leu Gly
850                 855                 860

Asp Pro Lys Ala Ser Thr Leu Pro Arg Ala Arg Glu Gln Gln Gln Gln
865                 870                 875                 880

Gln Gln Pro Leu Leu His Pro Pro Glu Pro Lys Ser Pro Gly Glu Tyr
                885                 890                 895

Val Asn Ile Glu Phe Gly Ser Asp Gln Ser Gly Tyr Leu Ser Gly Pro
                900                 905                 910

Val Ala Phe His Ser Ser Pro Ser Val Arg Cys Pro Ser Gln Leu Gln
                915                 920                 925

Pro Ala Pro Arg Glu Glu Glu Thr Gly Thr Glu Tyr Met Lys Met
                930                 935                 940

Asp Leu Gly Pro Gly Arg Arg Ala Ala Trp Gln Glu Ser Thr Gly Val
945                 950                 955                 960

Glu Met Gly Arg Leu Gly Pro Ala Pro Pro Gly Ala Ala Ser Ile Cys
                965                 970                 975

Arg Pro Thr Arg Ala Val Pro Ser Ser Arg Gly Asp Tyr Met Thr Met
                980                 985                 990

Gln Met Ser Cys Pro Arg Gln Ser Tyr Val Asp Thr Ser Pro Ala Ala
                995                 1000                1005

Pro Val Ser Tyr Ala Asp Met Arg Thr Gly Ile Ala Ala Glu Glu
    1010                1015                1020

Val Ser Leu Pro Arg Ala Thr Met Ala Ala Ala Ser Ser Ser
    1025                1030                1035

Ala Ala Ser Ala Ser Pro Thr Gly Pro Gln Gly Ala Ala Glu Leu
    1040                1045                1050

Ala Ala His Ser Ser Leu Leu Gly Gly Pro Gln Gly Pro Gly Gly
    1055                1060                1065

Met Ser Ala Phe Thr Arg Val Asn Leu Ser Pro Asn Arg Asn Gln
    1070                1075                1080

Ser Ala Lys Val Ile Arg Ala Asp Pro Gln Gly Cys Arg Arg Arg
    1085                1090                1095

His Ser Ser Glu Thr Phe Ser Ser Thr Pro Ser Ala Thr Arg Val
    1100                1105                1110

Gly Asn Thr Val Pro Phe Gly Ala Gly Ala Ala Val Gly Gly Gly
    1115                1120                1125

Gly Gly Ser Ser Ser Ser Ser Glu Asp Val Lys Arg His Ser Ser
    1130                1135                1140

Ala Ser Phe Glu Asn Val Trp Leu Arg Pro Gly Glu Leu Gly Gly
    1145                1150                1155

Ala Pro Lys Glu Pro Ala Lys Leu Cys Gly Ala Ala Gly Gly Leu
    1160                1165                1170

Glu Asn Gly Leu Asn Tyr Ile Asp Leu Asp Leu Val Lys Asp Phe
    1175                1180                1185
```

<210> SEQ ID NO 47
<211> LENGTH: 489
<212> TYPE: PRT
<213> ORGANISM: Mus musculus

<400> SEQUENCE: 47

```
Lys Gln Cys Pro Gln Glu Cys Thr Pro Glu Pro Gln Pro Pro Pro
    1190            1195                1200
Pro Pro Pro Pro His Gln Pro Leu Gly Ser Gly Glu Ser Ser Ser
    1205            1210                1215
Thr Arg Arg Ser Ser Glu Asp Leu Ser Ala Tyr Ala Ser Ile Ser
    1220            1225                1230
Phe Gln Lys Gln Pro Glu Asp Arg Gln
    1235            1240

Met Cys Asn Thr Asn Met Ser Val Ser Thr Glu Gly Ala Ala Ser Thr
1               5                   10                  15
Ser Gln Ile Pro Ala Ser Glu Gln Glu Thr Leu Val Arg Pro Lys Pro
                20                  25                  30
Leu Leu Leu Lys Leu Leu Lys Ser Val Gly Ala Gln Asn Asp Thr Tyr
            35                  40                  45
Thr Met Lys Glu Ile Ile Phe Tyr Ile Gly Gln Tyr Ile Met Thr Lys
        50                  55                  60
Arg Leu Tyr Asp Glu Lys Gln Gln His Ile Val Tyr Cys Ser Asn Asp
65                  70                  75                  80
Leu Leu Gly Asp Val Phe Gly Val Pro Ser Phe Ser Val Lys Glu His
                85                  90                  95
Arg Lys Ile Tyr Ala Met Ile Tyr Arg Asn Leu Val Ala Val Ser Gln
            100                 105                 110
Gln Asp Ser Gly Thr Ser Leu Ser Glu Ser Arg Arg Gln Pro Glu Gly
        115                 120                 125
Gly Ser Asp Leu Lys Asp Pro Leu Gln Ala Pro Pro Glu Glu Lys Pro
    130                 135                 140
Ser Ser Ser Asp Leu Ile Ser Arg Leu Ser Thr Ser Ser Arg Arg Arg
145                 150                 155                 160
Ser Ile Ser Glu Thr Glu Glu Asn Thr Asp Glu Leu Pro Gly Glu Arg
                165                 170                 175
His Arg Lys Arg Arg Ser Leu Ser Phe Asp Pro Ser Leu Gly Leu
            180                 185                 190
Cys Glu Leu Arg Glu Met Cys Ser Gly Gly Ser Ser Ser Ser Ser Ser
        195                 200                 205
Ser Ser Ser Glu Ser Thr Glu Thr Pro Ser His Gln Asp Leu Asp Asp
    210                 215                 220
Gly Val Ser Glu His Ser Gly Asp Cys Leu Asp Gln Asp Ser Val Ser
225                 230                 235                 240
Asp Gln Phe Ser Val Glu Phe Glu Val Glu Ser Leu Asp Ser Glu Asp
                245                 250                 255
Tyr Ser Leu Ser Asp Glu Gly His Glu Leu Ser Asp Glu Asp Asp Glu
            260                 265                 270
Val Tyr Arg Val Thr Val Tyr Gln Thr Gly Glu Ser Asp Thr Asp Ser
        275                 280                 285
Phe Glu Gly Asp Pro Glu Ile Ser Leu Ala Asp Tyr Trp Lys Cys Thr
    290                 295                 300
Ser Cys Asn Glu Met Asn Pro Pro Leu Pro Ser His Cys Lys Arg Cys
305                 310                 315                 320
```

```
Trp Thr Leu Arg Glu Asn Trp Leu Pro Asp Asp Lys Gly Lys Asp Lys
                325                 330                 335

Val Glu Ile Ser Glu Lys Ala Lys Leu Glu Asn Ser Ala Gln Ala Glu
            340                 345                 350

Glu Gly Leu Asp Val Pro Asp Gly Lys Lys Leu Thr Glu Asn Asp Ala
        355                 360                 365

Lys Glu Pro Cys Ala Glu Asp Ser Glu Glu Lys Ala Glu Gln Thr
370                 375                 380

Pro Leu Ser Gln Glu Ser Asp Asp Tyr Ser Gln Pro Ser Thr Ser Ser
385                 390                 395                 400

Ser Ile Val Tyr Ser Ser Gln Glu Ser Val Lys Glu Leu Lys Glu Glu
                405                 410                 415

Thr Gln Asp Lys Asp Glu Ser Val Glu Ser Ser Phe Ser Leu Asn Ala
            420                 425                 430

Ile Glu Pro Cys Val Ile Cys Gln Gly Arg Pro Lys Asn Gly Cys Ile
        435                 440                 445

Val His Gly Lys Thr Gly His Leu Met Ser Cys Phe Thr Cys Ala Lys
    450                 455                 460

Lys Leu Lys Lys Arg Asn Lys Pro Cys Pro Val Cys Arg Gln Pro Ile
465                 470                 475                 480

Gln Met Ile Val Leu Thr Tyr Phe Asn
                485

<210> SEQ ID NO 48
<211> LENGTH: 497
<212> TYPE: PRT
<213> ORGANISM: Homo Sapiens

<400> SEQUENCE: 48

Met Val Arg Ser Arg Gln Met Cys Asn Thr Asn Met Ser Val Pro Thr
1               5                   10                  15

Asp Gly Ala Val Thr Thr Ser Gln Ile Pro Ala Ser Glu Gln Glu Thr
            20                  25                  30

Leu Val Arg Pro Lys Pro Leu Leu Leu Lys Leu Leu Lys Ser Val Gly
        35                  40                  45

Ala Gln Lys Asp Thr Tyr Thr Met Lys Glu Val Leu Phe Tyr Leu Gly
    50                  55                  60

Gln Tyr Ile Met Thr Lys Arg Leu Tyr Asp Glu Lys Gln Gln His Ile
65                  70                  75                  80

Val Tyr Cys Ser Asn Asp Leu Leu Gly Asp Leu Phe Gly Val Pro Ser
                85                  90                  95

Phe Ser Val Lys Glu His Arg Lys Ile Tyr Thr Met Ile Tyr Arg Asn
                100                 105                 110

Leu Val Val Val Asn Gln Gln Glu Ser Ser Asp Ser Gly Thr Ser Val
            115                 120                 125

Ser Glu Asn Arg Cys His Leu Glu Gly Gly Ser Asp Gln Lys Asp Leu
        130                 135                 140

Val Gln Glu Leu Gln Glu Glu Lys Pro Ser Ser Ser His Leu Val Ser
145                 150                 155                 160

Arg Pro Ser Thr Ser Ser Arg Arg Arg Ala Ile Ser Glu Thr Glu Glu
                165                 170                 175

Asn Ser Asp Glu Leu Ser Gly Glu Arg Gln Arg Lys Arg His Lys Ser
            180                 185                 190

Asp Ser Ile Ser Leu Ser Phe Asp Glu Ser Leu Ala Leu Cys Val Ile
```

```
                195                 200                 205
Arg Glu Ile Cys Cys Glu Arg Ser Ser Ser Glu Ser Thr Gly Thr
210                 215                 220

Pro Ser Asn Pro Asp Leu Asp Ala Gly Val Ser Glu His Ser Gly Asp
225                 230                 235                 240

Trp Leu Asp Gln Asp Ser Val Ser Asp Gln Phe Ser Val Glu Phe Glu
                245                 250                 255

Val Glu Ser Leu Asp Ser Glu Asp Tyr Ser Leu Ser Glu Glu Gly Gln
            260                 265                 270

Glu Leu Ser Asp Glu Asp Asp Glu Val Tyr Gln Val Thr Val Tyr Gln
        275                 280                 285

Ala Gly Glu Ser Asp Thr Asp Ser Phe Glu Glu Asp Pro Glu Ile Ser
    290                 295                 300

Leu Ala Asp Tyr Trp Lys Cys Thr Ser Cys Asn Glu Met Asn Pro Pro
305                 310                 315                 320

Leu Pro Ser His Cys Asn Arg Cys Trp Ala Leu Arg Glu Asn Trp Leu
                325                 330                 335

Pro Glu Asp Lys Gly Lys Asp Lys Gly Glu Ile Ser Glu Lys Ala Lys
            340                 345                 350

Leu Glu Asn Ser Thr Gln Ala Glu Glu Gly Phe Asp Val Pro Asp Cys
        355                 360                 365

Lys Lys Thr Ile Val Asn Asp Ser Arg Glu Ser Cys Val Glu Glu Asn
    370                 375                 380

Asp Asp Lys Ile Thr Gln Ala Ser Gln Ser Gln Glu Ser Glu Asp Tyr
385                 390                 395                 400

Ser Gln Pro Ser Thr Ser Ser Ile Ile Tyr Ser Ser Gln Glu Asp
                405                 410                 415

Val Lys Glu Phe Glu Arg Glu Gly Thr Gln Asp Lys Gly Glu Ser Val
            420                 425                 430

Glu Ser Ser Leu Pro Leu Asn Ala Ile Glu Pro Cys Val Ile Cys Gln
        435                 440                 445

Gly Arg Pro Lys Asn Gly Cys Ile Val His Gly Lys Thr Gly His Leu
    450                 455                 460

Met Ala Cys Phe Thr Cys Ala Lys Lys Leu Lys Lys Arg Asn Lys Pro
465                 470                 475                 480

Cys Pro Val Cys Arg Gln Pro Ile Gln Met Ile Val Leu Thr Tyr Phe
                485                 490                 495

Pro

<210> SEQ ID NO 49
<211> LENGTH: 847
<212> TYPE: PRT
<213> ORGANISM: Homo Sapiens

<400> SEQUENCE: 49

Met Glu Pro Leu Lys Ser Leu Phe Leu Lys Ser Pro Leu Gly Ser Trp
1               5                   10                  15

Asn Gly Ser Gly Ser Gly Gly Gly Gly Gly Gly Gly Gly Arg Pro
                20                  25                  30

Glu Gly Ser Pro Lys Ala Ala Gly Tyr Ala Asn Pro Val Trp Thr Ala
            35                  40                  45

Leu Phe Asp Tyr Glu Pro Ser Gly Gln Asp Glu Leu Ala Leu Arg Lys
        50                  55                  60

Gly Asp Arg Val Glu Val Leu Ser Arg Asp Ala Ala Ile Ser Gly Asp
```

-continued

Glu Gly Trp Trp Ala Gly Gln Val Gly Gln Val Gly Ile Phe Pro
65                  70                  75                  80

Ser Asn Tyr Val Ser Arg Gly Gly Pro Pro Cys Glu Val Ala
            85                  90                  95

Ser Phe Gln Glu Leu Arg Leu Glu Val Ile Gly Ile Gly Gly Phe
            100                 105                 110

Gly Lys Val Tyr Arg Gly Ser Trp Arg Gly Glu Leu Val Ala Val Lys
            115                 120                 125

Ala Ala Arg Gln Asp Pro Asp Glu Asp Ile Ser Val Thr Ala Glu Ser
130                 135                 140

Val Arg Gln Glu Ala Arg Leu Phe Ala Met Leu Ala His Pro Asn Ile
145                 150                 155                 160

Ile Ala Leu Lys Ala Val Cys Leu Glu Glu Pro Asn Leu Cys Leu Val
                165                 170                 175

Met Glu Tyr Ala Ala Gly Gly Pro Leu Ser Arg Ala Leu Ala Gly Arg
            180                 185                 190

Arg Val Pro Pro His Val Leu Val Asn Trp Ala Val Gln Ile Ala Arg
                195                 200                 205

Gly Met His Tyr Leu His Cys Glu Ala Leu Val Pro Val Ile His Arg
210                 215                 220

Asp Leu Lys Ser Asn Asn Ile Leu Leu Leu Gln Pro Ile Glu Ser Asp
                225                 230                 235                 240

Asp Met Glu His Lys Thr Leu Lys Ile Thr Asp Phe Gly Leu Ala Arg
            245                 250                 255

Glu Trp His Lys Thr Thr Gln Met Ser Ala Ala Gly Thr Tyr Ala Trp
            260                 265                 270

Met Ala Pro Glu Val Ile Lys Ala Ser Thr Phe Ser Lys Gly Ser Asp
            275                 280                 285

Val Trp Ser Phe Gly Val Leu Leu Trp Glu Leu Leu Thr Gly Glu Val
290                 295                 300

Pro Tyr Arg Gly Ile Asp Cys Leu Ala Val Ala Tyr Gly Val Ala Val
                305                 310                 315                 320

Asn Lys Leu Thr Leu Pro Ile Pro Ser Thr Cys Pro Glu Pro Phe Ala
            325                 330                 335

Gln Leu Met Ala Asp Cys Trp Ala Gln Asp Pro His Arg Arg Pro Asp
            340                 345                 350

Phe Ala Ser Ile Leu Gln Gln Leu Glu Ala Leu Glu Ala Gln Val Leu
            355                 360                 365

Arg Glu Met Pro Arg Asp Ser Phe His Ser Met Gln Glu Gly Trp Lys
370                 375                 380

Arg Glu Ile Gln Gly Leu Phe Asp Glu Leu Arg Ala Lys Glu Lys Glu
                385                 390                 395                 400

Leu Leu Ser Arg Glu Glu Glu Leu Thr Arg Ala Ala Arg Glu Gln Arg
            405                 410                 415

Ser Gln Ala Glu Gln Leu Arg Arg Arg Glu His Leu Leu Ala Gln Trp
            420                 425                 430

Glu Leu Glu Val Phe Glu Arg Glu Leu Thr Leu Leu Gln Gln Val
            435                 440                 445

Asp Arg Glu Arg Pro His Val Arg Arg Arg Gly Thr Phe Lys Arg
465                 470                 475                 480

Ser Lys Leu Arg Ala Arg Asp Gly Gly Glu Arg Ile Ser Met Pro Leu
                485                 490                 495

Asp Phe Lys His Arg Ile Thr Val Gln Ala Ser Pro Gly Leu Asp Arg
            500                 505                 510

Arg Arg Asn Val Phe Glu Val Gly Pro Gly Asp Ser Pro Thr Phe Pro
        515                 520                 525

Arg Phe Arg Ala Ile Gln Leu Glu Pro Ala Glu Pro Gly Gln Ala Trp
    530                 535                 540

Gly Arg Gln Ser Pro Arg Arg Leu Glu Asp Ser Ser Asn Gly Glu Arg
545                 550                 555                 560

Arg Ala Cys Trp Ala Trp Gly Pro Ser Ser Pro Lys Pro Gly Glu Ala
                565                 570                 575

Gln Asn Gly Arg Arg Arg Ser Arg Met Asp Glu Ala Thr Trp Tyr Leu
            580                 585                 590

Asp Ser Asp Asp Ser Ser Pro Leu Gly Ser Pro Ser Thr Pro Pro Ala
        595                 600                 605

Leu Asn Gly Asn Pro Pro Arg Pro Ser Leu Glu Pro Glu Glu Pro Lys
    610                 615                 620

Arg Pro Val Pro Ala Glu Arg Gly Ser Ser Ser Gly Thr Pro Lys Leu
625                 630                 635                 640

Ile Gln Arg Ala Leu Leu Arg Gly Thr Ala Leu Leu Ala Ser Leu Gly
                645                 650                 655

Leu Gly Arg Asp Leu Gln Pro Gly Gly Pro Gly Arg Glu Arg Gly
            660                 665                 670

Glu Ser Pro Thr Thr Pro Pro Thr Pro Thr Pro Ala Pro Cys Pro Thr
        675                 680                 685

Glu Pro Pro Ser Pro Leu Ile Cys Phe Ser Leu Lys Thr Pro Asp
    690                 695                 700

Ser Pro Pro Thr Pro Ala Pro Leu Leu Leu Asp Leu Gly Ile Pro Val
705                 710                 715                 720

Gly Gln Arg Ser Ala Lys Ser Pro Arg Arg Glu Glu Glu Pro Arg Gly
                725                 730                 735

Gly Thr Val Ser Pro Pro Gly Thr Ser Arg Ser Ala Pro Gly Thr
            740                 745                 750

Pro Gly Thr Pro Arg Ser Pro Pro Leu Gly Leu Ile Ser Arg Pro Arg
        755                 760                 765

Pro Ser Pro Leu Arg Ser Arg Ile Asp Pro Trp Ser Phe Val Ser Ala
    770                 775                 780

Gly Pro Arg Pro Ser Pro Leu Pro Ser Pro Gln Pro Ala Pro Arg Arg
785                 790                 795                 800

Ala Pro Trp Thr Leu Phe Pro Asp Ser Asp Pro Phe Trp Asp Ser Pro
                805                 810                 815

Pro Ala Asn Pro Phe Gln Gly Gly Pro Gln Asp Cys Arg Ala Gln Thr
            820                 825                 830

Lys Asp Met Gly Ala Gln Ala Pro Trp Val Pro Glu Ala Gly Pro
        835                 840                 845

<210> SEQ ID NO 50
<211> LENGTH: 2549
<212> TYPE: PRT
<213> ORGANISM: Homo Sapiens

<400> SEQUENCE: 50

Met Leu Gly Thr Gly Pro Ala Ala Ala Thr Thr Ala Ala Thr Thr Ser
1               5                   10                  15

Ser Asn Val Ser Val Leu Gln Gln Phe Ala Ser Gly Leu Lys Ser Arg

```
                    20                  25                  30

Asn Glu Glu Thr Arg Ala Lys Ala Ala Lys Glu Leu Gln His Tyr Val
                35                  40                  45

Thr Met Glu Leu Arg Glu Met Ser Gln Glu Glu Ser Thr Arg Phe Tyr
        50                  55                  60

Asp Gln Leu Asn His His Ile Phe Glu Leu Val Ser Ser Ser Asp Ala
 65                  70                  75                  80

Asn Glu Arg Lys Gly Gly Ile Leu Ala Ile Ala Ser Leu Ile Gly Val
                85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
        130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
            195                 200                 205

Ala Val Ala Ala Leu Arg Ala Cys Leu Ile Leu Thr Thr Gln Arg Glu
        210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
        290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Thr Ser Pro Ser Pro Ala
            340                 345                 350

Lys Ser Thr Leu Val Glu Ser Arg Cys Cys Arg Asp Leu Met Glu Glu
        355                 360                 365

Lys Phe Asp Gln Val Cys Gln Trp Val Leu Lys Cys Arg Asn Ser Lys
        370                 375                 380

Asn Ser Leu Ile Gln Met Thr Ile Leu Asn Leu Pro Arg Leu Ala
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445
```

```
Lys Val Tyr Leu Pro Arg Val Leu Asp Ile Ile Arg Ala Ala Leu Pro
    450                 455                 460

Pro Lys Asp Phe Ala His Lys Arg Gln Lys Ala Met Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
                500                 505                 510

Leu Ser Pro Ala Leu Thr Ala Val Leu Tyr Asp Leu Ser Arg Gln Ile
            515                 520                 525

Pro Gln Leu Lys Lys Asp Ile Gln Asp Gly Leu Leu Lys Met Leu Ser
        530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Gly Ser Ile Thr Leu Ala Leu Arg Thr Leu Gly Ser Phe
                580                 585                 590

Glu Phe Glu Gly His Ser Leu Thr Gln Phe Val Arg His Cys Ala Asp
    595                 600                 605

His Phe Leu Asn Ser Glu His Lys Glu Ile Arg Met Glu Ala Ala Arg
    610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
                675                 680                 685

Gln Ala Glu Asn Leu Gln Ala Leu Phe Val Ala Leu Asn Asp Gln Val
            690                 695                 700

Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
                740                 745                 750

Ser Ala Arg Met Leu Gly His Leu Val Ser Asn Ala Pro Arg Leu Ile
            755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Met Asp Met Leu Gln Asp Ser Ser
                820                 825                 830

Leu Leu Ala Lys Arg Gln Val Ala Leu Trp Thr Leu Gly Gln Leu Val
            835                 840                 845

Ala Ser Thr Gly Tyr Val Val Glu Pro Tyr Arg Lys Tyr Pro Thr Leu
    850                 855                 860
```

-continued

```
Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
            885                 890                 895

Tyr Lys His Lys Val Asn Ile Gly Met Ile Asp Gln Ser Arg Asp Ala
            900                 905                 910

Ser Ala Val Ser Leu Ser Glu Ser Lys Ser Ser Gln Asp Ser Ser Asp
            915                 920                 925

Tyr Ser Thr Ser Glu Met Leu Val Asn Met Gly Asn Leu Pro Leu Asp
        930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
            980                 985                 990

Val Met Pro Thr Phe Leu Asn Val Ile Arg Val Cys Asp Gly Ala Ile
            995                 1000                1005

Arg Glu Phe Leu Phe Gln Gln Leu Gly Met Leu Val Ser Phe Val
    1010                1015                1020

Lys Ser His Ile Arg Pro Tyr Met Asp Glu Ile Val Thr Leu Met
    1025                1030                1035

Arg Glu Phe Trp Val Met Asn Thr Ser Ile Gln Ser Thr Ile Ile
    1040                1045                1050

Leu Leu Ile Glu Gln Ile Val Val Ala Leu Gly Gly Glu Phe Lys
    1055                1060                1065

Leu Tyr Leu Pro Gln Leu Ile Pro His Met Leu Arg Val Phe Met
    1070                1075                1080

His Asp Asn Ser Pro Gly Arg Ile Val Ser Ile Lys Leu Leu Ala
    1085                1090                1095

Ala Ile Gln Leu Phe Gly Ala Asn Leu Asp Asp Tyr Leu His Leu
    1100                1105                1110

Leu Leu Pro Pro Ile Val Lys Leu Phe Asp Ala Pro Glu Ala Pro
    1115                1120                1125

Leu Pro Ser Arg Lys Ala Ala Leu Glu Thr Val Asp Arg Leu Thr
    1130                1135                1140

Glu Ser Leu Asp Phe Thr Asp Tyr Ala Ser Arg Ile Ile His Pro
    1145                1150                1155

Ile Val Arg Thr Leu Asp Gln Ser Pro Glu Leu Arg Ser Thr Ala
    1160                1165                1170

Met Asp Thr Leu Ser Ser Leu Val Phe Gln Leu Gly Lys Lys Tyr
    1175                1180                1185

Gln Ile Phe Ile Pro Met Val Asn Lys Val Leu Val Arg His Arg
    1190                1195                1200

Ile Asn His Gln Arg Tyr Asp Val Leu Ile Cys Arg Ile Val Lys
    1205                1210                1215

Gly Tyr Thr Leu Ala Asp Glu Glu Asp Pro Leu Ile Tyr Gln
    1220                1225                1230

His Arg Met Leu Arg Ser Gly Gln Gly Asp Ala Leu Ala Ser Gly
    1235                1240                1245

Pro Val Glu Thr Gly Pro Met Lys Lys Leu His Val Ser Thr Ile
    1250                1255                1260

Asn Leu Gln Lys Ala Trp Gly Ala Ala Arg Arg Val Ser Lys Asp
```

-continued

```
            1265                1270                1275

Asp Trp Leu Glu Trp Leu Arg Arg Leu Ser Leu Glu Leu Leu Lys
        1280                1285                1290

Asp Ser Ser Ser Pro Ser Leu Arg Ser Cys Trp Ala Leu Ala Gln
        1295                1300                1305

Ala Tyr Asn Pro Met Ala Arg Asp Leu Phe Asn Ala Ala Phe Val
        1310                1315                1320

Ser Cys Trp Ser Glu Leu Asn Glu Asp Gln Gln Asp Glu Leu Ile
        1325                1330                1335

Arg Ser Ile Glu Leu Ala Leu Thr Ser Gln Asp Ile Ala Glu Val
        1340                1345                1350

Thr Gln Thr Leu Leu Asn Leu Ala Glu Phe Met Glu His Ser Asp
        1355                1360                1365

Lys Gly Pro Leu Pro Leu Arg Asp Asp Asn Gly Ile Val Leu Leu
        1370                1375                1380

Gly Glu Arg Ala Ala Lys Cys Arg Ala Tyr Ala Lys Ala Leu His
        1385                1390                1395

Tyr Lys Glu Leu Glu Phe Gln Lys Gly Pro Thr Pro Ala Ile Leu
        1400                1405                1410

Glu Ser Leu Ile Ser Ile Asn Asn Lys Leu Gln Gln Pro Glu Ala
        1415                1420                1425

Ala Ala Gly Val Leu Glu Tyr Ala Met Lys His Phe Gly Glu Leu
        1430                1435                1440

Glu Ile Gln Ala Thr Trp Tyr Glu Lys Leu His Glu Trp Glu Asp
        1445                1450                1455

Ala Leu Val Ala Tyr Asp Lys Lys Met Asp Thr Asn Lys Asp Asp
        1460                1465                1470

Pro Glu Leu Met Leu Gly Arg Met Arg Cys Leu Glu Ala Leu Gly
        1475                1480                1485

Glu Trp Gly Gln Leu His Gln Gln Cys Cys Glu Lys Trp Thr Leu
        1490                1495                1500

Val Asn Asp Glu Thr Gln Ala Lys Met Ala Arg Met Ala Ala Ala
        1505                1510                1515

Ala Ala Trp Gly Leu Gly Gln Trp Asp Ser Met Glu Glu Tyr Thr
        1520                1525                1530

Cys Met Ile Pro Arg Asp Thr His Asp Gly Ala Phe Tyr Arg Ala
        1535                1540                1545

Val Leu Ala Leu His Gln Asp Leu Phe Ser Leu Ala Gln Gln Cys
        1550                1555                1560

Ile Asp Lys Ala Arg Asp Leu Leu Asp Ala Glu Leu Thr Ala Met
        1565                1570                1575

Ala Gly Glu Ser Tyr Ser Arg Ala Tyr Gly Ala Met Val Ser Cys
        1580                1585                1590

His Met Leu Ser Glu Leu Glu Glu Val Ile Gln Tyr Lys Leu Val
        1595                1600                1605

Pro Glu Arg Arg Glu Ile Ile Arg Gln Ile Trp Trp Glu Arg Leu
        1610                1615                1620

Gln Gly Cys Gln Arg Ile Val Glu Asp Trp Gln Lys Ile Leu Met
        1625                1630                1635

Val Arg Ser Leu Val Val Ser Pro His Glu Asp Met Arg Thr Trp
        1640                1645                1650

Leu Lys Tyr Ala Ser Leu Cys Gly Lys Ser Gly Arg Leu Ala Leu
        1655                1660                1665
```

```
Ala His Lys Thr Leu Val Leu Leu Leu Gly Val Asp Pro Ser Arg
    1670            1675                1680

Gln Leu Asp His Pro Leu Pro Thr Val His Pro Gln Val Thr Tyr
    1685            1690                1695

Ala Tyr Met Lys Asn Met Trp Lys Ser Ala Arg Lys Ile Asp Ala
    1700            1705                1710

Phe Gln His Met Gln His Phe Val Gln Thr Met Gln Gln Gln Ala
    1715            1720                1725

Gln His Ala Ile Ala Thr Glu Asp Gln Gln His Lys Gln Glu Leu
    1730            1735                1740

His Lys Leu Met Ala Arg Cys Phe Leu Lys Leu Gly Glu Trp Gln
    1745            1750                1755

Leu Asn Leu Gln Gly Ile Asn Glu Ser Thr Ile Pro Lys Val Leu
    1760            1765                1770

Gln Tyr Tyr Ser Ala Ala Thr Glu His Asp Arg Ser Trp Tyr Lys
    1775            1780                1785

Ala Trp His Ala Trp Ala Val Met Asn Phe Glu Ala Val Leu His
    1790            1795                1800

Tyr Lys His Gln Asn Gln Ala Arg Asp Glu Lys Lys Lys Leu Arg
    1805            1810                1815

His Ala Ser Gly Ala Asn Ile Thr Asn Ala Thr Thr Ala Ala Thr
    1820            1825                1830

Thr Ala Ala Thr Ala Thr Thr Thr Ala Ser Thr Glu Gly Ser Asn
    1835            1840                1845

Ser Glu Ser Glu Ala Glu Ser Thr Glu Asn Ser Pro Thr Pro Ser
    1850            1855                1860

Pro Leu Gln Lys Lys Val Thr Glu Asp Leu Ser Lys Thr Leu Leu
    1865            1870                1875

Met Tyr Thr Val Pro Ala Val Gln Gly Phe Phe Arg Ser Ile Ser
    1880            1885                1890

Leu Ser Arg Gly Asn Asn Leu Gln Asp Thr Leu Arg Val Leu Thr
    1895            1900                1905

Leu Trp Phe Asp Tyr Gly His Trp Pro Asp Val Asn Glu Ala Leu
    1910            1915                1920

Val Glu Gly Val Lys Ala Ile Gln Ile Asp Thr Trp Leu Gln Val
    1925            1930                1935

Ile Pro Gln Leu Ile Ala Arg Ile Asp Thr Pro Arg Pro Leu Val
    1940            1945                1950

Gly Arg Leu Ile His Gln Leu Leu Thr Asp Ile Gly Arg Tyr His
    1955            1960                1965

Pro Gln Ala Leu Ile Tyr Pro Leu Thr Val Ala Ser Lys Ser Thr
    1970            1975                1980

Thr Thr Ala Arg His Asn Ala Ala Asn Lys Ile Leu Lys Asn Met
    1985            1990                1995

Cys Glu His Ser Asn Thr Leu Val Gln Gln Ala Met Met Val Ser
    2000            2005                2010

Glu Glu Leu Ile Arg Val Ala Ile Leu Trp His Glu Met Trp His
    2015            2020                2025

Glu Gly Leu Glu Glu Ala Ser Arg Leu Tyr Phe Gly Glu Arg Asn
    2030            2035                2040

Val Lys Gly Met Phe Glu Val Leu Glu Pro Leu His Ala Met Met
    2045            2050                2055
```

```
Glu Arg Gly Pro Gln Thr Leu Lys Glu Thr Ser Phe Asn Gln Ala
    2060                2065                2070

Tyr Gly Arg Asp Leu Met Glu Ala Gln Glu Trp Cys Arg Lys Tyr
2075                2080                2085

Met Lys Ser Gly Asn Val Lys Asp Leu Thr Gln Ala Trp Asp Leu
2090                2095                2100

Tyr Tyr His Val Phe Arg Arg Ile Ser Lys Gln Leu Pro Gln Leu
2105                2110                2115

Thr Ser Leu Glu Leu Gln Tyr Val Ser Pro Lys Leu Leu Met Cys
2120                2125                2130

Arg Asp Leu Glu Leu Ala Val Pro Gly Thr Tyr Asp Pro Asn Gln
2135                2140                2145

Pro Ile Ile Arg Ile Gln Ser Ile Ala Pro Ser Leu Gln Val Ile
2150                2155                2160

Thr Ser Lys Gln Arg Pro Arg Lys Leu Thr Leu Met Gly Ser Asn
2165                2170                2175

Gly His Glu Phe Val Phe Leu Leu Lys Gly His Glu Asp Leu Arg
2180                2185                2190

Gln Asp Glu Arg Val Met Gln Leu Phe Gly Leu Val Asn Thr Leu
2195                2200                2205

Leu Ala Asn Asp Pro Thr Ser Leu Arg Lys Asn Leu Ser Ile Gln
2210                2215                2220

Arg Tyr Ala Val Ile Pro Leu Ser Thr Asn Ser Gly Leu Ile Gly
2225                2230                2235

Trp Val Pro His Cys Asp Thr Leu His Ala Leu Ile Arg Asp Tyr
2240                2245                2250

Arg Glu Lys Lys Lys Ile Leu Leu Asn Ile Glu His Arg Ile Met
2255                2260                2265

Leu Arg Met Ala Pro Asp Tyr Asp His Leu Thr Leu Met Gln Lys
2270                2275                2280

Val Glu Val Phe Glu His Ala Val Asn Asn Thr Ala Gly Asp Asp
2285                2290                2295

Leu Ala Lys Leu Leu Trp Leu Lys Ser Pro Ser Ser Glu Val Trp
2300                2305                2310

Phe Asp Arg Arg Thr Asn Tyr Thr Arg Ser Leu Ala Val Met Ser
2315                2320                2325

Met Val Gly Tyr Ile Leu Gly Leu Gly Asp Arg His Pro Ser Asn
2330                2335                2340

Leu Met Leu Asp Arg Leu Ser Gly Lys Ile Leu His Ile Asp Phe
2345                2350                2355

Gly Asp Cys Phe Glu Val Ala Met Thr Arg Glu Lys Phe Pro Glu
2360                2365                2370

Lys Ile Pro Phe Arg Leu Thr Arg Met Leu Thr Asn Ala Met Glu
2375                2380                2385

Val Thr Gly Leu Asp Gly Asn Tyr Arg Ile Thr Cys His Thr Val
2390                2395                2400

Met Glu Val Leu Arg Glu His Lys Asp Ser Val Met Ala Val Leu
2405                2410                2415

Glu Ala Phe Val Tyr Asp Pro Leu Leu Asn Trp Arg Leu Met Asp
2420                2425                2430

Thr Asn Thr Lys Gly Asn Lys Arg Ser Arg Thr Arg Thr Asp Ser
2435                2440                2445

Tyr Ser Ala Gly Gln Ser Val Glu Ile Leu Asp Gly Val Glu Leu
```

```
              2450                2455                2460
Gly Glu Pro Ala His Lys Lys Thr Gly Thr Thr Val Pro Glu Ser
        2465                2470                2475

Ile His Ser Phe Ile Gly Asp Gly Leu Val Lys Pro Glu Ala Leu
        2480                2485                2490

Asn Lys Lys Ala Ile Gln Ile Ile Asn Arg Val Arg Asp Lys Leu
        2495                2500                2505

Thr Gly Arg Asp Phe Ser His Asp Asp Thr Leu Asp Val Pro Thr
        2510                2515                2520

Gln Val Glu Leu Leu Ile Lys Gln Ala Thr Ser His Glu Asn Leu
        2525                2530                2535

Cys Gln Cys Tyr Ile Gly Trp Cys Pro Phe Trp
        2540                2545

<210> SEQ ID NO 51
<211> LENGTH: 1462
<212> TYPE: PRT
<213> ORGANISM: Homo Sapiens

<400> SEQUENCE: 51

Met Gly Ala Gln Asp Arg Pro Gln Cys His Phe Asp Ile Glu Ile Asn
1               5                   10                  15

Arg Glu Pro Val Gly Arg Ile Met Phe Gln Leu Phe Ser Asp Ile Cys
            20                  25                  30

Pro Lys Thr Cys Lys Asn Phe Leu Cys Leu Cys Ser Gly Glu Lys Gly
        35                  40                  45

Leu Gly Lys Thr Thr Gly Lys Lys Leu Cys Tyr Lys Gly Ser Thr Phe
    50                  55                  60

His Arg Val Val Lys Asn Phe Met Ile Gln Gly Gly Asp Phe Ser Glu
65                  70                  75                  80

Gly Asn Gly Lys Gly Gly Glu Ser Ile Tyr Gly Gly Tyr Phe Lys Asp
                85                  90                  95

Glu Asn Phe Ile Leu Lys His Asp Arg Ala Phe Leu Leu Ser Met Ala
            100                 105                 110

Asn Arg Gly Lys His Thr Asn Gly Ser Gln Phe Phe Ile Thr Thr Lys
        115                 120                 125

Pro Ala Pro His Leu Asp Gly His Val Val Phe Gly Leu Val Ile
    130                 135                 140

Ser Gly Phe Glu Val Ile Glu Gln Ile Glu Asn Leu Lys Thr Asp Ala
145                 150                 155                 160

Ala Ser Arg Pro Tyr Ala Asp Val Arg Val Ile Asp Cys Gly Val Leu
                165                 170                 175

Ala Thr Lys Ser Ile Lys Asp Val Phe Glu Lys Arg Lys Lys Pro
            180                 185                 190

Thr His Ser Glu Gly Ser Asp Ser Ser Asn Ser Ser Ser Ser
        195                 200                 205

Glu Ser Ser Ser Glu Ser Glu Leu Glu His Glu Arg Ser Arg Arg Arg
    210                 215                 220

Lys His Lys Arg Arg Pro Lys Val Lys Arg Ser Lys Lys Arg Arg Lys
225                 230                 235                 240

Glu Ala Ser Ser Glu Glu Pro Arg Asn Lys His Ala Met Asn Pro
                245                 250                 255

Lys Gly His Ser Glu Arg Ser Asp Thr Asn Glu Lys Arg Ser Val Asp
            260                 265                 270
```

```
Ser Ser Ala Lys Arg Glu Lys Pro Val Val Arg Pro Glu Ile Pro
        275                 280                 285
Pro Val Pro Glu Asn Arg Phe Leu Leu Arg Arg Asp Met Pro Val Val
        290                 295                 300
Thr Ala Glu Pro Glu Pro Lys Ile Pro Asp Val Ala Pro Ile Val Ser
305                 310                 315                 320
Asp Gln Lys Pro Ser Val Ser Lys Ser Gly Arg Lys Ile Lys Gly Arg
                325                 330                 335
Gly Thr Ile Arg Tyr His Thr Pro Arg Ser Arg Ser Cys Ser Glu
                340                 345                 350
Ser Asp Asp Asp Ser Ser Glu Thr Pro Pro His Trp Lys Glu Glu
        355                 360                 365
Met Gln Arg Leu Arg Ala Tyr Arg Pro Pro Ser Gly Glu Lys Trp Ser
        370                 375                 380
Lys Gly Asp Lys Leu Ser Asp Pro Cys Ser Ser Arg Trp Asp Glu Arg
385                 390                 395                 400
Ser Leu Ser Gln Arg Ser Arg Ser Trp Ser Tyr Asn Gly Tyr Tyr Ser
                405                 410                 415
Asp Leu Ser Thr Ala Arg His Ser Gly His Lys Arg Arg Lys
                420                 425                 430
Glu Lys Lys Val Lys His Lys Lys Gly Lys Lys Gln Lys His Cys
        435                 440                 445
Arg Arg His Lys Gln Thr Lys Lys Arg Ile Leu Ile Pro Ser Asp
        450                 455                 460
Ile Glu Ser Ser Lys Ser Ser Thr Arg Arg Met Lys Ser Ser Cys Asp
465                 470                 475                 480
Arg Glu Arg Ser Ser Arg Ser Ser Ser Leu Ser Ser His His Ser Ser
                485                 490                 495
Lys Arg Asp Trp Ser Lys Ser Asp Lys Asp Val Gln Ser Ser Leu Thr
                500                 505                 510
His Ser Ser Arg Asp Ser Tyr Arg Ser Lys Ser His Ser Gln Ser Tyr
        515                 520                 525
Ser Arg Gly Ser Ser Arg Ser Arg Thr Ala Ser Lys Ser Ser Ser His
530                 535                 540
Ser Arg Ser Arg Ser Lys Ser Arg Ser Ser Lys Ser Gly His Arg
545                 550                 555                 560
Lys Arg Ala Ser Lys Ser Pro Arg Lys Thr Ala Ser Gln Leu Ser Glu
                565                 570                 575
Asn Lys Pro Val Lys Thr Glu Pro Leu Arg Ala Thr Met Ala Gln Asn
                580                 585                 590
Glu Asn Val Val Val Gln Pro Val Ala Glu Asn Ile Pro Val Ile
        595                 600                 605
Pro Leu Ser Asp Ser Pro Pro Ser Arg Trp Lys Pro Gly Gln Lys
        610                 615                 620
Pro Trp Lys Pro Ser Tyr Glu Arg Ile Gln Glu Met Lys Ala Lys Thr
625                 630                 635                 640
Thr His Leu Leu Pro Ile Gln Ser Thr Tyr Ser Leu Ala Asn Ile Lys
                645                 650                 655
Glu Thr Gly Ser Ser Ser Tyr His Lys Arg Glu Lys Asn Ser Glu
                660                 665                 670
Ser Asp Gln Ser Thr Tyr Ser Lys Tyr Ser Asp Arg Ser Ser Glu Ser
        675                 680                 685
Ser Pro Arg Ser Arg Ser Arg Ser Ser Arg Ser Arg Ser Tyr Ser Arg
```

```
              690                 695                 700
Ser Tyr Thr Arg Ser Arg Ser Leu Ala Ser Ser His Ser Arg Ser Arg
705                 710                 715                 720

Ser Pro Ser Ser Arg Ser His Ser Arg Asn Lys Tyr Ser Asp His Ser
                    725                 730                 735

Gln Cys Ser Arg Ser Ser Tyr Thr Ser Ile Ser Ser Asp Asp Gly
                740                 745                 750

Arg Arg Ala Lys Arg Arg Leu Arg Ser Ser Gly Lys Lys Asn Ser Val
                755                 760                 765

Ser His Lys Lys His Ser Ser Ser Glu Lys Thr Leu His Ser Lys
770                 775                 780

Tyr Val Lys Gly Arg Asp Arg Ser Ser Cys Val Arg Lys Tyr Ser Glu
785                 790                 795                 800

Ser Arg Ser Ser Leu Asp Tyr Ser Asp Ser Glu Gln Ser Ser Val
                805                 810                 815

Gln Ala Thr Gln Ser Ala Gln Glu Lys Glu Lys Gln Gly Gln Met Glu
                820                 825                 830

Arg Thr His Asn Lys Gln Glu Lys Asn Arg Gly Glu Glu Lys Ser Lys
                835                 840                 845

Ser Glu Arg Glu Cys Pro His Ser Lys Lys Arg Thr Leu Lys Glu Asn
850                 855                 860

Leu Ser Asp His Leu Arg Asn Gly Ser Lys Pro Lys Arg Lys Asn Tyr
865                 870                 875                 880

Ala Gly Ser Lys Trp Asp Ser Glu Ser Asn Ser Glu Arg Asp Val Thr
                885                 890                 895

Lys Asn Ser Lys Asn Asp Ser His Pro Ser Ser Asp Lys Glu Glu Gly
                900                 905                 910

Glu Ala Thr Ser Asp Ser Glu Ser Glu Val Ser Glu Ile His Ile Lys
                915                 920                 925

Val Lys Pro Thr Thr Lys Ser Ser Thr Asn Thr Ser Leu Pro Asp Asp
                930                 935                 940

Asn Gly Ala Trp Lys Ser Ser Lys Gln Arg Gly Thr Ser Asp Ser
945                 950                 955                 960

Glu Gly Ser Cys Ser Asn Ser Glu Asn Asn Arg Gly Lys Pro Gln Lys
                965                 970                 975

His Lys His Gly Ser Lys Glu Asn Leu Lys Arg Glu His Thr Lys Lys
                980                 985                 990

Val Lys Glu Lys Leu Lys Gly Lys  Lys Asp Lys Lys His  Lys Ala Pro
                995                 1000                1005

Lys Arg  Lys Gln Ala Phe His  Trp Gln Pro Leu  Glu Phe Gly
    1010                1015                1020

Glu Glu  Glu Glu Glu Ile  Asp Asp Lys Gln Val  Thr Gln Glu
    1025                1030                1035

Ser Lys  Glu Lys Lys Val  Ser Glu Asn Asn Glu  Thr Ile Lys Asp
    1040                1045                1050

Asn Ile  Leu Lys Thr Glu  Lys Ser Ser Glu Glu  Asp Leu Ser Gly
    1055                1060                1065

Lys His  Asp Thr Val Thr  Val Ser Ser Asp Leu Asp  Gln Phe Thr
    1070                1075                1080

Lys Asp  Asp Ser Lys Leu Ser  Ile Ser Pro Thr Ala  Leu Asn Thr
    1085                1090                1095

Glu Glu  Asn Val Ala Cys Leu  Gln Asn Ile Gln His  Val Glu Glu
    1100                1105                1110
```

-continued

Ser Val Pro Asn Gly Val Glu Asp Val Leu Gln Thr Asp Asp Asn
1115                1120                1125

Met Glu Ile Cys Thr Pro Asp Arg Ser Pro Ala Lys Val Glu
1130                1135                1140

Glu Thr Ser Pro Leu Gly Asn Ala Arg Leu Asp Thr Pro Asp Ile
1145                1150                1155

Asn Ile Val Leu Lys Gln Asp Met Ala Thr Glu His Pro Gln Ala
1160                1165                1170

Glu Val Val Lys Gln Glu Ser Ser Met Ser Glu Ser Lys Val Leu
1175                1180                1185

Gly Glu Val Gly Lys Gln Asp Ser Ser Ala Ser Leu Ala Ser
1190                1195                1200

Ala Gly Glu Ser Thr Gly Lys Lys Glu Val Ala Glu Lys Ser Gln
1205                1210                1215

Ile Asn Leu Ile Asp Lys Lys Trp Lys Pro Leu Gln Gly Val Gly
1220                1225                1230

Asn Leu Ala Ala Pro Asn Ala Ala Thr Ser Ser Ala Val Glu Val
1235                1240                1245

Lys Val Leu Thr Thr Val Pro Glu Met Lys Pro Gln Gly Leu Arg
1250                1255                1260

Ile Glu Ile Lys Ser Lys Asn Lys Val Arg Pro Gly Ser Leu Phe
1265                1270                1275

Asp Glu Val Arg Lys Thr Ala Arg Leu Asn Arg Arg Pro Arg Asn
1280                1285                1290

Gln Glu Ser Ser Ser Asp Glu Gln Thr Pro Ser Arg Asp Asp Asp
1295                1300                1305

Ser Gln Ser Arg Ser Pro Ser Arg Ser Arg Ser Lys Ser Glu Thr
1310                1315                1320

Lys Ser Arg His Arg Thr Arg Ser Val Ser Tyr Ser His Ser Arg
1325                1330                1335

Ser Arg Ser Arg Ser Ser Thr Ser Ser Tyr Arg Ser Arg Ser Tyr
1340                1345                1350

Ser Arg Ser Arg Ser Arg Gly Trp Tyr Ser Arg Gly Arg Thr Arg
1355                1360                1365

Ser Arg Ser Ser Ser Tyr Arg Ser Tyr Lys Ser His Arg Thr Ser
1370                1375                1380

Ser Arg Ser Arg Ser Arg Ser Ser Tyr Asp Pro His Ser Arg
1385                1390                1395

Ser Arg Ser Tyr Thr Tyr Asp Ser Tyr Tyr Ser Arg Ser Arg Ser
1400                1405                1410

Arg Ser Arg Ser Gln Arg Ser Asp Ser Tyr His Arg Gly Arg Ser
1415                1420                1425

Tyr Asn Arg Arg Ser Arg Ser Cys Arg Ser Tyr Gly Ser Asp Ser
1430                1435                1440

Glu Ser Asp Arg Ser Tyr Ser His His Arg Ser Pro Ser Glu Ser
1445                1450                1455

Ser Arg Tyr Ser
1460

<210> SEQ ID NO 52
<211> LENGTH: 598
<212> TYPE: PRT
<213> ORGANISM: Homo Sapiens

<400> SEQUENCE: 52

```
Met Pro Cys Ile Gln Ala Gln Tyr Gly Thr Pro Ala Pro Ser Pro Gly
1               5                   10                  15

Pro Arg Asp His Leu Ala Ser Asp Pro Leu Thr Pro Glu Phe Ile Lys
            20                  25                  30

Pro Thr Met Asp Leu Ala Ser Pro Glu Ala Pro Ala Ala Pro Ala Thr
        35                  40                  45

Ala Leu Pro Ser Phe Ser Thr Phe Met Asp Gly Tyr Thr Gly Glu Phe
    50                  55                  60

Asp Thr Phe Leu Tyr Gln Leu Pro Gly Thr Val Gln Pro Cys Ser Ser
65                  70                  75                  80

Ala Ser Ser Ser Ala Ser Ser Thr Ser Ser Ser Ala Thr Ser Pro
                85                  90                  95

Ala Ser Ala Ser Phe Lys Phe Glu Asp Phe Gln Val Tyr Gly Cys Tyr
                100                 105                 110

Pro Gly Pro Leu Ser Gly Pro Val Asp Glu Ala Leu Ser Ser Ser Gly
            115                 120                 125

Ser Asp Tyr Tyr Gly Ser Pro Cys Ser Ala Pro Ser Pro Ser Thr Pro
    130                 135                 140

Ser Phe Gln Pro Pro Gln Leu Ser Pro Trp Asp Gly Ser Phe Gly His
145                 150                 155                 160

Phe Ser Pro Ser Gln Thr Tyr Glu Gly Leu Arg Ala Trp Thr Glu Gln
                165                 170                 175

Leu Pro Lys Ala Ser Gly Pro Pro Gln Pro Pro Ala Phe Phe Ser Phe
            180                 185                 190

Ser Pro Pro Thr Gly Pro Ser Pro Ser Leu Ala Gln Ser Pro Leu Lys
        195                 200                 205

Leu Phe Pro Ser Gln Ala Thr His Gln Leu Gly Glu Gly Glu Ser Tyr
    210                 215                 220

Ser Met Pro Thr Ala Phe Pro Gly Leu Ala Pro Thr Ser Pro His Leu
225                 230                 235                 240

Glu Gly Ser Gly Ile Leu Asp Thr Pro Val Thr Ser Thr Lys Ala Arg
                245                 250                 255

Ser Gly Ala Pro Gly Gly Ser Glu Gly Arg Cys Ala Val Cys Gly Asp
            260                 265                 270

Asn Ala Ser Cys Gln His Tyr Gly Val Arg Thr Cys Glu Gly Cys Lys
        275                 280                 285

Gly Phe Phe Lys Arg Thr Val Gln Lys Asn Ala Lys Tyr Ile Cys Leu
    290                 295                 300

Ala Asn Lys Asp Cys Pro Val Asp Lys Arg Arg Arg Asn Arg Cys Gln
305                 310                 315                 320

Phe Cys Arg Phe Gln Lys Cys Leu Ala Val Gly Met Val Lys Glu Val
                325                 330                 335

Val Arg Thr Asp Ser Leu Lys Gly Arg Arg Gly Arg Leu Pro Ser Lys
            340                 345                 350

Pro Lys Gln Pro Pro Asp Ala Ser Pro Ala Asn Leu Leu Thr Ser Leu
        355                 360                 365

Val Arg Ala His Leu Asp Ser Gly Pro Ser Thr Ala Lys Leu Asp Tyr
    370                 375                 380

Ser Lys Phe Gln Glu Leu Val Leu Pro His Phe Gly Lys Glu Asp Ala
385                 390                 395                 400

Gly Asp Val Gln Gln Phe Tyr Asp Leu Leu Ser Gly Ser Leu Glu Val
                405                 410                 415
```

```
Ile Arg Lys Trp Ala Glu Lys Ile Pro Gly Phe Ala Glu Leu Ser Pro
            420                 425                 430

Ala Asp Gln Asp Leu Leu Glu Ser Ala Phe Leu Glu Leu Phe Ile
            435                 440                 445

Leu Arg Leu Ala Tyr Arg Ser Lys Pro Gly Glu Gly Lys Leu Ile Phe
450                 455                 460

Cys Ser Gly Leu Val Leu His Arg Leu Gln Cys Ala Arg Gly Phe Gly
465                 470                 475                 480

Asp Trp Ile Asp Ser Ile Leu Ala Phe Ser Arg Ser Leu His Ser Leu
                485                 490                 495

Leu Val Asp Val Pro Ala Phe Ala Cys Leu Ser Ala Leu Val Leu Ile
            500                 505                 510

Thr Asp Arg His Gly Leu Gln Glu Pro Arg Arg Val Glu Glu Leu Gln
            515                 520                 525

Asn Arg Ile Ala Ser Cys Leu Lys Glu His Val Ala Ala Val Ala Gly
            530                 535                 540

Glu Pro Gln Pro Ala Ser Cys Leu Ser Arg Leu Leu Gly Lys Leu Pro
545                 550                 555                 560

Glu Leu Arg Thr Leu Cys Thr Gln Gly Leu Gln Arg Ile Phe Tyr Leu
                565                 570                 575

Lys Leu Glu Asp Leu Val Pro Pro Pro Ile Ile Asp Lys Ile Phe
            580                 585                 590

Met Asp Thr Leu Pro Phe
            595

<210> SEQ ID NO 53
<211> LENGTH: 164
<212> TYPE: PRT
<213> ORGANISM: Homo Sapiens

<400> SEQUENCE: 53

Met Ser Glu Pro Ala Gly Asp Val Arg Gln Asn Pro Cys Gly Ser Lys
1               5                   10                  15

Ala Cys Arg Arg Leu Phe Gly Pro Val Asp Ser Glu Gln Leu Ser Arg
            20                  25                  30

Asp Cys Asp Ala Leu Met Ala Gly Cys Ile Gln Glu Ala Arg Glu Arg
        35                  40                  45

Trp Asn Phe Asp Phe Val Thr Glu Thr Pro Leu Glu Gly Asp Phe Ala
    50                  55                  60

Trp Glu Arg Val Arg Gly Leu Gly Leu Pro Lys Leu Tyr Leu Pro Thr
65                  70                  75                  80

Gly Pro Arg Arg Gly Arg Asp Glu Leu Gly Gly Arg Arg Pro Gly
                85                  90                  95

Thr Ser Pro Ala Leu Leu Gln Gly Thr Ala Glu Glu Asp His Val Asp
            100                 105                 110

Leu Ser Leu Ser Cys Thr Leu Val Pro Arg Ser Gly Glu Gln Ala Glu
        115                 120                 125

Gly Ser Pro Gly Gly Pro Gly Asp Ser Gln Gly Arg Lys Arg Arg Gln
    130                 135                 140

Thr Ser Met Thr Asp Phe Tyr His Ser Lys Arg Arg Leu Ile Phe Ser
145                 150                 155                 160

Lys Arg Lys Pro

<210> SEQ ID NO 54
```

<211> LENGTH: 198
<212> TYPE: PRT
<213> ORGANISM: Homo Sapiens

<400> SEQUENCE: 54

Met Ser Asn Val Arg Val Ser Asn Gly Ser Pro Ser Leu Glu Arg Met
1               5                   10                  15

Asp Ala Arg Gln Ala Glu His Pro Lys Pro Ser Ala Cys Arg Asn Leu
            20                  25                  30

Phe Gly Pro Val Asp His Glu Leu Thr Arg Asp Leu Glu Lys His
        35                  40                  45

Cys Arg Asp Met Glu Glu Ala Ser Gln Arg Lys Trp Asn Phe Asp Phe
50                  55                  60

Gln Asn His Lys Pro Leu Glu Gly Lys Tyr Glu Trp Gln Glu Val Glu
65                  70                  75                  80

Lys Gly Ser Leu Pro Glu Phe Tyr Tyr Arg Pro Arg Pro Pro Lys
                85                  90                  95

Gly Ala Cys Lys Val Pro Ala Gln Glu Ser Gln Asp Val Ser Gly Ser
            100                 105                 110

Arg Pro Ala Ala Pro Leu Ile Gly Ala Pro Ala Asn Ser Glu Asp Thr
        115                 120                 125

His Leu Val Asp Pro Lys Thr Asp Pro Ser Asp Ser Gln Thr Gly Leu
130                 135                 140

Ala Glu Gln Cys Ala Gly Ile Arg Lys Arg Pro Ala Thr Asp Asp Ser
145                 150                 155                 160

Ser Thr Gln Asn Lys Arg Ala Asn Arg Thr Glu Glu Asn Val Ser Asp
                165                 170                 175

Gly Ser Pro Asn Ala Gly Ser Val Glu Gln Thr Pro Lys Lys Pro Gly
            180                 185                 190

Leu Arg Arg Arg Gln Thr
        195

<210> SEQ ID NO 55
<211> LENGTH: 390
<212> TYPE: PRT
<213> ORGANISM: Homo Sapiens

<400> SEQUENCE: 55

Met Gly Asp Thr Phe Ile Arg His Ile Ala Leu Leu Gly Phe Glu Lys
1               5                   10                  15

Arg Phe Val Pro Ser Gln His Tyr Val Tyr Met Phe Leu Val Lys Trp
            20                  25                  30

Gln Asp Leu Ser Glu Lys Val Val Tyr Arg Arg Phe Thr Glu Ile Tyr
        35                  40                  45

Glu Phe His Lys Thr Leu Lys Glu Met Phe Pro Ile Glu Ala Gly Ala
50                  55                  60

Ile Asn Pro Glu Asn Arg Ile Ile Pro His Leu Pro Ala Pro Lys Trp
65                  70                  75                  80

Phe Asp Gly Gln Arg Ala Ala Glu Asn Arg Gln Gly Thr Leu Thr Glu
                85                  90                  95

Tyr Cys Ser Thr Leu Met Ser Leu Pro Thr Lys Ile Ser Arg Cys Pro
            100                 105                 110

His Leu Leu Asp Phe Phe Lys Val Arg Pro Asp Asp Leu Lys Leu Pro
        115                 120                 125

Thr Asp Asn Gln Thr Lys Lys Pro Glu Thr Tyr Leu Met Pro Lys Asp
130                 135                 140

```
Gly Lys Ser Thr Ala Thr Asp Ile Thr Gly Pro Ile Ile Leu Gln Ser
145                 150                 155                 160

Tyr Arg Ala Ile Ala Asn Tyr Glu Lys Thr Ser Gly Ser Glu Met Ala
                165                 170                 175

Leu Ser Thr Gly Asp Val Val Glu Val Val Glu Lys Ser Glu Ser Gly
            180                 185                 190

Trp Trp Phe Cys Gln Met Lys Ala Lys Arg Gly Trp Ile Pro Ala Ser
        195                 200                 205

Phe Leu Glu Pro Leu Asp Ser Pro Asp Glu Thr Glu Asp Pro Glu Pro
    210                 215                 220

Asn Tyr Ala Gly Glu Pro Tyr Val Ala Ile Lys Ala Tyr Thr Ala Val
225                 230                 235                 240

Glu Gly Asp Glu Val Ser Leu Leu Glu Gly Glu Ala Val Glu Val Ile
                245                 250                 255

His Lys Leu Leu Asp Gly Trp Trp Val Ile Arg Lys Asp Asp Val Thr
            260                 265                 270

Gly Tyr Phe Pro Ser Met Tyr Leu Gln Lys Ser Gly Gln Asp Val Ser
        275                 280                 285

Gln Ala Gln Arg Gln Ile Lys Arg Gly Ala Pro Pro Arg Arg Ser Ser
    290                 295                 300

Ile Arg Asn Val His Ser Ile His Gln Arg Ser Arg Lys Arg Leu Ser
305                 310                 315                 320

Gln Asp Ala Tyr Arg Arg Asn Ser Val Arg Phe Leu Gln Gln Arg Arg
                325                 330                 335

Arg Gln Ala Arg Pro Gly Pro Gln Ser Pro Gly Ser Pro Leu Glu Glu
            340                 345                 350

Glu Arg Gln Thr Gln Arg Ser Lys Pro Gln Pro Ala Val Pro Pro Arg
        355                 360                 365

Pro Ser Ala Asp Leu Ile Leu Asn Arg Cys Ser Glu Ser Thr Lys Arg
    370                 375                 380

Lys Leu Ala Ser Ala Val
385                 390

<210> SEQ ID NO 56
<211> LENGTH: 130
<212> TYPE: PRT
<213> ORGANISM: Homo Sapiens

<400> SEQUENCE: 56

Met Ala Glu Tyr Gly Thr Leu Leu Gln Asp Leu Thr Asn Asn Ile Thr
1               5                   10                  15

Leu Glu Asp Leu Glu Gln Leu Lys Ser Ala Cys Lys Glu Asp Ile Pro
            20                  25                  30

Ser Glu Lys Ser Glu Glu Ile Thr Thr Gly Ser Ala Trp Phe Ser Phe
        35                  40                  45

Leu Glu Ser His Asn Lys Leu Asp Lys Asp Asn Leu Ser Tyr Ile Glu
    50                  55                  60

His Ile Phe Glu Ile Ser Arg Arg Pro Asp Leu Leu Thr Met Val Val
65                  70                  75                  80

Asp Tyr Arg Thr Arg Val Leu Lys Ile Ser Glu Asp Glu Leu Asp
                85                  90                  95

Thr Lys Leu Thr Arg Ile Pro Ser Ala Lys Lys Tyr Lys Asp Ile Ile
            100                 105                 110

Arg Gln Pro Ser Glu Glu Glu Ile Ile Lys Leu Ala Pro Pro Pro Lys
```

-continued

```
                115                 120                 125
Lys Ala
    130

<210> SEQ ID NO 57
<211> LENGTH: 291
<212> TYPE: PRT
<213> ORGANISM: Homo Sapiens

<400> SEQUENCE: 57

Met Ser Cys Gln Ala Phe Thr Ser Ala Asp Thr Phe Ile Pro Leu Asn
1               5                   10                  15

Ser Asp Ala Ser Ala Thr Leu Pro Leu Ile Met His His Ser Ala Ala
            20                  25                  30

Glu Cys Leu Pro Val Ser Asn His Ala Thr Asn Val Met Ser Thr Ala
        35                  40                  45

Thr Gly Leu His Tyr Ser Val Pro Ser Cys His Tyr Gly Asn Gln Pro
    50                  55                  60

Ser Thr Tyr Gly Val Met Ala Gly Ser Leu Thr Pro Cys Leu Tyr Lys
65                  70                  75                  80

Phe Pro Asp His Thr Leu Ser His Gly Phe Pro Ile His Gln Pro
                85                  90                  95

Leu Leu Ala Glu Asp Pro Thr Ala Ala Asp Phe Lys Gln Glu Leu Arg
            100                 105                 110

Arg Lys Ser Lys Leu Val Glu Glu Pro Ile Asp Met Asp Ser Pro Glu
        115                 120                 125

Ile Arg Glu Leu Glu Lys Phe Ala Asn Glu Phe Lys Val Arg Arg Ile
    130                 135                 140

Lys Leu Gly Tyr Thr Gln Thr Asn Val Gly Glu Ala Leu Ala Ala Val
145                 150                 155                 160

His Gly Ser Glu Phe Ser Gln Thr Thr Ile Cys Arg Phe Glu Asn Leu
                165                 170                 175

Gln Leu Ser Phe Lys Asn Ala Cys Lys Leu Lys Ala Ile Leu Ser Lys
            180                 185                 190

Trp Leu Glu Glu Ala Glu Gln Val Gly Ala Leu Tyr Asn Glu Lys Val
        195                 200                 205

Gly Ala Asn Glu Arg Lys Arg Lys Arg Thr Thr Ile Ser Ile Ala
    210                 215                 220

Ala Lys Asp Ala Leu Glu Arg His Phe Gly Glu Gln Asn Lys Pro Ser
225                 230                 235                 240

Ser Gln Glu Ile Met Arg Met Ala Glu Glu Leu Asn Leu Glu Lys Glu
                245                 250                 255

Val Val Arg Val Trp Phe Cys Asn Arg Arg Gln Arg Glu Lys Arg Val
            260                 265                 270

Lys Thr Ser Leu Asn Gln Ser Leu Phe Ser Ile Ser Lys Glu His Leu
        275                 280                 285

Glu Cys Arg
    290

<210> SEQ ID NO 58
<211> LENGTH: 505
<212> TYPE: PRT
<213> ORGANISM: Homo Sapiens

<400> SEQUENCE: 58

Met Ser Gly Ala Ser Ser Ser Glu Gln Asn Asn Asn Ser Tyr Glu Thr
```

-continued

```
1               5                   10                  15
Lys Thr Pro Asn Leu Arg Met Ser Glu Lys Cys Ser Trp Ala Ser
            20                  25                  30
Tyr Met Thr Asn Ser Pro Thr Leu Ile Val Met Ile Gly Leu Pro Ala
                35                  40                  45
Arg Gly Lys Thr Tyr Val Ser Lys Lys Leu Thr Arg Tyr Leu Asn Trp
    50                  55                  60
Ile Gly Val Pro Thr Lys Val Phe Asn Leu Gly Val Tyr Arg Arg Glu
65                  70                  75                  80
Ala Val Lys Ser Tyr Lys Ser Tyr Asp Phe Phe Arg His Asp Asn Glu
                85                  90                  95
Glu Ala Met Lys Ile Arg Lys Gln Cys Ala Leu Val Ala Leu Glu Asp
                100                 105                 110
Val Lys Ala Tyr Leu Thr Glu Glu Asn Gly Gln Ile Ala Val Phe Asp
                115                 120                 125
Ala Thr Asn Thr Thr Arg Glu Arg Arg Asp Met Ile Leu Asn Phe Ala
                130                 135                 140
Glu Gln Asn Ser Phe Lys Val Phe Phe Val Glu Ser Val Cys Asp Asp
145                 150                 155                 160
Pro Asp Val Ile Ala Ala Asn Ile Leu Glu Val Lys Val Ser Ser Pro
                165                 170                 175
Asp Tyr Pro Glu Arg Asn Arg Glu Asn Val Met Glu Asp Phe Leu Lys
                180                 185                 190
Arg Ile Glu Cys Tyr Lys Val Thr Tyr Arg Pro Leu Asp Pro Asp Asn
                195                 200                 205
Tyr Asp Lys Asp Leu Ser Phe Ile Lys Val Ile Asn Val Gly Gln Arg
                210                 215                 220
Phe Leu Val Asn Arg Val Gln Asp Tyr Ile Gln Ser Lys Ile Val Tyr
225                 230                 235                 240
Tyr Leu Met Asn Ile His Val Gln Pro Arg Thr Ile Tyr Leu Cys Arg
                245                 250                 255
His Gly Glu Ser Glu Phe Asn Leu Leu Gly Lys Ile Gly Gly Asp Ser
                260                 265                 270
Gly Leu Ser Val Arg Gly Lys Gln Phe Ala Gln Ala Leu Arg Lys Phe
                275                 280                 285
Leu Glu Glu Gln Glu Ile Thr Asp Leu Lys Val Trp Thr Ser His Val
                290                 295                 300
Lys Arg Thr Ile Gln Thr Ala Glu Ser Leu Gly Val Pro Tyr Glu Gln
305                 310                 315                 320
Trp Lys Ile Leu Asn Glu Ile Asp Ala Gly Val Cys Glu Glu Met Thr
                325                 330                 335
Tyr Ala Glu Ile Glu Lys Arg Tyr Pro Glu Glu Phe Ala Leu Arg Asp
                340                 345                 350
Gln Glu Lys Tyr Leu Tyr Arg Tyr Pro Gly Gly Glu Ser Tyr Gln Asp
                355                 360                 365
Leu Val Gln Leu Leu Glu Pro Val Ile Met Glu Leu Glu Arg Gln Gly
                370                 375                 380
Asn Val Leu Val Ile Ser His Gln Ala Val Met His Cys Leu Leu Ala
385                 390                 395                 400
Tyr Phe Leu Asp Lys Asp Ala Asp Glu Leu Pro Tyr Leu Arg Cys Pro
                405                 410                 415
Leu His Thr Ile Phe Lys Leu Thr Pro Val Thr Tyr Gly Cys Lys Val
                420                 425                 430
```

```
Glu Thr Ile Lys Leu Asn Val Glu Ala Val Asn Thr His Arg Asp Lys
            435                 440                 445

Pro Thr Asn Asn Phe Pro Lys Asn Gln Thr Pro Val Arg Met Arg Arg
    450                 455                 460

Asn Ser Phe Thr Pro Leu Ser Ser Ser Asn Thr Ile Arg Arg Pro Arg
465                 470                 475                 480

Asn Tyr Ser Val Gly Ser Arg Pro Leu Lys Pro Leu Ser Pro Leu Arg
                485                 490                 495

Ala Gln Asp Met Gln Glu Gly Ala Asp
            500                 505

<210> SEQ ID NO 59
<211> LENGTH: 1100
<212> TYPE: PRT
<213> ORGANISM: Mus musculus

<400> SEQUENCE: 59

Met Arg Lys Asp Glu Arg Glu Arg Asp Ala Pro Ala Met Arg Ser Pro
1               5                   10                  15

Pro Pro Pro Pro Ala Ser Ala Ala Ser Pro Pro Glu Ser Leu Arg Asn
                20                  25                  30

Gly Tyr Val Lys Ser Cys Val Ser Pro Leu Arg Gln Asp Pro Pro Arg
            35                  40                  45

Ser Phe Phe His Leu Cys Arg Phe Cys Asn Val Glu Pro Pro Ala
    50                  55                  60

Ala Ser Leu Arg Ala Gly Ala Arg Leu Ser Leu Gly Val Leu Ala Ala
65                  70                  75                  80

Phe Val Leu Ala Ala Leu Leu Gly Ala Arg Pro Glu Arg Trp Ala Ala
                85                  90                  95

Ala Ala Ala Gly Leu Arg Thr Leu Leu Ser Ala Cys Ser Leu Ser Leu
            100                 105                 110

Ser Pro Leu Phe Ser Ile Ala Cys Ala Phe Phe Phe Leu Thr Cys Phe
            115                 120                 125

Leu Thr Arg Ala Gln Arg Gly Pro Gly Arg Gly Ala Gly Ser Trp Trp
    130                 135                 140

Leu Leu Ala Leu Pro Ala Cys Cys Tyr Leu Gly Asp Phe Ala Ala Trp
145                 150                 155                 160

Gln Trp Trp Ser Trp Leu Arg Gly Glu Pro Ala Ala Gly Arg Leu
                165                 170                 175

Cys Leu Val Leu Ser Cys Val Gly Leu Leu Thr Leu Ala Pro Arg Val
            180                 185                 190

Arg Leu Arg His Gly Val Leu Val Leu Leu Phe Ala Gly Leu Val Trp
    195                 200                 205

Trp Val Ser Phe Ser Gly Leu Gly Ala Leu Pro Pro Ala Leu Arg Pro
    210                 215                 220

Leu Leu Ser Cys Leu Val Gly Gly Ala Gly Cys Leu Leu Ala Leu Gly
225                 230                 235                 240

Leu Asp His Phe Phe His Val Arg Gly Ala Ser Pro Pro Arg Ser
                245                 250                 255

Ala Ser Thr Ala Glu Glu Lys Val Pro Val Ile Arg Pro Arg Arg Arg
            260                 265                 270

Ser Ser Cys Val Ser Leu Gly Glu Ser Ala Ala Gly Tyr Tyr Gly Ser
            275                 280                 285

Gly Lys Met Phe Arg Arg Pro Ser Leu Pro Cys Ile Ser Arg Glu Gln
```

```
            290                 295                 300
Met Ile Leu Trp Asp Trp Asp Leu Lys Gln Trp Cys Lys Pro His Tyr
305                 310                 315                 320

Gln Asn Ser Gly Gly Gly Asn Gly Val Asp Leu Ser Val Leu Asn Glu
                325                 330                 335

Ala Arg Asn Met Val Ser Asp Leu Leu Ile Asp Pro Ser Leu Pro Pro
                340                 345                 350

Gln Val Ile Ser Ser Leu Arg Ser Ile Ser Ser Leu Met Gly Ala Phe
                355                 360                 365

Ser Gly Ser Cys Arg Pro Lys Ile Asn Ser Phe Thr Pro Phe Pro Gly
                370                 375                 380

Phe Tyr Pro Cys Ser Glu Val Glu Asp Pro Val Glu Lys Gly Asp Arg
385                 390                 395                 400

Lys Leu His Lys Gly Leu Ser Gly Arg Thr Ser Phe Pro Thr Pro Gln
                405                 410                 415

Leu Arg Arg Ser Ser Gly Ala Ser Ser Leu Leu Thr Asn Glu His Cys
                420                 425                 430

Ser Arg Trp Asp Arg Ser Ser Gly Lys Arg Ser Tyr Gln Glu Leu Ser
                435                 440                 445

Val Ser Ser His Gly Cys His Leu Asn Gly Pro Phe Ser Ser Asn Leu
                450                 455                 460

Phe Thr Ile Pro Lys Gln Arg Ser Ser Val Ser Leu Thr His His
465                 470                 475                 480

Ala Gly Leu Arg Arg Ala Gly Ala Leu Pro Ser His Ser Leu Leu Asn
                485                 490                 495

Ser Ser Ser His Val Pro Val Ser Ala Gly Ser Leu Thr Asn Arg Ser
                500                 505                 510

Pro Ile Gly Phe Pro Asp Thr Thr Asp Phe Leu Thr Lys Pro Asn Ile
                515                 520                 525

Ile Leu His Arg Ser Leu Gly Ser Val Ser Ser Ala Ala Asp Phe His
                530                 535                 540

Gln Tyr Leu Arg Asn Ser Asp Ser Asn Leu Cys Ser Ser Cys Gly His
545                 550                 555                 560

Gln Ile Leu Lys Tyr Val Ser Thr Cys Glu Pro Asp Gly Thr Asp His
                565                 570                 575

Pro Ser Glu Lys Ser Gly Glu Glu Asp Ser Ser Val Phe Ser Lys Glu
                580                 585                 590

Pro Leu Asn Ile Val Glu Thr Gln Glu Glu Thr Met Lys Lys Ala
                595                 600                 605

Cys Arg Glu Leu Phe Leu Glu Gly Asp Ser His Leu Met Glu Glu Ala
                610                 615                 620

Gln Gln Pro Asn Ile Asp Gln Glu Val Ser Leu Asp Pro Met Leu Val
625                 630                 635                 640

Glu Asp Tyr Asp Ser Leu Ile Glu Lys Met Asn Asn Trp Asn Phe Gln
                645                 650                 655

Ile Phe Glu Leu Val Glu Lys Met Gly Glu Lys Ser Gly Arg Ile Leu
                660                 665                 670

Ser Gln Val Met Tyr Thr Leu Phe Gln Asp Thr Gly Leu Leu Glu Thr
                675                 680                 685

Phe Lys Ile Pro Thr Gln Glu Phe Met Asn Tyr Phe Arg Ala Leu Glu
                690                 695                 700

Asn Gly Tyr Arg Asp Ile Pro Tyr His Asn Arg Val His Ala Thr Asp
705                 710                 715                 720
```

-continued

```
Val Leu His Ala Val Trp Tyr Leu Thr Thr Arg Pro Ile Pro Gly Leu
            725                 730                 735

Pro Gln Ile His Asn Asn His Glu Thr Glu Thr Lys Ala Asp Ser Asp
            740                 745                 750

Gly Arg Leu Gly Ser Gly Gln Ile Ala Tyr Ile Ser Ser Lys Ser Cys
            755                 760                 765

Cys Ile Pro Asp Met Ser Tyr Gly Cys Leu Ser Ser Asn Ile Pro Ala
    770                 775                 780

Leu Glu Leu Met Ala Leu Tyr Val Ala Ala Met His Asp Tyr Asp
785                 790                 795                 800

His Pro Gly Arg Thr Asn Ala Phe Leu Val Ala Thr Asn Ala Pro Gln
                805                 810                 815

Ala Val Leu Tyr Asn Asp Arg Ser Val Leu Glu Asn His His Ala Ala
                820                 825                 830

Ser Ala Trp Asn Leu Tyr Leu Ser Arg Pro Glu Tyr Asn Phe Leu Leu
                835                 840                 845

Asn Leu Asp His Met Glu Phe Lys Arg Phe Arg Phe Leu Val Ile Glu
    850                 855                 860

Ala Ile Leu Ala Thr Asp Leu Lys Lys His Phe Asp Phe Leu Ala Glu
865                 870                 875                 880

Phe Asn Ala Lys Ala Asn Asp Val Asn Ser Asn Gly Ile Glu Trp Ser
                885                 890                 895

Ser Glu Asn Asp Arg Leu Leu Val Cys Gln Val Cys Ile Lys Leu Ala
                900                 905                 910

Asp Ile Asn Gly Pro Ala Lys Asp Arg Asp Leu His Leu Arg Trp Thr
                915                 920                 925

Glu Gly Ile Val Asn Glu Phe Tyr Glu Gln Gly Asp Glu Glu Ala Ala
    930                 935                 940

Leu Gly Leu Pro Ile Ser Pro Phe Met Asp Arg Ser Ser Pro Gln Leu
945                 950                 955                 960

Ala Lys Leu Gln Glu Ser Phe Ile Thr His Ile Val Gly Pro Leu Cys
                965                 970                 975

Asn Ser Tyr Asp Ala Ala Gly Leu Leu Pro Gly Gln Trp Ile Glu Thr
                980                 985                 990

Glu Glu Gly Asp Asp Thr Glu Ser  Asp Asp Asp Asp  Asp Asp Asp
    995                 1000                1005

Gly Asp  Gly Gly Glu Glu Leu  Asp Ser Asp Asp Glu  Glu Thr Glu
    1010                1015                1020

Asp Asn  Leu Asn Pro Lys Pro  Gln Arg Arg Lys Gly  Arg Arg Arg
    1025                1030                1035

Ile Phe  Cys Gln Leu Met His  His Leu Thr Glu Asn  His Lys Ile
    1040                1045                1050

Trp Lys  Glu Ile Ile Glu Glu  Glu Glu Lys Cys  Lys Ala Glu
    1055                1060                1065

Gly Asn  Lys Leu Gln Val Asp  Asn Ala Ser Leu Pro  Gln Ala Asp
    1070                1075                1080

Glu Ile  Gln Val Ile Glu Glu  Ala Asp Glu Glu Glu  Glu Gln Met
    1085                1090                1095

Phe Glu
    1100

<210> SEQ ID NO 60
<211> LENGTH: 1112
```

<212> TYPE: PRT
<213> ORGANISM: Homo Sapiens

<400> SEQUENCE: 60

```
Met Arg Arg Asp Glu Arg Asp Ala Lys Ala Met Arg Ser Leu Gln Pro
1               5                   10                  15

Pro Asp Gly Ala Gly Ser Pro Pro Glu Ser Leu Arg Asn Gly Tyr Val
            20                  25                  30

Lys Ser Cys Val Ser Pro Leu Arg Gln Asp Pro Pro Arg Gly Phe Phe
        35                  40                  45

Phe His Leu Cys Arg Phe Cys Asn Val Glu Leu Arg Pro Pro Pro Ala
    50                  55                  60

Ser Pro Gln Gln Pro Arg Arg Cys Ser Pro Phe Cys Arg Ala Arg Leu
65              70                  75                  80

Ser Leu Gly Ala Leu Ala Ala Phe Val Leu Ala Leu Leu Leu Gly Ala
                85                  90                  95

Glu Pro Glu Ser Trp Ala Ala Gly Ala Ala Trp Leu Arg Thr Leu Leu
            100                 105                 110

Ser Val Cys Ser His Ser Leu Ser Pro Leu Phe Ser Ile Ala Cys Ala
        115                 120                 125

Phe Phe Phe Leu Thr Cys Phe Leu Thr Arg Thr Lys Arg Gly Pro Gly
    130                 135                 140

Pro Gly Arg Ser Cys Gly Ser Trp Trp Leu Leu Ala Leu Pro Ala Cys
145             150                 155                 160

Cys Tyr Leu Gly Asp Phe Leu Val Trp Gln Trp Ser Trp Pro Trp Trp
                165                 170                 175

Gly Asp Gly Asp Ala Gly Ser Ala Ala Pro His Thr Pro Pro Glu Ala
            180                 185                 190

Ala Ala Gly Arg Leu Leu Leu Val Leu Ser Cys Val Gly Leu Leu Leu
        195                 200                 205

Thr Leu Ala His Pro Leu Arg Leu Arg His Cys Val Leu Val Leu Leu
    210                 215                 220

Leu Ala Ser Phe Val Trp Trp Val Ser Phe Thr Ser Leu Gly Ser Leu
225                 230                 235                 240

Pro Ser Ala Leu Arg Pro Leu Leu Ser Gly Leu Val Gly Gly Ala Gly
                245                 250                 255

Cys Leu Leu Ala Leu Gly Leu Asp His Phe Gln Ile Arg Glu Ala
            260                 265                 270

Pro Leu His Pro Arg Leu Ser Ser Ala Ala Glu Glu Lys Val Pro Val
        275                 280                 285

Ile Arg Pro Arg Arg Ser Ser Cys Val Ser Leu Gly Glu Thr Ala
    290                 295                 300

Ala Ser Tyr Tyr Gly Ser Cys Lys Ile Phe Arg Pro Ser Leu Pro
305                 310                 315                 320

Cys Ile Ser Arg Glu Gln Met Ile Leu Trp Asp Trp Asp Leu Lys Gln
                325                 330                 335

Trp Tyr Lys Pro His Tyr Gln Asn Ser Gly Gly Asn Gly Val Asp
            340                 345                 350

Leu Ser Val Leu Asn Glu Ala Arg Asn Met Val Ser Asp Leu Leu Thr
        355                 360                 365

Asp Pro Ser Leu Pro Pro Gln Val Ile Ser Ser Leu Arg Ser Ile Ser
    370                 375                 380

Ser Leu Met Gly Ala Phe Ser Gly Ser Cys Arg Pro Lys Ile Asn Pro
385                 390                 395                 400
```

```
Leu Thr Pro Phe Pro Gly Phe Tyr Pro Cys Ser Glu Ile Glu Asp Pro
            405                 410                 415

Ala Glu Lys Gly Asp Arg Lys Leu Asn Lys Gly Leu Asn Arg Asn Ser
        420                 425                 430

Leu Pro Thr Pro Gln Leu Arg Arg Ser Ser Gly Thr Ser Gly Leu Leu
            435                 440                 445

Pro Val Glu Gln Ser Ser Arg Trp Asp Arg Asn Asn Gly Lys Arg Pro
        450                 455                 460

His Gln Glu Phe Gly Ile Ser Ser Gln Gly Cys Tyr Leu Asn Gly Pro
465                 470                 475                 480

Phe Asn Ser Asn Leu Leu Thr Ile Pro Lys Gln Arg Ser Ser Ser Val
                485                 490                 495

Ser Leu Thr His His Val Gly Leu Arg Arg Ala Gly Val Leu Ser Ser
            500                 505                 510

Leu Ser Pro Val Asn Ser Ser Asn His Gly Pro Val Ser Thr Gly Ser
            515                 520                 525

Leu Thr Asn Arg Ser Pro Ile Glu Phe Pro Asp Thr Ala Asp Phe Leu
            530                 535                 540

Asn Lys Pro Ser Val Ile Leu Gln Arg Ser Leu Gly Asn Ala Pro Asn
545                 550                 555                 560

Thr Pro Asp Phe Tyr Gln Gln Leu Arg Asn Ser Asp Ser Asn Leu Cys
                565                 570                 575

Asn Ser Cys Gly His Gln Met Leu Lys Tyr Val Ser Thr Ser Glu Ser
            580                 585                 590

Asp Gly Thr Asp Cys Cys Ser Gly Lys Ser Gly Glu Glu Glu Asn Ile
            595                 600                 605

Phe Ser Lys Glu Ser Phe Lys Leu Met Glu Thr Gln Gln Glu Glu Glu
            610                 615                 620

Thr Glu Lys Lys Asp Ser Arg Lys Leu Phe Gln Glu Gly Asp Lys Trp
625                 630                 635                 640

Leu Thr Glu Glu Ala Gln Ser Glu Gln Gln Thr Asn Ile Glu Gln Glu
                645                 650                 655

Val Ser Leu Asp Leu Ile Leu Val Glu Glu Tyr Asp Ser Leu Ile Glu
            660                 665                 670

Lys Met Ser Asn Trp Asn Phe Pro Ile Phe Glu Leu Val Glu Lys Met
            675                 680                 685

Gly Glu Lys Ser Gly Arg Ile Leu Ser Gln Val Met Tyr Thr Leu Phe
        690                 695                 700

Gln Asp Thr Gly Leu Leu Glu Ile Phe Lys Ile Pro Thr Gln Gln Phe
705                 710                 715                 720

Met Asn Tyr Phe Arg Ala Leu Glu Asn Gly Tyr Arg Asp Ile Pro Tyr
                725                 730                 735

His Asn Arg Ile His Ala Thr Asp Val Leu His Ala Val Trp Tyr Leu
            740                 745                 750

Thr Thr Arg Pro Val Pro Gly Leu Gln Gln Ile His Asn Gly Cys Gly
            755                 760                 765

Thr Gly Asn Glu Thr Asp Ser Asp Gly Arg Ile Asn His Gly Arg Ile
        770                 775                 780

Ala Tyr Ile Ser Ser Lys Ser Cys Ser Asn Pro Asp Glu Ser Tyr Gly
785                 790                 795                 800

Cys Leu Ser Ser Asn Ile Pro Ala Leu Glu Leu Met Ala Leu Tyr Val
                805                 810                 815
```

Ala Ala Ala Met His Asp Tyr Asp His Pro Gly Arg Thr Asn Ala Phe
            820                 825                 830

Leu Val Ala Thr Asn Ala Pro Gln Ala Val Leu Tyr Asn Asp Arg Ser
        835                 840                 845

Val Leu Glu Asn His His Ala Ala Ser Ala Trp Asn Leu Tyr Leu Ser
    850                 855                 860

Arg Pro Glu Tyr Asn Phe Leu His Leu Asp His Val Glu Phe Lys
865                 870                 875                 880

Arg Phe Arg Phe Leu Val Ile Glu Ala Ile Leu Ala Thr Asp Leu Lys
                885                 890                 895

Lys His Phe Asp Phe Leu Ala Glu Phe Asn Ala Lys Ala Asn Asp Val
            900                 905                 910

Asn Ser Asn Gly Ile Glu Trp Ser Asn Glu Asn Asp Arg Leu Leu Val
        915                 920                 925

Cys Gln Val Cys Ile Lys Leu Ala Asp Ile Asn Gly Pro Ala Lys Val
    930                 935                 940

Arg Asp Leu His Leu Lys Trp Thr Glu Gly Ile Val Asn Glu Phe Tyr
945                 950                 955                 960

Glu Gln Gly Asp Glu Glu Ala Asn Leu Gly Leu Pro Ile Ser Pro Phe
                965                 970                 975

Met Asp Arg Ser Ser Pro Gln Leu Ala Lys Leu Gln Glu Ser Phe Ile
            980                 985                 990

Thr His Ile Val Gly Pro Leu Cys Asn Ser Tyr Asp Ala Ala Gly Leu
        995                 1000                1005

Leu Pro Gly Gln Trp Leu Glu Ala Glu Glu Asp Asn Asp Thr Glu
    1010                1015                1020

Ser Gly Asp Asp Glu Asp Gly Glu Glu Leu Asp Thr Glu Asp Glu
    1025                1030                1035

Glu Met Glu Asn Asn Leu Asn Pro Lys Pro Pro Arg Arg Lys Ser
    1040                1045                1050

Arg Arg Arg Ile Phe Cys Gln Leu Met His His Leu Thr Glu Asn
    1055                1060                1065

His Lys Ile Trp Lys Glu Ile Val Glu Glu Glu Lys Cys Lys
    1070                1075                1080

Ala Asp Gly Asn Lys Leu Gln Val Glu Asn Ser Ser Leu Pro Gln
    1085                1090                1095

Ala Asp Glu Ile Gln Val Ile Glu Glu Ala Asp Glu Glu Glu
    1100                1105                1110

<210> SEQ ID NO 61
<211> LENGTH: 256
<212> TYPE: PRT
<213> ORGANISM: Homo Sapiens

<400> SEQUENCE: 61

Met Ala Ser Gly Arg Pro Glu Glu Leu Trp Glu Ala Val Val Gly Ala
1               5                   10                  15

Ala Glu Arg Phe Arg Ala Arg Thr Gly Thr Glu Leu Val Leu Leu Thr
            20                  25                  30

Ala Ala Pro Pro Pro Pro Arg Pro Gly Pro Cys Ala Tyr Pro Ala
        35                  40                  45

His Gly Arg Gly Ala Leu Ala Glu Ala Ala Arg Arg Cys Leu His Asp
    50                  55                  60

Ile Ala Leu Ala His Arg Ala Ala Thr Ala Ala Arg Pro Pro Ala Pro
65                  70                  75                  80

```
Pro Pro Ala Pro Gln Pro Pro Ser Pro Thr Pro Ser Pro Pro Arg Pro
                85                  90                  95

Thr Leu Ala Arg Glu Asp Asn Glu Glu Asp Glu Asp Glu Pro Thr Glu
            100                 105                 110

Thr Glu Thr Ser Gly Glu Gln Leu Gly Ile Ser Asp Asn Gly Gly Leu
        115                 120                 125

Phe Val Met Asp Glu Asp Ala Thr Leu Gln Asp Leu Pro Pro Phe Cys
130                 135                 140

Glu Ser Asp Pro Glu Ser Thr Asp Asp Gly Ser Leu Ser Glu Glu Thr
145                 150                 155                 160

Pro Ala Gly Pro Pro Thr Cys Ser Val Pro Ala Ser Ala Leu Pro
                165                 170                 175

Thr Gln Gln Tyr Ala Lys Ser Leu Pro Val Ser Val Pro Val Trp Gly
            180                 185                 190

Phe Lys Glu Lys Arg Thr Glu Ala Arg Ser Ser Asp Glu Glu Asn Gly
        195                 200                 205

Pro Pro Ser Ser Pro Asp Leu Asp Arg Ile Ala Ala Ser Met Arg Ala
210                 215                 220

Leu Val Leu Arg Glu Ala Glu Asp Thr Gln Val Phe Gly Asp Leu Pro
225                 230                 235                 240

Arg Pro Arg Leu Asn Thr Ser Asp Phe Gln Lys Leu Lys Arg Lys Tyr
                245                 250                 255

<210> SEQ ID NO 62
<211> LENGTH: 435
<212> TYPE: PRT
<213> ORGANISM: Homo Sapiens

<400> SEQUENCE: 62

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
```

```
                195                 200                 205
Gly Pro Val Val His Cys Ser Ala Gly Ile Gly Arg Ser Gly Thr
    210                 215                 220
Phe Cys Leu Ala Asp Thr Cys Leu Leu Met Asp Lys Arg Lys Asp
225                 230                 235                 240
Pro Ser Ser Val Asp Ile Lys Lys Val Leu Glu Met Arg Lys Phe
                245                 250                 255
Arg Met Gly Leu Ile Gln Thr Ala Asp Gln Leu Arg Phe Ser Tyr Leu
            260                 265                 270
Ala Val Ile Glu Gly Ala Lys Phe Ile Met Gly Asp Ser Ser Val Gln
        275                 280                 285
Asp Gln Trp Lys Glu Leu Ser His Glu Asp Leu Glu Pro Pro Glu
    290                 295                 300
His Ile Pro Pro Pro Arg Pro Lys Arg Ile Leu Glu Pro His
305                 310                 315                 320
Asn Gly Lys Cys Arg Glu Phe Phe Pro Asn His Gln Trp Val Lys Glu
                325                 330                 335
Glu Thr Gln Glu Asp Lys Asp Cys Pro Ile Lys Glu Glu Lys Gly Ser
            340                 345                 350
Pro Leu Asn Ala Ala Pro Tyr Gly Ile Glu Ser Met Ser Gln Asp Thr
        355                 360                 365
Glu Val Arg Ser Arg Val Val Gly Gly Ser Leu Arg Gly Ala Gln Ala
    370                 375                 380
Ala Ser Pro Ala Lys Gly Glu Pro Ser Leu Pro Glu Lys Asp Glu Asp
385                 390                 395                 400
His Ala Leu Ser Tyr Trp Lys Pro Phe Leu Val Asn Met Cys Val Ala
                405                 410                 415
Thr Val Leu Thr Ala Gly Ala Tyr Leu Cys Tyr Arg Phe Leu Phe Asn
            420                 425                 430
Ser Asn Thr
        435

<210> SEQ ID NO 63
<211> LENGTH: 192
<212> TYPE: PRT
<213> ORGANISM: Homo Sapiens

<400> SEQUENCE: 63

Met Gln Ala Ile Lys Cys Val Val Val Gly Asp Gly Ala Val Gly Lys
1               5                   10                  15
Thr Cys Leu Leu Ile Ser Tyr Thr Thr Asn Ala Phe Pro Gly Glu Tyr
                20                  25                  30
Ile Pro Thr Val Phe Asp Asn Tyr Ser Ala Asn Val Met Val Asp Gly
            35                  40                  45
Lys Pro Val Asn Leu Gly Leu Trp Asp Thr Ala Gly Gln Glu Asp Tyr
        50                  55                  60
Asp Arg Leu Arg Pro Leu Ser Tyr Pro Gln Thr Asp Val Phe Leu Ile
65                  70                  75                  80
Cys Phe Ser Leu Val Ser Pro Ala Ser Phe Glu Asn Val Arg Ala Lys
                85                  90                  95
Trp Tyr Pro Glu Val Arg His His Cys Pro Asn Thr Pro Ile Ile Leu
            100                 105                 110
Val Gly Thr Lys Leu Asp Leu Arg Asp Asp Lys Asp Thr Ile Glu Lys
        115                 120                 125
```

```
Leu Lys Glu Lys Lys Leu Thr Pro Ile Thr Tyr Pro Gln Gly Leu Ala
            130                 135                 140

Met Ala Lys Glu Ile Gly Ala Val Lys Tyr Leu Glu Cys Ser Ala Leu
145                 150                 155                 160

Thr Gln Arg Gly Leu Lys Thr Val Phe Asp Glu Ala Ile Arg Ala Val
                165                 170                 175

Leu Cys Pro Pro Val Lys Lys Arg Lys Arg Lys Cys Leu Leu Leu
                180                 185                 190

<210> SEQ ID NO 64
<211> LENGTH: 648
<212> TYPE: PRT
<213> ORGANISM: Mus musculus

<400> SEQUENCE: 64

Met Glu His Ile Gln Gly Ala Trp Lys Thr Ile Ser Asn Gly Phe Gly
1               5                   10                  15

Leu Lys Asp Ala Val Phe Asp Gly Ser Ser Cys Ile Ser Pro Thr Ile
                20                  25                  30

Val Gln Gln Phe Gly Tyr Gln Arg Arg Ala Ser Asp Asp Gly Lys Leu
            35                  40                  45

Thr Asp Ser Ser Lys Thr Ser Asn Thr Ile Arg Val Phe Leu Pro Asn
50                  55                  60

Lys Gln Arg Thr Val Val Asn Val Arg Asn Gly Met Ser Leu His Asp
65                  70                  75                  80

Cys Leu Met Lys Ala Leu Lys Val Arg Gly Leu Gln Pro Glu Cys Cys
                85                  90                  95

Ala Val Phe Arg Leu Leu Gln Glu His Lys Gly Lys Lys Ala Arg Leu
            100                 105                 110

Asp Trp Asn Thr Asp Ala Ala Ser Leu Ile Gly Glu Glu Leu Gln Val
        115                 120                 125

Asp Phe Leu Asp His Val Pro Leu Thr Thr His Asn Phe Ala Arg Lys
    130                 135                 140

Thr Phe Leu Lys Leu Ala Phe Cys Asp Ile Cys Gln Lys Phe Leu Leu
145                 150                 155                 160

Asn Gly Phe Arg Cys Gln Thr Cys Gly Tyr Lys Phe His Glu His Cys
                165                 170                 175

Ser Thr Lys Val Pro Thr Met Cys Val Asp Trp Ser Asn Ile Arg Gln
            180                 185                 190

Leu Leu Leu Phe Pro Asn Ser Thr Val Gly Asp Ser Gly Val Pro Ala
        195                 200                 205

Pro Pro Ser Phe Pro Met Arg Arg Met Arg Glu Ser Val Ser Arg Met
    210                 215                 220

Pro Ala Ser Ser Gln His Arg Tyr Ser Thr Pro His Ala Phe Thr Phe
225                 230                 235                 240

Asn Thr Ser Ser Pro Ser Ser Glu Gly Ser Leu Ser Gln Arg Gln Arg
                245                 250                 255

Ser Thr Ser Thr Pro Asn Val His Met Val Ser Thr Thr Leu His Val
            260                 265                 270

Asp Ser Arg Met Ile Glu Asp Ala Ile Arg Ser His Ser Glu Ser Ala
        275                 280                 285

Ser Pro Ser Ala Leu Ser Ser Ser Pro Asn Asn Leu Ser Pro Thr Gly
    290                 295                 300

Trp Ser Gln Pro Lys Thr Pro Val Pro Ala Gln Arg Glu Arg Ala Pro
305                 310                 315                 320
```

```
Gly Ser Gly Thr Gln Glu Lys Asn Lys Ile Arg Pro Arg Gly Gln Arg
                325                 330                 335

Asp Ser Ser Tyr Tyr Trp Glu Ile Glu Ala Ser Glu Val Met Leu Ser
            340                 345                 350

Thr Arg Ile Gly Ser Gly Ser Phe Gly Thr Val Tyr Lys Gly Lys Trp
        355                 360                 365

His Gly Asp Val Ala Val Lys Ile Leu Lys Val Asp Pro Thr Pro
    370                 375                 380

Glu Gln Leu Gln Ala Phe Arg Asn Glu Val Ala Val Leu Arg Lys Thr
385                 390                 395                 400

Arg His Val Asn Ile Leu Leu Phe Met Gly Tyr Met Thr Lys Asp Asn
                405                 410                 415

Leu Ala Ile Val Thr Gln Trp Cys Glu Gly Ser Ser Leu Tyr Lys His
            420                 425                 430

Leu His Val Gln Glu Thr Lys Phe Gln Met Phe Gln Leu Ile Asp Ile
        435                 440                 445

Ala Arg Gln Thr Ala Gln Gly Met Asp Tyr Leu His Ala Lys Asn Ile
    450                 455                 460

Ile His Arg Asp Met Lys Ser Asn Asn Ile Phe Leu His Glu Gly Leu
465                 470                 475                 480

Thr Val Lys Ile Gly Asp Phe Gly Leu Ala Thr Val Lys Ser Arg Trp
                485                 490                 495

Ser Gly Ser Gln Gln Val Glu Gln Pro Thr Gly Ser Val Leu Trp Met
            500                 505                 510

Ala Pro Glu Val Ile Arg Met Gln Asp Asn Asn Pro Phe Ser Phe Gln
        515                 520                 525

Ser Asp Val Tyr Ser Tyr Gly Ile Val Leu Tyr Glu Leu Met Thr Gly
    530                 535                 540

Glu Leu Pro Tyr Ala His Ile Asn Asn Arg Asp Gln Ile Ile Phe Met
545                 550                 555                 560

Val Gly Arg Gly Tyr Ala Ser Pro Asp Leu Ser Arg Leu Tyr Lys Asn
                565                 570                 575

Cys Pro Lys Ala Met Lys Arg Leu Val Ala Asp Cys Val Lys Lys Val
            580                 585                 590

Lys Glu Glu Arg Pro Leu Phe Pro Gln Ile Leu Ser Ser Ile Glu Leu
        595                 600                 605

Leu Gln His Ser Leu Pro Lys Ile Asn Arg Ser Ala Ser Glu Pro Ser
    610                 615                 620

Leu His Arg Ala Ala His Thr Glu Asp Ile Asn Ala Cys Thr Leu Thr
625                 630                 635                 640

Thr Ser Pro Arg Leu Pro Val Phe
                645

<210> SEQ ID NO 65
<211> LENGTH: 399
<212> TYPE: PRT
<213> ORGANISM: Homo Sapiens

<400> SEQUENCE: 65

Met Ala Ala Pro Ser Pro Ser Gly Gly Gly Gly Ser Gly Gly Gly Ser
1               5                   10                  15

Gly Ser Gly Thr Pro Gly Pro Val Gly Ser Pro Ala Pro Gly His Pro
            20                  25                  30

Ala Val Ser Ser Met Gln Gly Lys Arg Lys Ala Leu Lys Leu Asn Phe
```

```
                    35                  40                  45
Ala Asn Pro Pro Phe Lys Ser Thr Ala Arg Phe Thr Leu Asn Pro Asn
 50                  55                  60

Pro Thr Gly Val Gln Asn Pro His Ile Glu Arg Leu Arg Thr His Ser
 65                  70                  75                  80

Ile Glu Ser Ser Gly Lys Leu Lys Ile Ser Pro Glu Gln His Trp Asp
                 85                  90                  95

Phe Thr Ala Glu Asp Leu Lys Asp Leu Gly Glu Ile Gly Arg Gly Ala
                100                 105                 110

Tyr Gly Ser Val Asn Lys Met Val His Lys Pro Ser Gly Gln Ile Met
                115                 120                 125

Ala Val Lys Arg Ile Arg Ser Thr Val Asp Glu Lys Glu Gln Lys Gln
            130                 135                 140

Leu Leu Met Asp Leu Asp Val Val Met Arg Ser Ser Asp Cys Pro Tyr
145                 150                 155                 160

Ile Val Gln Phe Tyr Gly Ala Leu Phe Arg Glu Gly Asp Cys Trp Ile
                165                 170                 175

Cys Met Glu Leu Met Ser Thr Ser Phe Asp Lys Phe Tyr Lys Tyr Val
                180                 185                 190

Tyr Ser Val Leu Asp Asp Val Ile Pro Glu Glu Ile Leu Gly Lys Ile
            195                 200                 205

Thr Leu Ala Thr Val Lys Ala Leu Asn His Leu Lys Glu Asn Leu Lys
210                 215                 220

Ile Ile His Arg Asp Ile Lys Pro Ser Asn Ile Leu Leu Asp Arg Ser
225                 230                 235                 240

Gly Asn Ile Lys Leu Cys Asp Phe Gly Ile Ser Gly Gln Leu Val Asp
                245                 250                 255

Ser Ile Ala Lys Thr Arg Asp Ala Gly Cys Arg Pro Tyr Met Ala Pro
            260                 265                 270

Glu Arg Ile Asp Pro Ser Ala Ser Arg Gln Gly Tyr Asp Val Arg Ser
        275                 280                 285

Asp Val Trp Ser Leu Gly Ile Thr Leu Tyr Glu Leu Ala Thr Gly Arg
290                 295                 300

Phe Pro Tyr Pro Lys Trp Asn Ser Val Phe Asp Gln Leu Thr Gln Val
305                 310                 315                 320

Val Lys Gly Asp Pro Pro Gln Leu Ser Asn Ser Glu Glu Arg Glu Phe
                325                 330                 335

Ser Pro Ser Phe Ile Asn Phe Val Asn Leu Cys Leu Thr Lys Asp Glu
            340                 345                 350

Ser Lys Arg Pro Lys Tyr Lys Glu Leu Leu Lys His Pro Phe Ile Leu
        355                 360                 365

Met Tyr Glu Glu Arg Ala Val Glu Val Ala Cys Tyr Val Cys Lys Ile
    370                 375                 380

Leu Asp Gln Met Pro Ala Thr Pro Ser Ser Pro Met Tyr Val Asp
385                 390                 395

<210> SEQ ID NO 66
<211> LENGTH: 1132
<212> TYPE: PRT
<213> ORGANISM: Homo Sapiens

<400> SEQUENCE: 66

Met Pro Arg Ala Pro Arg Cys Arg Ala Val Arg Ser Leu Leu Arg Ser
 1               5                  10                  15
```

His Tyr Arg Glu Val Leu Pro Leu Ala Thr Phe Val Arg Arg Leu Gly
            20                  25                  30

Pro Gln Gly Trp Arg Leu Val Gln Arg Gly Asp Pro Ala Ala Phe Arg
        35                  40                  45

Ala Leu Val Ala Gln Cys Leu Val Cys Val Pro Trp Asp Ala Arg Pro
50                  55                  60

Pro Pro Ala Ala Pro Ser Phe Arg Gln Val Ser Cys Leu Lys Glu Leu
65                  70                  75                  80

Val Ala Arg Val Leu Gln Arg Leu Cys Glu Arg Gly Ala Lys Asn Val
                85                  90                  95

Leu Ala Phe Gly Phe Ala Leu Leu Asp Gly Ala Arg Gly Gly Pro Pro
            100                 105                 110

Glu Ala Phe Thr Thr Ser Val Arg Ser Tyr Leu Pro Asn Thr Val Thr
            115                 120                 125

Asp Ala Leu Arg Gly Ser Gly Ala Trp Gly Leu Leu Leu Arg Arg Val
            130                 135                 140

Gly Asp Asp Val Leu Val His Leu Leu Ala Arg Cys Ala Leu Phe Val
145                 150                 155                 160

Leu Val Ala Pro Ser Cys Ala Tyr Gln Val Cys Gly Pro Pro Leu Tyr
                165                 170                 175

Gln Leu Gly Ala Ala Thr Gln Ala Arg Pro Pro Pro His Ala Ser Gly
            180                 185                 190

Pro Arg Arg Arg Leu Gly Cys Glu Arg Ala Trp Asn His Ser Val Arg
            195                 200                 205

Glu Ala Gly Val Pro Leu Gly Leu Pro Ala Pro Gly Ala Arg Arg Arg
210                 215                 220

Gly Gly Ser Ala Ser Arg Ser Leu Pro Leu Pro Lys Arg Pro Arg Arg
225                 230                 235                 240

Gly Ala Ala Pro Glu Pro Glu Arg Thr Pro Val Gly Gln Gly Ser Trp
                245                 250                 255

Ala His Pro Gly Arg Thr Arg Gly Pro Ser Asp Arg Gly Phe Cys Val
            260                 265                 270

Val Ser Pro Ala Arg Pro Ala Glu Glu Ala Thr Ser Leu Glu Gly Ala
            275                 280                 285

Leu Ser Gly Thr Arg His Ser His Pro Ser Val Gly Arg Gln His His
290                 295                 300

Ala Gly Pro Pro Ser Thr Ser Arg Pro Pro Arg Pro Trp Asp Thr Pro
305                 310                 315                 320

Cys Pro Pro Val Tyr Ala Glu Thr Lys His Phe Leu Tyr Ser Ser Gly
                325                 330                 335

Asp Lys Glu Gln Leu Arg Pro Ser Phe Leu Leu Ser Ser Leu Arg Pro
            340                 345                 350

Ser Leu Thr Gly Ala Arg Arg Leu Val Glu Thr Ile Phe Leu Gly Ser
            355                 360                 365

Arg Pro Trp Met Pro Gly Thr Pro Arg Arg Leu Pro Arg Leu Pro Gln
370                 375                 380

Arg Tyr Trp Gln Met Arg Pro Leu Phe Leu Glu Leu Leu Gly Asn His
385                 390                 395                 400

Ala Gln Cys Pro Tyr Gly Val Leu Leu Lys Thr His Cys Pro Leu Arg
                405                 410                 415

Ala Ala Val Thr Pro Ala Ala Gly Val Cys Ala Arg Glu Lys Pro Gln
            420                 425                 430

Gly Ser Val Ala Ala Pro Glu Glu Glu Asp Thr Asp Pro Arg Arg Leu

-continued

```
                435                 440                 445
Val Gln Leu Leu Arg Gln His Ser Ser Pro Trp Gln Val Tyr Gly Phe
450                 455                 460
Val Arg Ala Cys Leu Arg Arg Leu Val Pro Pro Gly Leu Trp Gly Ser
465                 470                 475                 480
Arg His Asn Glu Arg Arg Phe Leu Arg Asn Thr Lys Lys Phe Ile Ser
                485                 490                 495
Leu Gly Lys His Ala Lys Leu Ser Leu Gln Glu Leu Thr Trp Lys Met
                500                 505                 510
Ser Val Arg Asp Cys Ala Trp Leu Arg Arg Ser Pro Gly Val Gly Cys
                515                 520                 525
Val Pro Ala Ala Glu His Arg Leu Arg Glu Glu Ile Leu Ala Lys Phe
530                 535                 540
Leu His Trp Leu Met Ser Val Tyr Val Val Leu Leu Arg Ser Phe
545                 550                 555                 560
Phe Tyr Val Thr Glu Thr Thr Phe Gln Lys Asn Arg Leu Phe Phe Tyr
                565                 570                 575
Arg Lys Ser Val Trp Ser Lys Leu Gln Ser Ile Gly Ile Arg Gln His
                580                 585                 590
Leu Lys Arg Val Gln Leu Arg Glu Leu Ser Glu Ala Glu Val Arg Gln
                595                 600                 605
His Arg Glu Ala Arg Pro Ala Leu Leu Thr Ser Arg Leu Arg Phe Ile
                610                 615                 620
Pro Lys Pro Asp Gly Leu Arg Pro Ile Val Asn Met Asp Tyr Val Val
625                 630                 635                 640
Gly Ala Arg Thr Phe Arg Arg Glu Lys Arg Ala Glu Arg Leu Thr Ser
                645                 650                 655
Arg Val Lys Ala Leu Phe Ser Val Leu Asn Tyr Glu Arg Ala Arg Arg
                660                 665                 670
Pro Gly Leu Leu Gly Ala Ser Val Leu Gly Leu Asp Asp Ile His Arg
                675                 680                 685
Ala Trp Arg Thr Phe Val Leu Arg Val Arg Ala Gln Asp Pro Pro Pro
                690                 695                 700
Glu Leu Tyr Phe Val Lys Val Asp Val Thr Gly Ala Tyr Asp Thr Ile
705                 710                 715                 720
Pro Gln Asp Arg Leu Thr Glu Val Ile Ala Ser Ile Ile Lys Pro Gln
                725                 730                 735
Asn Thr Tyr Cys Val Arg Arg Tyr Ala Val Val Gln Lys Ala Ala His
                740                 745                 750
Gly His Val Arg Lys Ala Phe Lys Ser His Val Ser Thr Leu Thr Asp
                755                 760                 765
Leu Gln Pro Tyr Met Arg Gln Phe Val Ala His Leu Gln Glu Thr Ser
                770                 775                 780
Pro Leu Arg Asp Ala Val Val Ile Glu Gln Ser Ser Ser Leu Asn Glu
785                 790                 795                 800
Ala Ser Ser Gly Leu Phe Asp Val Phe Leu Arg Phe Met Cys His His
                805                 810                 815
Ala Val Arg Ile Arg Gly Lys Ser Tyr Val Gln Cys Gln Gly Ile Pro
                820                 825                 830
Gln Gly Ser Ile Leu Ser Thr Leu Leu Cys Ser Leu Cys Tyr Gly Asp
                835                 840                 845
Met Glu Asn Lys Leu Phe Ala Gly Ile Arg Arg Asp Gly Leu Leu Leu
850                 855                 860
```

```
Arg Leu Val Asp Asp Phe Leu Leu Val Thr Pro His Leu Thr His Ala
865                 870                 875                 880

Lys Thr Phe Leu Arg Thr Leu Val Arg Gly Val Pro Glu Tyr Gly Cys
            885                 890                 895

Val Val Asn Leu Arg Lys Thr Val Asn Phe Pro Val Glu Asp Glu
        900                 905                 910

Ala Leu Gly Gly Thr Ala Phe Val Gln Met Pro Ala His Gly Leu Phe
            915                 920                 925

Pro Trp Cys Gly Leu Leu Asp Thr Arg Thr Leu Glu Val Gln Ser
        930                 935                 940

Asp Tyr Ser Ser Tyr Ala Arg Thr Ser Ile Arg Ala Ser Leu Thr Phe
945                 950                 955                 960

Asn Arg Gly Phe Lys Ala Gly Arg Asn Met Arg Arg Lys Leu Phe Gly
            965                 970                 975

Val Leu Arg Leu Lys Cys His Ser Leu Phe Leu Asp Leu Gln Val Asn
            980                 985                 990

Ser Leu Gln Thr Val Cys Thr Asn Ile Tyr Lys Ile Leu Leu Leu Gln
            995                 1000                1005

Ala Tyr Arg Phe His Ala Cys Val Leu Gln Leu Pro Phe His Gln
    1010                1015                1020

Gln Val Trp Lys Asn Pro Thr Phe Phe Leu Arg Val Ile Ser Asp
    1025                1030                1035

Thr Ala Ser Leu Cys Tyr Ser Ile Leu Lys Ala Lys Asn Ala Gly
    1040                1045                1050

Met Ser Leu Gly Ala Lys Gly Ala Ala Gly Pro Leu Pro Ser Glu
    1055                1060                1065

Ala Val Gln Trp Leu Cys His Gln Ala Phe Leu Leu Lys Leu Thr
    1070                1075                1080

Arg His Arg Val Thr Tyr Val Pro Leu Leu Gly Ser Leu Arg Thr
    1085                1090                1095

Ala Gln Thr Gln Leu Ser Arg Lys Leu Pro Gly Thr Thr Leu Thr
    1100                1105                1110

Ala Leu Glu Ala Ala Ala Asn Pro Ala Leu Pro Ser Asp Phe Lys
    1115                1120                1125

Thr Ile Leu Asp
    1130

<210> SEQ ID NO 67
<211> LENGTH: 467
<212> TYPE: PRT
<213> ORGANISM: Homo Sapiens

<400> SEQUENCE: 67

Met Glu Tyr Met Ser Thr Gly Ser Asp Asn Lys Glu Glu Ile Asp Leu
1               5                   10                  15

Leu Ile Lys His Leu Asn Val Ser Asp Val Ile Asp Ile Met Glu Asn
                20                  25                  30

Leu Tyr Ala Ser Glu Glu Pro Ala Val Tyr Glu Pro Ser Leu Met Thr
            35                  40                  45

Met Cys Gln Asp Ser Asn Gln Asn Asp Glu Arg Ser Lys Ser Leu Leu
        50                  55                  60

Leu Ser Gly Gln Glu Val Pro Trp Leu Ser Ser Val Arg Tyr Gly Thr
65                  70                  75                  80

Val Glu Asp Leu Leu Ala Phe Ala Asn His Ile Ser Asn Thr Ala Lys
```

```
                85                  90                  95
His Phe Tyr Gly Gln Arg Pro Gln Glu Ser Gly Ile Leu Leu Asn Met
            100                 105                 110
Val Ile Thr Pro Gln Asn Gly Arg Tyr Gln Ile Asp Ser Asp Val Leu
            115                 120                 125
Leu Ile Pro Trp Lys Leu Thr Tyr Arg Asn Ile Gly Ser Asp Phe Ile
            130                 135                 140
Pro Arg Gly Ala Phe Gly Lys Val Tyr Leu Ala Gln Asp Ile Lys Thr
145                 150                 155                 160
Lys Lys Arg Met Ala Cys Lys Leu Ile Pro Val Asp Gln Phe Lys Pro
                165                 170                 175
Ser Asp Val Glu Ile Gln Ala Cys Phe Arg His Glu Asn Ile Ala Glu
                180                 185                 190
Leu Tyr Gly Ala Val Leu Trp Gly Glu Thr Val His Leu Phe Met Glu
                195                 200                 205
Ala Gly Glu Gly Gly Ser Val Leu Glu Lys Leu Glu Ser Cys Gly Pro
            210                 215                 220
Met Arg Glu Phe Glu Ile Ile Trp Val Thr Lys His Val Leu Lys Gly
225                 230                 235                 240
Leu Asp Phe Leu His Ser Lys Lys Val Ile His His Asp Ile Lys Pro
                245                 250                 255
Ser Asn Ile Val Phe Met Ser Thr Lys Ala Val Leu Val Asp Phe Gly
                260                 265                 270
Leu Ser Val Gln Met Thr Glu Asp Val Tyr Phe Pro Lys Asp Leu Arg
            275                 280                 285
Gly Thr Glu Ile Tyr Met Ser Pro Glu Val Ile Leu Cys Arg Gly His
            290                 295                 300
Ser Thr Lys Ala Asp Ile Tyr Ser Leu Gly Ala Thr Leu Ile His Met
305                 310                 315                 320
Gln Thr Gly Thr Pro Pro Trp Val Lys Arg Tyr Pro Arg Ser Ala Tyr
                325                 330                 335
Pro Ser Tyr Leu Tyr Ile Ile His Lys Gln Ala Pro Pro Leu Glu Asp
                340                 345                 350
Ile Ala Asp Asp Cys Ser Pro Gly Met Arg Glu Leu Ile Glu Ala Ser
            355                 360                 365
Leu Glu Arg Asn Pro Asn His Arg Pro Arg Ala Ala Asp Leu Leu Lys
            370                 375                 380
His Glu Ala Leu Asn Pro Pro Arg Glu Asp Gln Pro Arg Cys Gln Ser
385                 390                 395                 400
Leu Asp Ser Ala Leu Leu Glu Arg Lys Arg Leu Leu Ser Arg Lys Glu
                405                 410                 415
Leu Glu Leu Pro Glu Asn Ile Ala Asp Ser Ser Cys Thr Gly Ser Thr
            420                 425                 430
Glu Glu Ser Glu Met Leu Lys Arg Gln Arg Ser Leu Tyr Ile Asp Leu
            435                 440                 445
Gly Ala Leu Ala Gly Tyr Phe Asn Leu Val Arg Gly Pro Pro Thr Leu
        450                 455                 460
Glu Tyr Gly
465

<210> SEQ ID NO 68
<211> LENGTH: 1807
<212> TYPE: PRT
<213> ORGANISM: Homo Sapiens
```

<400> SEQUENCE: 68

```
Met Ala Lys Pro Thr Ser Lys Asp Ser Gly Leu Lys Glu Lys Phe Lys
1               5                   10                  15

Ile Leu Leu Gly Leu Gly Thr Pro Arg Pro Asn Pro Arg Ser Ala Glu
            20                  25                  30

Gly Lys Gln Thr Glu Phe Ile Ile Thr Ala Glu Ile Leu Arg Glu Leu
            35                  40                  45

Ser Met Glu Cys Gly Leu Asn Asn Arg Ile Arg Met Ile Gly Gln Ile
50                      55                  60

Cys Glu Val Ala Lys Thr Lys Lys Phe Glu Glu His Ala Val Glu Ala
65                  70                  75                  80

Leu Trp Lys Ala Val Ala Asp Leu Leu Gln Pro Glu Arg Thr Leu Glu
                85                  90                  95

Ala Arg His Ala Val Leu Ala Leu Leu Lys Ala Ile Val Gln Gly Gln
            100                 105                 110

Gly Glu Arg Leu Gly Val Leu Arg Ala Leu Phe Phe Lys Val Ile Lys
            115                 120                 125

Asp Tyr Pro Ser Asn Glu Asp Leu His Glu Arg Leu Glu Val Phe Lys
130                 135                 140

Ala Leu Thr Asp Asn Gly Arg His Ile Thr Tyr Leu Glu Glu Glu Leu
145                 150                 155                 160

Ala Asp Phe Val Leu Gln Trp Met Asp Val Gly Leu Ser Ser Glu Phe
                165                 170                 175

Leu Leu Val Leu Val Asn Leu Val Lys Phe Asn Ser Cys Tyr Leu Asp
            180                 185                 190

Glu Tyr Ile Ala Arg Met Val Gln Met Ile Cys Leu Leu Cys Val Arg
            195                 200                 205

Thr Ala Ser Ser Val Asp Ile Glu Val Ser Leu Gln Val Leu Asp Ala
210                 215                 220

Val Val Cys Tyr Asn Cys Leu Pro Ala Glu Ser Leu Pro Leu Phe Ile
225                 230                 235                 240

Val Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys His Leu Met Glu Asp Arg Ala Tyr Met Glu Asp
            275                 280                 285

Ala Pro Leu Leu Arg Gly Ala Val Phe Phe Val Gly Met Ala Leu Trp
290                 295                 300

Gly Ala His Arg Leu Tyr Ser Leu Arg Asn Ser Pro Thr Ser Val Phe
305                 310                 315                 320

Pro Ser Phe Tyr Gln Ala Met Ala Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Val Val Ala Trp Asp Ile Leu Leu Asn Ile Ile Glu Arg Leu
            355                 360                 365

Leu Gln Gln Leu Gln Thr Leu Asp Ser Pro Glu Leu Arg Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Phe Glu Leu Val Glu Arg Cys Ala Asp
```

-continued

```
            405                 410                 415
Gln Arg Pro Glu Ser Ser Leu Leu Asn Leu Ile Ser Tyr Arg Ala Gln
            420                 425                 430
Ser Ile His Pro Ala Lys Asp Gly Trp Ile Gln Asn Leu Gln Ala Leu
            435                 440                 445
Met Glu Arg Phe Phe Arg Ser Glu Ser Arg Gly Ala Val Arg Ile Lys
            450                 455                 460
Val Leu Asp Val Leu Ser Phe Val Leu Leu Ile Asn Arg Gln Phe Tyr
465                 470                 475                 480
Glu Glu Glu Leu Ile Asn Ser Val Val Ile Ser Gln Leu Ser His Ile
                485                 490                 495
Pro Glu Asp Lys Asp His Gln Val Arg Lys Leu Ala Thr Gln Leu Leu
            500                 505                 510
Val Asp Leu Ala Glu Gly Cys His Thr His His Phe Asn Ser Leu Leu
            515                 520                 525
Asp Ile Ile Glu Lys Val Met Ala Arg Ser Leu Ser Pro Pro Pro Glu
        530                 535                 540
Leu Glu Glu Arg Asp Val Ala Ala Tyr Ser Ala Ser Leu Glu Asp Val
545                 550                 555                 560
Lys Thr Ala Val Leu Gly Leu Leu Val Ile Leu Gln Thr Lys Leu Tyr
                565                 570                 575
Thr Leu Pro Ala Ser His Ala Thr Arg Val Tyr Glu Met Leu Val Ser
            580                 585                 590
His Ile Gln Leu His Tyr Lys His Ser Tyr Thr Leu Pro Ile Ala Ser
                595                 600                 605
Ser Ile Arg Leu Gln Ala Phe Asp Phe Leu Phe Leu Leu Arg Ala Asp
        610                 615                 620
Ser Leu His Arg Leu Gly Leu Pro Asn Lys Asp Gly Val Val Arg Phe
625                 630                 635                 640
Ser Pro Tyr Cys Val Cys Asp Tyr Met Glu Pro Glu Arg Gly Ser Glu
                645                 650                 655
Lys Lys Thr Ser Gly Pro Leu Ser Pro Pro Thr Gly Pro Pro Gly Pro
            660                 665                 670
Ala Pro Ala Gly Pro Ala Val Arg Leu Gly Ser Val Pro Tyr Ser Leu
            675                 680                 685
Leu Phe Arg Val Leu Leu Gln Cys Leu Lys Gln Glu Ser Asp Trp Lys
            690                 695                 700
Val Leu Lys Leu Val Leu Gly Arg Leu Pro Glu Ser Leu Arg Tyr Lys
705                 710                 715                 720
Val Leu Ile Phe Thr Ser Pro Cys Ser Val Asp Gln Leu Cys Ser Ala
                725                 730                 735
Leu Cys Ser Met Leu Ser Gly Pro Lys Thr Leu Glu Arg Leu Arg Gly
            740                 745                 750
Ala Pro Glu Gly Phe Ser Arg Thr Asp Leu His Leu Ala Val Val Pro
            755                 760                 765
Val Leu Thr Ala Leu Ile Ser Tyr His Asn Tyr Leu Asp Lys Thr Lys
            770                 775                 780
Gln Arg Glu Met Val Tyr Cys Leu Glu Gln Gly Leu Ile His Arg Cys
785                 790                 795                 800
Ala Arg Gln Cys Val Val Ala Leu Ser Ile Cys Ser Val Glu Met Pro
                805                 810                 815
Asp Ile Ile Lys Ala Leu Pro Val Leu Val Val Lys Leu Thr His
            820                 825                 830
```

```
Ile Ser Ala Thr Ala Ser Met Ala Val Pro Leu Leu Glu Phe Leu Ser
    835                 840                 845

Thr Leu Ala Arg Leu Pro His Leu Tyr Arg Asn Phe Ala Ala Glu Gln
850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Phe Ile
            900                 905                 910

Thr Lys Gly Leu Arg Ser Asn Val Leu Leu Ser Phe Asp Asp Thr Pro
        915                 920                 925

Glu Lys Asp Ser Phe Arg Ala Arg Ser Thr Ser Leu Asn Glu Arg Pro
930                 935                 940

Lys Ser Leu Arg Ile Ala Arg Pro Pro Lys Gln Gly Leu Asn Asn Ser
945                 950                 955                 960

Pro Pro Val Lys Glu Phe Lys Glu Ser Ala Ala Glu Ala Phe Arg
                965                 970                 975

Cys Arg Ser Ile Ser Val Ser Glu His Val Val Arg Ser Arg Ile Gln
                980                 985                 990

Thr Ser Leu Thr Ser Ala Ser Leu Gly Ser Ala Asp Glu Asn Ser Val
        995                 1000                1005

Ala Gln Ala Asp Asp Ser Leu Lys Asn Leu His Leu Glu Leu Thr
    1010                1015                1020

Glu Thr Cys Leu Asp Met Met Ala Arg Tyr Val Phe Ser Asn Phe
    1025                1030                1035

Thr Ala Val Pro Lys Arg Ser Pro Val Gly Glu Phe Leu Leu Ala
    1040                1045                1050

Gly Gly Arg Thr Lys Thr Trp Leu Val Gly Asn Lys Leu Val Thr
    1055                1060                1065

Val Thr Thr Ser Val Gly Thr Gly Thr Arg Ser Leu Leu Gly Leu
    1070                1075                1080

Asp Ser Gly Glu Leu Gln Ser Gly Pro Gly Ser Ser Ser Pro
    1085                1090                1095

Gly Val His Val Arg Gln Thr Lys Glu Ala Pro Ala Lys Leu Glu
    1100                1105                1110

Ser Gln Ala Gly Gln Gln Val Ser Arg Gly Ala Arg Asp Arg Val
    1115                1120                1125

Arg Ser Met Ser Gly Gly His Gly Leu Arg Val Gly Ala Leu Asp
    1130                1135                1140

Val Pro Ala Ser Gln Phe Leu Gly Ser Ala Thr Ser Pro Gly Pro
    1145                1150                1155

Arg Thr Ala Pro Ala Ala Lys Pro Glu Lys Ala Ser Ala Gly Thr
    1160                1165                1170

Arg Val Pro Val Gln Glu Lys Thr Asn Leu Ala Ala Tyr Val Pro
    1175                1180                1185

Leu Leu Thr Gln Gly Trp Ala Glu Ile Leu Val Arg Arg Pro Thr
    1190                1195                1200

Gly Asn Thr Ser Trp Leu Met Ser Leu Glu Asn Pro Leu Ser Pro
    1205                1210                1215

Phe Ser Ser Asp Ile Asn Asn Met Pro Leu Gln Glu Leu Ser Asn
    1220                1225                1230
```

```
Ala Leu Met Ala Ala Glu Arg Phe Lys Glu His Arg Asp Thr Ala
1235                1240                1245

Leu Tyr Lys Ser Leu Ser Val Pro Ala Ser Thr Ala Lys Pro
1250                1255                1260

Pro Pro Leu Pro Arg Ser Asn Thr Val Ala Ser Phe Ser Ser Leu
1265                1270                1275

Tyr Gln Ser Ser Cys Gln Gly Gln Leu His Arg Ser Val Ser Trp
1280                1285                1290

Ala Asp Ser Ala Val Val Met Glu Glu Gly Ser Pro Gly Glu Val
1295                1300                1305

Pro Val Leu Val Glu Pro Pro Gly Leu Glu Asp Val Glu Ala Ala
1310                1315                1320

Leu Gly Met Asp Arg Arg Thr Asp Ala Tyr Ser Arg Ser Ser Ser
1325                1330                1335

Val Ser Ser Gln Glu Glu Lys Ser Leu His Ala Glu Glu Leu Val
1340                1345                1350

Gly Arg Gly Ile Pro Ile Glu Arg Val Val Ser Glu Gly Gly
1355                1360                1365

Arg Pro Ser Val Asp Leu Ser Phe Gln Pro Ser Gln Pro Leu Ser
1370                1375                1380

Lys Ser Ser Ser Ser Pro Glu Leu Gln Thr Leu Gln Asp Ile Leu
1385                1390                1395

Gly Asp Pro Gly Asp Lys Ala Asp Val Gly Arg Leu Ser Pro Glu
1400                1405                1410

Val Lys Ala Arg Ser Gln Ser Gly Thr Leu Asp Gly Glu Ser Ala
1415                1420                1425

Ala Trp Ser Ala Ser Gly Glu Asp Ser Arg Gly Gln Pro Glu Gly
1430                1435                1440

Pro Leu Pro Ser Ser Ser Pro Arg Ser Pro Ser Gly Leu Arg Pro
1445                1450                1455

Arg Gly Tyr Thr Ile Ser Asp Ser Ala Pro Ser Arg Arg Gly Lys
1460                1465                1470

Arg Val Glu Arg Asp Ala Leu Lys Ser Arg Ala Thr Ala Ser Asn
1475                1480                1485

Ala Glu Lys Val Pro Gly Ile Asn Pro Ser Phe Val Phe Leu Gln
1490                1495                1500

Leu Tyr His Ser Pro Phe Phe Gly Asp Glu Ser Asn Lys Pro Ile
1505                1510                1515

Leu Leu Pro Asn Glu Ser Gln Ser Phe Glu Arg Ser Val Gln Leu
1520                1525                1530

Leu Asp Gln Ile Pro Ser Tyr Asp Thr His Lys Ile Ala Val Leu
1535                1540                1545

Tyr Val Gly Glu Gly Gln Ser Asn Ser Glu Leu Ala Ile Leu Ser
1550                1555                1560

Asn Glu His Gly Ser Tyr Arg Tyr Thr Glu Phe Leu Thr Gly Leu
1565                1570                1575

Gly Arg Leu Ile Glu Leu Lys Asp Cys Gln Pro Asp Lys Val Tyr
1580                1585                1590

Leu Gly Gly Leu Asp Val Cys Gly Glu Asp Gly Gln Phe Thr Tyr
1595                1600                1605

Cys Trp His Asp Asp Ile Met Gln Ala Val Phe His Ile Ala Thr
1610                1615                1620

Leu Met Pro Thr Lys Asp Val Asp Lys His Arg Cys Asp Lys Lys
```

-continued

```
              1625                1630                1635

Arg His Leu Gly Asn Asp Phe Val Ser Ile Val Tyr Asn Asp Ser
       1640                1645                1650

Gly Glu Asp Phe Lys Leu Gly Thr Ile Lys Gly Gln Phe Asn Phe
   1655                1660                1665

Val His Val Ile Val Thr Pro Leu Asp Tyr Glu Cys Asn Leu Val
   1670                1675                1680

Ser Leu Gln Cys Arg Lys Asp Met Glu Gly Leu Val Asp Thr Ser
   1685                1690                1695

Val Ala Lys Ile Val Ser Asp Arg Asn Leu Pro Phe Val Ala Arg
   1700                1705                1710

Gln Met Ala Leu His Ala Asn Met Ala Ser Gln Val His His Ser
   1715                1720                1725

Arg Ser Asn Pro Thr Asp Ile Tyr Pro Ser Lys Trp Ile Ala Arg
   1730                1735                1740

Leu Arg His Ile Lys Arg Leu Arg Gln Arg Ile Cys Glu Glu Ala
   1745                1750                1755

Ala Tyr Ser Asn Pro Ser Leu Pro Leu Val His Pro Pro Ser His
   1760                1765                1770

Ser Lys Ala Pro Ala Gln Thr Pro Ala Glu Pro Thr Pro Gly Tyr
   1775                1780                1785

Glu Val Gly Gln Arg Lys Arg Leu Ile Ser Ser Val Glu Asp Phe
   1790                1795                1800

Thr Glu Phe Val
   1805

<210> SEQ ID NO 69
<211> LENGTH: 1814
<212> TYPE: PRT
<213> ORGANISM: Mus musculus

<400> SEQUENCE: 69

Met Ala Lys Pro Thr Ser Lys Asp Ser Gly Leu Lys Glu Lys Phe Lys
1               5                   10                  15

Ile Leu Leu Gly Leu Gly Thr Ser Arg Pro Asn Pro Arg Cys Ala Glu
            20                  25                  30

Gly Lys Gln Thr Glu Phe Ile Ile Thr Ser Glu Ile Leu Arg Glu Leu
        35                  40                  45

Ser Gly Glu Cys Gly Leu Asn Asn Arg Ile Arg Met Ile Gly Gln Ile
    50                  55                  60

Cys Asp Val Ala Lys Thr Lys Lys Leu Glu Glu His Ala Val Glu Ala
65                  70                  75                  80

Leu Trp Lys Ala Val Ser Asp Leu Leu Gln Pro Glu Arg Pro Pro Glu
                85                  90                  95

Ala Arg His Ala Val Leu Thr Leu Leu Lys Ala Ile Val Gln Gly Gln
            100                 105                 110

Gly Asp Arg Leu Gly Val Leu Arg Ala Leu Phe Phe Lys Val Ile Lys
        115                 120                 125

Asp Tyr Pro Ser Asn Glu Asp Leu His Glu Arg Leu Glu Val Phe Lys
    130                 135                 140

Ala Leu Thr Asp Asn Gly Arg His Ile Thr Tyr Leu Glu Glu Glu Leu
145                 150                 155                 160

Ala Glu Phe Val Leu Gln Trp Met Asp Val Gly Leu Ser Ser Glu Phe
                165                 170                 175
```

```
Leu Leu Val Leu Val Asn Leu Val Lys Phe Asn Ser Cys Tyr Leu Asp
                180                 185                 190

Glu Tyr Ile Ala Ser Met Val His Met Ile Cys Leu Leu Cys Ile Arg
            195                 200                 205

Thr Val Ser Ser Val Asp Ile Glu Val Ser Leu Gln Val Leu Asp Ala
        210                 215                 220

Val Val Cys Tyr Asn Cys Leu Pro Ala Glu Ser Leu Pro Leu Phe Ile
225                 230                 235                 240

Ile Thr Leu Cys Arg Thr Ile Asn Val Lys Glu Leu Cys Glu Pro Cys
                245                 250                 255

Trp Lys Leu Met Arg Asn Leu Leu Gly Thr His Leu Gly His Ser Ala
            260                 265                 270

Ile Tyr Asn Met Cys Arg Ile Met Glu Asp Arg Ser Tyr Met Glu Asp
        275                 280                 285

Ala Pro Leu Leu Arg Gly Ala Val Phe Phe Val Gly Met Ala Leu Trp
    290                 295                 300

Gly Ala His Arg Leu Tyr Ser Leu Lys Asn Ser Pro Thr Ser Val Leu
305                 310                 315                 320

Pro Ser Phe Tyr Glu Ala Met Thr Cys Pro Asn Glu Val Val Ser Tyr
                325                 330                 335

Glu Ile Val Leu Ser Ile Thr Arg Leu Ile Lys Lys Tyr Arg Lys Glu
            340                 345                 350

Leu Gln Ala Val Thr Trp Asp Ile Leu Leu Asp Ile Glu Arg Leu
        355                 360                 365

Leu Gln Gln Leu Gln Asn Leu Asp Ser Pro Glu Leu Lys Thr Ile Val
370                 375                 380

His Asp Leu Leu Thr Thr Val Glu Glu Leu Cys Asp Gln Asn Glu Phe
385                 390                 395                 400

His Gly Ser Gln Glu Arg Tyr Tyr Glu Leu Val Glu Ser Tyr Ala Asp
                405                 410                 415

Gln Arg Pro Glu Ser Ser Leu Leu Asn Leu Ile Ser Tyr Arg Ala Gln
            420                 425                 430

Ser Ile His Pro Ala Lys Asp Gly Trp Ile Gln Asn Leu Gln Leu Leu
        435                 440                 445

Met Glu Arg Phe Phe Arg Asn Glu Cys Arg Ser Ala Val Ala Ile Lys
    450                 455                 460

Val Leu Asp Val Leu Ser Phe Val Leu Leu Ile Ile Arg Gln Phe Tyr
465                 470                 475                 480

Glu Glu Glu Leu Ile Asn Ser Val Ile Ser Gln Leu Ser His Ile
                485                 490                 495

Pro Glu Asp Lys Asp His Gln Val Arg Lys Leu Ala Thr Gln Leu Leu
            500                 505                 510

Val Asp Leu Ala Glu Gly Cys His Thr His His Phe Asn Ser Leu Leu
        515                 520                 525

Asp Ile Ile Glu Lys Val Met Ala Arg Ser Leu Ser Pro Pro Glu
    530                 535                 540

Leu Glu Glu Arg Asp Leu Ala Val His Ser Ala Ser Leu Glu Asp Val
545                 550                 555                 560

Lys Thr Ala Val Leu Gly Leu Leu Val Ile Leu Gln Thr Lys Leu Tyr
                565                 570                 575

Thr Leu Pro Ala Ser His Ala Thr Arg Val Tyr Glu Ser Leu Ile Ser
            580                 585                 590

His Ile Gln Leu His Tyr Lys His Gly Tyr Ser Leu Pro Ile Ala Ser
```

```
                595                 600                 605
Ser Ile Arg Leu Gln Ala Phe Asp Phe Leu Leu Leu Arg Ala Asp
610                 615                 620

Ser Leu His Arg Leu Gly Leu Pro Asn Lys Asp Gly Val Val Arg Phe
625                 630                 635                 640

Ser Pro Tyr Cys Leu Cys Asp Cys Met Glu Leu Asp Arg Ala Ser Glu
                    645                 650                 655

Lys Lys Ala Ser Gly Pro Leu Ser Pro Pro Thr Gly Pro Pro Ser Pro
                660                 665                 670

Val Pro Met Gly Pro Ala Val Arg Leu Gly Tyr Leu Pro Tyr Ser Leu
                675                 680                 685

Leu Phe Arg Val Leu Leu Gln Cys Leu Lys Gln Glu Ser Asp Trp Lys
690                 695                 700

Val Leu Lys Leu Val Leu Ser Arg Leu Pro Glu Ser Leu Arg Tyr Lys
705                 710                 715                 720

Val Leu Ile Phe Thr Ser Pro Cys Ser Val Asp Gln Leu Ser Ser Ala
                725                 730                 735

Leu Cys Ser Met Leu Ser Ala Pro Lys Thr Leu Glu Arg Leu Arg Gly
                740                 745                 750

Thr Pro Glu Gly Phe Ser Arg Thr Asp Leu His Leu Ala Val Val Pro
                755                 760                 765

Val Leu Thr Ala Leu Ile Ser Tyr His Asn Tyr Leu Asp Lys Thr Arg
770                 775                 780

Gln Arg Glu Met Val Tyr Cys Leu Glu Gln Gly Leu Ile Tyr Arg Cys
785                 790                 795                 800

Ala Ser Gln Cys Val Val Ala Leu Ala Ile Cys Ser Val Glu Met Pro
                805                 810                 815

Asp Ile Ile Ile Lys Ala Leu Pro Val Leu Val Val Lys Leu Thr His
                820                 825                 830

Ile Ser Ala Thr Ala Ser Met Ala Ile Pro Leu Leu Glu Phe Leu Ser
                835                 840                 845

Thr Leu Ala Arg Leu Pro His Leu Tyr Arg Asn Phe Val Pro Glu Gln
850                 855                 860

Tyr Ala Ser Val Phe Ala Ile Ser Leu Pro Tyr Thr Asn Pro Ser Lys
865                 870                 875                 880

Phe Asn Gln Tyr Ile Val Cys Leu Ala His His Val Ile Ala Met Trp
                885                 890                 895

Phe Ile Arg Cys Arg Leu Pro Phe Arg Lys Asp Phe Val Pro Tyr Ile
                900                 905                 910

Thr Lys Gly Leu Arg Ser Asn Val Leu Leu Ser Phe Asp Asp Thr Pro
                915                 920                 925

Glu Lys Asp Ser Phe Arg Arg Ser Thr Ser Leu Asn Glu Arg Pro
930                 935                 940

Lys Ser Leu Arg Ile Ala Arg Ala Pro Lys Gln Gly Leu Asn Asn Ser
945                 950                 955                 960

Pro Pro Val Lys Glu Phe Lys Glu Ser Cys Ala Ala Glu Ala Phe Arg
                965                 970                 975

Cys Arg Ser Ile Ser Val Ser Glu His Val Val Arg Ser Arg Ile Gln
                980                 985                 990

Thr Ser Leu Thr Ser Ala Ser Leu  Gly Ser Ala Asp Glu  Asn Ser Met
            995                 1000                1005

Ala Gln  Ala Asp Asp Asn Leu  Lys Asn Leu His Leu  Glu Leu Thr
    1010                1015                1020
```

```
Glu Thr Cys Leu Asp Met Met Ala Arg Tyr Val Phe Ser Asn Phe
1025                1030                1035

Thr Ala Val Pro Lys Arg Ser Pro Val Gly Glu Phe Leu Leu Ala
1040                1045                1050

Gly Gly Arg Thr Lys Thr Trp Leu Val Gly Asn Lys Leu Val Thr
1055                1060                1065

Val Thr Thr Ser Val Gly Thr Gly Thr Arg Ser Leu Leu Gly Leu
1070                1075                1080

Asp Ser Gly Asp Leu Gln Gly Gly Ser Asp Ser Ser Asp Pro
1085                1090                1095

Ser Thr His Val Arg Gln Thr Lys Glu Ala Pro Ala Lys Leu Glu
1100                1105                1110

Ser Gln Ala Gly Gln Gln Val Ser Arg Gly Ala Arg Asp Arg Val
1115                1120                1125

Arg Ser Met Ser Gly Gly His Gly Leu Arg Val Gly Val Leu Asp
1130                1135                1140

Thr Ser Ala Pro Tyr Ser Pro Gly Gly Ser Ala Ser Leu Gly Pro
1145                1150                1155

Gln Thr Ala Val Ala Ala Lys Pro Glu Lys Pro Pro Ala Gly Ala
1160                1165                1170

Gln Leu Pro Thr Ala Glu Lys Thr Asn Leu Ala Ala Tyr Val Pro
1175                1180                1185

Leu Leu Thr Gln Gly Trp Ala Glu Ile Leu Val Arg Arg Pro Thr
1190                1195                1200

Gly Asn Thr Ser Trp Leu Met Ser Leu Glu Asn Pro Leu Ser Pro
1205                1210                1215

Phe Ser Ser Asp Ile Asn Asn Met Pro Leu Gln Glu Leu Ser Asn
1220                1225                1230

Ala Leu Met Ala Ala Glu Arg Phe Lys Glu His Gly His Ala Pro
1235                1240                1245

Val Gln Val Ile Val Ser Ala Thr Gly Cys Thr Ala Lys Pro Pro
1250                1255                1260

Thr Leu Pro Arg Ser Asn Thr Val Ala Ser Phe Ser Ser Leu Tyr
1265                1270                1275

Gln Pro Ser Cys Gln Gly Gln Leu His Arg Ser Val Ser Trp Ala
1280                1285                1290

Asp Ser Ala Met Val Leu Glu Glu Gly Ser Pro Gly Glu Thr Gln
1295                1300                1305

Val Pro Val Glu Pro Pro Glu Leu Glu Asp Phe Glu Ala Ala Leu
1310                1315                1320

Gly Thr Asp Arg His Cys Gln Arg Pro Asp Thr Tyr Ser Arg Ser
1325                1330                1335

Ser Ser Ala Ser Ser Gln Glu Glu Lys Ser His Leu Glu Glu Leu
1340                1345                1350

Ala Ala Gly Gly Ile Pro Ile Glu Arg Ala Ile Ser Ser Glu Gly
1355                1360                1365

Ala Arg Pro Ala Val Asp Leu Ser Phe Gln Pro Ser Gln Pro Leu
1370                1375                1380

Ser Lys Ser Ser Ser Ser Pro Glu Leu Gln Thr Leu Gln Asp Ile
1385                1390                1395

Leu Gly Asp Leu Gly Asp Lys Ile Asp Ile Gly Arg Leu Ser Pro
1400                1405                1410
```

```
Glu Ala Lys Val Arg Ser Gln Ser Gly Ile Leu Asp Gly Glu Ala
1415                1420                1425

Ala Thr Trp Ser Ala Thr Gly Glu Glu Ser Arg Ile Thr Val Pro
1430                1435                1440

Pro Glu Gly Pro Leu Pro Ser Ser Ser Pro Arg Ser Pro Ser Gly
1445                1450                1455

Leu Arg Pro Arg Gly Tyr Thr Ile Ser Asp Ser Ala Pro Ser Arg
1460                1465                1470

Arg Gly Lys Arg Val Glu Arg Asp Asn Phe Lys Ser Arg Ala Ala
1475                1480                1485

Ala Ser Ser Ala Glu Lys Val Pro Gly Ile Asn Pro Ser Phe Val
1490                1495                1500

Phe Leu Gln Leu Tyr His Ser Pro Phe Phe Gly Asp Glu Ser Asn
1505                1510                1515

Lys Pro Ile Leu Leu Pro Asn Glu Ser Phe Glu Arg Ser Val Gln
1520                1525                1530

Leu Leu Asp Gln Ile Pro Ser Tyr Asp Thr His Lys Ile Ala Val
1535                1540                1545

Leu Tyr Val Gly Glu Gly Gln Ser Ser Ser Glu Leu Ala Ile Leu
1550                1555                1560

Ser Asn Glu His Gly Ser Tyr Arg Tyr Thr Glu Phe Leu Thr Gly
1565                1570                1575

Leu Gly Arg Leu Ile Glu Leu Lys Asp Cys Gln Pro Asp Lys Val
1580                1585                1590

Tyr Leu Gly Gly Leu Asp Val Cys Gly Glu Asp Gly Gln Phe Thr
1595                1600                1605

Tyr Cys Trp His Asp Asp Ile Met Gln Ala Val Phe His Ile Ala
1610                1615                1620

Thr Leu Met Pro Thr Lys Asp Val Asp Lys His Arg Cys Asp Lys
1625                1630                1635

Lys Arg His Leu Gly Asn Asp Phe Val Ser Ile Ile Tyr Asn Asp
1640                1645                1650

Ser Gly Glu Asp Phe Lys Leu Gly Thr Ile Lys Gln Gly Gln Phe
1655                1660                1665

Asn Phe Val His Val Ile Ile Thr Pro Leu Asp Tyr Lys Cys Asn
1670                1675                1680

Leu Leu Thr Leu Gln Cys Arg Lys Asp Gly Pro Ala Cys Lys Cys
1685                1690                1695

Glu Trp Trp Arg Gln Pro Gly Glu Ile Val Val Trp Ala Leu Pro
1700                1705                1710

Val Val Met Glu Leu Thr Val Thr Ile Leu Leu Cys His Leu Gln
1715                1720                1725

Met Ala Ser Gln Val His His Ser Arg Ser Asn Pro Thr Asp Ile
1730                1735                1740

Tyr Pro Ser Lys Trp Ile Ala Arg Leu Arg His Ile Lys Arg Leu
1745                1750                1755

Arg Gln Arg Ile Arg Glu Glu Val His Tyr Ser Asn Pro Ser Leu
1760                1765                1770

Pro Leu Met His Pro Pro Ala His Thr Lys Ala Pro Ala Gln Ala
1775                1780                1785

Pro Glu Ala Thr Pro Thr Tyr Glu Thr Gly Gln Arg Lys Arg Leu
1790                1795                1800

Ile Ser Ser Val Asp Asp Phe Thr Glu Phe Val
```

-continued

```
        1805              1810

<210> SEQ ID NO 70
<211> LENGTH: 2382
<212> TYPE: PRT
<213> ORGANISM: Homo Sapiens

<400> SEQUENCE: 70

Met Ser Gly Gly Ala Ala Glu Lys Gln Ser Ser Thr Pro Gly Ser Leu
1               5                   10                  15

Phe Leu Ser Pro Pro Ala Pro Ala Pro Lys Asn Gly Ser Ser Ser Asp
            20                  25                  30

Ser Ser Val Gly Glu Lys Leu Gly Ala Ala Ala Asp Ala Val Thr
        35                  40                  45

Gly Arg Thr Glu Glu Tyr Arg Arg Arg His Thr Met Asp Lys Asp
    50                  55                  60

Ser Arg Gly Ala Ala Thr Thr Thr Thr Thr Glu His Arg Phe Phe
65                  70                  75                  80

Arg Arg Ser Val Ile Cys Asp Ser Asn Ala Thr Ala Leu Glu Leu Pro
                85                  90                  95

Gly Leu Pro Leu Ser Leu Pro Gln Pro Ser Ile Pro Ala Val Pro
            100                 105                 110

Gln Ser Ala Pro Pro Glu Pro His Arg Glu Glu Thr Val Thr Ala Thr
            115                 120                 125

Ala Thr Ser Gln Val Ala Gln Gln Pro Ala Ala Ala Pro Gly
        130                 135                 140

Glu Gln Ala Val Ala Gly Pro Ala Pro Ser Thr Val Pro Ser Ser Thr
145                 150                 155                 160

Ser Lys Asp Arg Pro Val Ser Gln Pro Ser Leu Val Gly Ser Lys Glu
                165                 170                 175

Glu Pro Pro Pro Ala Arg Ser Gly Ser Gly Gly Ser Ala Lys Glu
            180                 185                 190

Pro Gln Glu Glu Arg Ser Gln Gln Gln Asp Asp Ile Glu Glu Leu Glu
        195                 200                 205

Thr Lys Ala Val Gly Met Ser Asn Asp Gly Arg Phe Leu Lys Phe Asp
    210                 215                 220

Ile Glu Ile Gly Arg Gly Ser Phe Lys Thr Val Tyr Lys Gly Leu Asp
225                 230                 235                 240

Thr Glu Thr Thr Val Glu Val Ala Trp Cys Glu Leu Gln Asp Arg Lys
                245                 250                 255

Leu Thr Lys Ser Glu Arg Gln Arg Phe Lys Glu Glu Ala Glu Met Leu
            260                 265                 270

Lys Gly Leu Gln His Pro Asn Ile Val Arg Phe Tyr Asp Ser Trp Glu
        275                 280                 285

Ser Thr Val Lys Gly Lys Lys Cys Ile Val Leu Val Thr Glu Leu Met
    290                 295                 300

Thr Ser Gly Thr Leu Lys Thr Tyr Leu Lys Arg Phe Lys Val Met Lys
305                 310                 315                 320

Ile Lys Val Leu Arg Ser Trp Cys Arg Gln Ile Leu Lys Gly Leu Gln
                325                 330                 335

Phe Leu His Thr Arg Thr Pro Ile Ile His Arg Asp Leu Lys Cys
            340                 345                 350

Asp Asn Ile Phe Ile Thr Gly Pro Thr Gly Ser Val Lys Ile Gly Asp
        355                 360                 365
```

```
Leu Gly Leu Ala Thr Leu Lys Arg Ala Ser Phe Ala Lys Ser Val Ile
    370                 375                 380

Gly Thr Pro Glu Phe Met Ala Pro Glu Met Tyr Glu Glu Lys Tyr Asp
385                 390                 395                 400

Glu Ser Val Asp Val Tyr Ala Phe Gly Met Cys Met Leu Glu Met Ala
                405                 410                 415

Thr Ser Glu Tyr Pro Tyr Ser Glu Cys Gln Asn Ala Ala Gln Ile Tyr
                420                 425                 430

Arg Arg Val Thr Ser Gly Val Lys Pro Ala Ser Phe Asp Lys Val Ala
            435                 440                 445

Ile Pro Glu Val Lys Glu Ile Ile Glu Gly Cys Ile Arg Gln Asn Lys
450                 455                 460

Asp Glu Arg Tyr Ser Ile Lys Asp Leu Leu Asn His Ala Phe Phe Gln
465                 470                 475                 480

Glu Glu Thr Gly Val Arg Val Glu Leu Ala Glu Glu Asp Asp Gly Glu
                485                 490                 495

Lys Ile Ala Ile Lys Leu Trp Leu Arg Ile Glu Asp Ile Lys Lys Leu
                500                 505                 510

Lys Gly Lys Tyr Lys Asp Asn Glu Ala Ile Glu Phe Ser Phe Asp Leu
            515                 520                 525

Glu Arg Asp Val Pro Glu Asp Val Ala Gln Glu Met Val Glu Ser Gly
530                 535                 540

Tyr Val Cys Glu Gly Asp His Lys Thr Met Ala Lys Ala Ile Lys Asp
545                 550                 555                 560

Arg Val Ser Leu Ile Lys Arg Lys Arg Glu Gln Arg Gln Leu Val Arg
                565                 570                 575

Glu Glu Gln Glu Lys Lys Lys Gln Glu Glu Ser Ser Leu Lys Gln Gln
                580                 585                 590

Val Glu Gln Ser Ser Ala Ser Gln Thr Gly Ile Lys Gln Leu Pro Ser
            595                 600                 605

Ala Ser Thr Gly Ile Pro Thr Ala Ser Thr Ser Ala Ser Val Ser
            610                 615                 620

Thr Gln Val Glu Pro Glu Glu Pro Glu Ala Asp Gln His Gln Gln Leu
625                 630                 635                 640

Gln Tyr Gln Gln Pro Ser Ile Ser Val Leu Ser Asp Gly Thr Val Asp
                645                 650                 655

Ser Gly Gln Gly Ser Ser Val Phe Thr Glu Ser Arg Val Ser Ser Gln
                660                 665                 670

Gln Thr Val Ser Tyr Gly Ser Gln His Glu Gln Ala His Ser Thr Gly
            675                 680                 685

Thr Val Pro Gly His Ile Pro Ser Thr Val Gln Ala Gln Ser Gln Pro
690                 695                 700

His Gly Val Tyr Pro Pro Ser Ser Val Ala Gln Gly Gln Ser Gln Gly
705                 710                 715                 720

Gln Pro Ser Ser Ser Leu Thr Gly Val Ser Ser Gln Pro Ile
                725                 730                 735

Gln His Pro Gln Gln Gln Gly Ile Gln Gln Thr Ala Pro Pro Gln
            740                 745                 750

Gln Thr Val Gln Tyr Ser Leu Ser Gln Thr Ser Thr Ser Ser Glu Ala
            755                 760                 765

Thr Thr Ala Gln Pro Val Ser Gln Pro Gln Ala Pro Gln Val Leu Pro
770                 775                 780

Gln Val Ser Ala Gly Lys Gln Leu Pro Val Ser Gln Pro Val Pro Thr
```

-continued

```
            785                 790                 795                 800
Ile Gln Gly Glu Pro Gln Ile Pro Val Ala Thr Gln Pro Ser Val Val
                805                 810                 815
Pro Val His Ser Gly Ala His Phe Leu Pro Val Gly Gln Pro Leu Pro
                820                 825                 830
Thr Pro Leu Leu Pro Gln Tyr Pro Val Ser Gln Ile Pro Ile Ser Thr
                835                 840                 845
Pro His Val Ser Thr Ala Gln Thr Gly Phe Ser Ser Leu Pro Ile Thr
                850                 855                 860
Met Ala Ala Gly Ile Thr Gln Pro Leu Leu Thr Leu Ala Ser Ser Ala
865                 870                 875                 880
Thr Thr Ala Ala Ile Pro Gly Val Ser Thr Val Pro Ser Gln Leu
                    885                 890                 895
Pro Thr Leu Leu Gln Pro Val Thr Gln Leu Pro Ser Gln Val His Pro
                900                 905                 910
Gln Leu Leu Gln Pro Ala Val Gln Ser Met Gly Ile Pro Ala Asn Leu
                915                 920                 925
Gly Gln Ala Ala Glu Val Pro Leu Ser Ser Gly Asp Val Leu Tyr Gln
                930                 935                 940
Gly Phe Pro Pro Arg Leu Pro Pro Gln Tyr Pro Gly Asp Ser Asn Ile
945                 950                 955                 960
Ala Pro Ser Ser Asn Val Ala Ser Val Cys Ile His Ser Thr Val Leu
                965                 970                 975
Ser Pro Pro Met Pro Thr Glu Val Leu Ala Thr Pro Gly Tyr Phe Pro
                980                 985                 990
Thr Val Val Gln Pro Tyr Val Glu Ser Asn Leu Leu Val Pro Met Gly
                995                1000                1005
Gly Val Gly Gly Gln Val Gln  Val Ser Gln Pro Gly  Gly Ser Leu
            1010                1015                1020
Ala Gln  Ala Pro Thr Thr Ser  Ser Gln Gln Ala Val  Leu Glu Ser
            1025                1030                1035
Thr Gln  Gly Val Ser Gln Val  Ala Pro Ala Glu Pro  Val Ala Val
            1040                1045                1050
Ala Gln  Pro Gln Ala Thr Gln  Pro Thr Thr Leu Ala  Ser Ser Val
            1055                1060                1065
Asp Ser  Ala His Ser Asp Val  Ala Ser Gly Met Ser  Asp Gly Asn
            1070                1075                1080
Glu Asn  Val Pro Ser Ser Ser  Gly Arg His Glu Gly  Arg Thr Thr
            1085                1090                1095
Lys Arg  His Tyr Arg Lys Ser  Val Arg Ser Arg Ser  Arg His Glu
            1100                1105                1110
Lys Thr  Ser Arg Pro Lys Leu  Arg Ile Leu Asn Val  Ser Asn Lys
            1115                1120                1125
Gly Asp  Arg Val Val Glu Cys  Gln Leu Glu Thr His  Asn Arg Lys
            1130                1135                1140
Met Val  Thr Phe Lys Phe Asp  Leu Asp Gly Asp Asn  Pro Glu Glu
            1145                1150                1155
Ile Ala  Thr Ile Met Val Asn  Asn Asp Phe Ile Leu  Ala Ile Glu
            1160                1165                1170
Arg Glu  Ser Phe Val Asp Gln  Val Arg Glu Ile Ile  Glu Lys Ala
            1175                1180                1185
Asp Glu  Met Leu Ser Glu Asp  Val Ser Val Glu Pro  Glu Gly Asp
            1190                1195                1200
```

-continued

Gln Gly Leu Glu Ser Leu Gln Gly Lys Asp Asp Tyr Gly Phe Ser
1205                1210                1215

Gly Ser Gln Lys Leu Glu Gly Glu Phe Lys Gln Pro Ile Pro Ala
1220                1225                1230

Ser Ser Met Pro Gln Gln Ile Gly Ile Pro Thr Ser Ser Leu Thr
1235                1240                1245

Gln Val Val His Ser Ala Gly Arg Arg Phe Ile Val Ser Pro Val
1250                1255                1260

Pro Glu Ser Arg Leu Arg Glu Ser Lys Val Phe Pro Ser Glu Ile
1265                1270                1275

Thr Asp Thr Val Ala Ala Ser Thr Ala Gln Ser Pro Gly Met Asn
1280                1285                1290

Leu Ser His Ser Ala Ser Ser Leu Ser Leu Gln Gln Ala Phe Ser
1295                1300                1305

Glu Leu Arg Arg Ala Gln Met Thr Glu Gly Pro Asn Thr Ala Pro
1310                1315                1320

Pro Asn Phe Ser His Thr Gly Pro Thr Phe Pro Val Val Pro Pro
1325                1330                1335

Phe Leu Ser Ser Ile Ala Gly Val Pro Thr Thr Ala Ala Ala Thr
1340                1345                1350

Ala Pro Val Pro Ala Thr Ser Ser Pro Pro Asn Asp Ile Ser Thr
1355                1360                1365

Ser Val Ile Gln Ser Glu Val Thr Val Pro Thr Glu Glu Gly Ile
1370                1375                1380

Ala Gly Val Ala Thr Ser Thr Gly Val Val Thr Ser Gly Gly Leu
1385                1390                1395

Pro Ile Pro Pro Val Ser Glu Ser Pro Val Leu Ser Ser Val Val
1400                1405                1410

Ser Ser Ile Thr Ile Pro Ala Val Val Ser Ile Ser Thr Thr Ser
1415                1420                1425

Pro Ser Leu Gln Val Pro Thr Ser Thr Ser Glu Ile Val Val Ser
1430                1435                1440

Ser Thr Ala Leu Tyr Pro Ser Val Thr Val Ser Ala Thr Ser Ala
1445                1450                1455

Ser Ala Gly Gly Ser Thr Ala Thr Pro Gly Pro Lys Pro Pro Ala
1460                1465                1470

Val Val Ser Gln Gln Ala Ala Gly Ser Thr Thr Val Gly Ala Thr
1475                1480                1485

Leu Thr Ser Val Ser Thr Thr Thr Ser Phe Pro Ser Thr Ala Ser
1490                1495                1500

Gln Leu Ser Ile Gln Leu Ser Ser Ser Thr Ser Thr Pro Thr Leu
1505                1510                1515

Ala Glu Thr Val Val Ser Ala His Ser Leu Asp Lys Thr Ser
1520                1525                1530

His Ser Ser Thr Thr Gly Leu Ala Phe Ser Leu Ser Ala Pro Ser
1535                1540                1545

Ser Ser Ser Ser Pro Gly Ala Gly Val Ser Ser Tyr Ile Ser Gln
1550                1555                1560

Pro Gly Gly Leu His Pro Leu Val Ile Pro Ser Val Ile Ala Ser
1565                1570                1575

Thr Pro Ile Leu Pro Gln Ala Ala Gly Pro Thr Ser Thr Pro Leu
1580                1585                1590

-continued

```
Leu Pro Gln Val Pro Ser Ile Pro Pro Leu Val Gln Pro Val Ala
1595                1600                1605

Asn Val Pro Ala Val Gln Gln Thr Leu Ile His Ser Gln Pro Gln
    1610                1615                1620

Pro Ala Leu Leu Pro Asn Gln Pro His Thr His Cys Pro Glu Val
    1625                1630                1635

Asp Ser Asp Thr Gln Pro Lys Ala Pro Gly Ile Asp Asp Ile Lys
    1640                1645                1650

Thr Leu Glu Glu Lys Leu Arg Ser Leu Phe Ser Glu His Ser Ser
    1655                1660                1665

Ser Gly Ala Gln His Ala Ser Val Ser Leu Glu Thr Ser Leu Val
    1670                1675                1680

Ile Glu Ser Thr Val Thr Pro Gly Ile Pro Thr Thr Ala Val Ala
    1685                1690                1695

Pro Ser Lys Leu Leu Thr Ser Thr Thr Ser Thr Cys Leu Pro Pro
    1700                1705                1710

Thr Asn Leu Pro Leu Gly Thr Val Ala Leu Pro Val Thr Pro Val
    1715                1720                1725

Val Thr Pro Gly Gln Val Ser Thr Pro Val Ser Thr Thr Thr Ser
    1730                1735                1740

Gly Val Lys Pro Gly Thr Ala Pro Ser Lys Pro Leu Thr Lys
    1745                1750                1755

Ala Pro Val Leu Pro Val Gly Thr Glu Leu Pro Ala Gly Thr Leu
    1760                1765                1770

Pro Ser Glu Gln Leu Pro Pro Phe Pro Gly Pro Ser Leu Thr Gln
    1775                1780                1785

Ser Gln Gln Pro Leu Glu Asp Leu Asp Ala Gln Leu Arg Arg Thr
    1790                1795                1800

Leu Ser Pro Glu Ile Ile Thr Val Thr Ser Ala Val Gly Pro Val
    1805                1810                1815

Ser Met Ala Ala Pro Thr Ala Ile Thr Glu Ala Gly Thr Gln Pro
    1820                1825                1830

Gln Lys Gly Val Ser Gln Val Lys Glu Gly Pro Val Leu Ala Thr
    1835                1840                1845

Ser Ser Gly Ala Gly Val Phe Lys Met Gly Arg Phe Gln Val Ser
    1850                1855                1860

Val Ala Ala Asp Gly Ala Gln Lys Glu Gly Lys Asn Lys Ser Glu
    1865                1870                1875

Asp Ala Lys Ser Val His Phe Glu Ser Ser Thr Ser Glu Ser Ser
    1880                1885                1890

Val Leu Ser Ser Ser Ser Pro Glu Ser Thr Leu Val Lys Pro Glu
    1895                1900                1905

Pro Asn Gly Ile Thr Ile Pro Gly Ile Ser Ser Asp Val Pro Glu
    1910                1915                1920

Ser Ala His Lys Thr Thr Ala Ser Glu Ala Lys Ser Asp Thr Gly
    1925                1930                1935

Gln Pro Thr Lys Val Gly Arg Phe Gln Val Thr Thr Thr Ala Asn
    1940                1945                1950

Lys Val Gly Arg Phe Ser Val Ser Lys Thr Glu Asp Lys Ile Thr
    1955                1960                1965

Asp Thr Lys Lys Glu Gly Pro Val Ala Ser Pro Pro Phe Met Asp
    1970                1975                1980

Leu Glu Gln Ala Val Leu Pro Ala Val Ile Pro Lys Lys Glu Lys
```

-continued

```
            1985                1990                1995

Pro Glu Leu Ser Glu Pro Ser His Leu Asn Gly Pro Ser Ser Asp
            2000                2005                2010

Pro Glu Ala Ala Phe Leu Ser Arg Asp Val Asp Asp Gly Ser Gly
            2015                2020                2025

Ser Pro His Ser Pro His Gln Leu Ser Ser Lys Ser Leu Pro Ser
            2030                2035                2040

Gln Asn Leu Ser Gln Ser Leu Ser Asn Ser Phe Asn Ser Ser Tyr
            2045                2050                2055

Met Ser Ser Asp Asn Glu Ser Asp Ile Glu Asp Glu Asp Leu Lys
            2060                2065                2070

Leu Glu Leu Arg Arg Leu Arg Asp Lys His Leu Lys Glu Ile Gln
            2075                2080                2085

Asp Leu Gln Ser Arg Gln Lys His Glu Ile Glu Ser Leu Tyr Thr
            2090                2095                2100

Lys Leu Gly Lys Val Pro Pro Ala Val Ile Ile Pro Pro Ala Ala
            2105                2110                2115

Pro Leu Ser Gly Arg Arg Arg Arg Pro Thr Lys Ser Lys Gly Ser
            2120                2125                2130

Lys Ser Ser Arg Ser Ser Ser Leu Gly Asn Lys Ser Pro Gln Leu
            2135                2140                2145

Ser Gly Asn Leu Ser Gly Gln Ser Ala Ala Ser Val Leu His Pro
            2150                2155                2160

Gln Gln Thr Leu His Pro Pro Gly Asn Ile Pro Glu Ser Gly Gln
            2165                2170                2175

Asn Gln Leu Leu Gln Pro Leu Lys Pro Ser Pro Ser Ser Asp Asn
            2180                2185                2190

Leu Tyr Ser Ala Phe Thr Ser Asp Gly Ala Ile Ser Val Pro Ser
            2195                2200                2205

Leu Ser Ala Pro Gly Gln Gly Thr Ser Ser Thr Asn Thr Val Gly
            2210                2215                2220

Ala Thr Val Asn Ser Gln Ala Ala Gln Ala Gln Pro Pro Ala Met
            2225                2230                2235

Thr Ser Ser Arg Lys Gly Thr Phe Thr Asp Asp Leu His Lys Leu
            2240                2245                2250

Val Asp Asn Trp Ala Arg Asp Ala Met Asn Leu Ser Gly Arg Arg
            2255                2260                2265

Gly Ser Lys Gly His Met Asn Tyr Glu Gly Pro Gly Met Ala Arg
            2270                2275                2280

Lys Phe Ser Ala Pro Gly Gln Leu Cys Ile Ser Met Thr Ser Asn
            2285                2290                2295

Leu Gly Gly Ser Ala Pro Ile Ser Ala Ala Ser Ala Thr Ser Leu
            2300                2305                2310

Gly His Phe Thr Lys Ser Met Cys Pro Pro Gln Gln Tyr Gly Phe
            2315                2320                2325

Pro Ala Thr Pro Phe Gly Ala Gln Trp Ser Gly Thr Gly Gly Pro
            2330                2335                2340

Ala Pro Gln Pro Leu Gly Gln Phe Gln Pro Val Gly Thr Ala Ser
            2345                2350                2355

Leu Gln Asn Phe Asn Ile Ser Asn Leu Gln Lys Ser Ile Ser Asn
            2360                2365                2370

Pro Pro Gly Ser Asn Leu Arg Thr Thr
            2375                2380
```

<210> SEQ ID NO 71
<211> LENGTH: 454
<212> TYPE: PRT
<213> ORGANISM: Homo Sapiens

<400> SEQUENCE: 71

```
Met Asp Pro Gly Gln Gln Pro Pro Gln Pro Ala Pro Gln Gly Gln
1               5                   10                  15

Gly Gln Pro Pro Ser Gln Pro Pro Gln Gly Gln Gly Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
            50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
            130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
                180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
        210                 215                 220

Met Asn Ser Ala Ser Ala Met Asn Gln Arg Ile Ser Gln Ser Ala Pro
225                 230                 235                 240

Val Lys Gln Pro Pro Pro Leu Ala Pro Gln Ser Pro Gln Gly Gly Val
                245                 250                 255

Met Gly Gly Ser Asn Ser Asn Gln Gln Gln Gln Met Arg Leu Gln Gln
            260                 265                 270

Leu Gln Met Glu Lys Glu Arg Leu Arg Leu Lys Gln Gln Glu Leu Leu
        275                 280                 285

Arg Gln Val Arg Pro Gln Glu Leu Ala Leu Arg Ser Gln Leu Pro Thr
    290                 295                 300

Leu Glu Gln Asp Gly Gly Thr Gln Asn Pro Val Ser Ser Pro Gly Met
305                 310                 315                 320

Ser Gln Glu Leu Arg Thr Met Thr Thr Asn Ser Ser Asp Pro Phe Leu
                325                 330                 335

Asn Ser Gly Thr Tyr His Ser Arg Asp Glu Ser Thr Asp Ser Gly Leu
            340                 345                 350

Ser Met Ser Ser Tyr Ser Val Pro Arg Thr Pro Asp Asp Phe Leu Asn
        355                 360                 365

Ser Val Asp Glu Met Asp Thr Gly Asp Thr Ile Asn Gln Ser Thr Leu
```

```
                            370                 375                 380
Pro Ser Gln Gln Asn Arg Phe Pro Asp Tyr Leu Glu Ala Ile Pro Gly
385                 390                 395                 400

Thr Asn Val Asp Leu Gly Thr Leu Glu Gly Asp Gly Met Asn Ile Glu
                405                 410                 415

Gly Glu Glu Leu Met Pro Ser Leu Gln Glu Ala Leu Ser Ser Asp Ile
            420                 425                 430

Leu Asn Asp Met Glu Ser Val Leu Ala Ala Thr Lys Leu Asp Lys Glu
        435                 440                 445

Ser Phe Leu Thr Trp Leu
        450

<210> SEQ ID NO 72
<211> LENGTH: 245
<212> TYPE: PRT
<213> ORGANISM: Homo Sapiens

<400> SEQUENCE: 72

Met Asp Lys Asn Glu Leu Val Gln Lys Ala Lys Leu Ala Glu Gln Ala
1               5                   10                  15

Glu Arg Tyr Asp Asp Met Ala Ala Cys Met Lys Ser Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Ala Arg Arg Ser Ser Trp Arg Val Val Ser Ser
    50                  55                  60

Ile Glu Gln Lys Thr Glu Gly Ala Glu Lys Lys Gln Gln Met Ala Arg
65                  70                  75                  80

Glu Tyr Arg Glu Lys Ile Glu Thr Glu Leu Arg Asp Ile Cys Asn Asp
                85                  90                  95

Val Leu Ser Leu Leu Glu Lys Phe Leu Ile Pro Asn Ala Ser Gln Ala
            100                 105                 110

Glu Ser Lys Val Phe Tyr Leu Lys Met Lys Gly Asp Tyr Tyr Arg Tyr
        115                 120                 125

Leu Ala Glu Val Ala Ala Gly Asp Asp Lys Lys Gly Ile Val Asp Gln
    130                 135                 140

Ser Gln Gln Ala Tyr Gln Glu Ala Phe Glu Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Ser Pro Glu Lys Ala Cys Ser Leu Ala
            180                 185                 190

Lys Thr Ala Phe Asp Glu Ala Ile Ala Glu Leu Asp Thr Leu Ser Glu
        195                 200                 205

Glu Ser Tyr Lys Asp Ser Thr Leu Ile Met Gln Leu Leu Arg Asp Asn
    210                 215                 220

Leu Thr Leu Trp Thr Ser Asp Thr Gln Gly Asp Glu Ala Glu Ala Gly
225                 230                 235                 240

Glu Gly Gly Glu Asn
                245

<210> SEQ ID NO 73
<211> LENGTH: 480
<212> TYPE: PRT
<213> ORGANISM: Homo Sapiens
```

<400> SEQUENCE: 73

```
Met Ser Asp Val Ala Ile Val Lys Glu Gly Trp Leu His Lys Arg Gly
1               5                   10                  15

Glu Tyr Ile Lys Thr Trp Arg Pro Arg Tyr Phe Leu Leu Lys Asn Asp
            20                  25                  30

Gly Thr Phe Ile Gly Tyr Lys Glu Arg Pro Gln Asp Val Asp Gln Arg
        35                  40                  45

Glu Ala Pro Leu Asn Asn Phe Ser Val Ala Gln Cys Gln Leu Met Lys
    50                  55                  60

Thr Glu Arg Pro Arg Pro Asn Thr Phe Ile Ile Arg Cys Leu Gln Trp
65                  70                  75                  80

Thr Thr Val Ile Glu Arg Thr Phe His Val Glu Thr Pro Glu Glu Arg
                85                  90                  95

Glu Glu Trp Thr Thr Ala Ile Gln Thr Val Ala Asp Gly Leu Lys Lys
            100                 105                 110

Gln Glu Glu Glu Met Asp Phe Arg Ser Gly Ser Pro Ser Asp Asn
        115                 120                 125

Ser Gly Ala Glu Glu Met Glu Val Ser Leu Ala Lys Pro Lys His Arg
    130                 135                 140

Val Thr Met Asn Glu Phe Glu Tyr Leu Lys Leu Leu Gly Lys Gly Thr
145                 150                 155                 160

Phe Gly Lys Val Ile Leu Val Lys Glu Lys Ala Thr Gly Arg Tyr Tyr
                165                 170                 175

Ala Met Lys Ile Leu Lys Lys Glu Val Ile Val Ala Lys Asp Glu Val
            180                 185                 190

Ala His Thr Leu Thr Glu Asn Arg Val Leu Gln Asn Ser Arg His Pro
        195                 200                 205

Phe Leu Thr Ala Leu Lys Tyr Ser Phe Gln Thr His Asp Arg Leu Cys
    210                 215                 220

Phe Val Met Glu Tyr Ala Asn Gly Gly Glu Leu Phe Phe His Leu Ser
225                 230                 235                 240

Arg Glu Arg Val Phe Ser Glu Asp Arg Ala Arg Phe Tyr Gly Ala Glu
                245                 250                 255

Ile Val Ser Ala Leu Asp Tyr Leu His Ser Glu Lys Asn Val Val Tyr
            260                 265                 270

Arg Asp Leu Lys Leu Glu Asn Leu Met Leu Asp Lys Asp Gly His Ile
        275                 280                 285

Lys Ile Thr Asp Phe Gly Leu Cys Lys Glu Gly Ile Lys Asp Gly Ala
    290                 295                 300

Thr Met Lys Thr Phe Cys Gly Thr Pro Glu Tyr Leu Ala Pro Glu Val
305                 310                 315                 320

Leu Glu Asp Asn Asp Tyr Gly Arg Ala Val Asp Trp Trp Gly Leu Gly
                325                 330                 335

Val Val Met Tyr Glu Met Met Cys Gly Arg Leu Pro Phe Tyr Asn Gln
            340                 345                 350

Asp His Glu Lys Leu Phe Glu Leu Ile Leu Met Glu Glu Ile Arg Phe
        355                 360                 365

Pro Arg Thr Leu Gly Pro Glu Ala Lys Ser Leu Leu Ser Gly Leu Leu
    370                 375                 380

Lys Lys Asp Pro Lys Gln Arg Leu Gly Gly Gly Ser Glu Asp Ala Lys
385                 390                 395                 400

Glu Ile Met Gln His Arg Phe Phe Ala Gly Ile Val Trp Gln His Val
                405                 410                 415
```

```
Tyr Glu Lys Lys Leu Ser Pro Pro Phe Lys Pro Gln Val Thr Ser Glu
            420                 425                 430

Thr Asp Thr Arg Tyr Phe Asp Glu Glu Phe Thr Ala Gln Met Ile Thr
            435                 440                 445

Ile Thr Pro Pro Asp Gln Asp Asp Ser Met Glu Cys Val Asp Ser Glu
        450                 455                 460

Arg Arg Pro His Phe Pro Gln Phe Ser Tyr Ser Ala Ser Gly Thr Ala
465                 470                 475                 480

<210> SEQ ID NO 74
<211> LENGTH: 14
<212> TYPE: PRT
<213> ORGANISM: Artificial Sequence
<220> FEATURE:
<223> OTHER INFORMATION: Synthetic Monomeric Ligand

<400> SEQUENCE: 74

Ala Arg Lys Arg Glu Arg Ala Tyr Ala Phe Gly His His Ala
1               5                   10

<210> SEQ ID NO 75
<211> LENGTH: 7
<212> TYPE: PRT
<213> ORGANISM: Artificial Sequence
<220> FEATURE:
<223> OTHER INFORMATION: Synthetic Monomeric Ligand

<400> SEQUENCE: 75

Arg Pro Arg Ala Ala Ala Phe
1               5

<210> SEQ ID NO 76
<211> LENGTH: 12
<212> TYPE: PRT
<213> ORGANISM: Artificial Sequence
<220> FEATURE:
<223> OTHER INFORMATION: Synthetic Monomeric Ligand

<400> SEQUENCE: 76

Ala Asn Arg Met Arg Gly Arg Leu Gly Ala Val Asp
1               5                   10

<210> SEQ ID NO 77
<211> LENGTH: 13
<212> TYPE: PRT
<213> ORGANISM: Artificial Sequence
<220> FEATURE:
<223> OTHER INFORMATION: Synthetic Monomeric Ligand

<400> SEQUENCE: 77

Gly Asp Leu Pro Arg Pro Arg Leu Asn Ala Ala Asp Phe
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Monomeric Ligand

<400> SEQUENCE: 78

Ala Arg Lys Arg Glu Arg Thr Tyr Ser Phe Gly His His Ala
1               5                   10
```

```
<210> SEQ ID NO 79
<211> LENGTH: 14
<212> TYPE: PRT
<213> ORGANISM: Artificial Sequence
<220> FEATURE:
<223> OTHER INFORMATION: Synthetic Monomeric Ligand
<220> FEATURE:
<221> NAME/KEY: misc_feature
<222> LOCATION: (9)..(9)
<223> OTHER INFORMATION: Xaa can be any naturally occurring amino acid

<400> SEQUENCE: 79

Ala Arg Lys Arg Glu Arg Ala Tyr Xaa Phe Gly His His Ala
1               5                   10

<210> SEQ ID NO 80
<211> LENGTH: 11
<212> TYPE: PRT
<213> ORGANISM: Artificial Sequence
<220> FEATURE:
<223> OTHER INFORMATION: Synthetic Monomeric Ligand
<220> FEATURE:
<221> NAME/KEY: misc_feature
<222> LOCATION: (7)..(7)
<223> OTHER INFORMATION: Xaa can be any naturally occurring amino acid

<400> SEQUENCE: 80

Gly Arg Pro Arg Thr Ser Xaa Phe Ala Glu Gly
1               5                   10

<210> SEQ ID NO 81
<211> LENGTH: 7
<212> TYPE: PRT
<213> ORGANISM: Artificial Sequence
<220> FEATURE:
<223> OTHER INFORMATION: Synthetic Monomeric Ligand
<220> FEATURE:
<221> NAME/KEY: misc_feature
<222> LOCATION: (6)..(6)
<223> OTHER INFORMATION: Xaa can be any naturally occurring amino acid

<400> SEQUENCE: 81

Arg Pro Arg Thr Ser Xaa Phe
1               5

<210> SEQ ID NO 82
<211> LENGTH: 7
<212> TYPE: PRT
<213> ORGANISM: Artificial Sequence
<220> FEATURE:
<223> OTHER INFORMATION: Synthetic Monomeric Ligand
<220> FEATURE:
<221> NAME/KEY: misc_feature
<222> LOCATION: (6)..(6)
<223> OTHER INFORMATION: Xaa can be any naturally occurring amino acid

<400> SEQUENCE: 82

Arg Pro Arg Ala Ala Xaa Phe
1               5

<210> SEQ ID NO 83
<211> LENGTH: 7
<212> TYPE: PRT
<213> ORGANISM: Artificial Sequence
<220> FEATURE:
<223> OTHER INFORMATION: mammalian
<220> FEATURE:
<221> NAME/KEY: misc_feature
<222> LOCATION: (6)..(6)
<223> OTHER INFORMATION: Xaa can be any naturally occurring amino acid
```

```
<400> SEQUENCE: 83

Arg Ala Arg Glu Ala Xaa Gly
1               5

<210> SEQ ID NO 84
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 84

Glu Ala Val Ser Glu Gly Ser Ser Gly Arg Ala Arg Glu Ala Xaa
1               5                   10                  15

Gly Ala Pro Thr Ser Ser Lys Asp Asn Tyr Leu
            20                  25

<210> SEQ ID NO 85
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 85

Arg Met Arg His Leu Xaa Gln
1               5

<210> SEQ ID NO 86
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 86

His Lys Ser Arg Met Tyr Ser Gln Cys Val Arg Met Arg His Leu Xaa
1               5                   10                  15

Gln Glu Arg Arg Phe Tyr Gln Leu Thr Lys Leu
            20                  25

<210> SEQ ID NO 87
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 87

Arg Gln Arg Ile Arg Xaa Cys
1               5

<210> SEQ ID NO 88
<211> LENGTH: 27
<212> TYPE: PRT
<213> ORGANISM: mammalian
<220> FEATURE:
<221> NAME/KEY: misc_feature
<222> LOCATION: (16)..(16)
```

<223> OTHER INFORMATION: Xaa can be any naturally occurring amino acid

<400> SEQUENCE: 88

Leu Leu Asp Leu Gln Glu Asn Arg Pro Ala Arg Gln Arg Ile Arg Xaa
1               5                   10                  15

Cys Val Ser Ala Glu Asn Phe Leu Gln Ile Gln
            20                  25

<210> SEQ ID NO 89
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 89

Arg Gly Arg Leu Gly Xaa Val
1               5

<210> SEQ ID NO 90
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 90

Asn Ile Phe Ser Arg Gly Ala Asn Arg Met Arg Gly Arg Leu Gly Xaa
1               5                   10                  15

Val Asp Ser Phe Glu Arg Ser Asn Ser Leu Ala
            20                  25

<210> SEQ ID NO 91
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 91

Arg Arg Arg Ala His Xaa Phe
1               5

<210> SEQ ID NO 92
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 92

Pro Glu Glu Asp Ser Asp Ser Pro Gln Phe Arg Arg Arg Ala His Xaa
1               5                   10                  15

Phe Ser His Pro Pro Ser Ser Thr Lys Arg Lys
            20                  25

<210> SEQ ID NO 93
<211> LENGTH: 7

<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 93

Arg Ser Arg Cys Ser Xaa Val
1               5

<210> SEQ ID NO 94
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 94

Asp Cys Gly Phe Asp Glu Gln Gln Glu Phe Arg Ser Arg Cys Ser Xaa
1               5                   10                  15

Val Thr Gly Val Met Gln Lys Lys Val His Glu
            20                  25

<210> SEQ ID NO 95
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 95

Arg Arg Arg His Ala Xaa Ala
1               5

<210> SEQ ID NO 96
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 96

Val His Glu Asn Asn Gln Lys Thr Gln Pro Arg Arg Arg His Ala Xaa
1               5                   10                  15

Ala Pro Ser His Val Gln Pro Ser Asp Ser Glu
            20                  25

<210> SEQ ID NO 97
<211> LENGTH: 31
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 97

```
Arg Ser Arg Cys Ser Xaa Val Thr Gly Val Met Gln Lys Lys Val His
1               5                   10                  15

Glu Asn Asn Gln Lys Thr Gln Pro Arg Arg His Ala Xaa Ala
            20                  25                  30
```

```
<210> SEQ ID NO 98
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 98
```

```
Arg Ser Leu Thr Ser Xaa Leu
1               5
```

```
<210> SEQ ID NO 99
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 99
```

```
Lys Leu Asp Val Leu Lys Asn Lys Ala Lys Arg Ser Leu Thr Ser Xaa
1               5                   10                  15

Leu Glu Asn Ile Phe Ser Arg Gly Ala Asn Arg
            20                  25
```

```
<210> SEQ ID NO 100
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 100
```

```
Arg Gly Arg Leu Gly Xaa Met
1               5
```

```
<210> SEQ ID NO 101
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 101
```

```
Asn Ile Phe Ser Arg Gly Ala Asn Arg Met Arg Gly Arg Leu Gly Xaa
1               5                   10                  15

Met Asp Ser Phe Glu Arg Ala Asn Ser Leu Ala
            20                  25
```

```
<210> SEQ ID NO 102
<211> LENGTH: 25
<212> TYPE: PRT
<213> ORGANISM: mammalian
<220> FEATURE:
<221> NAME/KEY: misc_feature
```

```
<222> LOCATION: (6)..(6)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid

<400> SEQUENCE: 102

Arg Ser Leu Thr Ser Xaa Leu Glu Asn Ile Phe Ser Arg Gly Ala Asn
1               5                   10                  15

Arg Met Arg Gly Arg Leu Gly Xaa Met
            20                  25

<210> SEQ ID NO 103
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 103

Arg Arg Arg Ala His Xaa Phe
1               5

<210> SEQ ID NO 104
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 104

Pro Glu Glu Asp Ser Asp Ser Pro Gln Phe Arg Arg Ala His Xaa
1               5                   10                  15

Phe Ser His Pro Pro Ser Ser Ser Arg Arg Lys
            20                  25

<210> SEQ ID NO 105
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 105

Arg Lys Arg Thr Ser Xaa Thr
1               5

<210> SEQ ID NO 106
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 106

Thr Ala Ser Glu Ser Ser Asp Gly Glu Gly Arg Lys Arg Thr Ser Xaa
1               5                   10                  15

Thr Cys Ser Asn Glu Ser Leu Asn Ala Gly Gly
```

```
                20                  25

<210> SEQ ID NO 107
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 107

Arg Gly Arg Gly Ser Xaa Val
1               5

<210> SEQ ID NO 108
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 108

Pro Ala Ala Thr Ser Ser Ser Ala Thr Arg Gly Arg Gly Ser Xaa
1               5                   10                  15

Val Gly Gly Gly Ser Arg Arg Thr Thr Val Ala
            20                  25

<210> SEQ ID NO 109
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 109

Arg Lys Arg Arg Trp Xaa Ala
1               5

<210> SEQ ID NO 110
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 110

Lys Ile Glu Pro Ser Lys Pro Ala Ala Thr Arg Lys Arg Arg Trp Xaa
1               5                   10                  15

Ala Pro Glu Ser Arg Lys Leu Glu Lys Ser Glu
            20                  25

<210> SEQ ID NO 111
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 111
```

```
Pro Ser Arg Thr Ala Xaa Phe
1               5

<210> SEQ ID NO 112
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 112

Asn Ala Ser Gly Ser Thr Ser Thr Pro Ala Pro Ser Arg Thr Ala Xaa
1               5                   10                  15

Phe Ser Glu Ser Arg Ala Asp Glu Val Ala Pro
            20                  25

<210> SEQ ID NO 113
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 113

Arg Ser Arg His Ser Xaa Tyr
1               5

<210> SEQ ID NO 114
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 114

His His Gly Gly Ala Gly Ala Met Glu Thr Arg Ser Arg His Ser Xaa
1               5                   10                  15

Tyr Pro Ala Gly Thr Glu Glu Asp Glu Gly Met
            20                  25

<210> SEQ ID NO 115
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 115

Arg Gly Arg Ser Arg Xaa Ala
1               5

<210> SEQ ID NO 116
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid
```

<400> SEQUENCE: 116

Glu Gly Met Glu Glu Leu Ser Pro Phe Arg Gly Arg Ser Arg Xaa
1               5                   10                  15

Ala Pro Pro Asn Leu Trp Ala Ala Gln Arg Tyr
            20                  25

<210> SEQ ID NO 117
<211> LENGTH: 31
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 117

Arg Ser Arg His Ser Xaa Tyr Pro Ala Gly Thr Glu Glu Asp Glu Gly
1               5                   10                  15

Met Glu Glu Leu Ser Pro Phe Arg Gly Arg Ser Arg Xaa Ala
            20                  25                  30

<210> SEQ ID NO 118
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 118

Arg Lys Arg Arg Pro Xaa Ser
1               5

<210> SEQ ID NO 119
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 119

Gln Glu Arg Pro Leu Thr Asn Lys Leu Lys Arg Lys Arg Arg Pro Xaa
1               5                   10                  15

Ser Gly Leu His Pro Glu Asp Phe Ile Lys Lys
            20                  25

<210> SEQ ID NO 120
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 120

Arg Asp Arg Asn Gly Xaa His
1               5

```
<210> SEQ ID NO 121
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 121

Arg Glu Lys Val Pro Lys Leu His Ser Ile Arg Asp Arg Asn Gly Xaa
1               5                   10                  15

His Leu Asp Ala Gly Ala Leu Thr Thr Thr Phe
            20                  25

<210> SEQ ID NO 122
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 122

Arg Arg Arg Phe Ser Xaa Pro
1               5

<210> SEQ ID NO 123
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 123

Thr Gly Ser Asn Ile Asp Cys Glu Lys Leu Arg Arg Arg Phe Ser Xaa
1               5                   10                  15

Pro His Phe Met Val Glu Val Lys Gly Asp Leu
            20                  25

<210> SEQ ID NO 124
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 124

Arg Arg Arg Phe Ser Xaa Leu
1               5

<210> SEQ ID NO 125
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 125

Thr Gly Ser Asn Ile Asp Cys Glu Lys Leu Arg Arg Arg Phe Ser Xaa
```

```
                1               5                   10                  15
Leu His Phe Met Val Glu Val Lys Gly Asp Leu
                20                  25

<210> SEQ ID NO 126
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 126

Arg Arg Arg Ser Arg Xaa Phe
1               5

<210> SEQ ID NO 127
<211> LENGTH: 28
<212> TYPE: PRT
<213> ORGANISM: mammalian
<220> FEATURE:
<221> NAME/KEY: misc_feature
<222> LOCATION: (17)..(17)
<223> OTHER INFORMATION: Xaa can be any naturally occurring amino acid

<400> SEQUENCE: 127

Gln Arg Ser Ser Arg Arg Lys His Arg Arg Arg Arg Arg Arg Ser Arg
1               5                   10                  15
Xaa Phe Ser Arg Ser Ser Ser Gln His Ser Ser Arg
                20                  25

<210> SEQ ID NO 128
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 128

Leu Ser Arg Arg Pro Xaa Tyr
1               5

<210> SEQ ID NO 129
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 129

Val Thr Asp Ser Gln Lys Arg Arg Glu Ile Leu Ser Arg Arg Pro Xaa
1               5                   10                  15
Tyr Arg Lys Ile Leu Asn Asp Leu Ser Ser Asp
                20                  25

<210> SEQ ID NO 130
<211> LENGTH: 7
<212> TYPE: PRT
<213> ORGANISM: mammalian
<220> FEATURE:
<221> NAME/KEY: misc_feature
<222> LOCATION: (6)..(6)
```

<223> OTHER INFORMATION: Xaa can be any naturally occurring amino acid

<400> SEQUENCE: 130

Arg Ser Arg Arg Leu Xaa Phe
1               5

<210> SEQ ID NO 131
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 131

Tyr Cys Arg Ile Tyr Ser Leu Val Arg Thr Arg Ser Arg Arg Leu Xaa
1               5                   10                  15

Phe Arg Lys Asn Ile Ser Lys Ala Ser Arg Ser
            20                  25

<210> SEQ ID NO 132
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 132

Arg Ile Arg Thr Gln Xaa Phe
1               5

<210> SEQ ID NO 133
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 133

Leu Thr Leu Arg Thr Gln Glu Val Thr Ser Arg Ile Arg Thr Gln Xaa
1               5                   10                  15

Phe Ser Leu Gln Glu Arg Gln Leu Arg Gly Ala
            20                  25

<210> SEQ ID NO 134
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 134

Arg Lys Arg Val Lys Xaa Glu
1               5

<210> SEQ ID NO 135
<211> LENGTH: 27
<212> TYPE: PRT
<213> ORGANISM: mammalian
<220> FEATURE:

```
<221> NAME/KEY: misc_feature
<222> LOCATION: (16)..(16)
<223> OTHER INFORMATION: Xaa can be any naturally occurring amino acid

<400> SEQUENCE: 135

Lys Lys Ser Glu Lys Gly Pro Val Cys Trp Arg Lys Arg Val Lys Xaa
1               5                   10                  15

Glu Tyr Met Arg Leu Arg Gln Leu Lys Arg Phe
            20                  25

<210> SEQ ID NO 136
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 136

Arg Pro Arg Ser Cys Xaa Trp
1               5

<210> SEQ ID NO 137
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 137

Glu Ile Asp Pro Asp Phe Glu Pro Leu Pro Arg Pro Arg Ser Cys Xaa
1               5                   10                  15

Trp Pro Leu Pro Arg Pro Glu Phe Ser Gln Ser
            20                  25

<210> SEQ ID NO 138
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 138

Arg Arg Arg Ala Ala Xaa Met
1               5

<210> SEQ ID NO 139
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 139

Pro Glu Gly Gly Lys Ser Gly Lys Ser Pro Arg Arg Arg Ala Ala Xaa
1               5                   10                  15

Met Asp Asn Asn Ser Lys Phe Ala Lys Ser Arg
            20                  25
```

```
<210> SEQ ID NO 140
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 140

Arg Pro Arg Thr Ser Xaa Asn
1               5

<210> SEQ ID NO 141
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 141

Asn Asp Asp Phe Asp Asn Trp Ser Thr Phe Arg Pro Arg Thr Ser Xaa
1               5                   10                  15
Asn Ala Ser Thr Ile Ser Gly Arg Leu Ser Pro
            20                  25

<210> SEQ ID NO 142
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 142

Arg Pro Arg Ser Cys Xaa Trp
1               5

<210> SEQ ID NO 143
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 143

Glu Leu Asp Pro Glu Phe Glu Pro Gln Ser Arg Pro Arg Ser Cys Xaa
1               5                   10                  15
Trp Pro Leu Gln Arg Pro Glu Leu Gln Ala Ser
            20                  25

<210> SEQ ID NO 144
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 144

Arg Arg Arg Ala Val Xaa Met
1               5
```

```
<210> SEQ ID NO 145
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 145

Pro Asp Gly Gly Lys Ser Gly Lys Ala Pro Arg Arg Arg Ala Val Xaa
1               5                   10                  15

Met Asp Asn Ser Asn Lys Tyr Thr Lys Ser Arg
            20                  25

<210> SEQ ID NO 146
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 146

Arg Ser Arg Thr Asn Xaa Asn
1               5

<210> SEQ ID NO 147
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 147

Ser Asp Glu Leu Asp Ala Trp Thr Asp Phe Arg Ser Arg Thr Asn Xaa
1               5                   10                  15

Asn Ala Ser Thr Val Ser Gly Arg Leu Ser Pro
            20                  25

<210> SEQ ID NO 148
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 148

Arg Pro Arg Ser Cys Xaa Trp
1               5

<210> SEQ ID NO 149
<211> LENGTH: 26
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 149
```

Asp Leu Asp Pro Asp Phe Glu Pro Gln Ser Arg Pro Arg Ser Cys Xaa
1               5                   10                  15

Trp Pro Leu Pro Arg Pro Glu Ile Ala Asn
            20                  25

<210> SEQ ID NO 150
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 150

Arg Pro Arg Ser Ser Xaa Asn
1               5

<210> SEQ ID NO 151
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 151

Arg Glu Glu Ala Asp Met Trp Thr Thr Phe Arg Pro Arg Ser Ser Xaa
1               5                   10                  15

Asn Ala Ser Ser Val Ser Thr Arg Leu Ser Pro
            20                  25

<210> SEQ ID NO 152
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 152

Tyr Arg Arg Ser Tyr Xaa His
1               5

<210> SEQ ID NO 153
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 153

Gly Leu Ser Arg Ala Arg Asp Pro Lys Thr Tyr Arg Arg Ser Tyr Xaa
1               5                   10                  15

His Ala Lys Pro Pro Tyr Ser Tyr Ile Ser Leu
            20                  25

<210> SEQ ID NO 154
<211> LENGTH: 7
<212> TYPE: PRT
<213> ORGANISM: mammalian
<220> FEATURE:
<221> NAME/KEY: misc_feature

```
<222> LOCATION: (6)..(6)
<223> OTHER INFORMATION: Xaa can be any naturally occurring amino acid

<400> SEQUENCE: 154

Arg Gln Arg Ser Cys Xaa Trp
1               5

<210> SEQ ID NO 155
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 155

Glu Thr Asp Pro Asp Phe Glu Pro Leu Pro Arg Gln Arg Ser Cys Xaa
1               5                   10                  15

Trp Pro Leu Pro Arg Pro Glu Phe Asn Gln Ser
            20                  25

<210> SEQ ID NO 156
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 156

Arg Arg Arg Ala Ala Xaa Met
1               5

<210> SEQ ID NO 157
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 157

Pro Glu Gly Gly Lys Ser Gly Lys Ser Pro Arg Arg Ala Ala Xaa
1               5                   10                  15

Met Asp Asn Asn Ser Lys Phe Ala Lys Ser Arg
            20                  25

<210> SEQ ID NO 158
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 158

Arg Pro Arg Thr Ser Xaa Asn
1               5

<210> SEQ ID NO 159
<211> LENGTH: 27
<212> TYPE: PRT
<213> ORGANISM: mammalian
```

```
<220> FEATURE:
<221> NAME/KEY: misc_feature
<222> LOCATION: (16)..(16)
<223> OTHER INFORMATION: Xaa can be any naturally occurring amino acid

<400> SEQUENCE: 159

Asn Asp Asp Phe Asp Asn Trp Ser Thr Phe Arg Pro Arg Thr Ser Xaa
1               5                   10                  15

Asn Ala Ser Thr Ile Ser Gly Arg Leu Ser Pro
            20                  25

<210> SEQ ID NO 160
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 160

Arg Pro Arg Ser Cys Xaa Trp
1               5

<210> SEQ ID NO 161
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 161

Glu Leu Asp Pro Glu Phe Glu Pro Gln Ser Arg Pro Arg Ser Cys Xaa
1               5                   10                  15

Trp Pro Leu Gln Arg Pro Glu Leu Gln Ala Ser
            20                  25

<210> SEQ ID NO 162
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 162

Arg Arg Arg Ala Val Xaa Met
1               5

<210> SEQ ID NO 163
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 163

Pro Asp Gly Gly Lys Ser Gly Lys Ala Pro Arg Arg Arg Ala Val Xaa
1               5                   10                  15

Met Asp Asn Ser Asn Lys Tyr Thr Lys Ser Arg
            20                  25
```

```
<210> SEQ ID NO 164
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 164

Arg Glu Arg Lys Ser Xaa Ala
1               5

<210> SEQ ID NO 165
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 165

Glu Leu Ser Ser Ser Ser Gln His Leu Leu Arg Glu Arg Lys Ser Xaa
1               5                   10                  15

Ala Pro Ser His Ser Ser Gln Pro Thr Leu Phe
            20                  25

<210> SEQ ID NO 166
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 166

Ala Glu Phe Ser Ser Ser Gln His Leu Leu Arg Glu Arg Lys Ser Xaa
1               5                   10                  15

Ala Pro Ser His Ser Ser Gln Pro Thr Leu Phe
            20                  25

<210> SEQ ID NO 167
<211> LENGTH: 8
<212> TYPE: PRT
<213> ORGANISM: mammalian
<220> FEATURE:
<221> NAME/KEY: misc_feature
<222> LOCATION: (7)..(7)
<223> OTHER INFORMATION: Xaa can be any naturally occurring amino acid

<400> SEQUENCE: 167

Arg Leu Arg Arg Arg Ala Xaa Gln
1               5

<210> SEQ ID NO 168
<211> LENGTH: 28
<212> TYPE: PRT
<213> ORGANISM: mammalian
<220> FEATURE:
<221> NAME/KEY: misc_feature
<222> LOCATION: (17)..(17)
<223> OTHER INFORMATION: Xaa can be any naturally occurring amino acid

<400> SEQUENCE: 168

Leu Glu Arg His Val Ala Gln Lys Lys Ser Arg Leu Arg Arg Arg Ala
```

-continued

```
                1               5                  10                  15
Xaa Gln Leu Lys Ile Thr Ile Pro Asp Leu Thr Asp
            20                  25
```

<210> SEQ ID NO 169
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 169

```
Arg Ala Arg Thr Ser Xaa Phe
1               5
```

<210> SEQ ID NO 170
<211> LENGTH: 26
<212> TYPE: PRT
<213> ORGANISM: mammalian
<220> FEATURE:
<221> NAME/KEY: misc_feature
<222> LOCATION: (15)..(15)
<223> OTHER INFORMATION: Xaa can be any naturally occurring amino acid

<400> SEQUENCE: 170

```
Ser Gly Gly Gly Pro Gly Gly Ser Gly Arg Ala Arg Thr Ser Xaa Phe
1               5                  10                  15
Ala Glu Pro Gly Gly Gly Gly Gly Gly
            20                  25
```

<210> SEQ ID NO 171
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 171

```
Arg Pro Arg Thr Thr Xaa Phe
1               5
```

<210> SEQ ID NO 172
<211> LENGTH: 20
<212> TYPE: PRT
<213> ORGANISM: mammalian
<220> FEATURE:
<221> NAME/KEY: misc_feature
<222> LOCATION: (9)..(9)
<223> OTHER INFORMATION: Xaa can be any naturally occurring amino acid

<400> SEQUENCE: 172

```
Met Ser Gly Arg Pro Arg Thr Thr Xaa Phe Ala Glu Ser Cys Lys Pro
1               5                  10                  15
Val Gln Gln Pro
            20
```

<210> SEQ ID NO 173
<211> LENGTH: 7
<212> TYPE: PRT
<213> ORGANISM: mammalian
<220> FEATURE:
<221> NAME/KEY: misc_feature
<222> LOCATION: (6)..(6)

```
<223> OTHER INFORMATION: Xaa can be any naturally occurring amino acid

<400> SEQUENCE: 173

Arg Ser Arg Lys Glu Xaa Tyr
1               5

<210> SEQ ID NO 174
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 174

Ala Gln Lys Lys Asp Gly Lys Lys Arg Lys Arg Ser Arg Lys Glu Xaa
1               5                   10                  15

Tyr Ser Ile Tyr Val Tyr Lys Val Leu Lys Gln
            20                  25

<210> SEQ ID NO 175
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 175

Ala Gln Lys Lys Asp Gly Lys Lys Arg Lys Arg Ser Arg Lys Glu Xaa
1               5                   10                  15

Tyr Ser Val Tyr Val Tyr Lys Val Leu Lys Gln
            20                  25

<210> SEQ ID NO 176
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 176

Arg Ser Arg Ser Gly Xaa Ile
1               5

<210> SEQ ID NO 177
<211> LENGTH: 26
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 177

Leu Thr Ala Ala Lys Glu Glu Ser Gly Gly Arg Ser Arg Ser Gly Xaa
1               5                   10                  15

Ile Val Glu Leu Ile Ala Gly Gly Gly Ser
            20                  25

<210> SEQ ID NO 178
<211> LENGTH: 7
```

```
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 178

Arg Glu Arg Leu Gly Xaa Gly
1               5

<210> SEQ ID NO 179
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 179

Arg Pro Gly Ala Gly Gly Pro Trp Glu Met Arg Glu Arg Leu Gly Xaa
1               5                   10                  15

Gly Gly Phe Gly Asn Val Cys Leu Tyr Gln His
            20                  25

<210> SEQ ID NO 180
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 180

Arg Pro Arg Ser Lys Xaa Gln
1               5

<210> SEQ ID NO 181
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 181

Glu Ala Met Arg Ala Met Ser Asp Glu Phe Pro Arg Ser Lys Xaa
1               5                   10                  15

Gln Ser Ser Ser Asn Cys Ser Asn Pro Ile Ser
            20                  25

<210> SEQ ID NO 182
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 182

Arg Ser Arg Thr Glu Xaa Ile
1               5
```

<210> SEQ ID NO 183
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 183

Pro Pro Pro Ser Gln Val Gly Leu Thr Arg Arg Ser Arg Thr Glu Xaa
1               5                   10                  15

Ile Thr Ala Thr Ser Pro Ala Ser Met Val Gly
            20                  25

<210> SEQ ID NO 184
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 184

Arg Val Arg Ala Ser Xaa Asp
1               5

<210> SEQ ID NO 185
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 185

Ser Met Val Gly Gly Lys Pro Gly Ser Phe Arg Val Arg Ala Ser Xaa
1               5                   10                  15

Asp Gly Glu Gly Thr Met Ser Arg Pro Ala Ser
            20                  25

<210> SEQ ID NO 186
<211> LENGTH: 30
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (29)..(29)
<223> OTHER INFORMATION: Xaa can be any naturally occurring amino acid

<400> SEQUENCE: 186

Arg Ser Arg Thr Glu Xaa Ile Thr Ala Thr Ser Pro Ala Ser Met Val
1               5                   10                  15

Gly Gly Lys Pro Gly Ser Phe Arg Val Arg Ala Ser Xaa Asp
            20                  25                  30

<210> SEQ ID NO 187
<211> LENGTH: 9
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 187

Arg Phe Arg Lys Arg Xaa His Xaa Ala
1               5

<210> SEQ ID NO 188
<211> LENGTH: 29
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 188

Glu Ala Ala Ser Ala Ala Asp Leu Asp Asn Arg Phe Arg Lys Arg Xaa
1               5                   10                  15

His Xaa Ala Gly Thr Ser Pro Thr Ile Thr His Gln Lys
            20                  25

<210> SEQ ID NO 189
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 189

Arg Arg Arg His Ser Xaa Glu
1               5

<210> SEQ ID NO 190
<211> LENGTH: 28
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 190

Lys Val Ile Arg Ala Asp Pro Gln Gly Cys Arg Arg Arg His Ser Xaa
1               5                   10                  15

Glu Thr Phe Ser Ser Thr Pro Ser Ala Thr Arg Val
            20                  25

<210> SEQ ID NO 191
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 191

```
Arg Arg Arg Ser Ile Xaa Glu
1               5
```

<210> SEQ ID NO 192
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 192

```
Asp Leu Ile Ser Arg Leu Ser Thr Ser Ser Arg Arg Arg Ser Ile Xaa
1               5                   10                  15

Glu Thr Glu Glu Asn Thr Asp Glu Leu Pro Gly
            20                  25
```

<210> SEQ ID NO 193
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 193

```
Arg Arg Arg Ser Leu Xaa Phe
1               5
```

<210> SEQ ID NO 194
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 194

```
Asp Glu Leu Pro Gly Glu Arg His Arg Lys Arg Arg Arg Ser Leu Xaa
1               5                   10                  15

Phe Asp Pro Ser Leu Gly Leu Cys Glu Leu Arg
            20                  25
```

<210> SEQ ID NO 195
<211> LENGTH: 29
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid

<400> SEQUENCE: 195

```
Arg Arg Arg Ser Ile Xaa Glu Thr Glu Glu Asn Thr Asp Glu Leu Pro
1               5                   10                  15

Gly Glu Arg His Arg Lys Arg Arg Arg Ser Leu Xaa Phe
            20                  25
```

<210> SEQ ID NO 196
<211> LENGTH: 7

```
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 196

Arg Arg Arg Ala Ile Xaa Glu
1               5

<210> SEQ ID NO 197
<211> LENGTH: 28
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 197

His Leu Val Ser Arg Pro Ser Thr Ser Ser Arg Arg Arg Ala Ile Xaa
1               5                   10                  15
Glu Thr Glu Glu Asn Ser Asp Glu Leu Ser Gly Glu
            20                  25

<210> SEQ ID NO 198
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 198

Arg Lys Arg His Lys Xaa Asp
1               5

<210> SEQ ID NO 199
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 199

Asn Ser Asp Glu Leu Ser Gly Glu Arg Gln Arg Lys Arg His Lys Xaa
1               5                   10                  15
Asp Ser Ile Ser Leu Ser Phe Asp Glu Ser Leu
            20                  25

<210> SEQ ID NO 200
<211> LENGTH: 27
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (26)..(26)
<223> OTHER INFORMATION: Xaa can be any naturally occurring amino acid

<400> SEQUENCE: 200
```

```
Arg Arg Arg Ala Ile Xaa Glu Thr Glu Asn Ser Asp Glu Leu Ser
1               5                   10                  15

Gly Glu Arg Gln Arg Lys Arg His Lys Xaa Asp
            20                  25

<210> SEQ ID NO 201
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 201

Arg Glu Arg Gly Glu Xaa Pro
1               5

<210> SEQ ID NO 202
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 202

Arg Asp Leu Gln Pro Pro Gly Gly Pro Gly Arg Glu Arg Gly Glu Xaa
1               5                   10                  15

Pro Thr Thr Pro Pro Thr Pro Thr Pro Ala Pro
            20                  25

<210> SEQ ID NO 203
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 203

Arg Thr Arg Thr Asp Xaa Tyr
1               5

<210> SEQ ID NO 204
<211> LENGTH: 27
<212> TYPE: PRT
<213> ORGANISM: mammalian
<220> FEATURE:
<221> NAME/KEY: misc_feature
<222> LOCATION: (15)..(15)
<223> OTHER INFORMATION: Xaa can be any naturally occurring amino acid

<400> SEQUENCE: 204

Thr Asn Thr Lys Gly Asn Lys Arg Ser Arg Thr Arg Thr Asp Xaa Tyr
1               5                   10                  15

Ser Ala Gly Gln Ser Val Glu Ile Leu Asp Gly
            20                  25

<210> SEQ ID NO 205
<211> LENGTH: 7
<212> TYPE: PRT
<213> ORGANISM: mammalian
<220> FEATURE:
<221> NAME/KEY: misc_feature
```

<222> LOCATION: (6)..(6)
<223> OTHER INFORMATION: Xaa can be any naturally occurring amino acid

<400> SEQUENCE: 205

Arg Ser Arg Ser Tyr Xaa Tyr
1               5

<210> SEQ ID NO 206
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 206

Ser Arg Ser Ser Ser Tyr Asp Pro His Ser Arg Ser Arg Ser Tyr Xaa
1               5                   10                  15

Tyr Asp Ser Tyr Tyr Ser Arg Ser Arg Ser Arg
            20                  25

<210> SEQ ID NO 207
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 207

Arg Gly Arg Leu Pro Xaa Lys
1               5

<210> SEQ ID NO 208
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 208

Val Val Arg Thr Asp Ser Leu Lys Gly Arg Arg Gly Arg Leu Pro Xaa
1               5                   10                  15

Lys Pro Lys Gln Pro Pro Asp Ala Ser Pro Ala
            20                  25

<210> SEQ ID NO 209
<211> LENGTH: 8
<212> TYPE: PRT
<213> ORGANISM: mammalian
<220> FEATURE:
<221> NAME/KEY: misc_feature
<222> LOCATION: (7)..(7)
<223> OTHER INFORMATION: Xaa can be any naturally occurring amino acid

<400> SEQUENCE: 209

Arg Lys Arg Arg Gln Thr Xaa Met
1               5

<210> SEQ ID NO 210
<211> LENGTH: 28
<212> TYPE: PRT
<213> ORGANISM: mammalian

```
<220> FEATURE:
<221> NAME/KEY: misc_feature
<222> LOCATION: (17)..(17)
<223> OTHER INFORMATION: Xaa can be any naturally occurring amino acid

<400> SEQUENCE: 210

Ser Pro Gly Gly Pro Gly Asp Ser Gln Gly Arg Lys Arg Arg Gln Thr
1               5                   10                  15

Xaa Met Thr Asp Phe Tyr His Ser Lys Arg Arg Leu
            20                  25

<210> SEQ ID NO 211
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 211

Arg Lys Arg Pro Ala Xaa Asp
1               5

<210> SEQ ID NO 212
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 212

Thr Gly Leu Ala Glu Gln Cys Ala Gly Ile Arg Lys Arg Pro Ala Xaa
1               5                   10                  15

Asp Asp Ser Ser Thr Gln Asn Lys Arg Ala Asn
            20                  25

<210> SEQ ID NO 213
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 213

Pro Pro Arg Arg Ser Xaa Ile
1               5

<210> SEQ ID NO 214
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 214

Gln Ala Gln Arg Gln Ile Lys Arg Gly Ala Pro Pro Arg Arg Ser Xaa
1               5                   10                  15

Ile Arg Asn Val His Ser Ile His Gln Arg Ser
            20                  25
```

```
<210> SEQ ID NO 215
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 215

Ala Tyr Arg Arg Asn Xaa Val
1               5

<210> SEQ ID NO 216
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 216

Gln Arg Ser Arg Lys Arg Leu Ser Gln Asp Ala Tyr Arg Arg Asn Xaa
1               5                   10                  15

Val Arg Phe Leu Gln Gln Arg Arg Gln Ala
            20                  25

<210> SEQ ID NO 217
<211> LENGTH: 31
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid

<400> SEQUENCE: 217

Pro Pro Arg Arg Ser Xaa Ile Arg Asn Val His Ser Ile His Gln Arg
1               5                   10                  15

Ser Arg Lys Arg Leu Ser Gln Asp Ala Tyr Arg Arg Asn Xaa Val
            20                  25                  30

<210> SEQ ID NO 218
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 218

Ile Ile Arg Gln Pro Xaa Glu
1               5

<210> SEQ ID NO 219
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid
```

<400> SEQUENCE: 219

Arg Ile Pro Ser Ala Lys Lys Tyr Lys Asp Ile Ile Arg Gln Pro Xaa
1               5                   10                  15

Glu Glu Glu Ile Ile Lys Leu Ala Pro Pro Pro
            20                  25

<210> SEQ ID NO 220
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 220

Arg Lys Arg Arg Thr Xaa Ile
1               5

<210> SEQ ID NO 221
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 221

Asn Glu Lys Val Gly Ala Asn Glu Arg Lys Arg Lys Arg Arg Thr Xaa
1               5                   10                  15

Ile Ser Ile Ala Ala Lys Asp Ala Leu Glu Arg
            20                  25

<210> SEQ ID NO 222
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 222

Arg Met Arg Arg Asn Xaa Phe
1               5

<210> SEQ ID NO 223
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 223

Asn Asn Phe Pro Lys Asn Gln Thr Pro Val Arg Met Arg Arg Asn Xaa
1               5                   10                  15

Phe Thr Pro Leu Ser Ser Ser Asn Thr Ile Arg
            20                  25

<210> SEQ ID NO 224
<211> LENGTH: 7
<212> TYPE: PRT

```
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 224

Arg Pro Arg Asn Tyr Xaa Val
1               5

<210> SEQ ID NO 225
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 225

Thr Pro Leu Ser Ser Ser Asn Thr Ile Arg Arg Pro Arg Asn Tyr Xaa
1               5                   10                  15

Val Gly Ser Arg Pro Leu Lys Pro Leu Ser Pro
            20                  25

<210> SEQ ID NO 226
<211> LENGTH: 24
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid

<400> SEQUENCE: 226

Arg Met Arg Arg Asn Xaa Phe Thr Pro Leu Ser Ser Ser Asn Thr Ile
1               5                   10                  15

Arg Arg Pro Arg Asn Tyr Xaa Val
            20

<210> SEQ ID NO 227
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 227

Arg Pro Arg Arg Arg Xaa Ser
1               5

<210> SEQ ID NO 228
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 228

Ser Thr Ala Glu Glu Lys Val Pro Val Ile Arg Pro Arg Arg Arg Xaa
```

```
                1               5                  10                  15
Ser Cys Val Ser Leu Gly Glu Ser Ala Ala Gly
            20                  25

<210> SEQ ID NO 229
<211> LENGTH: 28
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 229

Ser Ala Ala Glu Glu Lys Val Pro Val Ile Arg Pro Arg Arg Arg Xaa
1               5                  10                  15

Ser Cys Val Ser Leu Gly Glu Thr Ala Ala Ser Tyr
            20                  25

<210> SEQ ID NO 230
<211> LENGTH: 9
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (8)..(8)
<223> OTHER INFORMATION: Xaa can be any naturally occurring amino acid

<400> SEQUENCE: 230

Arg Phe Arg Ala Arg Xaa Gly Xaa Glu
1               5

<210> SEQ ID NO 231
<211> LENGTH: 29
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 231

Leu Trp Glu Ala Val Val Gly Ala Ala Glu Arg Phe Arg Ala Arg Xaa
1               5                  10                  15

Gly Xaa Glu Leu Val Leu Leu Thr Ala Ala Pro Pro Pro
            20                  25

<210> SEQ ID NO 232
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 232

Arg Pro Arg Leu Asn Xaa Ser
1               5
```

```
<210> SEQ ID NO 233
<211> LENGTH: 23
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 233

Glu Asp Thr Gln Val Phe Gly Asp Leu Pro Arg Pro Arg Leu Asn Xaa
1               5                   10                  15

Ser Asp Phe Gln Lys Leu Lys
            20

<210> SEQ ID NO 234
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 234

Arg Tyr Arg Asp Val Xaa Pro
1               5

<210> SEQ ID NO 235
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 235

Ala Lys Leu Pro Lys Asn Lys Asn Arg Asn Arg Tyr Arg Asp Val Xaa
1               5                   10                  15

Pro Phe Asp His Ser Arg Ile Lys Leu His Gln
            20                  25

<210> SEQ ID NO 236
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 236

Arg Leu Arg Pro Leu Xaa Tyr
1               5

<210> SEQ ID NO 237
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 237

Trp Asp Thr Ala Gly Gln Glu Asp Tyr Asp Arg Leu Arg Pro Leu Xaa
```

```
                 1               5                  10                 15
Tyr Pro Gln Thr Asp Val Phe Leu Ile Cys Phe
                20                 25

<210> SEQ ID NO 238
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 238

Arg Gln Arg Ser Thr Xaa Thr
1               5

<210> SEQ ID NO 239
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 239

Ser Pro Ser Ser Glu Gly Ser Leu Ser Gln Arg Gln Arg Ser Thr Xaa
1               5                  10                 15
Thr Pro Asn Val His Met Val Ser Thr Thr Leu
                20                 25

<210> SEQ ID NO 240
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 240

Arg Leu Arg Thr His Xaa Ile
1               5

<210> SEQ ID NO 241
<211> LENGTH: 26
<212> TYPE: PRT
<213> ORGANISM: mammalian
<220> FEATURE:
<221> NAME/KEY: misc_feature
<222> LOCATION: (15)..(15)
<223> OTHER INFORMATION: Xaa can be any naturally occurring amino acid

<400> SEQUENCE: 241

Thr Gly Val Gln Asn Pro His Ile Glu Arg Leu Arg Thr His Xaa Ile
1               5                  10                 15
Glu Ser Ser Gly Lys Leu Lys Ile Ser Pro
                20                 25

<210> SEQ ID NO 242
<211> LENGTH: 7
<212> TYPE: PRT
<213> ORGANISM: mammalian
<220> FEATURE:
<221> NAME/KEY: misc_feature
<222> LOCATION: (6)..(6)
```

```
<223> OTHER INFORMATION: Xaa can be any naturally occurring amino acid

<400> SEQUENCE: 242

Arg Arg Arg Gly Gly Xaa Ala
1               5

<210> SEQ ID NO 243
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 243

Val Pro Leu Gly Leu Pro Ala Pro Gly Ala Arg Arg Arg Gly Gly Xaa
1               5                   10                  15

Ala Ser Arg Ser Leu Pro Leu Pro Lys Arg Pro
            20                  25

<210> SEQ ID NO 244
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 244

Arg Lys Arg Leu Leu Xaa Arg
1               5

<210> SEQ ID NO 245
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 245

Cys Gln Ser Leu Asp Ser Ala Leu Leu Glu Arg Lys Arg Leu Leu Xaa
1               5                   10                  15

Arg Lys Glu Leu Glu Leu Pro Glu Asn Ile Ala
            20                  25

<210> SEQ ID NO 246
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 246

Arg Ala Arg Ser Thr Xaa Leu
1               5

<210> SEQ ID NO 247
<211> LENGTH: 27
<212> TYPE: PRT
<213> ORGANISM: mammalian
<220> FEATURE:
```

```
<221> NAME/KEY: misc_feature
<222> LOCATION: (16)..(16)
<223> OTHER INFORMATION: Xaa can be any naturally occurring amino acid

<400> SEQUENCE: 247

Phe Asp Asp Thr Pro Glu Lys Asp Ser Phe Arg Ala Arg Ser Thr Xaa
1               5                   10                  15

Leu Asn Glu Arg Pro Lys Ser Leu Arg Ile Ala
            20                  25

<210> SEQ ID NO 248
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 248

Arg Cys Arg Ser Ile Xaa Val
1               5

<210> SEQ ID NO 249
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 249

Phe Lys Glu Ser Ser Ala Ala Glu Ala Phe Arg Cys Arg Ser Ile Xaa
1               5                   10                  15

Val Ser Glu His Val Val Arg Ser Arg Ile Gln
            20                  25

<210> SEQ ID NO 250
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 250

Arg Asp Arg Val Arg Xaa Met
1               5

<210> SEQ ID NO 251
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 251

Gln Ala Gly Gln Gln Val Ser Arg Gly Ala Arg Asp Arg Val Arg Xaa
1               5                   10                  15

Met Ser Gly Gly His Gly Leu Arg Val Gly Ala
            20                  25
```

```
<210> SEQ ID NO 252
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 252

Arg Pro Arg Gly Tyr Xaa Ile
1               5

<210> SEQ ID NO 253
<211> LENGTH: 26
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 253

Ser Ser Ser Pro Arg Ser Pro Ser Gly Leu Arg Pro Arg Gly Tyr Xaa
1               5                   10                  15

Ile Ser Asp Ser Ala Pro Ser Arg Arg Gly
            20                  25

<210> SEQ ID NO 254
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 254

Arg Arg Arg Arg His Xaa Met
1               5

<210> SEQ ID NO 255
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 255

Asp Ala Val Thr Gly Arg Thr Glu Glu Tyr Arg Arg Arg His Xaa
1               5                   10                  15

Met Asp Lys Asp Ser Arg Gly Ala Ala Ala Thr
            20                  25

<210> SEQ ID NO 256
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 256

His Val Arg Ala His Xaa Ser
1               5
```

<210> SEQ ID NO 257
<211> LENGTH: 27
<212> TYPE: PRT
<213> ORGANISM: mammalian
<220> FEATURE:
<221> NAME/KEY: misc_feature
<222> LOCATION: (16)..(16)
<223> OTHER INFORMATION: Xaa can be any naturally occurring amino acid

<400> SEQUENCE: 257

Ala Gly Thr Ala Gly Ala Leu Thr Pro Gln His Val Arg Ala His Xaa
1               5                   10                  15

Ser Pro Ala Ser Leu Gln Leu Gly Ala Val Ser
            20                  25

<210> SEQ ID NO 258
<211> LENGTH: 7
<212> TYPE: PRT
<213> ORGANISM: mammalian
<220> FEATURE:
<221> NAME/KEY: misc_feature
<222> LOCATION: (6)..(6)
<223> OTHER INFORMATION: Xaa can be any naturally occurring amino acid

<400> SEQUENCE: 258

Gly Ala Arg Arg Ser Xaa Trp
1               5

<210> SEQ ID NO 259
<211> LENGTH: 27
<212> TYPE: PRT
<213> ORGANISM: mammalian
<220> FEATURE:
<221> NAME/KEY: misc_feature
<222> LOCATION: (15)..(15)
<223> OTHER INFORMATION: Xaa can be any naturally occurring amino acid

<400> SEQUENCE: 259

Leu Leu Ser Val Ala Tyr Lys Asn Val Val Gly Ala Arg Arg Xaa Ser
1               5                   10                  15

Trp Arg Val Val Ser Ser Ile Glu Gln Lys Thr
            20                  25

<210> SEQ ID NO 260
<211> LENGTH: 10
<212> TYPE: PRT
<213> ORGANISM: mammalian
<220> FEATURE:
<221> NAME/KEY: misc_feature
<222> LOCATION: (9)..(9)
<223> OTHER INFORMATION: Xaa can be any naturally occurring amino acid

<400> SEQUENCE: 260

Arg Arg Pro His Phe Pro Gln Phe Xaa Tyr
1               5                   10

<210> SEQ ID NO 261
<211> LENGTH: 24
<212> TYPE: PRT
<213> ORGANISM: mammalian
<220> FEATURE:
<221> NAME/KEY: misc_feature
<222> LOCATION: (17)..(17)
<223> OTHER INFORMATION: Xaa can be any naturally occurring amino acid

<400> SEQUENCE: 261

-continued

```
Ser Met Glu Cys Val Asp Ser Glu Arg Arg Pro His Phe Pro Gln Phe
1               5                   10                  15
Xaa Tyr Ser Ala Ser Gly Thr Ala
                20
```

AKT LIGANDS AND POLYNUCLEOTIDES ENCODING AKT LIGANDS

CROSS-REFERENCE TO RELATED APPLICATIONS

This application claims the benefit of U.S. Provisional Application No. 60/803,913, filed Jun. 5, 2006, the entirety of which is hereby incorporated by reference.

REFERENCE TO SEQUENCE LISTING SUBMITTED ELECTRONICALLY

The content of the electronically submitted substitute sequence listing, file name 2584_0290004_UpdatedSequenceListing_ascii.txt, size 488,000 bytes; and date of creation Jan. 5, 2015, filed herewith, is incorporated herein by reference in its entirety.

BACKGROUND OF THE INVENTION

1. Field of the Invention

The invention relates to mammalian kinase ligands, substrates and modulators. In particular, the invention relates to polypeptides, polypeptide compositions and polynucleotides that encode polypeptides that are ligands, substrates, and/or modulators of AKT. The invention also relates to polyligands that are homopolyligands or heteropolyligands that modulate AKT activity.

This application has subject matter related to application Ser. No. 10/724,532 (US 2004/0203027), Ser. No. 10/682,764 (US2004/0185556, PCT/US2004/013517, WO2005/040336), Ser. No. 11/233,246, and US20040572011P (WO2005116231). Each of these applications is hereby incorporated by reference.

2. Background of the Invention

Kinases are enzymes that catalyze the addition of phosphate to a molecule. The addition of phosphate by a kinase is called phosphorylation. When the kinase substrate is a protein molecule, the amino acids commonly phosphorylated are serine, threonine and tyrosine. Phosphatases are enzymes that remove phosphate from a molecule. The removal of phosphate is called dephosphorylation. Kinases and phosphatases often represent competing forces within a cell to transmit, attenuate, or otherwise modulate cellular signals and cellular control mechanisms. Kinases and phosphatases have both overlapping and unique natural substrates. Cellular signals and control mechanisms, as regulated by kinases, phosphatases, and their natural substrates are a target of research tool design and drug design.

Mammalian Protein Kinase B is also known as AKT. The enzymatic activity, activation and autoregulation of AKT have been studied. Several cellular substrates of AKT have been identified. A pharmacological agent that inhibits AKT activity has been disclosed in the literature by Martelli et al. (*Leukemia* (2003) 17:1794-1805). Natural and synthetic polypeptides have been studied to examine AKT substrate specificity. While polypeptides and variants thereof have been studied as individual AKT substrates or ligands, mixed ligands linked together as polyligands that modulate AKT activity have not been demonstrated before this invention. An aspect of the invention is to provide novel, modular, inhibitors of AKT activity by modifying one or more natural substrates either by truncation or by amino acid substitution. A further aspect of the invention is the subcellular localization of an AKT inhibitor, ligand, or polyligand by linking to a subcellular localization signal.

Design and synthesis of polypeptide ligands that modulate calcium/calmodulin-dependent protein kinase and that localize to the cardiac sarco(endo)plasmic reticulum was performed by Ji et al. (*J Biol Chem* (2003) 278:25063-71). Ji et al. accomplished this by generating expression constructs that localized calcium/calmodulin-dependent protein kinase inhibitory polypeptide ligands to the sarcoplasmic reticulum by fusing a sarcoplasmic reticulum localization signal derived from phospholamban to a polypeptide ligand. See also US 2004/0203027.

The following references are hereby incorporated in their entirety: Altiok et al. 1999 J Biol Chem 274:32274-32278; Alessi et al. 1996 J FEBS Letters 399:333-338; Berwick et al. 2002 J Biol Chem 277:33895-33900; Biggs III et al. 1999 Genetics 96:7421-7426; Blume-Jensen et al. 1998 Current Biol 8:779-782; Brazil et al. 2002 Cell 111:293-303; Brunet et al. 1999 Cell 96:857-868; Cardone et al. 1998 Science 282:1318-1321; Cha et al. 2005 Science 310: 306-310; Chen et al. 2003 Cell 133:457-468; Cross et al. 1995 Nature 378:785-789; Datta et al. 1999 J Genes and Dev. 13:2905-2927; Deprez et al. 1997 J Biol Chem; Du et al. 2003 Science 300:1574-1577; Gingras et al. 1998 Genes and Dev. 12:502-513; Hanada et al. 2004 Biochimica 1697:3-16; Humbert et al. 2002 Dev Cell 2(6):831-837; Hurt et al. 2002 J PNAS 99:4061-4066; Lee et al. 2001 mol. Cell 8(3):693-704; Li et al. 1999 J Biol Chem 274:9351-9356; Jiang et al. 2005 J Biol Chem 280:21622-21628; Kane et al. 2002 J Biol Chem 277:22115-22118; Kitamura et al. 1999 Mol cell Biol 19:6286-6296; Kovacina et al. 2003 J Biol Chem 278: 10189-10194; Kwon et al. 2000 J Biol Chem 275:423-428; Lawlor et al. 2001 J Cell Science 114:2903-2910; Lynch et al. 2002 EMBO 21:72-82; Maira et al. 2001 Science 294: 374-380; Michell et al. 1999 Current Biol 9:845-848; Miinea et al. 2005 Biochem 391:87-93; Nakae et al. 2001 J Clin. Invest. 108:1359-1367; Obata et al. 2000 J Biol Chem 275:36108-36115; Ozes et al. 1999 Nature 401:82-85; Peso et al. 1997 Science 278:687-689; Plomgaard et al. 2005 Diabetes 54:2939-2945; Powell et al. 2002 J Biol Chem 277:21639-21642; Rena et al. 1999 J Biol Chem 274:17179-17183; Saito et al. 2004 J Neuroscience 24:1584-1593; Sano et al. 2003 J Biol Chem 278:14599-14602; Song et al. 2005 J Cell. Mol. Med. 9:59-71; Tee et al. 2003 J Biol Chem 278:37288-37296; Toker et al. 2000 J Biol Chem 275:8271-8274; Viglietto et al. 2002 Nature Medicine 8:1136-1144; Vitari et al. 2004 J Biochem 378:257-268; Wang et al. 2005 Mol Pharmacol 67:489-498; Wolfrum et al. 2003 PNAS 100:11624-11629; Yang et al. 2005 J Biol Chem 280:33558-33565; Yang et al. 2002 J Nature Structural Biol 9:940-944; Zheng et al. 2000 J Biol Chem 275:39152-39158; Zhou et al. 2002 Semin. Oncology 3(11):62-70; Zhou et al. 2003 Mol Cell Biol 23(22):8058-8069; Zimmerman et al. 1999 Science 286:1741-1744.

SUMMARY OF THE INVENTION

The invention relates to mammalian kinase ligands, substrates and modulators. In particular, the invention relates to polypeptides, polypeptide compositions and polynucleotides that encode polypeptides that are ligands, substrates, and/or modulators of AKT. The invention also relates to polyligands that are homopolyligands or heteropolyligands that modulate AKT activity.

BRIEF DESCRIPTION OF THE D WINGS

FIGS. 1A-1C show examples of homopolymeric ligands without spacers.

FIGS. 2A-2C show examples of homopolymeric ligands with spacers.

FIGS. 3A-3E show examples of heteropolymeric ligands without spacers.

FIGS. 4A-4E show examples of heteropolymeric ligands with spacers.

FIGS. 8A-8G show examples of ligands and polymeric ligands linked to a localization signal and an epitope tag.

FIGS. 9A-9G show examples of gene constructs where ligands and polyligands are linked to a localization signal, an epitope tag, and a reporter.

Figure 13:
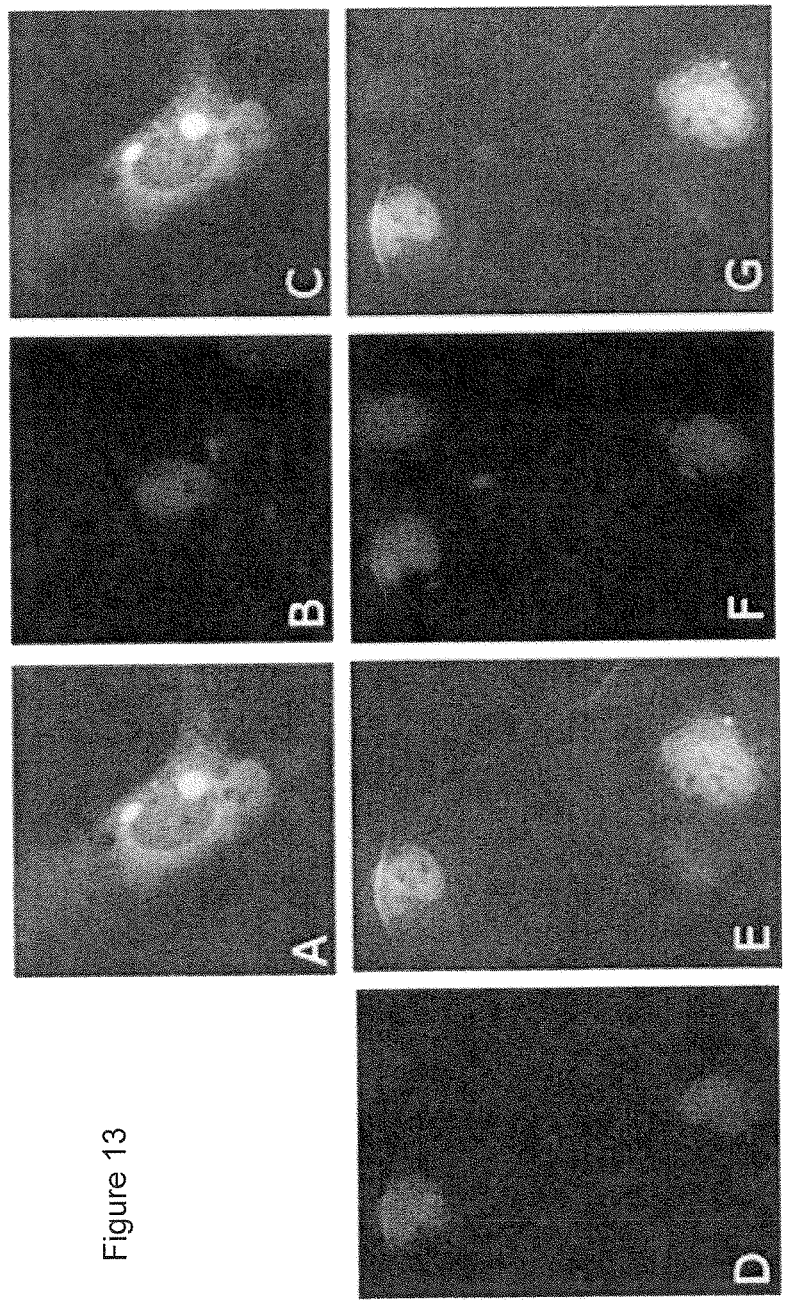

FIG. 13 shows an example of the effects of a nuclear-localized AKT polyligand on FKHRL1-GFP cellular distribution. Inhibition of AKT kinase using the AKT polyligand changed the translocation of the Forkhead transcription factor (FKHRL1), causing nuclear retention in Huh7 cells. Panels A-C represent Huh7 cells transfected with a FKHRL1-Green Fluorescent Protein (GFP) fusion protein, under normal growth conditions, 24 hours posttransfection. Panels D-G represent Huh7 cells co-transfected with the AKT polyligand and FKHRL1-GFP fusion protein 24 hours posttransfection. Panel D represents anti c-Myc primary and secondary antibody staining specific to the c-Myc epitope tag linked to the AKT polyligand. Panels A and E represent GFP fluorescent imaging to recognize the FKHRL1-GFP fusion protein. Panel B and F represent DAPI nuclear DNA staining, (4',6-diamidino-2-phenylindole) staining, a standard fluorescent stain for visualizing nuclear DNA, to determine the number and position of Huh7 cell nuclei. Panel C and G represent a co-localization of all panels in that represented row. Panel C shows that under normal growth conditions, the concentration of FKHRL1-GFP is primarily outside the nucleus. Panel G shows the FKHRL1-GFP fusion protein inside the nucleus, in those cells where the AKT polyligand is also present.

DETAILED DESCRIPTION OF THE INVENTION

The present invention relates to ligands and polyligands that are AKT modulators. The ligands and polyligands comprise SEQ ID NOS:1-261. Polyligands are chimeric ligands comprising two or more monomeric polypeptide ligands. An example of a monomeric ligand is the polypeptide represented by SEQ ID NO:83, wherein Xaa is any amino acid. SEQ ID NO:83 is a selected subsequence of wildtype full length SEQ ID NO:10, wherein the amino acid corresponding to Xaa in the wildtype sequence is a serine or threonine phosphorylatable by AKT. Another example of a monomeric ligand is the polypeptide represented by SEQ ID NO:74. Each of SEQ ID NOS:74-261 represents an individual polypeptide ligand in monomeric form, wherein Xaa is any amino acid. SEQ ID NOS:83-261 are selected examples of subsequences of SEQ ID NOS:10-73, however, other subsequences of SEQ ID NOS:10-73 may also be utilized as monomeric ligands. Monomeric ligand subsequences of SEQ ID NOS:10-73 may be wildtype subsequences. Additionally, monomeric ligand subsequences of SEQ ID NOS:10-73 may have the AKT phosphorylatable amino acids replaced by other amino acids. Furthermore, monomeric ligands and polyligands may have at least about 80%, 85%, 90%, 95%, 96%, 97%, 98% or 99% sequence identity to a ligand comprising an amino acid sequence in one or more of SEQ ID NOS:74-261. Furthermore, monomeric ligands and polyligands may have at least about 80%, 85%, 90%, 95%, 96%, 97%, 98% and 99% sequence identity to a subsequence of SEQ ID NOS:10-73.

Figure 12:
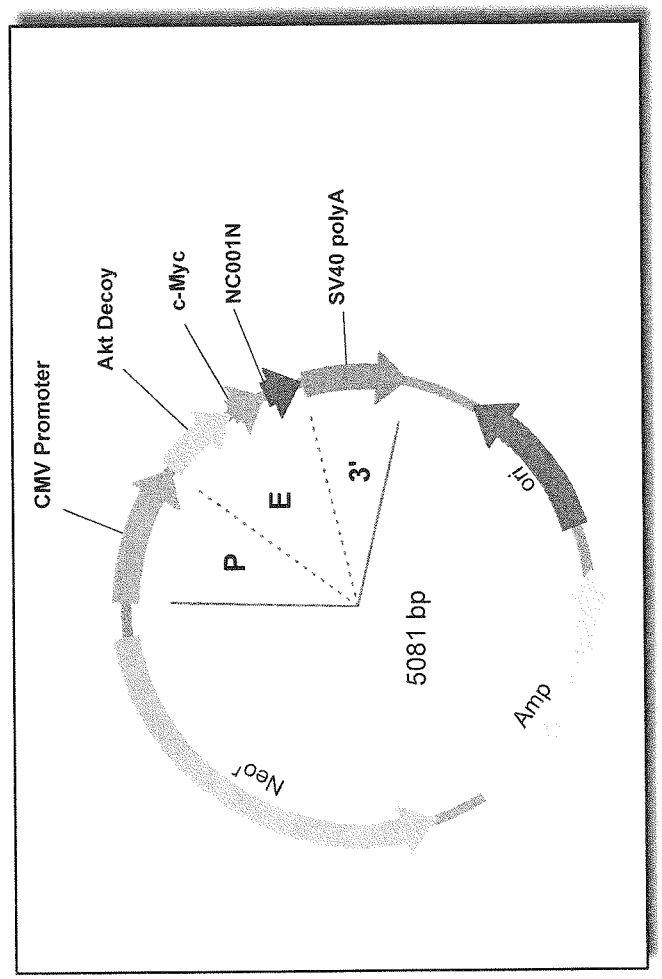
FIG. 12 shows a diagram of the vector used to transform the Huh7 cells of FIG. 13.

SEQ ID NOS:1-9 are example polyligands and polynucleotides encoding them. Specifically, the AKT polyligand of SEQ ID NO:1 is encoded by SEQ ID NO:2 and by SEQ ID NO:3, wherein the the codons of SEQ ID NO:3 have been optimized for vector insertion. A vector map of a vector containing SEQ ID NO:3 is shown in FIG. 12 (labeled AKT decoy). SEQ ID NO:1 was expressed in Huh7 cells as shown in FIG. 13. SEQ ID NO:1 is an embodiment of a polyligand of the structure A-B-C-D, wherein A is SEQ ID NO:74, B is SEQ ID NO:75, C is SEQ ID NO:76, and D is SEQ ID NO:77. A polyligand of structure A-B-C-D is also called herein a heteropolyligand.

SEQ ID NO:4 is an embodiment of a polyligand of the structure X-Y-Z, wherein X is SEQ ID NO:84, Y is SEQ ID NO:119, and Z is SEQ ID NO:86, and wherein Xaa is Alanine. The AKT polyligand of SEQ ID NO:4 is encoded by SEQ ID NO:5 and by SEQ ID NO:6, wherein the the codons of SEQ ID NO:6 have been optimized for vector insertion. A polyligand of structure X-Y-Z is also called herein a heteropolyligand.

SEQ ID NO:7 is an embodiment of a polyligand of the structure X-S1-Y-S2-Z, wherein X is SEQ ID NO:131, Y is SEQ ID NO:88, Z is SEQ ID NO: 137, wherein Xaa is Alanine, and wherein S1 is a five amino acid spacer with the sequence AlaGlyAlaGlyPro, and S2 is a five amino acid spacer with the sequence GlyAlaGlyAlaPro. The AKT polyligand of SEQ ID NO:7 is encoded by SEQ ID NO:8 and by SEQ ID NO:9, wherein the the codons of SEQ ID NO:9 have been optimized for vector insertion. A polyligand of structure X-S1-Y-S2-Z is also called herein a heteropolyligand.

SEQ ID NOS:10-73 are full length AKT protein substrates. These sequences have the following public database accession numbers: AAA51780, NP_055655, NP_055647, Q8BYJ6, Q99683, NP_000323, NP_058683, NP_001087, NP_031548, AAC37594, AAD24962, BAA82697, AAC51817, NP_604391, CAA53712, P21453, O08530, NP_000594, AAS09975, NP_002006, NP_963853, CAA63819, NP_710141, NP_062713, NP_062714, BAA76737, BAA76738, NP_000804, NP_001026837, AAA62432, AAH00251, NP_062801, AAH61044, AAI06721, NP_002102, O15111, NP_005535, AAB09030, NP_002383, NP_002410, P42345, P30414, NP_775180, AAB29246, NP_004055, AAB95193, Q15121, NP_000297, CAA06606, NP_035185, NP_000913, AAH07416, NP_002818, CAB53579, AAH92040, NP_003001, NP_003210, NP_005195, P49815, Q61037, Q9H4A3, P46937, NP_663723, P31749. Each of the sequences represented by these accession numbers is incorporated by reference herein.

SEQ ID NOS:74-82 represent examples of monomeric peptide ligand sequences, wherein Xaa is any amino acid.

SEQ ID NOS:83-261 are partial sequences of SEQ ID NOS:10-73, which represent examples of peptide ligand sequences where the location of the AKT phosphorylatable serine or threonine in the natural polypeptide is designated as Xaa.

SEQ ID NOS:79-261 encompass peptides where Xaa is any amino acid. In some embodiments, Xaa is serine or threonine.

An example of a homopolyligand is a polypeptide comprising a dimer or multimer of SEQ ID N0:83, wherein Xaa is any amino acid. An example of a heteropolyligand is a polypeptide comprising SEQ ID NO:74 and one or more of SEQ ID NOS:75-261, wherein Xaa is any amino acid. There are numerous ways to combine SEQ ID NOS:74-261 into homopolymeric or heteropolymeric ligands. Furthermore, there are numerous ways to combine additional subsequences of SEQ ID NOS:10-73 with each other and with SEQ ID NOS:74-261 to make polymeric ligands.

Polyligands may comprise any two or more of SEQ ID NOS:74-261, wherein Xaa is any amino acid. A dimer or multimer of SEQ ID NO:118 is an example of a homopolyligand. An example of a heteropolyligand is a polypeptide comprising SEQ ID NO:261 and one or more of SEQ ID NOS:74-260. There are numerous ways to combine SEQ ID NOS:74-261 into homopolymeric or heteropolymeric ligands. SEQ ID NOS:83-261 are selected examples of subsequences of SEQ ID NOS:10-73, however, additional subsequences, wildtype or mutated, may be utilized to form polyligands. The instant invention is directed to all possible combinations of homopolyligands and heteropolyligands without limitation.

SEQ ID NOS:10-73 show proteins that contain at least one serine or threonine residue phosphorylatable by AKT. SEQ ID NOS:83-261 are subsequences of SEQ ID NOS:10-73 where the locations of the AKT phosphorylatable residues are represented by Xaa. In nature, Xaa is, generally speaking, serine or threonine. In one embodiment of the instant invention, Xaa can be any amino acid. Ligands where Xaa is serine or threonine can be used as part of a polyligand, however in one embodiment, the phosphorylatable serine or threonine is replaced with another amino acid, such as one of the naturally occurring amino acids including, alanine, aspartate, asparagine, cysteine, glutamate, glutamine, phenylalanine, glycine, histidine, isoleucine, leucine, lysine, methionine, proline, arginine, valine, tryptophan, or tyrosine. The Xaa may also be a non-naturally occurring amino acid. In another embodiment, the AKT phosphorylatable serine(s) or threonine(s) are replaced by alanine. As shown by SEQ ID NO:1 and FIG. 13 and Example 4 below, the polyligands of the invention are capable of modulating endogenous effects of AKT.

In general, ligand monomers are built by isolating a putative AKT phosphorylation recognition motif in an AKT substrate. Sometimes it is desirable to modify the phosphorylatable residue to an amino acid other than serine or threonine. Additional monomers include the AKT recognition motif as well as amino acids adjacent and contiguous on either side of the AKT recognition motif Monomers may therefore be any length provided the monomer includes the AKT recognition motif. For example, the monomer may comprise an AKT recognition motif and at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30-100 or more amino acids adjacent to the recognition motif.

For example, in one embodiment, the invention comprises an inhibitor of AKT comprising at least one copy of a peptide selected from the group consisting of: a) a peptide at least 80%, 85%, 90%, 95%, 96%, 97%, 98% or 99% identical to a peptide comprising amino acid residues corresponding to amino acid residues 203-209 of the amino acid sequence of SEQ ID NO:10, wherein the amino acid residue corresponding to amino acid residue 208 of SEQ ID NO:10 has been mutated to an amino acid residue other than serine or threonine; b) a peptide at least 80%, 85%, 90%, 95%, 96%, 97%, 98% or 99% identical to a peptide comprising amino acid residues corresponding to amino acid residues 200-212 of the amino acid sequence of SEQ ID NO:10, wherein the amino acid residue corresponding to amino acid residue 208 of SEQ ID NO:10 has been mutated to an amino acid residue other than serine or threonine; c) a peptide at least 80%, 85%, 90%, 95%, 96%, 97%, 98% or 99% identical to a peptide comprising amino acid residues corresponding to amino acid residues 193-219 of the amino acid sequence of SEQ ID NO:10, wherein the amino acid residue corresponding to amino acid residue 208 of SEQ ID NO:10 has been mutated to an amino acid residue other than serine or threonine; and d) a peptide at least 80%, 85%, 90%, 95%, 96%, 97%, 98% or 99% identical to a peptide comprising amino acid residues corresponding to amino acid residues 183-229 of the amino acid sequence of SEQ ID NO:10, wherein the amino acid residue corresponding to amino acid residue 208 of SEQ ID NO:10 has been mutated to an amino acid residue other than serine or threonine.

As used herein, the term "correspond(s) to" and "corresponding to," as they relate to sequence alignment, are intended to mean enumerated positions within a reference protein, e.g., Androgen Receptor (SEQ ID NO:10), and those positions that align with the positions on the reference protein. Thus, when the amino acid sequence of a subject peptide is aligned with the amino acid sequence of a reference peptide, e.g., SEQ ID NO:10, the amino acids in the subject peptide sequence that "correspond to" certain enumerated positions of the reference peptide sequence are those that align with these positions of the reference peptide sequence, but are not necessarily in these exact numerical positions of the reference sequence. Methods for aligning sequences for determining corresponding amino acids between sequences are described below.

Additional embodiments of the invention include monomers (as described above) based on any putative or real substrate for AKT, such as substrates identified by SEQ ID NOS:11-73. Furthermore, if the substrate has more than one recognition motif, then more than one monomer may be identified therein.

Another embodiment of the invention is a nucleic acid molecule comprising a polynucleotide sequence encoding at least one copy of a ligand peptide.

Another embodiment of the invention is a nucleic acid molecule wherein the polynucleotide sequence encodes one or more copies of one or more peptide ligands.

Another embodiment of the invention is a nucleic acid molecule wherein the polynucleotide sequence encodes at least a number of copies of the peptide selected from the group consisting of: 2, 3, 4, 5, 6, 7, 8, 9 or 10.

Another embodiment of the invention is a vector comprising a nucleic acid molecule encoding at least one copy of a ligand peptide.

Another embodiment of the invention is a recombinant host cell comprising a vector comprising a nucleic acid molecule encoding at least one copy of a ligand peptide.

Another embodiment of the invention is a method of inhibiting AKT in a cell comprising transfecting a vector comprising a nucleic acid molecule encoding at least one copy of a ligand peptide into a host cell and culturing the transfected host cell under conditions suitable to produce at least one copy of the peptide.

The invention also relates to modified inhibitors that are at least about 80%, 85%, 90% 95%, 96%, 97%, 98% or 99% identical to a reference inhibitor. A "modified inhibitor" is used to mean a peptide that can be created by addition, deletion or substitution of one or more amino acids in the primary structure (amino acid sequence) of a inhibitor protein or polypeptide. A "modified recognition motif" is a naturally occurring AKT recognition motif that has been modified by addition, deletion, or substitution of one or more amino acids in the primary structure (amino acid sequence) of the motif. For example, a modified AKT recognition motif may be a motif where the phosphorylatable amino acid as been modified to a non-phosphorylatable amino acid. The terms "protein" and "polypeptide" are used interchangeably herein. The reference inhibitor is not necessarily a wild-type protein or a portion thereof. Thus, the reference inhibitor may be a protein or peptide whose sequence was previously modified over a wild-type protein. The reference inhibitor may or may not be the wild-type protein from a particular organism. Furthermore, the term "wild-type protein" includes the wild-type protein with or without a leader sequence.

A polypeptide having an amino acid sequence at least, for example, about 95% "identical" to a reference an amino acid sequence is understood to mean that the amino acid sequence of the polypeptide is identical to the reference sequence except that the amino acid sequence may include up to about five modifications per each 100 amino acids of the reference amino acid sequence encoding the reference peptide. In other words, to obtain a peptide having an amino acid sequence at least about 95% identical to a reference amino acid sequence, up to about 5% of the amino acid residues of the reference sequence may be deleted or substituted with another amino acid or a number of amino acids up to about 5% of the total amino acids in the reference sequence may be inserted into the reference sequence. These modifications of the reference sequence may occur at the N-terminus or C-terminus positions of the reference amino acid sequence or anywhere between those terminal positions, interspersed either individually among amino acids in the reference sequence or in one or more contiguous groups within the reference sequence.

As used herein, "identity" is a measure of the identity of nucleotide sequences or amino acid sequences compared to a reference nucleotide or amino acid sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While there exist several methods to measure identity between two polynucleotide or polypeptide sequences, the term "identity" is well known to skilled artisans (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCG program package (Devereux, J., et al., Nucleic Acids Research 12(i):387 (1984)), BLASTP, ExPASy, BLASTN, FASTA (Atschul, S. F., et al., J Molec Biol 215:403 (1990)) and FASTDB. Examples of methods to determine identity and similarity are discussed in Michaels, G. and Garian, R., *Current Protocols in Protein Science*, Vol 1, John Wiley & Sons, Inc. (2000), which is incorporated by reference. In one embodiment of the present invention, the algorithm used to determine identity between two or more polypeptides is BLASTP.

In another embodiment of the present invention, the algorithm used to determine identity between two or more polypeptides is FASTDB, which is based upon the algorithm of Brutlag et al. (Comp. App. Biosci. 6:237-245 (1990), incorporated by reference). In a FASTDB sequence alignment, the query and subject sequences are amino sequences. The result of sequence alignment is in percent identity. Parameters that may be used in a FASTDB alignment of amino acid sequences to calculate percent identity include, but are not limited to: Matrix=PAM, k-tuple=2, Mismatch Penalty=1, Joining Penalty=20, Randomization Group Length=0, Cutoff Score=1, Gap Penalty=5, Gap Size Penalty 0.05, Window Size=500 or the length of the subject amino sequence, whichever is shorter.

If the subject sequence is shorter or longer than the query sequence because of N-terminus or C-terminus additions or deletions, not because of internal additions or deletions, a manual correction can be made, because the FASTDB program does not account for N-terminus and C-terminus truncations or additions of the subject sequence when calculating percent identity. For subject sequences truncated at the 5' or 3' ends, relative to the query sequence, the percent identity is corrected by calculating the number of bases of the query sequence that are N- and C-terminus to the reference sequence that are not matched/aligned, as a percent of the total bases of the query sequence. The results of the FASTDB sequence alignment determine matching/alignment. The alignment percentage is then subtracted from the percent identity, calculated by the above FASTDB program using the specified parameters, to arrive at a final percent identity score. This corrected score can be used for the purposes of determining how alignments "correspond" to each other, as well as percentage identity. Residues of the query (subject) sequences or the reference sequence that extend past the N- or C-termini of the reference or subject sequence, respectively, may be considered for the purposes of manually adjusting the percent identity score. That is, residues that are not matched/aligned with the N- or C-termini of the comparison sequence may be counted when manually adjusting the percent identity score or alignment numbering.

For example, a 90 amino acid residue subject sequence is aligned with a 100 residue reference sequence to determine percent identity. The deletion occurs at the N-terminus of the subject sequence and therefore, the FASTDB alignment does not show a match/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 reference sequence. This time the deletions are internal deletions so there are no residues at the N- or C-termini of the subject sequence which are not matched/aligned with the query. In this case the percent identity calculated by FASTDB is not manually corrected.

The polyligands of the invention optionally comprise spacer amino acids between monomers. The length and composition of the spacer may vary. An example of a spacer is glycine, alanine, polyglycine, or polyalanine. Specific examples of spacers used between monomers in SEQ ID NO:7 are the five amino acid peptides GlyAlaGlyAlaPro and AlaGlyAlaGlyPro. In the instance of SEQ ID NO:7, the proline-containing spacer is intended to break an alpha helical secondary structure. Spacer amino acids may be any amino acid and are not limited to alanine, glycine and proline. SEQ ID NO:7, depicted generically in FIG. 4B, represents a specific example of a heteropolyligand with the structure X-S1-Y-S2-Z, where X is SEQ ID NO:131, Y is SEQ ID NO:88, Z is SEQ ID NO: 137, wherein Xaa is Alanine, and wherein S1 is a five amino acid spacer with the sequence AlaGlyAlaGlyPro, and S2 is a five amino acid spacer with the sequence GlyAlaGlyAlaPro. The instant invention is directed to all combinations of homopolyligands and heteropolyligands, with or without spacers, and without limitation to the examples given above or below.

The ligands and polyligands of the invention are optionally linked to additional molecules or amino acids that provide an epitope tag, a reporter, and/or localize the ligand to a region of a cell. Non-limiting examples of epitope tags are FLAG™ (Kodak; Rochester, N.Y.), HA (hemagluttinin), c-Myc and His6. Additional examples of epitope tags are given in Jarvik & Telmer 1998 Annual Reviw of Genetics 32:601-18. Non-limiting examples of reporters are alkaline phosphatase, galactosidase, peroxidase, luciferase and green fluorescent protein (GFP). Non-limiting examples of cellular localizations are sarcoplamic reticulum, endoplasmic reticulum, mitochondria, golgi apparatus, nucleus, plasma membrane, apical membrane, and basolateral membrane. The epitopes, reporters and localization signals are given by way of example and without limitation. The epitope tag, reporter and/or localization signal may be the same molecule. The epitope tag, reporter and/or localization signal may also be different molecules.

Ligands and polyligands and optional amino acids linked thereto can be synthesized chemically or recombinantly using techniques known in the art. Chemical synthesis techniques include but are not limited to peptide synthesis which is often performed using an automated peptide synthesizer. Pepetides can also be synthesized utilizing non-automated peptide synthesis methods known in the art. Recombinant techniques include insertion of ligand-encoding nucleic acids into expression vectors, wherein nucleic acid expression products are synthesized using cellular factors and processes.

Linkage of a cellular localization signal, epitope tag, or reporter to a ligand or polyligand can include covalent or enzymatic linkage to the ligand. When the localization signal comprises material other than a polypeptide, such as a lipid or carbohydrate, a chemical reaction to link molecules may be utilized. Additionally, non-standard amino acids and amino acids modified with lipids, carbohydrates, phosphate or other molecules may be used as precursors to peptide synthesis. The ligands of the invention have therapeutic utility with or without localization signals. For example, the ligands generically depicted in FIGS. 1A-1C, FIGS. 2A-2C, FIGS. 3A-3C, FIGS. 4A-4C and FIGS. 7A-7G represent embodiments of conventional polypeptide therapeutics. However, ligands linked to localization signals have utility as subcellular tools or therapeutics. For example, ligands depicted generically in FIGS. 7A-7G represent ligands with utility as subcellular tools or therapeutics. AKT ligand-containing gene constructs are also delivered via gene therapy. FIGS. 10B and 10C depict embodiments of gene therapy vectors for delivering and controlling polypeptide expression in vivo. Polynucleotide sequences linked to the gene construct in FIGS. 10B and 10C include genome integration domains to facilitate integration of the transgene into a viral genome and/or host genome.

Figure 5A:
FIGS. 5A-5G show examples of ligands and polymeric ligands linked to an epitope tag.
Figure 5B:
Figure 5C:
Figure 5D:
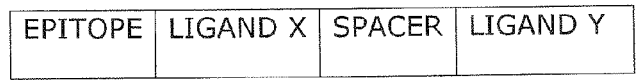
Figure 5E:
Figure 5F:
Figure 5G:
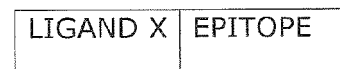
Figure 6A:
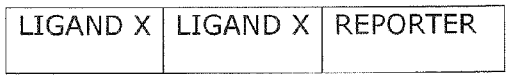
FIGS. 6A-6G show examples of ligands and polymeric ligands linked to a reporter.
Figure 6B:
Figure 6C:
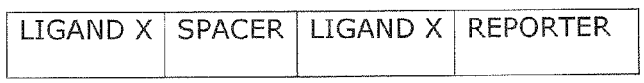
Figure 6D:
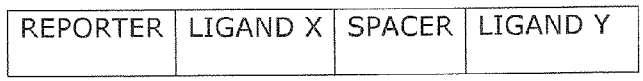
Figure 6E:
Figure 6F:
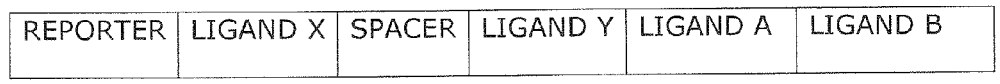
Figure 6G:
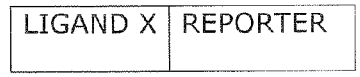
Figure 7A:
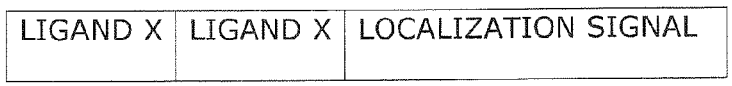
FIGS. 7A-7G show examples of ligands and polymeric ligands linked to a localization signal.
Figure 7B:
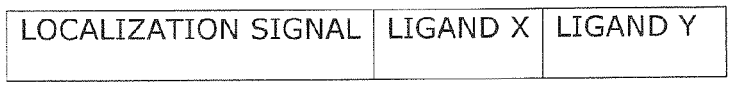
Figure 7C:
Figure 7D:
Figure 7E:
Figure 7F:
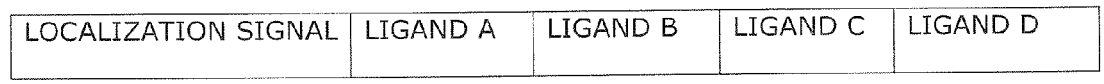
Figure 7G:
Figure 10A:
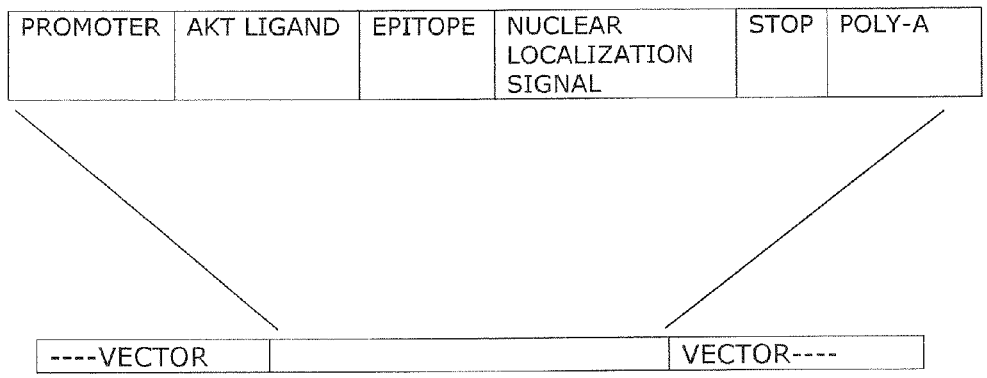
FIGS. 10A-10D show examples of vectors containing ligand gene constructs.
Figure 10B:
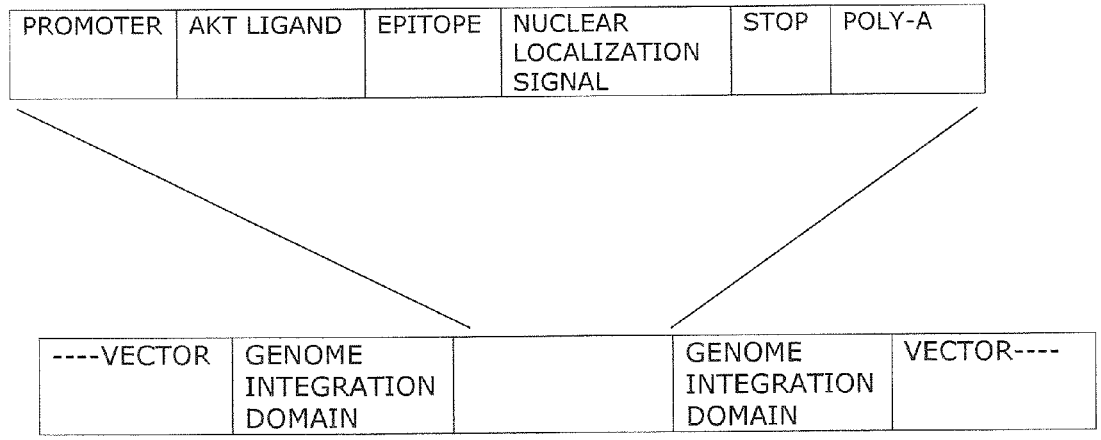
Figure 10C:
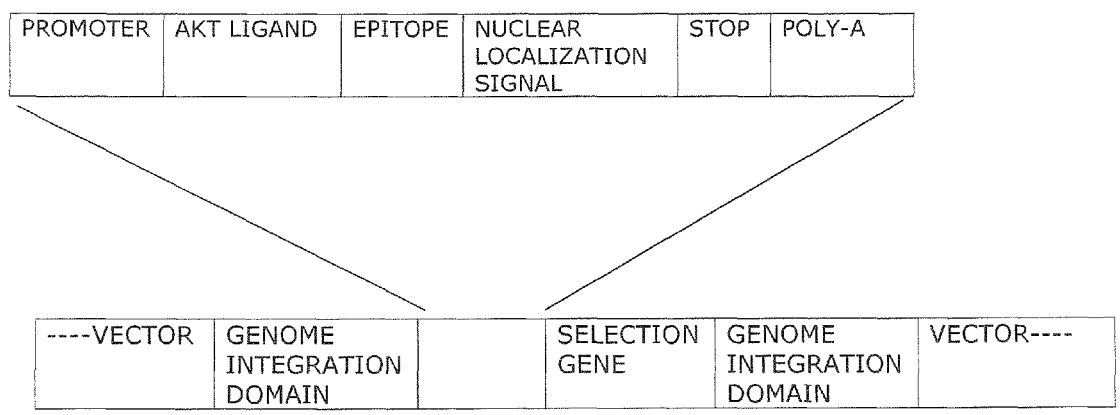

FIG. 10A shows a vector containing an AKT ligand gene construct, wherein the ligand gene construct is releasable from the vector as a unit useful for generating transgenic animals. For example, the ligand gene construct, or transgene, is released from the vector backbone by restriction endonuclease digestion. The released transgene is then injected into pronuclei of fertilized mouse eggs; or the transgene is used to transform embryonic stem cells. The vector containing a ligand gene construct of FIG. 10A is also useful for transient transfection of the trangene, wherein the promoter and codons of the transgene are optimized for the host organism. The vector containing a ligand gene construct of FIG. 10A is also useful for recombinant expression of polypeptides in fermentible organisms adaptable for small or large scale production, wherein the promoter and codons of the transgene are optimized for the fermentation host organism.

Figure 10D:
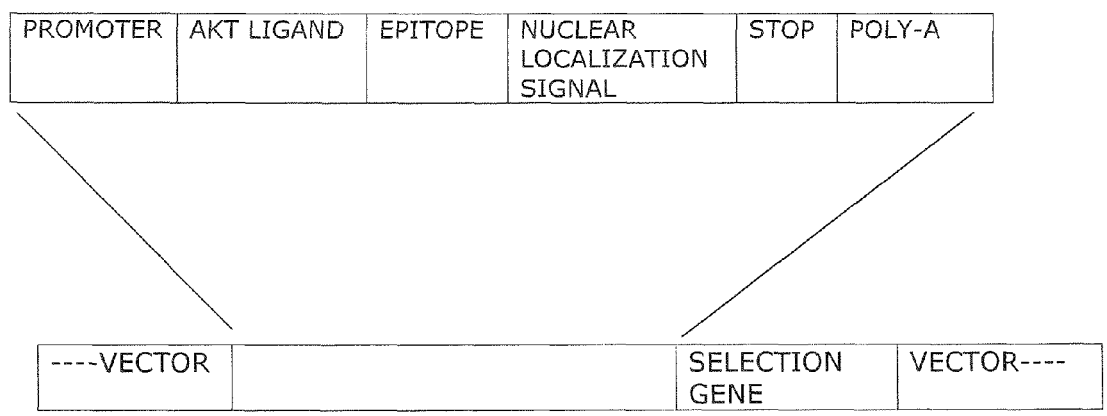

FIG. 10D shows a vector containing an AKT ligand gene construct useful for generating stable cell lines.

The invention also encompasses polynucleotides comprising nucleotide sequences encoding ligands, homopolyligands, and heteropolyligands. The polynucleotides of the invention are optionally linked to additional nucleotide sequences encoding epitopes, reporters and/or localization signals. Further, the nucleic acids of the invention are optionally incorporated into vector polynucleotides. The polynucleotides are optionally flanked by nucleotide sequences comprising restriction endonuclease sites and other nucleotides needed for restriction endonuclease activity. The flanking sequences optionally provide cloning sites within a vector. The restriction sites can include, but are not limited to, any of the commonly used sites in most commercially available cloning vectors. Examples of such sites are those recognized by BamHI, ClaI, EcoRI, EcoRV, SpeI, AflII, NdeI, NheI, XbaI, XhoI, SphI, NaeI, SexAI, HindIII, HpaI, and PstI restriction endonucleases. Sites for cleavage by other restriction enzymes, including homing endonucleases, are also used for this purpose. The polynucleotide flanking sequences also optionally provide directionality of subsequence cloning. It is preferred that 5' and 3' restriction endonuclease sites differ from each other so that double-stranded DNA can be directionally cloned into corresponding complementary sites of a cloning vector.

Ligands and polyligands with or without localization signals, epitopes or reporters are alternatively synthesized by recombinant techniques. Polynucleotide expression constructs are made containing desired components and inserted into an expression vector. The expression vector is then transfected into cells and the polypeptide products are expressed and isolated. Ligands made according to recombinant DNA techniques have utility as research tools and/or therapeutics.

The following is an example of how polynucleotides encoding ligands and polyligands are produced. Complimentary oligonucleotides encoding the ligands and flanking sequences are synthesized and annealled. The resulting double-stranded DNA molecule is inserted into a cloning vector using techniques known in the art. When the ligands and polyligands are placed in-frame adjacent to sequences within a transgenic gene construct that is translated into a protein product, they form part of a fusion protein when expressed in cells or transgenic animals.

Another embodiment of the invention relates to selective control of transgene expression in a desired cell or organism. The promotor portion of the recombinant gene can be a constitutive promotor, a non-constitutive promotor, a tissue-specific promotor (constitutive or non-constitutive) or a selectively controlled promotor. Different selectively controlled promotors are controlled by different mechanisms. For example, a tetracycline-inducible promotor is activated to express a downstream coding sequence when the cell containing the promotor and other necessary cellular factors is treated with tetracycline. When tetracycline is removed, gene expression is subsequently reduced. Other inducible promotors are activated by other drugs or factors. Rheo-Switch® is an inducible promotor system available from RheoGene. Temperature sensitive promotors can also be used to increase or decrease gene expression. An embodiment of the invention comprises a ligand or polyligand gene construct whose expression is controlled by an inducible promotor. In one embodiment, the inducible promotor is tetracycline inducible.

Figure 11:
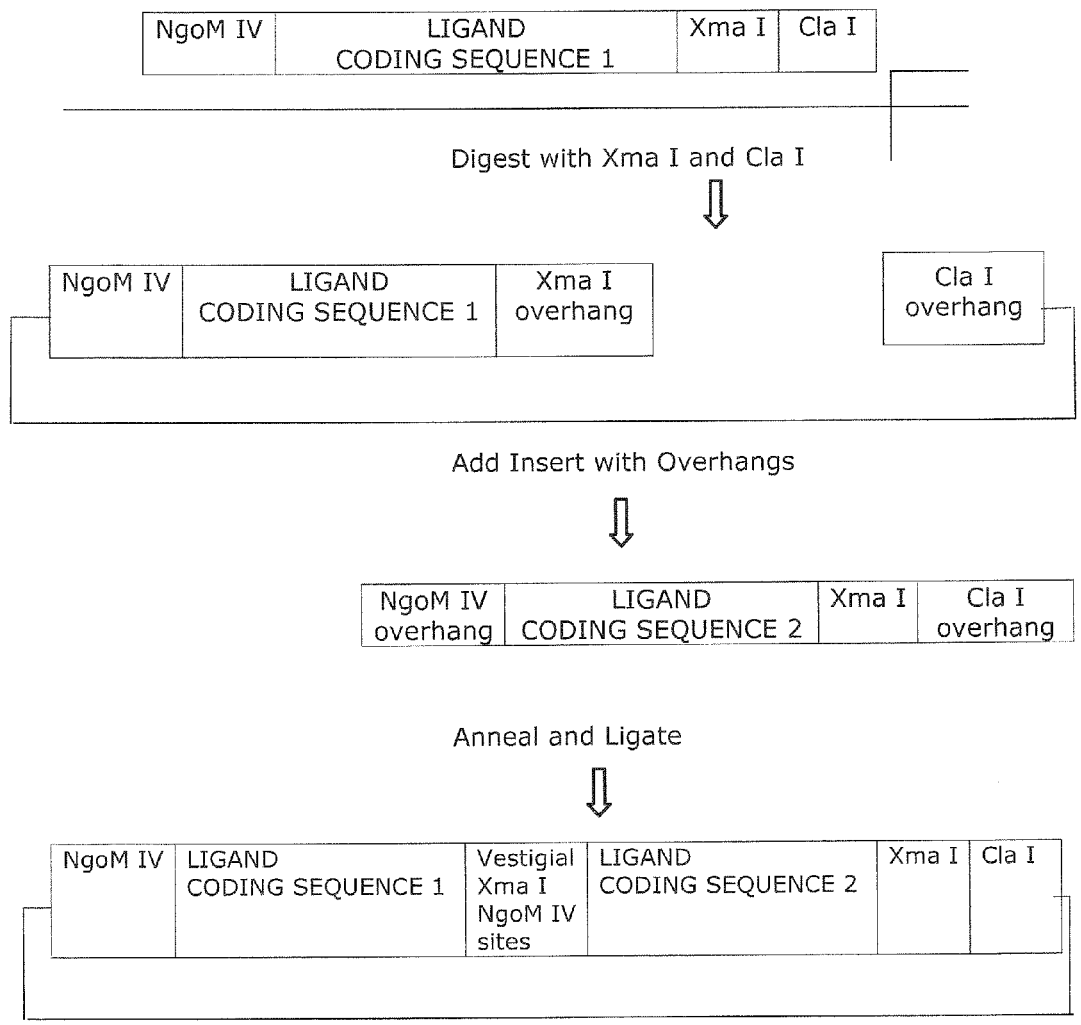
FIG. 11 shows an example of a sequential cloning process useful for combinatorial synthesis of polyligands.

Polyligands are modular in nature. An aspect of the instant invention is the combinatorial modularity of the disclosed polyligands. Another aspect of the invention are methods of making these modular polyligands easily and conveniently. In this regard, an embodiment of the invention comprises methods of modular subsequence cloning of genetic expression components. When the ligands, homopolyligands, heteropolyligands and optional amino acid expression components are synthesized recombinantly, one can consider each clonable element as a module. For speed and convenience of cloning, it is desirable to make modular elements that are compatible at cohesive ends and are easy to insert and clone sequentially. This is accomplished by exploiting the natural properties of restriction endonuclease site recognition and cleavage. One aspect of the invention encompasses module flanking sequences that, at one end of the module, are utilized for restriction enzyme digestion once, and at the other end, utilized for restriction enzyme digestion as many times as desired. In other words, a restriction site at one end of the module is utilized and destroyed in order to effect sequential cloning of modular elements. An example of restriction sites flanking a coding region module are sequences recognized by the restriction enzymes NgoM IV and Cla I; or Xma I and Cla I. Cutting a first circular DNA with NgoM IV and Cla I to yield linear DNA with a 5' NgoM IV overhang and a 3' Cla I overhang; and cutting a second circular DNA with Xma I and Cla I to yield linear DNA with a 5' Cla I overhang and a 3' Xma I overhang generates first and second DNA fragments with compatible cohesive ends. When these first and second DNA fragments are mixed together, annealed, and ligated to form a third circular DNA fragment, the NgoM IV site that was in the first DNA and the Xma I site that was in the second DNA are destroyed in the third circular DNA. Now this vestigial region of DNA is protected from further Xma I or NgoM IV digestion, but flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences. This process is depicted in FIG. 11.

Another way to assemble coding region modules directionally and sequentially employs linear DNA in addition to circular DNA. For example, like the sequential cloning process described above, restriction sites flanking a coding region module are sequences recognized by the restriction enzymes NgoM IV and Cla I; or Xma I and Cla I. A first circular DNA is cut with NgoM IV and Cla I to yield linear DNA with a 5' NgoM IV overhang and a 3' Cla I overhang. A second linear double-stranded DNA is generated by PCR amplification or by synthesizing and annealing complimentary oligonucleotides. The second linear DNA has 5' Cla I overhang and a 3' Xma I overhang, which are compatible cohesive ends with the first DNA linearized. When these first and second DNA fragments are mixed together, annealed, and ligated to form a third circular DNA fragment, the NgoM IV site that was in the first DNA and the Xma I site that was in the second DNA are destroyed in the third circular DNA. Flanking sequences remaining in the third circular DNA still contain intact 5' NgoM IV and 3' Cla I sites. This process can be repeated numerous times to achieve directional, sequential, modular cloning events. Restriction sites recognized by NgoM IV, Xma I, and Cla I endonucleases represent a group of sites that permit sequential cloning when used as flanking sequences.

One of ordinary skill in the art recognizes that other restriction site groups can accomplish sequential, directional cloning as described herein. Preferred criteria for restriction endonuclease selection are selecting a pair of endonucleases that generate compatible cohesive ends but whose sites are destroyed upon ligation with each other. Another criteria is to select a third endouclease site that does not generate sticky ends compatible with either of the first two. When such criteria are utilized as a system for sequential, directional cloning, ligands, polyligands and other coding regions or expression components can be combinatorially assembled as desired. The same sequential process can be utilized for epitope, reporter, and/or localization signals.

Polyligands and methods of making polyligands that modulate AKT activity are disclosed. Therapeutics include delivery of purified ligand or polyligand with or without a localization signal to a cell. Alternatively, ligands and polyligands with or without a localization signals are delivered via adenovirus, lentivirus, adeno-associated virus, or other viral constructs that express protein product in a cell.

Ligands of the invention can be assayed for kinase modulating activity several methods.

In one embodiment, a biochemical assay can be performed employing commercially-obtained kinase, commercially-obtained substrate, commercially-obtained kinase inhibitor (control), and semi-purified inhibitor ligand of the invention (decoy ligand). Decoy ligands can be linked to an epitope tag at one end of the polypeptide for purification and/or immobilization, for example, on a microtiter plate. The tagged decoy ligand can be made using an in vitro transcription/translation system such as a reticulocyte lysate system well known in the art. A vector polynucleotide comprising a promotor, such as T7 and/or T3 and/or SP6 promotor, a decoy ligand coding sequence, and an epitope tag coding sequence can be employed to synthesize the tagged decoy ligand in an in vitro transcription/translation system. In vitro transcription/translation protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Immunoreagent-containing methods such as western blots, elisas, and immunoprecipitations can be performed as described in: Using Antibodies: A Laboratory Manual (Harlow and Lane Cold Spring Harbor Laboratory Press, 1999).

In another embodiment, specifically, tagged decoy ligand synthesized using an in vitro transcription/translation system can be semi-purified and added to a microtiter plate containing kinase enzyme and substrate immobilized by an anti-substrate specific antibody. Microtiter plates can be rinsed to substantially remove non-immobilized components. Kinase activity is a direct measure of the phosphorylation of substrate by kinase employing a phospho-substrate specific secondary antibody conjugated to horseradish peroxidase (HRP) followed by the addition of 3,3',5,5'-tetramethylbenzidine (TMB) substrate solution. The catalysis of TMB by HRP results in a blue color that changes to yellow upon addition of phosphoric or sulfuric acid with a maximum absorbance at 450 nm. Control experiments can include the absence of kinase enzyme, and/or absence of decoy ligand, and/or presence/absence of known kinase inhibitors. A known kinase inhibitor useful in the assay is staurosporine.

A similar assay can be performed employing the same reagents as above but the substrate can be biotinylated and immobilized by binding to a streptavidin-coated plate.

In another embodiment, a biochemical assay can be performed employing commercially-obtained kinase, commercially-obtained substrate, commercially-obtained kinase inhibitor (control), and semi-purified inhibitor ligand of the invention (decoy ligand) in a microtiter plate. A luminescent-based detection system, such as Promega's Kinase-Glo, can then be added to inversely measure kinase activity.

In yet another embodiment, specifically, tagged decoy ligand synthesized using an in vitro transcription/translation system can be semi-purified and added to a microtiter plate containing kinase enzyme and substrate. After the kinase assay is performed, luciferase and luciferin are added to the reaction. Luciferase utilizes any remaining ATP not used by the kinase to catalyze luciferin. The luciferase reaction results in the production of light which is inversely related to kinase activity. Control experiments can include the absence of kinase enzyme, and/or absence of decoy ligand, and/or presence/absence of known kinase inhibitors. A known kinase inhibitor useful in the assay is staurosporine.

In another embodiment still, a similar cell-based assay can be performed employing the same reagents as above, but synthesizing the decoy ligand in a mammalian cell system instead of an in vitro transcription/translation system. Decoy ligands can be linked to an epitope tag at one end of the polypeptide for immobilization and/or for purification and/or for identification in a western blot. Optionally, tagged decoy ligands can also be linked to a cellular localization signal for phenotypic comparison of pan-cellular and localized kinase modulation. A vector polynucleotide comprising a constitutive promotor, such as the CMV promotor, a decoy ligand coding sequence, an epitope tag coding sequence, and optionally a localization signal coding sequence can be employed to express the decoy ligand in cells. Transfection and expression protocols are disclosed in reference manuals such as: Current Protocols in Molecular Biology (eds. Ausubel et al., Wiley, 2004 edition.) and Molecular Cloning: A Laboratory Manual (Sambrook and Russell (Cold Spring Harbor Laboratory Press, 2001, third edition). Western Blots and immunoreagent-containing methods can be performed as described in: Using Antibodies: A Laboratory Manual (Harlow and Lane Cold Spring Harbor Laboratory Press, 1999).

EXAMPLES

Example 1

A polypeptide comprising a heteropolyligand, an endoplasmic reticulum cellular localization signal, and a His6 epitope is synthesized. The structure of such a polypeptide is generically represented by FIG. 8E. The polypeptide is synthesized on an automated peptide synthesizer or is recombinantly expressed and purified. Purified polypeptide is solubilized in media and added to cells. The polypeptide is endocytosed by the cells, and transported to the endoplasmic reticulum. Verification is performed by immunohistochemical staining using an anti-His6 antibody.

Example 2

A transgene is constructed using a human cytomegalovirus (CMV) promoter to direct expression of a fusion protein comprising SEQ ID NO:84, SEQ ID NO:119, SEQ ID NO:86 (POLYLIGAND), green fluorescent protein (REPORTER), and a plasma membrane localization signal (LOCALIZATION SIGNAL). Such a transgene is generically represented by FIG. 9C. The transgene is transfected into cells for transient expression. Verification of expression and location is performed by visualization of green fluorescent protein (GFP) by confocal microscopy.

Example 3

A transgene construct is built to produce a protein product with expression driven by a tissue-specific promoter. The transgene comprises a synthetic gene expression unit engineered to encode three domains. Each of these three domains is synthesized as a pair of complimentary polynucleotides that are annealed in solution, ligated and inserted into a vector. Starting at the amino-terminus, the three domains in the expression unit are nucleotide sequences that encode an AKT ligand, a FLAG™ epitope, and a nuclear localization signal. The AKT ligand is a monomeric ligand, homopolymeric ligand or heteropolymeric ligand as described herein. Nucleotide sequences encoding a FLAG™ epitope (amino acids DYKDDDDK) are placed downstream of nucleotide sequences encoding the AKT ligand. Finally, nucleotide sequences encoding the localization signal are placed downstream of those encoding the FLAG™ epitope. The assembled gene expression unit is subsequently subcloned into an expression vector, such as that shown in FIG. 10A, and used to transiently transfect cells. Verification is performed by immunohistochemical staining using an anti-FLAG™ antibody.

Example 4

Modulation of AKT cellular function by subcellularly localized AKT polyligand was demonstrated in Huh7 cells. A transgene construct containing a polyligand fusion protein, epitope, and nuclear localization signal was made. The expressed portion of the transgene construct is generically shown in FIG. 8A. The expression unit contains nucleotides that encode SEQ ID NO:1 (POLYLIGAND), a c-Myc epitope (EPITOPE), and a nuclear localization signal (LOCALIZATION SIGNAL). This expression unit is subsequently subcloned into a vector between a CMV promoter and an SV40 polyadenylation signal (Generically depicted in FIG. 10A). The completed transgene-containing expression vector is then used to transfect Huh7 cells co-transfected with FKHRL1-GFP fusion expression construct. FIG. 13 illustrates the change in cellular location of FKHRL1-GFP when co-expressed with nuclear-localized AKT ligand. In the absence of nuclear-localized AKT ligand, FKHRL1-GFP is primarily outside the nucleus. However, in the presence of nuclear-localized AKT ligand, FKHRL1-GFP is primarily inside the nucleus.

Example 5

Ligand function and localization is demonstrated in vivo by making a transgene construct used to generate mice expressing a ligand fusion protein targeted to the endoplasmic reticulum. The transgene construct is shown generically in FIG. 10B. The expression unit contains nucleotides that encode a tetramer of SEQ ID NO:74, a hemagluttinin epitope, and a mitochondrial localization signal. This expression unit is subsequently subcloned into a vector between nucleotide sequences including an inducible promoter and an SV40 polyadenylation signal. The completed transgene is then injected into pronuclei of fertilized mouse oocytes. The resultant pups are screened for the presence of the transgene by PCR. Transgenic founder mice are bred with wild-type mice. Heterozygous transgenic animals from at least the third generation are used for the following tests, with their non-transgenic littermates serving as controls.

Test 1: Southern blotting analysis is performed to determine the copy number. Southern blots are hybridized with a radio-labeled probe generated from a fragment of the transgene. The probe detects bands containing DNA from transgenic mice, but does not detect bands containing DNA from non-transgenic mice. Intensities of the transgenic mice bands are measured and compared with the transgene plasmid control bands to estimate copy number. This demonstrates that mice in Example 4 harbor the transgene in their genomes.

Test 2: Tissue homogenates are prepared for Western blot analysis. This experiment demonstrates the transgene is expressed in tissues of transgenic mice because hemagluttinin epitope is detected in transgenic homogenates but not in non-transgenic homogenates.

These examples demonstrate delivery of ligands to a localized region of a cell for therapeutic or experimental purposes. The purified polypeptide ligands can be formulated for oral or parenteral administration, topical administration, or in tablet, capsule, or liquid form, intranasal or inhaled aerosol, subcutaneous, intramuscular, intraperitoneal, or other injection; intravenous instillation; or any other routes of administration. Furthermore, the nucleotide sequences encoding the ligands permit incorporation into a vector designed to deliver and express a gene product in a cell. Such vectors include plasmids, cosmids, artificial chromosomes, and modified viruses. Delivery to eukaryotic cells can be accomplished in vivo or ex vivo. Ex vivo delivery methods include isolation of the intended recipient's cells or donor cells and delivery of the vector to those cells, followed by treatment of the recipient with the cells.

Disclosed are ligands and polyligands that modulate AKT activity and methods of making and using these ligands. The ligands and polyligands are synthesized chemically or recombinantly and are utilized as research tools or as therapeutics. The invention includes linking the ligands and polyligands to cellular localization signals for subcellular therapeutics.

What is claimed is:

1. An isolated polynucleotide comprising a polynucleotide sequence encoding a polypeptide heteropolyligand wherein said polypeptide heteropolyligand comprises
   (a) a sequence at least 90% identical to SEQ ID NO:90 and SEQ ID NO:174;
   (b) a sequence at least 90% identical to SEQ ID NO:102 and SEQ ID NO:174;
   (c) a sequence at least 90% identical to SEQ ID NO:194 and SEQ ID NO:174; or
   (d) a sequence at least 90% identical to SEQ ID NO:195 and SEQ ID NO:174;
   wherein Xaa is any amino acid, and wherein the polypeptide heteropolyligand inhibits the kinase activity of mammalian protein kinase B (AKT).

2. The isolated polynucleotide of claim 1, wherein at least one amino acid designated as Xaa is an amino acid other than serine or threonine.

3. The isolated polynucleotide of claim 1, wherein said polypeptide heteropolyligand is linked to one or more of a localization signal, an epitope tag, or a reporter.

4. A vector comprising the isolated polynucleotide of claim 1.

5. A host cell comprising the vector of claim 4.

6. The isolated polynucleotide of claim 1, operably linked to a promoter.

7. The isolated polynucleotide of claim 6, wherein said promoter is an inducible promoter.

8. The isolated polynucleotide of claim 1, wherein said encoded polypeptide heteropolyligand comprises (a) a sequence at least 95% identical to SEQ ID NO:90; (b) a sequence at least 95% identical to SEQ ID NO:102; (c) a sequence at least 95% identical to SEQ ID NO:194; or (d) a sequence at least 95% identical to SEQ ID NO:195, wherein the polypeptide heteropolyligand inhibits the kinase activity of mammalian protein kinase B (AKT).

9. The isolated polynucleotide of claim 1, wherein said encoded polypeptide heteropolyligand comprises (a) a sequence at least 96% identical to SEQ ID NO:90; (b) a sequence at least 96% identical to SEQ ID NO:102; (c) a sequence at least 96% identical to SEQ ID NO:194; or (d) a sequence at least 96% identical to SEQ ID NO:195, wherein the polypeptide heteropolyligand inhibits the kinase activity of mammalian protein kinase B (AKT).

10. The isolated polynucleotide of claim 1, wherein said encoded polypeptide heteropolyligand comprises (a) a sequence at least 97% identical to SEQ ID NO:90; (b) a sequence at least 97% identical to SEQ ID NO:102; (c) a sequence at least 97% identical to SEQ ID NO:194; or (d) a sequence at least 97% identical to SEQ ID NO:195, wherein the polypeptide heteropolyligand inhibits the kinase activity of mammalian protein kinase B (AKT).

11. The isolated polynucleotide of claim 1, wherein said encoded polypeptide heteropolyligand comprises (a) a sequence at least 98% identical to SEQ ID NO:90; (b) a sequence at least 98% identical to SEQ ID NO:102; (c) a sequence at least 98% identical to SEQ ID NO:194; or (d) a sequence at least 98% identical to SEQ ID NO:195, wherein the polypeptide heteropolyligand inhibits the kinase activity of mammalian protein kinase B (AKT).

12. The isolated polynucleotide of claim 1, wherein said encoded polypeptide heteropolyligand comprises (a) a sequence at least 99% identical to SEQ ID NO:90; (b) a sequence at least 99% identical to SEQ ID NO:102; (c) a sequence at least 99% identical to SEQ ID NO:194; or (d) a sequence at least 99% identical to SEQ ID NO:195, wherein the polypeptide heteropolyligand inhibits the kinase activity of mammalian protein kinase B (AKT).

13. The isolated polynucleotide of claim 1, wherein said encoded polypeptide heteropolyligand comprises (a) SEQ ID NO: 90; (b) SEQ ID NO:101; (c) SEQ ID NO: 102; (d) SEQ ID NO:194; or (e) SEQ ID NO:195.

14. A method of inhibiting AKT in a cell, said method comprising
   (a) transfecting the vector of claim 4 into a host cell, and
   (b) culturing the transfected host cell under conditions suitable to produce at least one copy of the polypeptide polyligand.

15. The isolated polynucleotide of claim 1, wherein said encoded polypeptide heteropolyligand comprises a sequence at least 95% identical to SEQ ID NO:174, and wherein the polypeptide heteropolyligand inhibits the kinase activity of mammalian protein kinase B (AKT).

16. The isolated polynucleotide of claim 1, wherein said encoded polypeptide heteropolyligand comprises a sequence at least 96% identical to SEQ ID NO:174, and wherein the polypeptide heteropolyligand inhibits the kinase activity of mammalian protein kinase B (AKT).

17. The isolated polynucleotide of claim 1, wherein said encoded polypeptide heteropolyligand comprises a sequence at least 97% identical to SEQ ID NO:174, and wherein the polypeptide heteropolyligand inhibits the kinase activity of mammalian protein kinase B (AKT).

18. The isolated polynucleotide of claim 1, wherein said encoded polypeptide heteropolyligand comprises a sequence at least 98% identical to SEQ ID NO:174, and wherein the polypeptide heteropolyligand inhibits the kinase activity of mammalian protein kinase B (AKT).

19. The isolated polynucleotide of claim 1, wherein said encoded polypeptide heteropolyligand comprises a sequence at least 99% identical to SEQ ID NO:174, and wherein the polypeptide heteropolyligand inhibits the kinase activity of mammalian protein kinase B (AKT).

20. The isolated polynucleotide of claim 1, wherein said encoded polypeptide heteropolyligand comprises SEQ ID NO: 174 or 175, and wherein the polypeptide heteropolyligand inhibits the kinase activity of mammalian protein kinase B (AKT).

* * * * *